US011147852B2

(12) United States Patent
Marquette et al.

(10) Patent No.: US 11,147,852 B2
(45) Date of Patent: Oct. 19, 2021

(54) ENGINEERED ANTIBODY CONSTANT REGIONS FOR SITE-SPECIFIC CONJUGATION AND METHODS AND USES THEREFOR

(71) Applicant: Pfizer Inc., New York, NY (US)

(72) Inventors: Kimberly Marquette, Somerville, MA (US); Eric Bennett, Arlington, MA (US); Lioudmila Tchistiakova, Andover, MA (US); L. Nathan Tumey, Pawcatuck, CT (US); Jack Bikker, Little Silver, NJ (US); Valerie Calabro, Carro (FR); Edmund Graziani, Chestnut Ridge, NY (US)

(73) Assignee: Pfizer Inc., New York, NY (US)

( * ) Notice: Subject to any disclaimer, the term of this patent is extended or adjusted under 35 U.S.C. 154(b) by 117 days.

(21) Appl. No.: 14/367,861

(22) PCT Filed: Dec. 19, 2012

(86) PCT No.: PCT/IB2012/057491
§ 371 (c)(1),
(2) Date: Jun. 20, 2014

(87) PCT Pub. No.: WO2013/093809
PCT Pub. Date: Jun. 27, 2013

(65) Prior Publication Data
US 2016/0008485 A1    Jan. 14, 2016

Related U.S. Application Data

(60) Provisional application No. 61/580,169, filed on Dec. 23, 2011.

(51) Int. Cl.
| | |
|---|---|
| *A61K 38/08* | (2019.01) |
| *C07K 16/30* | (2006.01) |
| *C07K 16/32* | (2006.01) |
| *A61K 47/68* | (2017.01) |
| *C07K 16/00* | (2006.01) |
| *C07K 16/28* | (2006.01) |

(52) U.S. Cl.
CPC ............ *A61K 38/08* (2013.01); *A61K 47/68* (2017.08); *A61K 47/6803* (2017.08); *A61K 47/6849* (2017.08); *A61K 47/6851* (2017.08); *C07K 16/00* (2013.01); *C07K 16/2863* (2013.01); *C07K 16/30* (2013.01); *C07K 16/32* (2013.01); *C07K 2317/21* (2013.01); *C07K 2317/32* (2013.01); *C07K 2317/52* (2013.01); *C07K 2317/732* (2013.01); *C07K 2317/77* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,013,556 | A | 5/1991 | Woodle et al. |
| 5,208,020 | A | 5/1993 | Chari et al. |
| 5,648,095 | A | 7/1997 | Illum et al. |
| 5,821,337 | A | 10/1998 | Carter et al. |
| 5,981,568 | A | 11/1999 | Kunz et al. |
| 6,309,633 | B1 | 10/2001 | Ekwuribe et al. |
| 6,461,603 | B2 | 10/2002 | Bentley et al. |
| 7,521,541 | B2 | 4/2009 | Eigenbrot et al. |
| 7,855,275 | B2 | 12/2010 | Eigenbrot et al. |
| 7,989,594 | B2 | 8/2011 | Humphreys et al. |
| 8,337,856 | B2 | 12/2012 | Blättler et al. |
| 10,086,085 | B2 | 10/2018 | Maderna et al. |
| 2005/0249723 | A1* | 11/2005 | Lazar .................... C07K 16/00 424/133.1 |
| 2006/0205670 | A1 | 9/2006 | Bradshaw et al. |
| 2008/0306246 | A1 | 12/2008 | Heywood |
| 2009/0041770 | A1 | 2/2009 | Chamberlain et al. |
| 2009/0087478 | A1 | 4/2009 | Hansen et al. |
| 2009/0252729 | A1 | 10/2009 | Farrington et al. |
| 2009/0258420 | A1 | 10/2009 | van Vlijmen et al. |
| 2011/0301334 | A1 | 12/2011 | Bhakta et al. |
| 2015/0209445 | A1 | 7/2015 | Maderna et al. |

(Continued)

FOREIGN PATENT DOCUMENTS

| | | |
|---|---|---|
| EP | 2083017 | 7/2009 |
| JP | 2009095249 | 5/2009 |

(Continued)

OTHER PUBLICATIONS

Stimmel et al. (J. Biol. Chem., 275(39): 30445-30450, 2000).*
Boswell et al., "Impact of Drug Conjugation on Pharmacokinetics and Tissue Distribution of Anti-STEAP1 Antibody-Drug Conjugates in Rats.", Bioconjugate Chemistry, vol. 22, 2011, pp. 1994-2004.
Boswell et al., "Impact of Drug Conjugation on Pharmacokinetics and Tissue Distribution of Anti-STEAP1 Antibody-Drug Conjugates in Rats.", Bioconjugate Chemistry, Supporting Information, 2011, pp. 1-7.
Chan et al., "A proprotein convertase subtilisin/kexin type 9 neutralizing antibody reduces serum cholesterol in mice and nonhuman primates." PNAS, vol. 106, No. 24, 2009, pp. 9820-9825.

(Continued)

*Primary Examiner* — Nelson B Moseley, II
(74) *Attorney, Agent, or Firm* — Austin W. Zhang

(57) ABSTRACT

The present invention is directed to antibodies, and antigen-binding portions thereof, engineered to introduce amino acids for site-specific conjugation. The invention relates to engineered antibody constant region (Fc, Cγ, Cκ, and Cλ) polypeptides, and portions thereof, and antibodies comprising the polypeptides. Further, the invention relates to Fc fusion proteins comprising an engineered Fc region. The invention also relates to methods and uses of the engineered antibodies and portions for, among other things, production of antibody-drug conjugate therapeutics.

27 Claims, 49 Drawing Sheets

Specification includes a Sequence Listing.

(56) References Cited

U.S. PATENT DOCUMENTS

| | | |
|---|---|---|
| 2015/0352225 A1 | 12/2015 | Rabuka et al. |
| 2016/0271270 A1 | 9/2016 | Maderna et al. |
| 2017/0151341 A1 | 6/2017 | Ma et al. |
| 2017/0216452 A1 | 8/2017 | Ma et al. |
| 2018/0339060 A1 | 11/2018 | Maderna et al. |
| 2019/0099499 A1 | 4/2019 | Katragadda et al. |

FOREIGN PATENT DOCUMENTS

| | | |
|---|---|---|
| WO | 2000053211 | 9/2000 |
| WO | 2005092925 A2 | 10/2005 |
| WO | 2006034488 A2 | 3/2006 |
| WO | 2007038658 | 4/2007 |
| WO | 200802833 | 3/2008 |
| WO | 2008038024 A1 | 4/2008 |
| WO | 2008141044 A2 | 11/2008 |
| WO | 2009009103 A2 | 1/2009 |
| WO | 2009092011 A1 | 7/2009 |
| WO | 2010141902 A2 | 12/2010 |
| WO | 2011005481 A1 | 1/2011 |
| WO | 2011044368 A1 | 4/2011 |
| WO | 2011044369 | 4/2011 |
| WO | 2011118739 | 9/2011 |
| WO | 2012/059882 | 5/2012 |
| WO | 2012162482 | 11/2012 |
| WO | 2013/072813 | 5/2013 |
| WO | 2013072813 A2 | 5/2013 |
| WO | 2013093809 | 6/2013 |
| WO | 2013/173337 | 11/2013 |
| WO | 2014/022592 | 2/2014 |
| WO | 2014/072888 | 5/2014 |
| WO | 2014/124316 | 8/2014 |
| WO | 2015023355 | 2/2015 |
| WO | 2015110935 | 7/2015 |
| WO | 2016151432 | 9/2016 |
| WO | 2017093844 | 6/2017 |
| WO | 2017093845 | 8/2017 |
| WO | 2018025168 | 8/2018 |

OTHER PUBLICATIONS

Cho et al., "Structure of the extracellular region of HER2 alone and in complex with the Herceptin Fab." Nature, vol. 421, 2003, pp. 756-760.
Edelman et al., "The Covalent Structure of an entire γG Immunoglobulin Molecule." Biochemistry, vol. 63, 1969, pp. 78-85.
Goldmacher et al., "Antibody-drug conjugates: using monoclonal antibodies for delivery of cytotoxic payloads to cancer cells", Therapeutic Delivery, vol. 2, No. 3, 2011, pp. 397-416.
Junutula et al., "Site-specific conjugation of a cytotoxic drug to an antibody improves the therapeutic index", Nature Biotechnology, vol. 26, No. 8, 2008, pp. 925-932.
Junutula et al., "Rapid identification of reactive cysteine residues for site-specific labeling of antibody-Fabs" J. of Immunological Methods, vol. 332, 2008, pp. 41-52.
Junutula et al., "Rapid identification of reactive cysteine residues for site-specific labeling of antibody-Fabs." J. of Immunological Methods, vol. 332, 2008, Supplementary data, pp. 1-12.
Junutula et al., "Engineered Thio-Trastuzumab-DM1 Conjugate with an Improved Therapeutic Index to Target Human Epidermal Growth Factor Receptor 2—Positive Breast Cancer.", Clinical Cancer Research, vol. 16, No. 19, 2010, pp. 4769-4778.
Krivov et al., "Improved prediction of protein side-chain conformations with SCWRL4." Proteins, vol. 77, 2009, pp. 778-795.
Kipriyanov et al., "Recombinant Single-chain Fv Fragments Carrying C-Terminal Cysteine Residues: Production of Bivalent and Biotinylated Miniantibodies.", Molecular Immunology, vol. 31, No. 4, 1994, pp. 1047-1058.
Shen et al., "Conjugation site modulates the in vivo stability and therapeutic activity of antibody-drug conjugates." Nature Biotechnology, vol. 30, No. 2, 2012, pp. 184-191.

Shen et al., "Conjugation site modulates the in vivo stability and therapeutic activity of antibody-drug conjugates." Nature Biotechnology, vol. 30, No. 2, 2012, Supplementary Data, pp. 1-26.
Sondermann et al., "The 3.2-Å crystal structure of the human IgG1 Fc fragment-FcγRIII complex." Nature, vol. 406, 2000, pp. 267-273.
Spassov and Yan, "A fast and accurate computational approach to protein ionization." Protein Science, vol. 17, 2008, pp. 1955-1970.
Teplyakov et al., "Epitope Mapping of Anti-Interleukin-13 Neutralizing Antibody CNTO607." J. Mol. Biol., vol. 389, 2009, pp. 115-123.
Voynov et al. "Design and application of antibody cysteine variants", Bioconjugate Chemistry, ACS, vol. 21, No. 2, 2010, pp. 385-392.
Ye et al., "Synthetic antibodies for specific recognition and crystallization of structured RNA." PNAS, vol. 105, No. 1, 2008, pp. 82-87.
Bird et al.; "Single-Chain Antigen-Binding Proteins" Science; vol. 242; pp. 424-426; 1988.
Brinkley; "A Brief Survey of Methods for Preparing Protein Conjugates with Dyes, Haptens, and Cross-Linking Reagents" Bioconj. Chem.; vol. 3; pp. 2-13; 1992.
Caceci et al.; "Fitting Curves to Data: The Simplex algorithm is the answer"; BYTE; vol. 3; pp. 340-362; 1984.
Eppstein et al.; "Biological activity of liposome-encapsulated murine interferon γ is mediated by a cell membrane receptor"; PNAS; vol. 82; pp. 3688-3692; 1985.
G. Hermanson; Modification of Nucleic Acids and Oligonucleotides, Bioconjugate Techniques, pp. 40-55, 1996.
G. Hermanson; "Chemical Modification of Nucleic Acids and Oligonucleotides", Bioconjugate Techniques, pp. 643-671, 1996.
Holliger et al.; "Diabodies": Small bivalent and bispecific antibody fragments; PNAS; vol. 90; pp. 6444-6448; 1993.
Hu et al; "Minibody: A Novel Engineered Anti-Carcinoembryonic Antigen Antibody Fragment (Single-Chain Fv-CH3) Which Exhibits Rapid, High-Level Targeting of Xenografts"; Cancer Res.; vol. 56; pp. 3055-3061; 1996.
Huston et al. "Protein engineering of antibody binding sites: Recovery of specific activity in an anti-digoxin single-chain Fv analogue produced in *Escherichia coli*" PNAS; vol. 85; pp. 5879-5883; 1988.
Hwang et al. "Hepatic uptake and degradation of unilamellar sphingomyelin/cholesterol liposomes: A kinetic study"; PNAS vol. 77; No. 7; pp. 4030-4034; 1980.
Kim et al.; "Statistical Modeling of the Drug Load Distribution on Trastuzumab Emtansine (Kadcyla), a Lysine-Linked Antibody Drug Conjugate" Bioconj. Chemistry; vol. 25; pp. 1223-1232; 2014.
Kunkel; "Rapid and efficient site-specific mutagenesis without phenotypic selection" PNAS; vol. 82; pp. 488-492; 1985.
Means & Feeney; "Chemical Modifications of Proteins: History and Applications"; Bioconj. Chemistry; vol. 1; pp. 2-12; 1990.
Olafsen et al.; "Characterization of engineered anti-p185HER-2 (scFv-CH3)2 antibody fragments (minibodies) for tumor targeting" Protein Engineering, Design & Selection; vol. 17; No. 4; pp. 315-323; 2004.
Poljak; "Production and structure of diabodies: The first crystal structure of a diabody, a bivalent antibody fragment, confirms previous predicted structures and techniques for generating bispecific bivalent antibody fragments of considerable therapeutic potential" Structure; vol. 2; No. 12; pp. 1121-1123; 1994.
Ward et al.; "Binding activities of a repertoire of single immunoglobulin variable domains secreted from *Escherichia coli*"; Nature; vol. 341; pp. 544-548; 1989.
Wong & Lohman; "A double-filter method for nitrocellulose-filter binding: Application to protein-nucleic acid interactions" PNAS; vol. 90; pp. 5428-5432; 1993.
Zoller & Smith; "Oligonucleotide-directed mutagenesis using M13-derived vectors: an efficient and general procedure for the production of point mutations in any fragment of DNA"; Nucleic Acids Res.; vol. 10; No. 20; pp. 6487-6500; 1982.
Stimmel et al. J. of Biological Chemistry, vol. 275, No. 39, pp. 30445-30450, 2000.
Burton, "Immunoglobulin G: Functional Sites", Molecular Immunology 22(3):161-206 (1985).

(56) References Cited

OTHER PUBLICATIONS

Carter et al, "Humanization of an anti-p185HER2 antibody for human cancer therapy", Proc. Natl. Acad. Sci. USA 89:4285-4289 (1992).
Chari et al, "Immunoconjugates Containing Novel Maytansinoids: Promising Anticancer Drugs", Cancer Research 52:127-131 (1992).
Chazin et al, "Transformation mediated by the human HER-2 gene independent of the epidermal growth factor receptor", Oncogene 7:1859-1866 (1992).
Christie et al, "Stabilization of cysteine-linked antibody drug conjugates with N-aryl maleimides", Journal of Controlled Release 220:660-670 (2015).
Database Genbank [online] (Mar. 30, 1995), "Human c-erb-B-2 mRNA [*Homo sapiens*]", retrieved from www.ncbi.nlm.nih.gov Database Accession No. X03363.1.
Di Fiore et al, "erbB-2 Is a Potent Oncogene When Overexpressed in NIH/3T3 Cells", Science 237(4811):178-182 (1987).
Di Joseph et al, "CMC-544 (inotuzamab ozogamicin): A CD22-targeted immunoconjugate of calicheamicin", Hematology Meeting Reports 5(6):74-77 (2008).
Dokter et al, "Impressive efficacy and safety profile of a novel generation duocarmycin-based HER2-targeting ADC", Presentation Abstract #2651, AACR Annual Meeting, San Diego, CA, Apr. 5-9, 2014.
Doronina et al, "Development of potent monoclonal antibody auristatin conjugates for cancer therapy", Nature Biotechnology 21(7):778-784 (2003).
Doronina et al, "Elucidating the role of drug-linker hydrophobicity in the disposition of antibody-drug conjugates", Presentation Abstract #4470, AACR Annual Meeting, San Diego, CA, Apr. 5-9, 2014.
Dorywalska et al, "Effect of Attachment Site on Stability of Cleavable Antibody Drug Conjugates", Bioconjugate Chemistry 26:650-659 (2015).
Erickson et al, "The Effect of Different Linkers on Target Cell Catabolism and Pharmacokinetics/Pharmacodynamics of Trastuzamab Maytansinoid Conjugates", Molecular Cancer Therapeutics 11(5):1133-1142 (2012).
Eustáquio et al, "Spliceostatin hemiketal biosynthesis in *Burkholderia* spp. is catalyzed by an iron/α-ketoglutarate-dependent dioxygenase", PNAS 111(33):E3376-E3385 (2014).
Fujimoto-Ouchi et al, "Antitumor activity of trastuzumab in combination with chemotherapy in human gastric cancer xenograft models", Cancer Chemother Pharmacol 59:795-805 (2007).
Gancberg et al, "Evaluation of HER-2/NEU protein expression in breast cancer by immunohistochemistry: an interlaboratory study assessing the reproducibility of HER-2/NEU testing", Breast Cancer Research and Treatment 74:113-120 (2002).
Guy et al, "Expression of the neu protooncogene in the mammary epithelium of transgenic mice induces metastatic disease", Proc. Natl. Acad. Sci. USA 89:10578-10582 (1992).
Hamblett et al, "Effects of Drug Loading on the Antitumor Activity of a Monoclonal Antibody Drug Conjugate", Clinical Cancer Research 10:7063-7070 (2004).
He et al, "Cytotoxic Spliceostatins from *Burkholderia* sp. and Their Semisynthetic Analogues", Journal of Natural Products 77:1864-1870 (2014).
Hudziak et al, "Increased expression of the putative growth factor receptor p185HER2 causes transformation and tumorigenesis of NIH 3T3 cells", Proc. Natl. Acad. Sci. USA 84:7159-7163 (1987).
Jackson et al, "In Vitro and In Vivo Evaluation of Cysteine and Site Specific Conjugated Herceptin Antibody-Drug Conjugates", PLOS ONE 9(1):E83865 (2014).
Jacobs et al, "Comparison of Fluorescence in Situ Hybridization and Immunohistochemistry for the Evaluation of HER-2/neu in Breast Cancer", Journal of Clinical Oncology 17(7):1974-1982 (1999).
Jeffrey et al, "Development and Properties of β-Glucuronide Linkers for Monoclonal Antibody-Drug Conjugates", Bioconjugate Chemistry 17:831-840 (2006).
Kellogg et al, "Disulfide-Linked Antibody-Maytansinoid Conjugates: Optimization of In Vivo Activity by Varying the Steric Hindrance at Carbon Atoms Adjacent to the Disulfide Linkage", Bioconjugate Chemistry 22:717-727 (2011).
Kern et al, "Discovery of Pyrophosphate Diesters as Tunable, Soluble, and Bioorthogonal Linkers for Site-Specific Antibody-Drug Conjugates", Journal of the American Chemical Society 138:1430-1445 (2016).
Kim et al, "Strategies and Advancement in Antibody-Drug Conjugate Optimization for Targeted Cancer Therapeutics", Biomolecules & Therapeutics 23(6):493-509 (2015).
Kovtun et al, "Antibody-Drug Conjugates Designed to Eradicate Tumors with Homogeneous and Heterogeneous Expression of the Target Antigen", Cancer Research 66(6):3214-3221 (2006).
Krop et al, "Phase I Study of Trastuzumab-DM1, an HER2 Antibody-Drug Conjugate, Given Every 3 Weeks to Patients With HER2-Positive Metastatic Breast Cancer", Journal of Clinical Oncology 28(16):2698-2704 (2010).
Lin et al, "Pharmacokinetic Considerations for Antibody Drug Conjugates", Pharm Res 29:2354-2366 (2012).
Lyon et al, "Self-hydrolyzing maleimides improve the stability and pharmacological properties of antibody-drug conjugates", Nature Biotechnology 32(10):1059-1062 (2014).
Lyon et al, "Self-stabilizing ADCs: antibody-drug conjugates prepared with maleimido drug-linkers that catalyze their own thiosuccinimide ring hydrolysis", Presentation Abstract #4333, AACR Annual Meeting, Washington, DC, Apr. 6-10, 2013.
Lyon et al, "Reducing hydrophobicity of homogeneous antibody-drug conjugates improves pharmacokinetics and therapeutic index", Nature Biotechnology 33:733-735 (2015).
Lyons et al, "Site-specific attachment to recombinant antibodies via introduced surface cystein residues", Protein Engineering 3(8):703-708 (1990).
Martin et al, "HER2 in solid tumors: more than 10 years under the microscope; where are they now?", Future Oncology 10(8):1469-1486 (2014).
Ménard et al, "HER2 overexpression in various tumor types, focussing on its relationship to the development of invasive breast cancer", Annals of Oncology 12(Suppl. 1):S15-S19 (2001).
Owens et al, "HER2 Amplification Ratios by Fluorescence In Situ Hybridization and Correlation with Immunohistochemistry in a Cohort of 6556 Breast Cancer Tissues", Clinical Breast Cancer 5(1):63-69 (2004).
PCT International Search Report and Written Opinion for International Patent Application No. PCT/IB2016/057017 dated Apr. 25, 2017.
Phillips et al, "Targeting HER2-Positive Breast Cancer with Trastuzumab-DM1, an Antibody-Cytotoxic Drug Conjugate", Cancer Research 68(22):9280-9290 (2008).
Poljak, "Production and structure of diabodies", Structure 2:1121-1123 (1994).
Polson et al, "Antibody-Drug Conjugates for the Treatment of Non-Hodgkin's Lymphoma: Target and Linker-Drug Selection", Cancer Research 69(6):2358-2364 (2009).
Press et al, "Diagnostic Evaluation of HER-2 as a Molecular Target: An Assessment of Accuracy and Reproducibility of Laboratory Testing in Large, Prospective, Randomized Clinical Trials", Clinical Cancer Research 11(18):6598-6607 (2005).
Remillard et al, "Antimitotic Activity of the Potent Tumor Inhibitor Maytansine", Science 189(4207):1002-1005 (1975).
Sapra, "A Novel Site-Specific HER2-ADC for Treatment of HER2+ Solid Tumors", Presentation #868, 2016 AACR Annual Meeting, New Orleans, LA, Apr. 17, 2016 (15 pages).
Sapra, "A Novel Site-Specific HER2-ADC for Treatment of HER2+ Solid Tumors", Bioconjugates: From Targets to Therapeutics, San Francisco, CA, Jun. 14, 2016 (18 pages).
Sauter et al, "Guidelines for Human Epidermal Growth Factor Receptor 2 Testing: Biologic and Methodologic Considerations", Journal of Clinical Oncology 27(8):1323-1333 (2009).
Scholl et al, "Targeting HER2 in other tumor types", Annals of Oncology 12(Suppl. 1):S81-S87 (2001).
Semba et al, "A v-erbB-related protooncogene, c-erbB-2, is distinct from the c-erbB-1/epidermal growth factor-receptor gene and is amplified in a human salivary gland adenocarcinoma", Proc. Natl. Acad. Sci. USA 82:6497-6501 (1985).

(56) References Cited

OTHER PUBLICATIONS

Senter et al, "The discovery and development of brentuximab vedotin for use in relapsed Hodgkin lymphoma and systemic anaplasitc large cell lymphoma", Nature Biotechnology 30(7):631-637 (2012).
Slamon et al, "Human Breast Cancer: Correlation of Relapse and Survival with Amplification of the HER-2/neu Oncogene", Science 235(4785):177-182 (1987).
Slamon et al, "Studies of the HER-2/neu Proto-oncogene in Human Breast and Ovarian Cancer", Science 244 (4905):707-712 (1989).
Strop et al, "Location Matters: Site of Conjugation Modulates Stability and Pharmacokinetics of Antibody Drug Conjugates", Chemistry & Biology 20:161-167 (2013).
Sung et al, "Caveolae-mediated endocytosis as a novel mechanism of resistance to T-DM1 ADC", Presentation Abstract #2113, AACR Annual Meeting, New Orleans, LA, Apr. 16-20, 2016.
Thomas et al, "Overcoming Multidrug Resistance in Cancer: An Update on the Clinical Strategy of Inhibiting P-Glycoprotein", Cancer Control 10(2)159-165 (2003).
Tian et al, "A general approach to site-specific antibody drug conjugates", PNAS 111(5):1766-1771 (2014).
Toda et al, "Rapid, Stable, Chemoselective Labeling of Thiols with Julia-Kocieński-like Reagents: A Serum-Stable Alternative to Maleimide-Based Protein Conjugation", Angew. Chem. Int. Ed. 52:12592-12596 (2013).
Tumey, "In Vivo ADC Stability", Hanson-Wade webinar, Jun. 3, 2014 (36 pages).
Tumey, "Metabolism of ADC Linkers & Payloads—How In Vivo & In Vitro Stability Data is Used to Advance Decision Making", ADC World Summit, San Diego, CA, Oct. 26-19, 2014 (29 pages).
Tumey et al, "Mild Method for Succinimide Hydrolysis on ADCs: Impact on ADc Potency, Stability, Exposure, and Efficacy", Bioconjugate Chemistry 25:1871-1880 (2014).
Tumey, "ADC Biotransformation: Metabolism of ADC Linkers & Payloads in vitro and in vivo", WRIB, Miami, FL, Mar. 2015 (25 pages).
Tumey, "Dreaming Big and Thinking Small: Applying Medicinal Chemistry Strategy to Antibody-Drug-Conjugates", ACS Webinar, Jun. 2016 (33 pages).
Tumey, "Site-specific Conjugation for the Advancement of New Linker-Payloads", ADC World Summit, Berlin, Germany, Feb. 2016 (30 pages).
Tumey et al.; "Optimization of Tubulysin Antibody-Drug Conjugates: A Study in Addressing ADC Metabolism", ACS Medicinal Chemistry Letters, vol. 7, No. 11, pp. 977-982, 2016.
Vogel et al, "Efficacy and Safety of Trastuzumab as a Single Agent in First-Line Treatment of HER2-Overexpressing Metastatic Breast Cancer", Journal of Clinical Oncology 20(3):719-726 (2002).
Von Pawel-Rammingen et al, "IdeS, a novel streptococcal cysteine proteinase with unique specificity for Immunoglobulin G", The EMBO Journal 21(7):1607-1615 (2002).
Wolff et al, "American Society of Clinical Oncology/College of American Pathologists Guideline Recommendations for Human Epidermal Growth Factor Receptor 2 Testing in Breast Cancer", Journal of Clinical Oncology 25(1):118-145 (2007).
Wolff et al, "Recommendations for Human Epidermal Growth Factor Receptor 2 Testing in Breast Cancer: American Society of Clinical Oncology/College of American Pathologists Clinical Practice Guideline Update", Journal of Clinical Oncology 31(31):3997-4013 (2013).
Xie et al, "Pharmacokinetics and Biodistribution of the Antitimor Immunoconjugate, Cantuzumab Mertansine (huC242-DM1), and Its Two Components in Mice", The Journal of Pharmacology and Experimental Therapeutics 308 (3):1073-1082 (2004).
Yamamoto et al, "Similarity of protein encoded by the human c-erb-B-2 gene to epidermal growth factor receptor", Nature 319:230-234 (1986).
Yu et al, "Engineering Hydrophobic Protein—Carbohydrate Interactions to Fine-Tune Monoclonal Antibodies", Journal of the American Chemical Society 135:9723-9732 (2013).
Partial International Serarch, PCT/IB2016/057018, dated Feb. 27, 2017, 9 pages.
Laguzza et al. "New antitumor monoclonal antibody-vinca conjugates ly203725 and related compounds: Design, preparation, and representative in vivo activity." J. Med. Chem. 32:548-555 (1989).
Lillo, A. et al. "A human single-chain antibody specific for integrin alpha 3 beta 1 capable of cell internalization and delivery of antitumor agents", Chemistry & Biology 11:897-906 (2004).
Langer, "New methods of drug delivery", Science 249:1527-1533 (1990).
Wu et al. "Arming antibodies: prospects and challenges for immunoconjugates", Nature Biotechnology 23 (9):1137-1146 (2005).
Alley et al, "Contribution of Linker Stability to the Activities of Anticancer Immunoconjugates", Bioconjugate Chemistry 19:759-765 (2008).
Anbazhagan et al, "Association of c-erbB-2 expression and S-phase fraction in the prognosis of node positive breast cancer", Annals of Oncology 2:47-53 (1991).
Andrulis et al, "neu/erbB-2 Amplification Identifies a Poor-Prognosis Group of Women With Node-Negative Breast Cancer", Journal of Clinical Oncology 16(4):1340-1349 (1998).
Badescu et al, "A New Reagent for Stable Thiol-Specific Conjugation", Bioconjugate Chemistry 25:460-469 (2014).
Badescu et al, "Bridging Disulfides for Stable and Defined Antibody Drug Conjugates", Bioconjugate Chemistry 25:1124-1136 (2014).
Bastiani et al, "Caveolae at a glance", Journal of Cell Science 123:3831-3836 (2010).
Béranger et al; "IMGT Scientific chart: Correspondence between the IMGT unique numbering for C-DOMAIN, the IMGT exon numbering, the Eu and Kabat numberings: Human IGHG" (May 17, 2001), Retrieved from the Internet: URL:http://www.imgt.org/IMGTScientificChart/Numbering/Hu_IGHGnber.html.
Boghaert et al, "Determination of pharmacokinetic values of calicheamicin-antibody conjugates in mice by plasmon resonance analysis of small (5 μl) blood samples", Cancer Chemother Pharmacol 61:1027-1035 (2008).
Boswell et al, "Effects of Charge on Antibody Tissue Distribution and Pharmacokinetics", Bioconjugate Chemistry 21:2153-2163 (2010).
Bumbaca et al, "Physiochemical and Biochemical Factors Influencing the Pharmacokinetics of Antibody Therapeutics", The AAPS Journal 14(3):554-558 (2012).
Burke et al, "Development and pharmacological properties of PEGylated glucuronide-auristatin linkers", Presentation Abstract #1786, AACR Annual Meeting, San Diego, CA, Apr. 5-9, 2014.
Burris et al, "Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy", Journal of Clinical Oncology 29(4):398-405 (2010).
Sandrine Beranger et al. "IMGT Scientific Chart: Correspondence between the IMGT unique numbering for C-DOMAIN, the IMGT exon numbering, the Eu and Kabat numbering: Human IGHG", 2001 XP055297333.

\* cited by examiner

Relative abundance of species:
LC: 96.3
LC+1: 3.7
HC: 14.6
HC+1: 85.4
HC+2: trace
Calculated total loading: 1.78
Estimated nonspecific loading: 0.15

5T4 A-E380-mcMMAD

Relative abundance of species:
LC: 100
LC+1: 0
HC: 12
HC+1: 88
HC+2: 0
Calculated total loading: 1.76
Estimated nonspecific loading: 0.0

5T4 A-L398C-vcMMAD

Figure 7
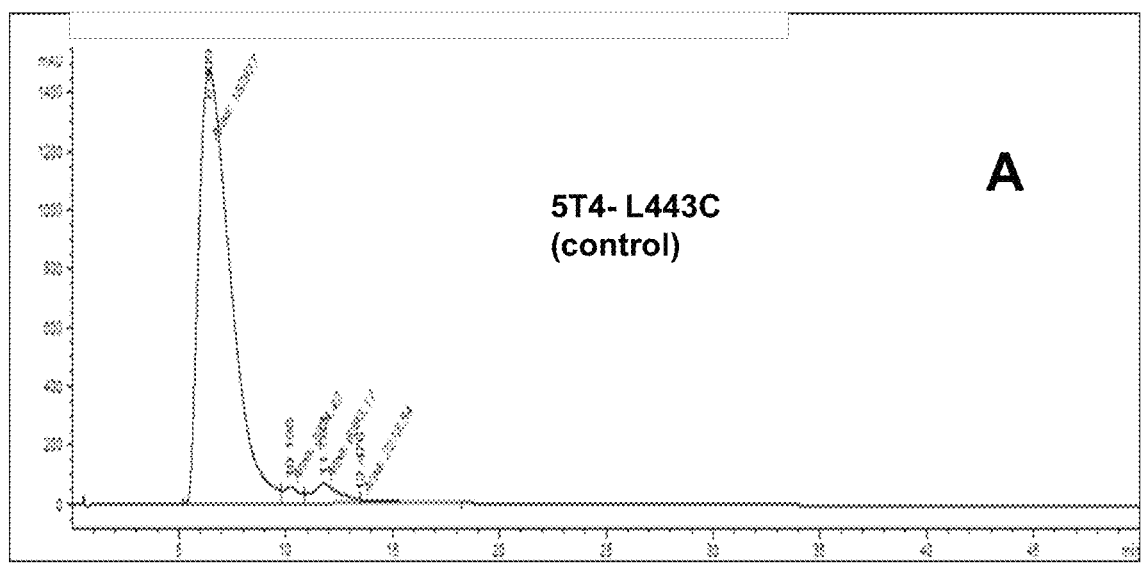
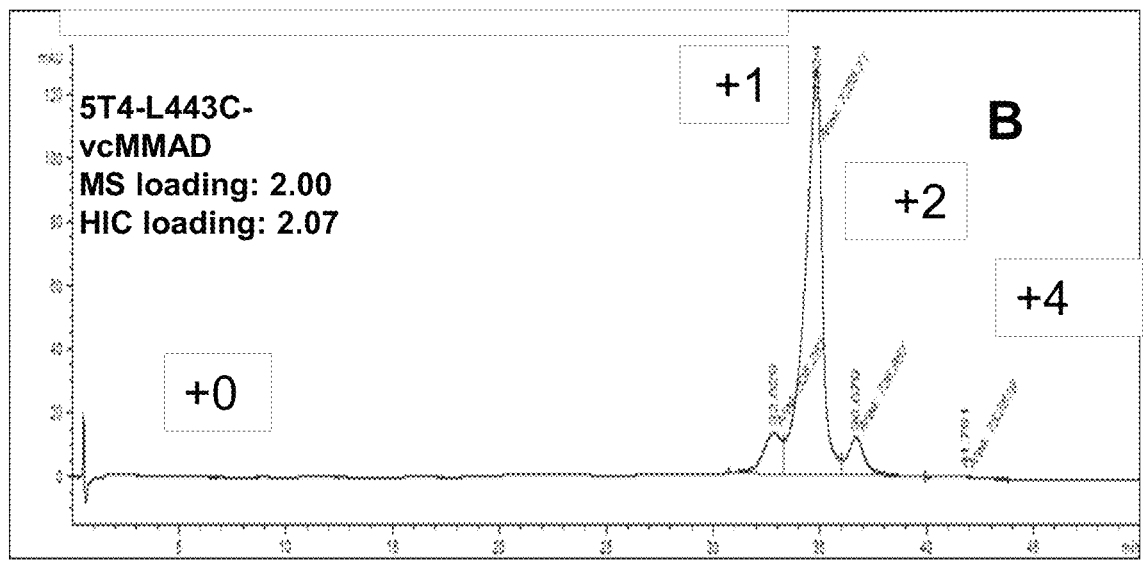

Figure 7
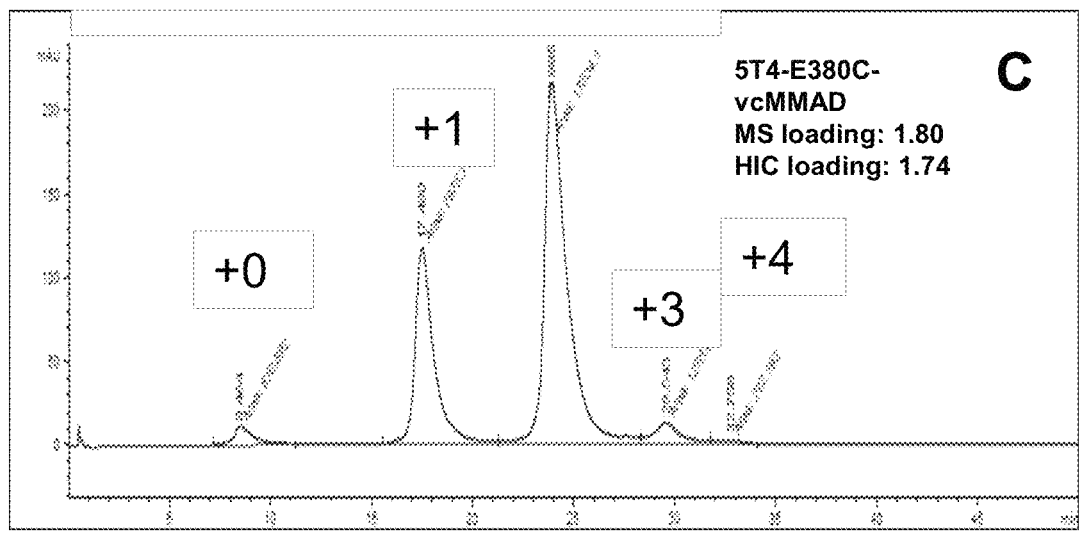
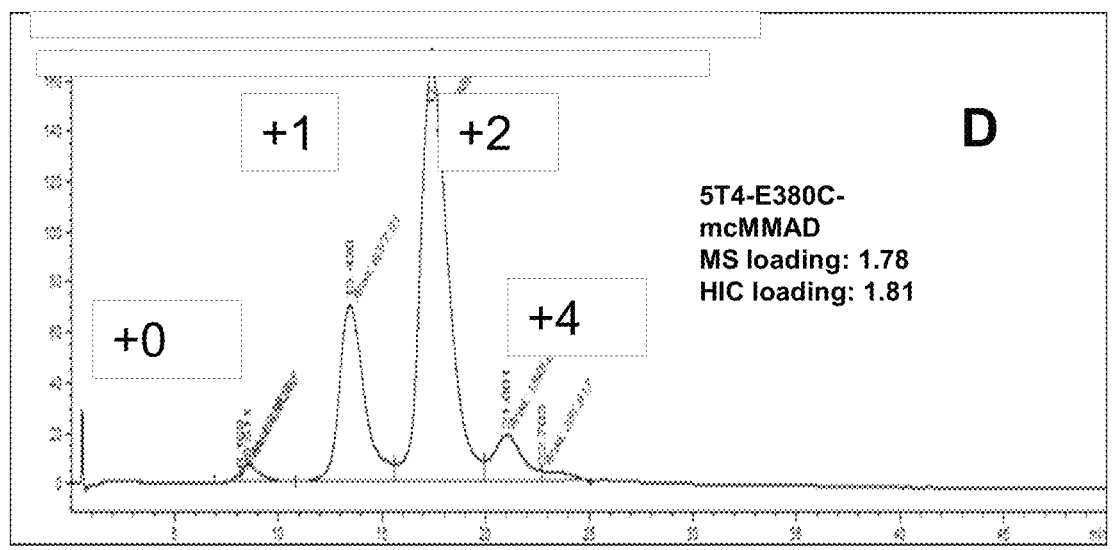

Figure 8
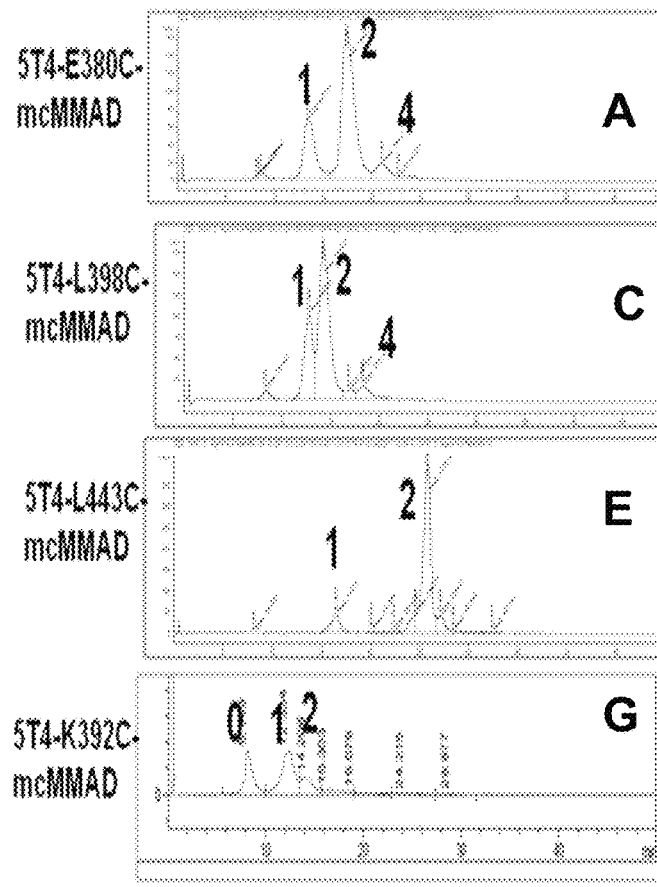
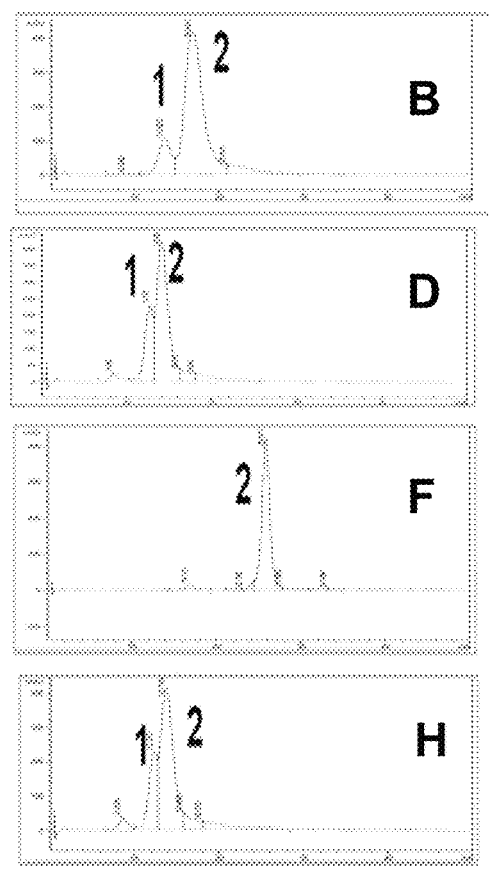

MDA435 /Neo ADCC

FIGURE 15

FIG. 15A. Amino acid sequence of human wild type IgG1 heavy chain constant domain comprising Fc region (SEQ ID NO:1)

```
ASTKGPSVFP LAPSSKSTSG GTAALGCLVK DYFPEPVTVS WNSGALTSGV  50
HTFPAVLQSS GLYSLSSVVT VPSSSLGTQT YICNVNHKPS NTKVDKKVEP 100
KSCDKTHTCP PCPAPELLGG PSVFLFPPKP KDTLMISRTP EVTCVVVDVS 150
HEDPEVKFNW YVDGVEVHNA KTKPREEQYN STYRVVSVLT VLHQDWLNGK 200
EYKCKVSNKA LPAPIEKTIS KAKGQPREPQ VYTLPPSREE MTKNQVSLTC 250
LVKGFYPSDI AVEWESNGQP ENNYKTTPPV LDSDGSFFLY SKLTVDKSRW 300
QQGNVFSCSV MHEALHNHYT QKSLSLSPGK 330
```

FIG. 15B, Nucleic acid sequence encoding human wild type IgG1 constant region (SEQ ID NO:2)

```
gcgtcgacca agggcccatc ggtcttcccc ctggcaccct cctccaagag cacctctggg
ggcacagcgg ccctgggctg cctggtcaag gactacttcc ccgaaccggt gacggtgtcg
tggaactcag gcgccctgac cagcggcgtg cacaccttcc cggctgtcct acagtcctca
ggactctact ccctcagcag cgtggtgacc gtgccctcca gcagcttggg cacccagacc
tacatctgca acgtgaatca caagcccagc aacaccaagg tggacaagaa agttgagccc
aaatcttgtg acaaaactca cacatgccca ccgtgcccag cacctgaact cctgggggga
ccgtcagtct tcctcttccc cccaaaaccc aaggacaccc tcatgatctc ccggacccct
gaggtcacat gcgtggtggt ggacgtgagc cacgaagacc ctgaggtcaa gttcaactgg
tacgtggacg gcgtggaggt gcataatgcc aagacaaagc cgcgggagga gcagtacaac
agcacgtacc gtgtggtcag cgtcctcacc gtcctgcacc aggactggct gaatggcaag
gagtacaagt gcaaggtctc caacaaagcc ctcccagccc ccatcgagaa aaccatctcc
aaagccaaag ggcagccccg agaaccacag gtgtacaccc tgcccccatc ccgggaggag
atgaccaaga accaggtcag cctgacctgc ctggtcaaag gcttctatcc cagcgacatc
gccgtggagt gggagagcaa tgggcagccg gagaacaact acaagaccac gcctcccgtg
ctggactccg acggctcctt cttcctctat agcaagctca ccgtggacaa gagcaggtgg
cagcaggga acgtcttctc atgctccgtg atgcatgagg ctctgcacaa ccactacacg
cagaagagcc tctccctgtc cccgggtaaa 990
```

FIG. 15C. Human wild type IgG2 constant region amino acid sequence (SEQ ID NO:3)

```
ASTKGPSVFP LAPCSRSTSE STAALGCLVK DYFPEPVTVS WNSGALTSGV HTFPAVLQSS 60
GLYSLSSVVT VPSSNFGTQT YTCNVDHKPS NTKVDKTVER KCCVECPPCP APPVAGPSVF
120
LFPPKPKDTL MISRTPEVTC VVVDVSHEDP EVQFNWYVDG VEVHNAKTKP REEQFNSTFR
180
VVSVLTVVHQ DWLNGKEYKC KVSNKGLPAP IEKTISKTKG QPREPQVYTL PPSREEMTKN
240
QVSLTCLVKG FYPSDISVEW ESNGQPENNY KTTPPMLDSD GSFFLYSKLT VDKSRWQQGN
300
VFSCSVMHEA LHNHYTQKSL SLSPGK 326
```

FIG. 15D. Human wild type IgG3 constant region amino acid sequence (SEQ ID NO:4)

```
ASTKGPSVFP LAPCSRSTSG GTAALGCLVK DYFPEPVTVS WNSGALTSGV HTFPAVLQSS 60
GLYSLSSVVT VPSSSLGTQT YTCNVNHKPS NTKVDKRVEL KTPLGDTTHT CPRCPEPKSC
120
DTPPPCPRCP EPKSCDTPPP CPRCPEPKSC DTPPPCPRCP APELLGGPSV FLFPPKPKDT
180
LMISRTPEVT CVVVDVSHED PEVQFKWYVD GVEVHNAKTK PREEQYNSTF RVVSVLTVLH
240
QDWLNGKEYK CKVSNKALPA PIEKTISKTK GQPREPQVYT LPPSREEMTK NQVSLTCLVK
300
GFYPSDIAVE WESSGQPENN YNTTPPMLDS DGSFFLYSKL TVDKSRWQQG NIFSCSVMHE
360
ALHNRFTQKS LSLSPGK 377
```

FIG. 15E. Human wild type IgG4 constant region amino acid sequence (SEQ ID NO:5)

```
ASTKGPSVFP LAPCSRSTSE STAALGCLVK DYFPEPVTVS WNSGALTSGV HTFPAVLQSS 60
GLYSLSSVVT VPSSSLGTKT YTCNVDHKPS NTKVDKRVES KYGPPCPSCP APEFLGGPSV
120
FLFPPKPKDT LMISRTPEVT CVVVDVSQED PEVQFNWYVD GVEVHNAKTK PREEQFNSTY
180
RVVSVLTVLH QDWLNGKEYK CKVSNKGLPS SIEKTISKAK GQPREPQVYT LPPSQEEMTK
240
NQVSLTCLVK GFYPSDIAVE WESNGQPENN YKTTPPVLDS DGSFFLYSRL TVDKSRWQEG
300
NVFSCSVMHE ALHNHYTQKS LSLSLGK 327
```

FIG. 15F. IgG1-K246C (SEQ ID NO 6)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPCPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15G. IgG1-D249C (SEQ ID NO:7)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKCTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15H. Human IgG1-S254C (SEQ ID NO:8)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMICRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK FIG. 15I. IgG1-D265C (SEQ ID NO:9)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVCVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK FIG. 15J. . IgG1-S267C (SEQ ID NO:10)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVCHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15K IgG1-D270C (SEQ ID NO:11)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHE<u>C</u>PEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15L. IgG1-N276C (SEQ ID NO:12)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKF<u>C</u>WYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15M IgG1-Y278C (SEQ ID NO:13)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNW<u>C</u>VDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15N IgG1-E283C (SEQ ID NO:14)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGV<u>C</u>VHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15O IgG1-V284C (SEQ ID NO:15)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVE<u>C</u>HNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15P. IgG1-A287C (SEQ ID NO:16)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNCKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15Q IgG1-R292C (SEQ ID NO:17)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPCEEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15R IgG1E293C (SEQ ID NO:18)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPRCEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15S IgG1-E294C (SEQ ID NO:19)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPRECQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15T. IgG1-Y300C (SEQ ID NO:20)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTCRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15U IgG1-V302C (SEQ ID NO:21)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRCV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15V IgG1-V303C (SEQ ID NO:22)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVC
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15W IgG1-L314C (SEQ ID NO:23)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWCNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15X IgG1-N315C (SEQ ID NO:24)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLCGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15Y IgG1-E318C (SEQ ID NO:25)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKCYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15Z IgG1-K320C (SEQ ID NO:26)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYCCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15AA IgG1-A327C (SEQ ID NO:27)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKCLPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15BB IgG1-I332C (SEQ ID NO:28)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPCEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15CC IgG1-E333C (SEQ ID NO:29)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPICKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15DD IgG1-K334C (SEQ ID NO:30)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIECTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15EE IgG1-I336C (SEQ ID NO:31)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTCSKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15FF IgG1-E345C (SEQ ID NO:32)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPRCPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15GG IgG1-Q347C (SEQ ID NO:33)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPCVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15HH IgG1-S354C (SEQ ID NO:34)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPCREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15II IgG1-R355C (SEQ ID NO:35)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSCEEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15JJ IgG1-M358C (SEQ ID NO:36)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREE<u>C</u>TKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15KK. IgG1-T359C (SEQ ID NO:37)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEM<u>C</u>KNQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15LL IgG1-K360C(SEQ ID NO:38)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMT<u>C</u>NQVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15MM IgG1-N361C(SEQ ID NO:39)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTK<u>C</u>QVSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15NN IgG1-Q362C (SEQ ID NO:40)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKN<u>C</u>VSL
TCLVKGFYPSDIAVEWESNGQPENNYKTTPPVLDSDGSFFLYSKLTVDKSRWQQGNVFSCSV
MHEALHNHYTQKSLSLSPGK

FIG. 15OO. IgG1-K370C (SEQ ID NO:41)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVCGFYPSDIAVEWESNGQPENNYKTTPPVLDSDGSFFLYSKLTVDKSRWQQGNVFSCSV
MHEALHNHYTQKSLSLSPGK

FIG. 15PP. IgG1-Y373C (SEQ ID NO:42)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFCPSDIAVEWESNGQPENNYKTTPPVLDSDGSFFLYSKLTVDKSRWQQGNVFSCSV
MHEALHNHYTQKSLSLSPGK

FIG. 15QQ. IgG1-D376C (SEQ ID NO:43)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSCIAVEWESNGQPENNYKTTPPVLDSDGSFFLYSKLTVDKSRWQQGNVFSCSV
MHEALHNHYTQKSLSLSPGK

FIG. 15RR. IgG1-A378C (SEQ ID NO:44)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDICVEWESNGQPENNYKTTPPVLDSDGSFFLYSKLTVDKSRWQQGNVFSCSV
MHEALHNHYTQKSLSLSPGK

FIG. 15SS. IgG1-E380C (SEQ ID NO:45)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVCWESNGQPENNYKTTPPVLDSDGSFFLYSKLTVDKSRWQQGNVFSCSV
MHEALHNHYTQKSLSLSPGK

FIG. 15TT. IgG1-E382C (SEQ ID NO:46)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWCSNGQPENNYKTTPPVLDSDGSFFLYSKLTVDKSRWQQGNVFSCSV
MHEALHNHYTQKSLSLSPGK

FIG. 15UU IgG1-S383C (SEQ ID NO:47)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWECNGQPENNYKTTPPVLDSDGSFFLYSKLTVDKSRWQQGNVFSCSV
MHEALHNHYTQKSLSLSPGK

FIG. 15VV IgG1-N384C (SEQ ID NO:48)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESCGQPENNYKTTPPVLDSDGSFFLYSKLTVDKSRWQQGNVFSCSV
MHEALHNHYTQKSLSLSPGK

FIG. 15 WW. IgG1-Q386C (SEQ ID NO:49)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGCPENNYKTTPPVLDSDGSFFLYSKLTVDKSRWQQGNVFSCSV
MHEALHNHYTQKSLSLSPGK

FIG. 15XX IgG1-E388C (SEQ ID NO:50)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPCNNYKTTPPVLDSDGSFFLYSKLTVDKSRWQQGNVFSCSV
MHEALHNHYTQKSLSLSPGK

FIG. 15YY IgG1-N390C (SEQ ID NO:51)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENCYKTTPPVLDSDGSFFLYSKLTVDKSRWQQGNVFSCSV
MHEALHNHYTQKSLSLSPGK

FIG. 15ZZ IgG1-K392C (SEQ ID NO:52)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYCTTPPVLDSDGSFFLYSKLTVDKSRWQQGNVFSCSV
MHEALHNHYTQKSLSLSPGK

FIG. 15AAA. IgG1-T393C (SEQ ID NO:53)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKCTPPVLDSDGSFFLYSKLTVDKSRWQQGNVFSCSV
MHEALHNHYTQKSLSLSPGK

FIG. 15BBB IgG1-L398C (SEQ ID NO:54)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVCDSDGSFFLYSKLTVDKSRWQQGNVFSCSV
MHEALHNHYTQKSLSLSPGK

FIG. 15CCC. IgG1-D401C (SEQ ID NO:55)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDS<ins>C</ins>GSFFLYSKLTVDKSRWQQGNVFSCSV
MHEALHNHYTQKSLSLSPGK FIG. 15DDD IgG1-F404C (SEQ ID NO:56)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGS<ins>C</ins>FLYSKLTVDKSRWQQGNVFSCSV
MHEALHNHYTQKSLSLSPGK FIG. 15EEE IgG1-T411C (SEQ ID NO:57)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKL<ins>C</ins>VDKSRWQQGNVFSCSV
MHEALHNHYTQKSLSLSPGK FIG. 15FFF. IgG1-D413C (SEQ ID NO:58)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTV<ins>C</ins>KSRWQQGNVFSCSV
MHEALHNHYTQKSLSLSPGK FIG. 15GGG IgG1-K414C (SEQ ID NO:59)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVD<ins>C</ins>SRWQQGNVFSCSV
MHEALHNHYTQKSLSLSPGK FIG 15HHH IgG1-R416C (SEQ ID NO:60)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKS<u>C</u>WQQGNVFSCSV
MHEALHNHYTQKSLSLSPGK FIG. 15III. IgG1-Q418C (SEQ ID NO:61)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRW<u>C</u>QGNVFSCSV
MHEALHNHYTQKSLSLSPGK FIG. 15JJJ IgG1-Q419 (SEQ ID NO:62)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQ<u>C</u>GNVFSCSV
MHEALHNHYTQKSLSLSPGK FIG. 15KKK. IgG1-N421C (SEQ ID NO:63)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQG<u>C</u>VFSCSV
MHEALHNHYTQKSLSLSPGK FIG. 15LLL IgG1-V422<u>C</u> (SEQ ID NO:64)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGN<u>C</u>FSCSV
MHEALHNHYTQKSLSLSPGK FIG. 15MMM. IgG1-M428C (SEQ ID NO:65)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
<u>C</u>HEALHNHYTQKSLSLSPGK FIG. 15NNN. IgG1-A431C (SEQ ID NO:66)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHE<u>C</u>LHNHYTQKSLSLSPGK FIG. 15OOO. IgG1-L432C (SEQ ID NO:67)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEA<u>C</u>HNHYTQKSLSLSPGK FIG. 15PPP. IgG1-T437C (SEQ ID NO:68)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHY<u>C</u>QKSLSLSPGK FIG. 15QQQ. IgG1-Q438C (SEQ ID NO:69)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYT<u>C</u>KSLSLSPGK FIG. 15RRR. IgG1-K439C (SEQ ID NO:70)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQCSLSLSPGK FIG. 15SSS. IgG1-S440C (SEQ ID NO:71)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKCLSLSPGK FIG. 15TTT. IgG1-L443C (SEQ ID NO:72)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSCSPGK FIG. 15UUU. IgG1-S444C (SEQ ID NO:73)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLCPGK

FIGURE 16

Double-Engineered Cysteine Mutation Sequences in Human IgG1 constant region

FIG. 16A. IgG1-E380C+L443C (SEQ ID NO:74)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVCWESNGQPENNYKTTPPVLDSDGSFFLYSKLTVDKSR
WQQGNVFSCSVMHEALHNHYTQKSLSCSPGK

FIG. 16B IgG1-L398C+L443C (SEQ ID NO:75)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVCDSDGSFFLYSKLTVDKSR
WQQGNVFSCSVMHEALHNHYTQKSLSCSPGK

FIG. 16C. IgG1- V422C+L443C (SEQ ID NO:76)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKSRW
QQGNCFSCSVMHEALHNHYTQKSLSCSPGK

FIG. 16D. IgG1- E380C+L398C (SEQ ID NO:77)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVCWESNGQPENNYKTTPPVCDSDGSFFLYSKLTVDKSR
WQQGNVFSCSVMHEALHNHYTQKSLSLSPGK

FIG. 16E. IgG1- L398C+V422C (SEQ ID NO:78)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVCDSDGSFFLYSKLTVDKSR
WQQGNCFSCSVMHEALHNHYTQKSLSLSPGK

FIG. 16F. IgG1-E380C+V422C (SEQ ID NO:79)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVCWESNGQPENNYKTTPPVLDSDGSFFLYSKLTVDKSR
WQQGNCFSCSVMHEALHNHYTQKSLSLSPGK

FIG. 16G IgG1-K392C+L443C (SEQ ID NO:80)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYCTTPPVLDSDGSFFLYSKLTVDKSR
WQQGNVFSCSVMHEALHNHYTQKSLSCSPGK

FIG. 16H IgG1-F404C+L443C (SEQ ID NO:81)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSCFLYSKLTVDKSR
WQQGNVFSCSVMHEALHNHYTQKSLSCSPGK

FIG. 16I IgG1-K392C+F404C (SEQ ID NO:82)

ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYCTTPPVLDSDGSCFLYSKLTVDKSR
WQQGNVFSCSVMHEALHNHYTQKSLSLSPGK

FIGURE 17

FIG. 17A. Amino acid sequence of anti-5T4 antibody heavy chain comprising wild type human IgG1 constant domain. (SEQ ID NO:83).

EVQLVESGGGLVQPGGSLRLSCAASGYTFTN<u>FGMN</u>WVRQAPGKGLEWVAW<u>INTNTGEPRYAE</u>
<u>EFKG</u>RFTISRDNAKNSLYLQMNSLRAEDTAVYYCARD<u>WDGAYFFDY</u>WGQGTLVTVSSastkg
psvfplapsskstsggtaalgclvkdyfpepvtvswnsgaltsgvhtfpavlqssglyslss
vvtvpssslgtqtyicnvnhkpsntkvdkkvepkscdkthtcppcpapellggpsvflfppk
pkdtlmisrtpevtcvvvdvshedpevkfnwyvdgvevhnaktkpreeqynstyrvvsvltv
lhqdwlngkeykckvsnkalpapiektiskakgqprepqvytlppsreemtknqvsltclvk
gfypsdiavewesngqpennykttppvldsdgsfflyskltvdksrwqqgnvfscsvmheal
hnhytqkslslspgk FIG. 17B Amino acid sequence of anti-5T4 light chain comprising wild type human wild type Kappa light chain (SEQ ID NO:84).

DIQMTQSPSSLSASVGDRVTITC<u>KASQSVSNDVA</u>WYQQKPGKAPKLLIY<u>FATNRYT</u>GVPSRF
SGSGYGTDFTLTISSLQPEDFATYYC<u>QQDYSSPWT</u>FGQGTKVEIKrtvaapsvfifppsdeq
lksgtasvvcllnnfypreakvqwkvdnalqsgnsqesvteqdskdstyslsstltlskady
ekhkvyacevthqglsspvtksfnrgec FIG. 17C. Amino acid sequence of anti-Her2 antibody heavy chain comprising wild type human IgG1 constant domain (SEQ ID NO:85).

EVQLVESGGGLVQPGGSLRLSCAASGFNIK<u>DTYIH</u>WVRQAPGKGLEWVAR<u>IYPTNGYTRYAD</u>
<u>SVKG</u>RFTISADTSKNTAYLQMNSLRAEDTAVYYCSR<u>WGGDGFYAMDY</u>WGQGTLVTVSSastk
gpsvfplapsskstsggtaalgclvkdyfpepvtvswnsgaltsgvhtfpavlqssglysls
svvtvpssslgtqtyicnvnhkpsntkvdkkvepkscdkthtcppcpapellggpsvflfpp
kpkdtlmisrtpevtcvvvdvshedpevkfnwyvdgvevhnaktkpreeqynstyrvvsvlt
vlhqdwlngkeykckvsnkalpapiektiskakgqprepqvytlppsreemtknqvsltclv
kgfypsdiavewesngqpennykttppvldsdgsfflyskltvdksrwqqgnvfscsvmhea
lhnhytqkslslspgk FIG. 17D Amino acid sequence of anti-Her2 light chain comprising wild type human wild type Kappa light chain constant domain (SEQ ID NO:86).

DIQMTQSPSSLSASVGDRVTITC<u>RASQDVNTAVA</u>WYQQKPGKAPKLLIY<u>SASFLYS</u>GVPSRF
SGSRSGTDFTLTISSLQPEDFATYYC<u>QQHYTTPPT</u>FGQGTKVEIKrtvaapsvfifppsdeq
lksgtasvvcllnnfypreakvqwkvdnalqsgnsqesvteqdskdstyslsstltlskady
ekhkvyacevthqglsspvtksfnrgec FIG. 17E. Amino acid sequence of anti-VEGFR2 antibody heavy chain comprising wild type human IgG1 constant domain (SEQ ID NO:87).

EVQLVQSGGGLVKPGGSLRLSCAAS<u>GFTFSSYSMN</u>WVRQAPGKGLEWVS<u>SISSSSSYIYYAD
SVKG</u>RFTISRDNAKNSLYLQMNSLRAEDTAVYYCAR<u>VTDAFDI</u>WGQGTMVTVSSastkgpsv
fplapsskstsggtaalgclvkdyfpepvtvswnsgaltsgvhtfpavlqssglyslssvvt
vpssslgtqtyicnvnhkpsntkvdkkvepkscdkthtcppcpapellggpsvflfppkpkd
tlmisrtpevtcvvvdvshedpevkfnwyvdgvevhnaktkpreeqynstyrvvsvltvlhq
dwlngkeykckvsnkalpapiektiskakgqprepqvytlppsreemtknqvsltclvkgfy
psdiavewesngqpennykttppvldsdgsfflyskltvdksrwqqgnvfscsvmhealhnh
ytqkslslspgk FIG. 17F Amino acid sequence of anti-VEGFR2 light chain comprising wild type human wild type Kappa light chain constant domain (SEQ ID NO:88).

DIQMTQSPSSVSASIGDRVTITC<u>RASQGIDNWLG</u>WYQQKPGKAPKLLIY<u>DASNLDT</u>GVPSRF
SGSGSGTYFTLTISSLQAEDFAVYFC<u>QQAKAFPPT</u>FGGGTKVDIKrtvaapsvfifppsdeq
lksgtasvvcllnnfypreakvqwkvdnalqsgnsqesvteqdskdstyslsstltlskady
ekhkvyacevthqglsspvtksfnrgec

FIGURE 18

FIG. 18A. Wild type human Kappa constant region (huKappa) (SEQ ID NO:89)

TVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

FIG. 18B. A111C-huKappa (SEQ ID NO:90)

TVCAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

FIG. 18C K183C-huKappa (SEQ ID NO:92)

TVAAPSVFIFPPSDEQLKSGTASVVCLLNNFYPREAKVQWKVDNALQSGNSQESVTEQDSKD
STYSLSSTLTLSCADYEKHKVYACEVTHQGLSSPVTKSFNRGEC

FIG. 18D N210C-huKappa (SEQ ID NO:95)

TVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFCRGEC

FIGURE 19A

Sequence alignment of Fc domain of wild type human IgG1, IgG2, IgG3, IgG4

```
          236
hIgG1   GGPSVFLFPPKPKDTLMISRTPEVTCVVVDVSHEDPEVKFNWYVDGVEVHNAKT
hIgG2   AGPSVFLFPPKPKDTLMISRTPEVTCVVVDVSHEDPEVQFNWYVDGVEVHNAKT
hIgG3   GGPSVFLFPPKPKDTLMISRTPEVTCVVVDVSHEDPEVQFKWYVDGVEVHNAKT
hIgG4   GGPSVFLFPPKPKDTLMISRTPEVTCVVVDVSQEDPEVQFNWYVDGVEVHNAKT 290
hIgG1   KPREEQYNSTYRVVSVLTVLHQDWLNGKEYKCKVSNKALPAPIEKTISKAKGQP
hIgG2   KPREEQFNSTFRVVSVLTVVHQDWLNGKEYKCKVSNKGLPAPIEKTISKTKGQP
hIgG3   KPREEQYNSTFRVVSVLTVLHQDWLNGKEYKCKVSNKALPAPIEKTISKTKGQP
hIgG4   KPREEQFNSTYRVVSVLTVLHQDWLNGKEYKCKVSNKGLPSSIEKTISKAKGQP 344
hIgG1   REPQVYTLPPSREEMTKNQVSLTCLVKGFYPSDIAVEWESNGQPENNYKTTP
hIgG2   REPQVYTLPPSREEMTKNQVSLTCLVKGFYPSDISVEWESNGQPENNYKTTP
hIgG3   REPQVYTLPPSREEMTKNQVSLTCLVKGFYPSDIAVEWESSGQPENNYNTTP
hIgG4   REPQVYTLPPSQEEMTKNQVSLTCLVKGFYPSDIAVEWESNGQPENNYKTTP 396
hIgG1   PVLDSDGSFFLYSKLTVDKSRWQQGNVFSCSVMHEALHNHYTQKSLSLSPGK
hIgG2   PMLDSDGSFFLYSKLTVDKSRWQQGNVFSCSVMHEALHNHYTQKSLSLSPGK
hIgG3   PMLDSDGSFFLYSKLTVDKSRWQQGNIFSCSVMHEALHNRFTQKSLSLSPGK
hIgG4   PVLDSDGSFFLYSRLTVDKSRWQEGNVFSCSVMHEALHNHYTQKSLSLSLGK
```

FIGURE 19B

Sequence alignment of constant domain of wild type human IgG1, IgG2, IgG3, and IgG4

FIGURE 20

FIG. 20A. Wild-type human Lambda constant region (huLambda) nucleic acid (SEQ ID NO: 170)
GGTCAGCCCAAGGCTGCCCCCTCGGTCACTCTGTTCCCGCCCTCCTCTGAGGAGCTTCAAGC
CAACAAGGCCACACTGGTGTGTCTCATAAGTGACTTCTACCCGGGAGCCGTGACAGTGGCCT
GGAAGGCAGATAGCAGCCCCGTCAAGGCGGGAGTGGAGACCACCACACCCTCCAAACAAAGC
AACAACAAGTACGCGGCCAGCAGCTATCTGAGCCTGACGCCTGAGCAGTGGAAGTCCCACAG
AAGCTACAGCTGCCAGGTCACGCATGAAGGGAGCACCGTGGAGAAGACAGTGGCCCCTACAG
AATGTTCA

FIG. 20B. Wild-type human Lambda constant region (huLambda) amino acid (SEQ ID NO: 171)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECS

FIG. 20C. K110C-huLambda (SEQ ID NO: 172)
GQPCAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECS

FIG. 20D. A111C-huLambda (SEQ ID NO: 173)
GQPKCAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECS

FIG. 20E. L125C-huLambda (SEQ ID NO: 174)
GQPKAAPSVTLFPPSSEECQANKATLVCLISDFYPGAVTVAWKADSSPVKAGVETTTPSKQS
NNKYAASSYLSLTPEQWKSHRSYSCQVTHEGSTVEKTVAPTECS

FIG. 20F. K149C-huLambda (SEQ ID NO: 175)
GQPKAAPSVTLFPPSSEELQANKATLVCLISDFYPGAVTVAWCADSSPVKAGVETTTPSKQS
NNKYAASSYLSLTPEQWKSHRSYSCQVTHEGSTVEKTVAPTECS

FIG. 20G. V155C-huLambda (SEQ ID NO: 176)
GQPKAAPSVTLFPPSSEELQANKATLVCLISDFYPGAVTVAWKADSSPCKAGVETTTPSKQS
NNKYAASSYLSLTPEQWKSHRSYSCQVTHEGSTVEKTVAPTECS

FIG. 20H. G158C-huLambda (SEQ ID NO: 177)
GQPKAAPSVTLFPPSSEELQANKATLVCLISDFYPGAVTVAWKADSSPVKACVETTTPSKQS
NNKYAASSYLSLTPEQWKSHRSYSCQVTHEGSTVEKTVAPTECS

FIG. 20I. T161C-huLambda (SEQ ID NO: 178)
GQPKAAPSVTLFPPSSEELQANKATLVCLISDFYPGAVTVAWKADSSPVKAGVECTTPSKQS
NNKYAASSYLSLTPEQWKSHRSYSCQVTHEGSTVEKTVAPTECS

FIG. 20J. Q185C-huLambda (SEQ ID NO: 179)
GQPKAAPSVTLFPPSSEELQANKATLVCLISDFYPGAVTVAWKADSSPVKAGVETTTPSKQS
NNKYAASSYLSLTPECWKSHRSYSCQVTHEGSTVEKTVAPTECS

FIG. 20K. S188C-huLambda (SEQ ID NO: 180)
GQPKAAPSVTLFPPSSEELQANKATLVCLISDFYPGAVTVAWKADSSPVKAGVETTTPSKQS
NNKYAASSYLSLTPEQWKCHRSYSCQVTHEGSTVEKTVAPTECS

FIG. 20L. H189C-huLambda (SEQ ID NO: 181)
GQPKAAPSVTLFPPSSEELQANKATLVCLISDFYPGAVTVAWKADSSPVKAGVETTTPSKQS
NNKYAASSYLSLTPEQWKSCRSYSCQVTHEGSTVEKTVAPTECS

FIG. 20M. S191C-huLambda (SEQ ID NO: 182)
GQPKAAPSVTLFPPSSEELQANKATLVCLISDFYPGAVTVAWKADSSPVKAGVETTTPSKQS
NNKYAASSYLSLTPEQWKSHRCYSCQVTHEGSTVEKTVAPTECS

FIG. 20N. T197C-huLambda (SEQ ID NO: 183)
GQPKAAPSVTLFPPSSEELQANKATLVCLISDFYPGAVTVAWKADSSPVKAGVETTTPSKQS
NNKYAASSYLSLTPEQWKSHRSYSCQVCHEGSTVEKTVAPTECS

FIG. 20O. V205C-huLambda (SEQ ID NO: 184)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTCEKTVAPTECS

FIG. 20P. E206C-huLambda (SEQ ID NO: 185)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTVCKTVAPTECS

FIG. 20Q. K207C-huLambda (SEQ ID NO: 186)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTVECTVAPTECS

FIG. 20R. T208C-huLambda (SEQ ID NO: 187)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKCVAPTECS

FIG. 20S. A210C -huLambda (SEQ ID NO: 188)
GQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVCPTECS

```
                        SEQUENCE LISTING

<160> NUMBER OF SEQ ID NOS: 205

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 2
<211> LENGTH: 990
<212> TYPE: DNA
<213> ORGANISM: Homo sapiens

<400> SEQUENCE: 2

```
gcgtcgacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                      990
```

<210> SEQ ID NO 3
<211> LENGTH: 326
<212> TYPE: PRT
<213> ORGANISM: HOMO SAPIENS

<400> SEQUENCE: 3

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

Val Glu Val His Asn Ala Lys Thr Lys Pro Arg Glu Glu Gln Phe Asn
145                 150                 155                 160

Ser Thr Phe Arg Val Val Ser Val Leu Thr Val Val His Gln Asp Trp
                165                 170                 175

Leu Asn Gly Lys Glu Tyr Lys Cys Lys Val Ser Asn Lys Gly Leu Pro
            180                 185                 190

Ala Pro Ile Glu Lys Thr Ile Ser Lys Thr Lys Gly Gln Pro Arg Glu
        195                 200                 205

Pro Gln Val Tyr Thr Leu Pro Pro Ser Arg Glu Glu Met Thr Lys Asn
210                 215                 220

Gln Val Ser Leu Thr Cys Leu Val Lys Gly Phe Tyr Pro Ser Asp Ile
225                 230                 235                 240

Ser Val Glu Trp Glu Ser Asn Gly Gln Pro Glu Asn Asn Tyr Lys Thr
            245                 250                 255

Thr Pro Pro Met Leu Asp Ser Asp Gly Ser Phe Phe Leu Tyr Ser Lys
        260                 265                 270

Leu Thr Val Asp Lys Ser Arg Trp Gln Gln Gly Asn Val Phe Ser Cys
    275                 280                 285

Ser Val Met His Glu Ala Leu His Asn His Tyr Thr Gln Lys Ser Leu
290                 295                 300

Ser Leu Ser Pro Gly Lys
305                 310                 315                 320

Ser Leu Ser Pro Gly Lys
            325

<210> SEQ ID NO 4
<211> LENGTH: 377
<212> TYPE: PRT
<213> ORGANISM: HOMO SAPIENS

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

```
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 5
<211> LENGTH: 327
<212> TYPE: PRT
<213> ORGANISM: HOMO SAPIENS

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 6
<211> LENGTH: 330
<212> TYPE: PRT
<213> ORGANISM: Artificial Sequence
<220> FEATURE:
<223> OTHER INFORMATION: IgG1-K246C

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Cys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 7
<211> LENGTH: 330
<212> TYPE: PRT
<213> ORGANISM: Artificial Sequence
<220> FEATURE:
<223> OTHER INFORMATION: IgG1-D249C

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Cys Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<223> OTHER INFORMATION: human IgG1-S254C

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Cys Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Artificial Sequence
<220> FEATURE:
<223> OTHER INFORMATION: human IgG1-D265C

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 10
<211> LENGTH: 330
<212> TYPE: PRT
<213> ORGANISM: Artificial Sequence
<220> FEATURE:
<223> OTHER INFORMATION: human IgG1-S267C

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Cys His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11

<211> LENGTH: 330
<212> TYPE: PRT
<213> ORGANISM: Artificial Sequence
<220> FEATURE:
<223> OTHER INFORMATION: human IgG1-D270C

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Cys Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 12
<211> LENGTH: 330
<212> TYPE: PRT
<213> ORGANISM: Artificial Sequence
<220> FEATURE:
<223> OTHER INFORMATION: human IgG1 N276C

```
<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Cys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: Artificial Sequence
<220> FEATURE:
<223> OTHER INFORMATION: human IgG1-Y278C

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

-continued

```
                20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Cys Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 330
<212> TYPE: PRT
<213> ORGANISM: Artificial Sequence
<220> FEATURE:
<223> OTHER INFORMATION: human IgG1-E283C

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Cys Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 330
<212> TYPE: PRT
<213> ORGANISM: Artificial Sequence
<220> FEATURE:
<223> OTHER INFORMATION: IgG1-V284C

<400> SEQUENCE: 15

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Cys His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: Artificial Sequence
<220> FEATURE:
<223> OTHER INFORMATION: human IgG1-A287C

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
               115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Cys Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 330
<212> TYPE: PRT
<213> ORGANISM: Artificial Sequence
<220> FEATURE:
<223> OTHER INFORMATION: human IgG1-R292C

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
145                 150                 155                 160
Tyr Val Asp Gly Val Glu Val His Asn Ala Lys Thr Lys Pro Cys Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 330
<212> TYPE: PRT
<213> ORGANISM: Artificial Sequence
<220> FEATURE:
<223> OTHER INFORMATION: human IgG1-E293C

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Cys
                165                 170                 175

Glu Gln Tyr Asn Ser Thr Tyr Arg Val Val Ser Val Leu Thr Val Leu
```

```
                180               185               190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 330
<212> TYPE: PRT
<213> ORGANISM: Artificial Sequence
<220> FEATURE:
<223> OTHER INFORMATION: human IgG1-E294C

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Cys Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
              210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 330
<212> TYPE: PRT
<213> ORGANISM: Artificial Sequence
<220> FEATURE:
<223> OTHER INFORMATION: human IgG1-Y300C

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Cys Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
            245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 21
<211> LENGTH: 330
<212> TYPE: PRT
<213> ORGANISM: Artificial Sequence
<220> FEATURE:
<223> OTHER INFORMATION: human IgG1-V302C

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Cys Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
            275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 330
<212> TYPE: PRT
<213> ORGANISM: Artificial Sequence
<220> FEATURE:
<223> OTHER INFORMATION: human IgG1-V303C

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Cys Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

Gln Lys Ser Leu Ser Leu Ser Pro Gly Lys
                325                 330

<210> SEQ ID NO 23
<211> LENGTH: 330
<212> TYPE: PRT
<213> ORGANISM: Artificial Sequence
<220> FEATURE:
<223> OTHER INFORMATION: human IgG1-L314C

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Cys Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 330
<212> TYPE: PRT
<213> ORGANISM: Artificial Sequence
<220> FEATURE:
<223> OTHER INFORMATION: human IgG1-N315C

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Cys Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 25
<211> LENGTH: 330
<212> TYPE: PRT
<213> ORGANISM: Artificial Sequence
<220> FEATURE:
<223> OTHER INFORMATION: human IgG1-E318C

<400> SEQUENCE: 25

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Cys Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 26
<211> LENGTH: 330
<212> TYPE: PRT
<213> ORGANISM: Artificial Sequence
<220> FEATURE:
<223> OTHER INFORMATION: human IgG1-K320C

<400> SEQUENCE: 26

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Cys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 330
<212> TYPE: PRT
<213> ORGANISM: Artificial Sequence
<220> FEATURE:
<223> OTHER INFORMATION: human IgG1-A327C

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Cys Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: Artificial Sequence
<220> FEATURE:
<223> OTHER INFORMATION: human IgG1-I332C

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Cys Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Artificial Sequence
<220> FEATURE:
<223> OTHER INFORMATION: human IgG1-E333C

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Cys Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 330
<212> TYPE: PRT
<213> ORGANISM: Artificial Sequence
<220> FEATURE:
<223> OTHER INFORMATION: human IgG1-K334C

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Cys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 31
<211> LENGTH: 330
<212> TYPE: PRT
<213> ORGANISM: Artificial Sequence
<220> FEATURE:
<223> OTHER INFORMATION: human IgG1-I336C

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Cys Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 330
<212> TYPE: PRT
<213> ORGANISM: Artificial Sequence
<220> FEATURE:
<223> OTHER INFORMATION: human IgG1-E345C

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

-continued

```
Lys Ala Leu Pro Ala Pro Ile Glu Lys Thr Ile Ser Lys Ala Lys Gly
        210                 215                 220

Gln Pro Arg Cys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 330
<212> TYPE: PRT
<213> ORGANISM: Artificial Sequence
<220> FEATURE:
<223> OTHER INFORMATION: 33 human GG IgG1-Q347C

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Cys Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 330
<212> TYPE: PRT
<213> ORGANISM: Artificial Sequence
<220> FEATURE:
<223> OTHER INFORMATION: 34 human HH  IgG1-S354C

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 330
<212> TYPE: PRT
<213> ORGANISM: Artificial Sequence
<220> FEATURE:
<223> OTHER INFORMATION: 35 human II IgG1-R355C

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Cys Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 36
<211> LENGTH: 330
<212> TYPE: PRT
<213> ORGANISM: Artificial Sequence
<220> FEATURE:
<223> OTHER INFORMATION: 36 human JJ  IgG1-M358C

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Cys Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 37
<211> LENGTH: 330
<212> TYPE: PRT
<213> ORGANISM: Artificial Sequence
<220> FEATURE:
<223> OTHER INFORMATION: 37 human KK. IgG1-T359C

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Cys Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 38
<211> LENGTH: 330
<212> TYPE: PRT
<213> ORGANISM: Artificial Sequence
<220> FEATURE:

<223> OTHER INFORMATION: 38 human LL IgG1-K360C

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Cys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 39
<211> LENGTH: 330
<212> TYPE: PRT
<213> ORGANISM: Artificial Sequence
<220> FEATURE:
<223> OTHER INFORMATION: MM IgG1-N361C

<400> SEQUENCE: 39

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Cys Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 40
<211> LENGTH: 330
<212> TYPE: PRT
<213> ORGANISM: Artificial Sequence
<220> FEATURE:
<223> OTHER INFORMATION: 40 human NN IgG1-Q362C

<400> SEQUENCE: 40

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Cys Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 330
<212> TYPE: PRT
<213> ORGANISM: Artificial Sequence
<220> FEATURE:
<223> OTHER INFORMATION: 41 human OO. IgG1-K370C

<400> SEQUENCE: 41

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Cys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 330
<212> TYPE: PRT
<213> ORGANISM: Artificial Sequence
<220> FEATURE:
<223> OTHER INFORMATION: 42 human PP.  IgG1-Y373C

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Cys
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 330
<212> TYPE: PRT
<213> ORGANISM: Artificial Sequence
<220> FEATURE:
<223> OTHER INFORMATION: 43 human QQ. IgG1-D376C

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Cys Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 44
<211> LENGTH: 330
<212> TYPE: PRT
<213> ORGANISM: Artificial Sequence
<220> FEATURE:
<223> OTHER INFORMATION: 44 human RR. IgG1-A378C

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Cys Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 330
<212> TYPE: PRT
<213> ORGANISM: Artificial Sequence
<220> FEATURE:
<223> OTHER INFORMATION: 45 human SS. IgG1-E380C

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Cys Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 330
<212> TYPE: PRT
<213> ORGANISM: Artificial Sequence
<220> FEATURE:
<223> OTHER INFORMATION: 46 human TT. IgG1-E382C

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Cys Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 47
<211> LENGTH: 330
<212> TYPE: PRT
<213> ORGANISM: Artificial Sequence
<220> FEATURE:
<223> OTHER INFORMATION: 47 human UU  IgG1-S383C

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Cys Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 330
<212> TYPE: PRT
<213> ORGANISM: Artificial Sequence
<220> FEATURE:
<223> OTHER INFORMATION: 48 human VV  IgG1-N384C

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Cys Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 330
<212> TYPE: PRT
<213> ORGANISM: Artificial Sequence
<220> FEATURE:
<223> OTHER INFORMATION: 49 human WW. IgG1-Q386C

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Cys Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 330
<212> TYPE: PRT
<213> ORGANISM: Artificial Sequence
<220> FEATURE:
<223> OTHER INFORMATION: 50 human XX  IgG1-E388C

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Cys Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 51
<211> LENGTH: 330
<212> TYPE: PRT
<213> ORGANISM: Artificial Sequence

```
<220> FEATURE:
<223> OTHER INFORMATION: 51 human YY  IgG1-N390C

<400> SEQUENCE: 51
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | 165 | | | | | 170 | | | | | 175 | | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Cys | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

```
<210> SEQ ID NO 52
<211> LENGTH: 330
<212> TYPE: PRT
<213> ORGANISM: Artificial Sequence
<220> FEATURE:
<223> OTHER INFORMATION: 52 human ZZ  IgG1-K392C

<400> SEQUENCE: 52
```

Ala Ser Thr Lys Gly Pro Ser Val Phe Pro Leu Ala Pro Ser Ser Lys

-continued

```
 1               5                  10                 15
Ser Thr Ser Gly Gly Thr Ala Ala Leu Gly Cys Leu Val Lys Asp Tyr
             20                 25                 30

Phe Pro Glu Pro Val Thr Val Ser Trp Asn Ser Gly Ala Leu Thr Ser
             35                 40                 45

Gly Val His Thr Phe Pro Ala Val Leu Gln Ser Ser Gly Leu Tyr Ser
             50                 55                 60

Leu Ser Ser Val Val Thr Val Pro Ser Ser Leu Gly Thr Gln Thr
 65                 70                 75                 80

Tyr Ile Cys Asn Val Asn His Lys Pro Ser Asn Thr Lys Val Asp Lys
                 85                 90                 95

Lys Val Glu Pro Lys Ser Cys Asp Lys Thr His Thr Cys Pro Pro Cys
             100                105                110

Pro Ala Pro Glu Leu Leu Gly Gly Pro Ser Val Phe Leu Phe Pro Pro
             115                120                125

Lys Pro Lys Asp Thr Leu Met Ile Ser Arg Thr Pro Glu Val Thr Cys
 130                135                140

Val Val Val Asp Val Ser His Glu Asp Pro Glu Val Lys Phe Asn Trp
 145                150                155                160

Tyr Val Asp Gly Val Glu Val His Asn Ala Lys Thr Lys Pro Arg Glu
             165                170                175

Glu Gln Tyr Asn Ser Thr Tyr Arg Val Val Ser Val Leu Thr Val Leu
             180                185                190

His Gln Asp Trp Leu Asn Gly Lys Glu Tyr Lys Cys Lys Val Ser Asn
             195                200                205

Lys Ala Leu Pro Ala Pro Ile Glu Lys Thr Ile Ser Lys Ala Lys Gly
             210                215                220

Gln Pro Arg Glu Pro Gln Val Tyr Thr Leu Pro Pro Ser Arg Glu Glu
 225                230                235                240

Met Thr Lys Asn Gln Val Ser Leu Thr Cys Leu Val Lys Gly Phe Tyr
             245                250                255

Pro Ser Asp Ile Ala Val Glu Trp Glu Ser Asn Gly Gln Pro Glu Asn
             260                265                270

Asn Tyr Cys Thr Thr Pro Pro Val Leu Asp Ser Asp Gly Ser Phe Phe
             275                280                285

Leu Tyr Ser Lys Leu Thr Val Asp Lys Ser Arg Trp Gln Gln Gly Asn
             290                295                300

Val Phe Ser Cys Ser Val Met His Glu Ala Leu His Asn His Tyr Thr
 305                310                315                320

Gln Lys Ser Leu Ser Leu Ser Pro Gly Lys
             325                330
```

<210> SEQ ID NO 53
<211> LENGTH: 330
<212> TYPE: PRT
<213> ORGANISM: Artificial Sequence
<220> FEATURE:
<223> OTHER INFORMATION: 53 human AAA. IgG1-T393C

<400> SEQUENCE: 53

```
Ala Ser Thr Lys Gly Pro Ser Val Phe Pro Leu Ala Pro Ser Ser Lys
 1               5                  10                 15

Ser Thr Ser Gly Gly Thr Ala Ala Leu Gly Cys Leu Val Lys Asp Tyr
             20                 25                 30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Cys Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 54
<211> LENGTH: 330
<212> TYPE: PRT
<213> ORGANISM: Artificial Sequence
<220> FEATURE:
<223> OTHER INFORMATION: 54 human BBB  IgG1-L398C

<400> SEQUENCE: 54

Ala Ser Thr Lys Gly Pro Ser Val Phe Pro Leu Ala Pro Ser Ser Lys
 1                5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Cys Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 55
<211> LENGTH: 330
<212> TYPE: PRT
<213> ORGANISM: Artificial Sequence
<220> FEATURE:
<223> OTHER INFORMATION: 55 human CCC.   IgG1-D401C

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Cys Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: Artificial Sequence
<220> FEATURE:
<223> OTHER INFORMATION: 56 human DDD  IgG1-F404C

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130             135             140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Cys Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 330
<212> TYPE: PRT
<213> ORGANISM: Artificial Sequence
<220> FEATURE:
<223> OTHER INFORMATION: 57 human EEE  IgG1-T411C

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                      165                 170                 175
Glu Gln Tyr Asn Ser Thr Tyr Arg Val Val Ser Val Leu Thr Val Leu
                  180                 185                 190

His Gln Asp Trp Leu Asn Gly Lys Glu Tyr Lys Cys Lys Val Ser Asn
              195                 200                 205

Lys Ala Leu Pro Ala Pro Ile Glu Lys Thr Ile Ser Lys Ala Lys Gly
          210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
              245                 250                 255

Pro Ser Asp Ile Ala Val Glu Trp Glu Ser Asn Gly Gln Pro Glu Asn
              260                 265                 270

Asn Tyr Lys Thr Thr Pro Pro Val Leu Asp Ser Asp Gly Ser Phe Phe
              275                 280                 285

Leu Tyr Ser Lys Leu Cys Val Asp Lys Ser Arg Trp Gln Gln Gly Asn
          290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                  325                 330

<210> SEQ ID NO 58
<211> LENGTH: 330
<212> TYPE: PRT
<213> ORGANISM: Artificial Sequence
<220> FEATURE:
<223> OTHER INFORMATION: 58 human FFF.  IgG1-D413C

<400> SEQUENCE: 58

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
          35                  40                  45

Gly Val His Thr Phe Pro Ala Val Leu Gln Ser Ser Gly Leu Tyr Ser
      50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
              85                  90                  95

Lys Val Glu Pro Lys Ser Cys Asp Lys Thr His Thr Cys Pro Pro Cys
          100                 105                 110

Pro Ala Pro Glu Leu Leu Gly Gly Pro Ser Val Phe Leu Phe Pro Pro
      115                 120                 125

Lys Pro Lys Asp Thr Leu Met Ile Ser Arg Thr Pro Glu Val Thr Cys
  130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
              165                 170                 175

Glu Gln Tyr Asn Ser Thr Tyr Arg Val Val Ser Val Leu Thr Val Leu
          180                 185                 190

His Gln Asp Trp Leu Asn Gly Lys Glu Tyr Lys Cys Lys Val Ser Asn
```

```
            195                 200                 205
Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Cys Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 59
<211> LENGTH: 330
<212> TYPE: PRT
<213> ORGANISM: Artificial Sequence
<220> FEATURE:
<223> OTHER INFORMATION: 59 human GGG IgG1-K414C

<400> SEQUENCE: 59

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
```

```
                225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Cys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 60
<211> LENGTH: 330
<212> TYPE: PRT
<213> ORGANISM: Artificial Sequence
<220> FEATURE:
<223> OTHER INFORMATION: 60 human HHH  IgG1-R416C

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Cys Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 61
<211> LENGTH: 330
<212> TYPE: PRT
<213> ORGANISM: Artificial Sequence
<220> FEATURE:
<223> OTHER INFORMATION: 61 human III.  IgG1-Q418C

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Cys Gln Gly Asn
```

```
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 330
<212> TYPE: PRT
<213> ORGANISM: Artificial Sequence
<220> FEATURE:
<223> OTHER INFORMATION: 62 human JJJ  IgG1-Q419

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Cys Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 63
<211> LENGTH: 330
<212> TYPE: PRT
<213> ORGANISM: Artificial Sequence
<220> FEATURE:
<223> OTHER INFORMATION: 63 human KKK.  IgG1-N421C

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Cys
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 330
<212> TYPE: PRT

<213> ORGANISM: Artificial Sequence
<220> FEATURE:
<223> OTHER INFORMATION: 64 human LLL IgG1-V422C

<400> SEQUENCE: 64

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Cys Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 65
<211> LENGTH: 330
<212> TYPE: PRT
<213> ORGANISM: Artificial Sequence
<220> FEATURE:
<223> OTHER INFORMATION: 65 human MMM. IgG1-M428C

<400> SEQUENCE: 65

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Cys His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 330
<212> TYPE: PRT
<213> ORGANISM: Artificial Sequence
<220> FEATURE:
<223> OTHER INFORMATION: 66 human NNN. IgG1-A431C

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
          35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Cys Leu His Asn His Tyr Thr
305                 310                 315                 320

Gln Lys Ser Leu Ser Leu Ser Pro Gly Lys
            325                 330

<210> SEQ ID NO 67
<211> LENGTH: 330
<212> TYPE: PRT
<213> ORGANISM: Artificial Sequence
<220> FEATURE:
<223> OTHER INFORMATION: 67 human OOO. IgG1-L432C

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
          35                  40                  45

Gly Val His Thr Phe Pro Ala Val Leu Gln Ser Ser Gly Leu Tyr Ser
 50                  55                  60

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Cys His Asn His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: Artificial Sequence
<220> FEATURE:
<223> OTHER INFORMATION: 68 human PPP.  IgG1-T437C

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Cys
305                 310                 315                 320

Gln Lys Ser Leu Ser Leu Ser Pro Gly Lys
                325                 330

<210> SEQ ID NO 69
<211> LENGTH: 330
<212> TYPE: PRT
<213> ORGANISM: Artificial Sequence
<220> FEATURE:
<223> OTHER INFORMATION: 69 human QQQ.  IgG1-Q438C

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Cys Lys Ser Leu Ser Leu Ser Pro Gly Lys
            325                 330

<210> SEQ ID NO 70
<211> LENGTH: 330
<212> TYPE: PRT
<213> ORGANISM: Artificial Sequence
<220> FEATURE:
<223> OTHER INFORMATION: 70 human RRR.  IgG1-K439C

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Cys Ser Leu Ser Leu Ser Pro Gly Lys
                325                 330

<210> SEQ ID NO 71
<211> LENGTH: 330
<212> TYPE: PRT
<213> ORGANISM: Artificial Sequence
<220> FEATURE:
<223> OTHER INFORMATION: IgG1 S440C

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Cys Leu Ser Leu Ser Pro Gly Lys
                325                 330

<210> SEQ ID NO 72
<211> LENGTH: 330
<212> TYPE: PRT
<213> ORGANISM: Artificial Sequence
<220> FEATURE:
<223> OTHER INFORMATION: 72 human TTT. IgG1-L443C

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

-continued

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Cys Ser Pro Gly Lys
            325                 330

<210> SEQ ID NO 73
<211> LENGTH: 330
<212> TYPE: PRT
<213> ORGANISM: Artificial Sequence
<220> FEATURE:
<223> OTHER INFORMATION: 73 human UUU.  IgG1-S444C

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Cys Pro Gly Lys
            325                 330

<210> SEQ ID NO 74
<211> LENGTH: 330
<212> TYPE: PRT
<213> ORGANISM: Artificial Sequence
<220> FEATURE:
<223> OTHER INFORMATION: 74 human IgG1-E380C+L443C

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Cys Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Cys Ser Pro Gly Lys
                325                 330

<210> SEQ ID NO 75
<211> LENGTH: 330
<212> TYPE: PRT
<213> ORGANISM: Artificial Sequence
<220> FEATURE:
<223> OTHER INFORMATION: 75 human IgG1-L398C+L443C

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Cys Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Cys Ser Pro Gly Lys
                325                 330

<210> SEQ ID NO 76
<211> LENGTH: 330
<212> TYPE: PRT
<213> ORGANISM: Artificial Sequence
<220> FEATURE:
<223> OTHER INFORMATION: 76 human IgG1- V422C+L443C

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Cys Phe Ser Cys Ser Val Met His Glu Ala Leu His Asn His Tyr Thr
305                 310                 315                 320

Gln Lys Ser Leu Ser Cys Ser Pro Gly Lys
                325                 330

<210> SEQ ID NO 77
<211> LENGTH: 330

```
<212> TYPE: PRT
<213> ORGANISM: Artificial Sequence
<220> FEATURE:
<223> OTHER INFORMATION: 77 human IgG1- E380C+L398C

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Cys Trp Glu Ser Asn Gly Gln Pro Glu Asn
            260                 265                 270

Asn Tyr Lys Thr Thr Pro Pro Val Cys Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 330
<212> TYPE: PRT
<213> ORGANISM: Artificial Sequence
<220> FEATURE:
<223> OTHER INFORMATION: 78 human IgG1- L398C+V422C

<400> SEQUENCE: 78
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Cys Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Cys Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 330
<212> TYPE: PRT
<213> ORGANISM: Artificial Sequence
<220> FEATURE:
<223> OTHER INFORMATION: 79 human IgG1-E380C+V422C

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Cys Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Cys Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 80
<211> LENGTH: 330
<212> TYPE: PRT
<213> ORGANISM: Artificial Sequence
<220> FEATURE:
<223> OTHER INFORMATION: human IgG1-K392C+L443C

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Cys Ser Pro Gly Lys
                325                 330

<210> SEQ ID NO 81
<211> LENGTH: 330
<212> TYPE: PRT
<213> ORGANISM: Artificial Sequence
<220> FEATURE:
<223> OTHER INFORMATION: human IgG1-F404C+L443C

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Cys Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Cys Ser Pro Gly Lys
                325                 330

<210> SEQ ID NO 82
<211> LENGTH: 330
<212> TYPE: PRT
<213> ORGANISM: Artificial Sequence
<220> FEATURE:
<223> OTHER INFORMATION: 82 human IgG1-K392C+F404C

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

Lys Pro Lys Asp Thr Leu Met Ile Ser Arg Thr Pro Glu Val Thr Cys
          130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Cys Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 449
<212> TYPE: PRT
<213> ORGANISM: Artificial Sequence
<220> FEATURE:
<223> OTHER INFORMATION: 83 anti-5T4 antibody heavy chain

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Phe
            20                  25                  30

Gly Met Asn Trp Val Arg Gln Ala Pro Gly Lys Gly Leu Glu Trp Val
        35                  40                  45

Ala Trp Ile Asn Thr Asn Thr Gly Glu Pro Arg Tyr Ala Glu Glu Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asp Gly Ala Tyr Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 84
<211> LENGTH: 214
<212> TYPE: PRT
<213> ORGANISM: Artificial Sequence
<220> FEATURE:
<223> OTHER INFORMATION: 84 anti-5T4 antibody light chain

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
    50                  55                  60
```

```
Ser Gly Tyr Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 85
<211> LENGTH: 450
<212> TYPE: PRT
<213> ORGANISM: Artificial Sequence
<220> FEATURE:
<223> OTHER INFORMATION: 85 anti-Her2 antibody heavy chain

<400> SEQUENCE: 85

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 86
<211> LENGTH: 214
<212> TYPE: PRT
<213> ORGANISM: Artificial Sequence
<220> FEATURE:
<223> OTHER INFORMATION: 86 anti-Her2 light chain

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 446
<212> TYPE: PRT
<213> ORGANISM: Artificial Sequence
<220> FEATURE:
<223> OTHER INFORMATION: 87 anti-VEGFR2 antibody heavy chain

<400> SEQUENCE: 87

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 88
<211> LENGTH: 214
<212> TYPE: PRT
<213> ORGANISM: Artificial Sequence
<220> FEATURE:
<223> OTHER INFORMATION: 88 anti-VEGFR2 light chan

<400> SEQUENCE: 88

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 106
<212> TYPE: PRT
<213> ORGANISM: Homo sapiens

<400> SEQUENCE: 89

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 90
<211> LENGTH: 106
<212> TYPE: PRT
<213> ORGANISM: Artificial Sequence
<220> FEATURE:
<223> OTHER INFORMATION: 90 A111C-huKappa

<400> SEQUENCE: 90

Thr Val Cys Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 91
<211> LENGTH: 106
<212> TYPE: PRT
<213> ORGANISM: Artificial Sequence
<220> FEATURE:
<223> OTHER INFORMATION: 91 K149C-huKappa

<400> SEQUENCE: 91

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Cys Val Asp Asn Ala Leu Gln Ser
            35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 92
<211> LENGTH: 106
<212> TYPE: PRT
<213> ORGANISM: Artificial Sequence
<220> FEATURE:
<223> OTHER INFORMATION: 92 K183C-huKappa

<400> SEQUENCE: 92

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Cys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 93
<211> LENGTH: 106
<212> TYPE: PRT
<213> ORGANISM: Artificial Sequence
<220> FEATURE:
<223> OTHER INFORMATION: 93 K188C-huKappa

<400> SEQUENCE: 93

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Cys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 94
<211> LENGTH: 106
<212> TYPE: PRT
<213> ORGANISM: Artificial Sequence
<220> FEATURE:
<223> OTHER INFORMATION: 94 K207C-huKappa

<400> SEQUENCE: 94

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Cys Ser Phe Asn Arg Gly Glu Cys
            100                 105

<210> SEQ ID NO 95
<211> LENGTH: 106
<212> TYPE: PRT
<213> ORGANISM: Artificial Sequence
<220> FEATURE:
<223> OTHER INFORMATION: 95 N210C-huKappa

<400> SEQUENCE: 95

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Cys Arg Gly Glu Cys
            100                 105

<210> SEQ ID NO 96
<211> LENGTH: 21
<212> TYPE: PRT
<213> ORGANISM: Artificial Sequence
<220> FEATURE:
<223> OTHER INFORMATION: 96 Partial S254C

<400> SEQUENCE: 96

Pro Pro Lys Pro Lys Asp Thr Leu Met Ile Cys Arg Thr Pro Glu Val
1               5                   10                  15

```
Thr Cys Val Val Val
        20

<210> SEQ ID NO 97
<211> LENGTH: 21
<212> TYPE: PRT
<213> ORGANISM: Artificial Sequence
<220> FEATURE:
<223> OTHER INFORMATION: 97 Partial T359C

<400> SEQUENCE: 97

Tyr Thr Leu Pro Pro Ser Arg Glu Glu Met Cys Lys Asn Gln Val Ser
1               5                   10                  15

Leu Thr Cys Leu Val
        20

<210> SEQ ID NO 98
<211> LENGTH: 21
<212> TYPE: PRT
<213> ORGANISM: Artificial Sequence
<220> FEATURE:
<223> OTHER INFORMATION: 98 Partial N361C

<400> SEQUENCE: 98

Leu Pro Pro Ser Arg Glu Glu Met Thr Lys Cys Gln Val Ser Leu Thr
1               5                   10                  15

Cys Leu Val Lys Gly
        20

<210> SEQ ID NO 99
<211> LENGTH: 21
<212> TYPE: PRT
<213> ORGANISM: Artificial Sequence
<220> FEATURE:
<223> OTHER INFORMATION: 99 Partial E380C

<400> SEQUENCE: 99

Lys Gly Phe Tyr Pro Ser Asp Ile Ala Val Cys Trp Glu Ser Asn Gly
1               5                   10                  15

Gln Pro Glu Asn Asn
        20

<210> SEQ ID NO 100
<211> LENGTH: 21
<212> TYPE: PRT
<213> ORGANISM: Artificial Sequence
<220> FEATURE:
<223> OTHER INFORMATION: 100 Partial S383C

<400> SEQUENCE: 100

Tyr Pro Ser Asp Ile Ala Val Glu Trp Glu Cys Asn Gly Gln Pro Glu
1               5                   10                  15

Asn Asn Tyr Lys Thr
        20

<210> SEQ ID NO 101
<211> LENGTH: 21
<212> TYPE: PRT
<213> ORGANISM: Artificial Sequence
<220> FEATURE:
<223> OTHER INFORMATION: 101 Partial N384C

<400> SEQUENCE: 101

Pro Ser Asp Ile Ala Val Glu Trp Glu Ser Cys Gly Gln Pro Glu Asn
1               5                   10                  15
```

```
<210> SEQ ID NO 102
<211> LENGTH: 21
<212> TYPE: PRT
<213> ORGANISM: Artificial Sequence
<220> FEATURE:
<223> OTHER INFORMATION: 102 Partial K392C

<400> SEQUENCE: 102

Glu Ser Asn Gly Gln Pro Glu Asn Asn Tyr Cys Thr Thr Pro Pro Val
1               5                   10                  15

Leu Asp Ser Asp Gly
            20

<210> SEQ ID NO 103
<211> LENGTH: 21
<212> TYPE: PRT
<213> ORGANISM: Artificial Sequence
<220> FEATURE:
<223> OTHER INFORMATION: 103 Partial L398C

<400> SEQUENCE: 103

Glu Asn Asn Tyr Lys Thr Thr Pro Pro Val Cys Asp Ser Asp Gly Ser
1               5                   10                  15

Phe Phe Leu Tyr Ser
            20

<210> SEQ ID NO 104
<211> LENGTH: 21
<212> TYPE: PRT
<213> ORGANISM: Artificial Sequence
<220> FEATURE:
<223> OTHER INFORMATION: 104 Partial F404C

<400> SEQUENCE: 104

Thr Pro Pro Val Leu Asp Ser Asp Gly Ser Cys Phe Leu Tyr Ser Lys
1               5                   10                  15

Leu Thr Val Asp Lys
            20

<210> SEQ ID NO 105
<211> LENGTH: 21
<212> TYPE: PRT
<213> ORGANISM: Artificial Sequence
<220> FEATURE:
<223> OTHER INFORMATION: 105 Partial V422C

<400> SEQUENCE: 105

Val Asp Lys Ser Arg Trp Gln Gln Gly Asn Cys Phe Ser Cys Ser Val
1               5                   10                  15

Met His Glu Ala Leu
            20

<210> SEQ ID NO 106
<211> LENGTH: 21
<212> TYPE: PRT
<213> ORGANISM: Artificial Sequence
<220> FEATURE:
<223> OTHER INFORMATION: 106 Partial S440C

<400> SEQUENCE: 106

Val Met His Glu Ala Leu His Asn His Tyr Thr Gln Lys Cys Leu Ser
```

```
1               5                   10                  15

Leu Ser Pro Gly Lys
            20

<210> SEQ ID NO 107
<211> LENGTH: 21
<212> TYPE: PRT
<213> ORGANISM: Artificial Sequence
<220> FEATURE:
<223> OTHER INFORMATION: 107 Partial L443C

<400> SEQUENCE: 107

Val Met His Glu Ala Leu His Asn His Tyr Thr Gln Lys Ser Leu Ser
1               5                   10                  15

Cys Ser Pro Gly Lys
            20

<210> SEQ ID NO 108
<211> LENGTH: 21
<212> TYPE: PRT
<213> ORGANISM: Artificial Sequence
<220> FEATURE:
<223> OTHER INFORMATION: 108 Partial K246C

<400> SEQUENCE: 108

Gly Gly Pro Ser Val Phe Leu Phe Pro Pro Cys Pro Lys Asp Thr Leu
1               5                   10                  15

Met Ile Ser Arg Thr
            20

<210> SEQ ID NO 109
<211> LENGTH: 21
<212> TYPE: PRT
<213> ORGANISM: Artificial Sequence
<220> FEATURE:
<223> OTHER INFORMATION: 109 Partial D249C

<400> SEQUENCE: 109

Ser Val Phe Leu Phe Pro Pro Lys Pro Lys Cys Thr Leu Met Ile Ser
1               5                   10                  15

Arg Thr Pro Glu Val
            20

<210> SEQ ID NO 110
<211> LENGTH: 21
<212> TYPE: PRT
<213> ORGANISM: Artificial Sequence
<220> FEATURE:
<223> OTHER INFORMATION: 110 Partial D265C

<400> SEQUENCE: 110

Arg Thr Pro Glu Val Thr Cys Val Val Val Cys Val Ser His Glu Asp
1               5                   10                  15

Pro Glu Val Lys Phe
            20

<210> SEQ ID NO 111
<211> LENGTH: 21
<212> TYPE: PRT
<213> ORGANISM: Artificial Sequence
<220> FEATURE:
<223> OTHER INFORMATION: 111 Partial S267C

<400> SEQUENCE: 111
```

```
Pro Glu Val Thr Cys Val Val Asp Val Cys His Glu Asp Pro Glu
1               5                   10                  15

Val Lys Phe Asn Trp
            20

<210> SEQ ID NO 112
<211> LENGTH: 21
<212> TYPE: PRT
<213> ORGANISM: Artificial Sequence
<220> FEATURE:
<223> OTHER INFORMATION: 112 Partial D270C

<400> SEQUENCE: 112

Thr Cys Val Val Val Asp Val Ser His Glu Cys Pro Glu Val Lys Phe
1               5                   10                  15

Asn Trp Tyr Val Asp
            20

<210> SEQ ID NO 113
<211> LENGTH: 21
<212> TYPE: PRT
<213> ORGANISM: Artificial Sequence
<220> FEATURE:
<223> OTHER INFORMATION: 113 Partial N276C

<400> SEQUENCE: 113

Val Ser His Glu Asp Pro Glu Val Lys Phe Cys Trp Tyr Val Asp Gly
1               5                   10                  15

Val Glu Val His Asn
            20

<210> SEQ ID NO 114
<211> LENGTH: 21
<212> TYPE: PRT
<213> ORGANISM: Artificial Sequence
<220> FEATURE:
<223> OTHER INFORMATION: 114 Partial Y278C

<400> SEQUENCE: 114

His Glu Asp Pro Glu Val Lys Phe Asn Trp Cys Val Asp Gly Val Glu
1               5                   10                  15

Val His Asn Ala Lys
            20

<210> SEQ ID NO 115
<211> LENGTH: 21
<212> TYPE: PRT
<213> ORGANISM: Artificial Sequence
<220> FEATURE:
<223> OTHER INFORMATION: 115 Partial E283C

<400> SEQUENCE: 115

Val Lys Phe Asn Trp Tyr Val Asp Gly Val Cys Val His Asn Ala Lys
1               5                   10                  15

Thr Lys Pro Arg Glu
            20

<210> SEQ ID NO 116
<211> LENGTH: 21
<212> TYPE: PRT
<213> ORGANISM: Artificial Sequence
<220> FEATURE:
<223> OTHER INFORMATION: 116 Partial V284C

<400> SEQUENCE: 116
```

-continued

```
Lys Phe Asn Trp Tyr Val Asp Gly Val Glu Cys His Asn Ala Lys Thr
1               5                   10                  15
Lys Pro Arg Glu Glu
            20

<210> SEQ ID NO 117
<211> LENGTH: 21
<212> TYPE: PRT
<213> ORGANISM: Artificial Sequence
<220> FEATURE:
<223> OTHER INFORMATION: 117 Partial A287C

<400> SEQUENCE: 117

Trp Tyr Val Asp Gly Val Glu Val His Asn Cys Lys Thr Lys Pro Arg
1               5                   10                  15
Glu Glu Gln Tyr Asn
            20

<210> SEQ ID NO 118
<211> LENGTH: 21
<212> TYPE: PRT
<213> ORGANISM: Artificial Sequence
<220> FEATURE:
<223> OTHER INFORMATION: 118 Partial R292C

<400> SEQUENCE: 118

Val Glu Val His Asn Ala Lys Thr Lys Pro Cys Glu Glu Gln Tyr Asn
1               5                   10                  15
Ser Thr Tyr Arg Val
            20

<210> SEQ ID NO 119
<211> LENGTH: 21
<212> TYPE: PRT
<213> ORGANISM: Artificial Sequence
<220> FEATURE:
<223> OTHER INFORMATION: 119 Partial E293C

<400> SEQUENCE: 119

Glu Val His Asn Ala Lys Thr Lys Pro Arg Cys Glu Gln Tyr Asn Ser
1               5                   10                  15
Thr Tyr Arg Val Val
            20

<210> SEQ ID NO 120
<211> LENGTH: 21
<212> TYPE: PRT
<213> ORGANISM: Artificial Sequence
<220> FEATURE:
<223> OTHER INFORMATION: 120 Partial E294C

<400> SEQUENCE: 120

Val His Asn Ala Lys Thr Lys Pro Arg Glu Cys Gln Tyr Asn Ser Thr
1               5                   10                  15
Tyr Arg Val Val Ser
            20

<210> SEQ ID NO 121
<211> LENGTH: 21
<212> TYPE: PRT
<213> ORGANISM: Artificial Sequence
<220> FEATURE:
<223> OTHER INFORMATION: 121 Partial Y300C
```

```
<400> SEQUENCE: 121

Lys Pro Arg Glu Glu Gln Tyr Asn Ser Thr Cys Arg Val Val Ser Val
1               5                   10                  15

Leu Thr Val Leu His
            20

<210> SEQ ID NO 122
<211> LENGTH: 21
<212> TYPE: PRT
<213> ORGANISM: Artificial Sequence
<220> FEATURE:
<223> OTHER INFORMATION: 122 Partial V302C

<400> SEQUENCE: 122

Arg Glu Glu Gln Tyr Asn Ser Thr Tyr Arg Cys Val Ser Val Leu Thr
1               5                   10                  15

Val Leu His Gln Asp
            20

<210> SEQ ID NO 123
<211> LENGTH: 21
<212> TYPE: PRT
<213> ORGANISM: Artificial Sequence
<220> FEATURE:
<223> OTHER INFORMATION: 123 Partial V303C

<400> SEQUENCE: 123

Glu Glu Gln Tyr Asn Ser Thr Tyr Arg Val Cys Ser Val Leu Thr Val
1               5                   10                  15

Leu His Gln Asp Trp
            20

<210> SEQ ID NO 124
<211> LENGTH: 21
<212> TYPE: PRT
<213> ORGANISM: Artificial Sequence
<220> FEATURE:
<223> OTHER INFORMATION: 124 Partial L314C

<400> SEQUENCE: 124

Ser Val Leu Thr Val Leu His Gln Asp Trp Cys Asn Gly Lys Glu Tyr
1               5                   10                  15

Lys Cys Lys Val Ser
            20

<210> SEQ ID NO 125
<211> LENGTH: 21
<212> TYPE: PRT
<213> ORGANISM: Artificial Sequence
<220> FEATURE:
<223> OTHER INFORMATION: 125 Partial N315C

<400> SEQUENCE: 125

Val Leu Thr Val Leu His Gln Asp Trp Leu Cys Gly Lys Glu Tyr Lys
1               5                   10                  15

Cys Lys Val Ser Asn
            20

<210> SEQ ID NO 126
<211> LENGTH: 21
<212> TYPE: PRT
<213> ORGANISM: Artificial Sequence
<220> FEATURE:
<223> OTHER INFORMATION: 126 Partial E318C
```

```
<400> SEQUENCE: 126

Val Leu His Gln Asp Trp Leu Asn Gly Lys Cys Tyr Lys Cys Lys Val
1               5                   10                  15

Ser Asn Lys Ala Leu
            20

<210> SEQ ID NO 127
<211> LENGTH: 21
<212> TYPE: PRT
<213> ORGANISM: Artificial Sequence
<220> FEATURE:
<223> OTHER INFORMATION: 127 Partial K320C

<400> SEQUENCE: 127

His Gln Asp Trp Leu Asn Gly Lys Glu Tyr Cys Cys Lys Val Ser Asn
1               5                   10                  15

Lys Ala Leu Pro Ala
            20

<210> SEQ ID NO 128
<211> LENGTH: 21
<212> TYPE: PRT
<213> ORGANISM: Artificial Sequence
<220> FEATURE:
<223> OTHER INFORMATION: 128 Partial A327C

<400> SEQUENCE: 128

Lys Glu Tyr Lys Cys Lys Val Ser Asn Lys Cys Leu Pro Ala Pro Ile
1               5                   10                  15

Glu Lys Thr Ile Ser
            20

<210> SEQ ID NO 129
<211> LENGTH: 21
<212> TYPE: PRT
<213> ORGANISM: Artificial Sequence
<220> FEATURE:
<223> OTHER INFORMATION: 129 Partial I332C

<400> SEQUENCE: 129

Lys Val Ser Asn Lys Ala Leu Pro Ala Pro Cys Glu Lys Thr Ile Ser
1               5                   10                  15

Lys Ala Lys Gly Gln
            20

<210> SEQ ID NO 130
<211> LENGTH: 21
<212> TYPE: PRT
<213> ORGANISM: Artificial Sequence
<220> FEATURE:
<223> OTHER INFORMATION: 130 Partial E333C

<400> SEQUENCE: 130

Val Ser Asn Lys Ala Leu Pro Ala Pro Ile Cys Lys Thr Ile Ser Lys
1               5                   10                  15

Ala Lys Gly Gln Pro
            20

<210> SEQ ID NO 131
<211> LENGTH: 21
<212> TYPE: PRT
<213> ORGANISM: Artificial Sequence
<220> FEATURE:
```

```
<223> OTHER INFORMATION: 131 Partial K334C

<400> SEQUENCE: 131

Ser Asn Lys Ala Leu Pro Ala Pro Ile Glu Cys Thr Ile Ser Lys Ala
1               5                   10                  15

Lys Gly Gln Pro Arg
            20

<210> SEQ ID NO 132
<211> LENGTH: 21
<212> TYPE: PRT
<213> ORGANISM: Artificial Sequence
<220> FEATURE:
<223> OTHER INFORMATION: 132 Partial I336

<400> SEQUENCE: 132

Lys Ala Leu Pro Ala Pro Ile Glu Lys Thr Cys Ser Lys Ala Lys Gly
1               5                   10                  15

Gln Pro Arg Glu Pro
            20

<210> SEQ ID NO 133
<211> LENGTH: 21
<212> TYPE: PRT
<213> ORGANISM: Artificial Sequence
<220> FEATURE:
<223> OTHER INFORMATION: 133 Partial E345C

<400> SEQUENCE: 133

Thr Ile Ser Lys Ala Lys Gly Gln Pro Arg Cys Pro Gln Val Tyr Thr
1               5                   10                  15

Leu Pro Pro Ser Arg
            20

<210> SEQ ID NO 134
<211> LENGTH: 21
<212> TYPE: PRT
<213> ORGANISM: Artificial Sequence
<220> FEATURE:
<223> OTHER INFORMATION: 134 Partial Q347

<400> SEQUENCE: 134

Ser Lys Ala Lys Gly Gln Pro Arg Glu Pro Cys Val Tyr Thr Leu Pro
1               5                   10                  15

Pro Ser Arg Glu Glu
            20

<210> SEQ ID NO 135
<211> LENGTH: 21
<212> TYPE: PRT
<213> ORGANISM: Artificial Sequence
<220> FEATURE:
<223> OTHER INFORMATION: 135 Partial S354C

<400> SEQUENCE: 135

Arg Glu Pro Gln Val Tyr Thr Leu Pro Pro Cys Arg Glu Glu Met Thr
1               5                   10                  15

Lys Asn Gln Val Ser
            20

<210> SEQ ID NO 136
<211> LENGTH: 21
<212> TYPE: PRT
<213> ORGANISM: Artificial Sequence
```

```
<220> FEATURE:
<223> OTHER INFORMATION: 136 Partial R355C

<400> SEQUENCE: 136

Glu Pro Gln Val Tyr Thr Leu Pro Pro Ser Cys Glu Met Thr Lys
1               5                   10                  15

Asn Gln Val Ser Leu
            20

<210> SEQ ID NO 137
<211> LENGTH: 21
<212> TYPE: PRT
<213> ORGANISM: Artificial Sequence
<220> FEATURE:
<223> OTHER INFORMATION: 137 Partial M358C

<400> SEQUENCE: 137

Val Tyr Thr Leu Pro Pro Ser Arg Glu Glu Cys Thr Lys Asn Gln Val
1               5                   10                  15

Ser Leu Thr Cys Leu
            20

<210> SEQ ID NO 138
<211> LENGTH: 21
<212> TYPE: PRT
<213> ORGANISM: Artificial Sequence
<220> FEATURE:
<223> OTHER INFORMATION: 138 Partial K360

<400> SEQUENCE: 138

Thr Leu Pro Pro Ser Arg Glu Glu Met Thr Cys Asn Gln Val Ser Leu
1               5                   10                  15

Thr Cys Leu Val Lys
            20

<210> SEQ ID NO 139
<211> LENGTH: 21
<212> TYPE: PRT
<213> ORGANISM: Artificial Sequence
<220> FEATURE:
<223> OTHER INFORMATION: 139 Partial Q362C

<400> SEQUENCE: 139

Pro Pro Ser Arg Glu Glu Met Thr Lys Asn Cys Val Ser Leu Thr Cys
1               5                   10                  15

Leu Val Lys Gly Phe
            20

<210> SEQ ID NO 140
<211> LENGTH: 21
<212> TYPE: PRT
<213> ORGANISM: Artificial Sequence
<220> FEATURE:
<223> OTHER INFORMATION: 140 Partial K370C

<400> SEQUENCE: 140

Lys Asn Gln Val Ser Leu Thr Cys Leu Val Cys Gly Phe Tyr Pro Ser
1               5                   10                  15

Asp Ile Ala Val Glu
            20

<210> SEQ ID NO 141
<211> LENGTH: 21
<212> TYPE: PRT
```

<213> ORGANISM: Artificial Sequence
<220> FEATURE:
<223> OTHER INFORMATION: 141 Partial Y373C

<400> SEQUENCE: 141

Val Ser Leu Thr Cys Leu Val Lys Gly Phe Cys Pro Ser Asp Ile Ala
1               5                   10                  15

Val Glu Trp Glu Ser
            20

<210> SEQ ID NO 142
<211> LENGTH: 21
<212> TYPE: PRT
<213> ORGANISM: Artificial Sequence
<220> FEATURE:
<223> OTHER INFORMATION: 142 Partial D376C

<400> SEQUENCE: 142

Thr Cys Leu Val Lys Gly Phe Tyr Pro Ser Cys Ile Ala Val Glu Trp
1               5                   10                  15

Glu Ser Asn Gly Gln
            20

<210> SEQ ID NO 143
<211> LENGTH: 21
<212> TYPE: PRT
<213> ORGANISM: Artificial Sequence
<220> FEATURE:
<223> OTHER INFORMATION: 143 Partial A378C

<400> SEQUENCE: 143

Leu Val Lys Gly Phe Tyr Pro Ser Asp Ile Cys Val Glu Trp Glu Ser
1               5                   10                  15

Asn Gly Gln Pro Glu
            20

<210> SEQ ID NO 144
<211> LENGTH: 21
<212> TYPE: PRT
<213> ORGANISM: Artificial Sequence
<220> FEATURE:
<223> OTHER INFORMATION: 144 Partial E382C

<400> SEQUENCE: 144

Phe Tyr Pro Ser Asp Ile Ala Val Glu Trp Cys Ser Asn Gly Gln Pro
1               5                   10                  15

Glu Asn Asn Tyr Lys
            20

<210> SEQ ID NO 145
<211> LENGTH: 21
<212> TYPE: PRT
<213> ORGANISM: Artificial Sequence
<220> FEATURE:
<223> OTHER INFORMATION: 145 Partial Q386C

<400> SEQUENCE: 145

Asp Ile Ala Val Glu Trp Glu Ser Asn Gly Cys Pro Glu Asn Asn Tyr
1               5                   10                  15

Lys Thr Thr Pro Pro
            20

<210> SEQ ID NO 146
<211> LENGTH: 21

<212> TYPE: PRT
<213> ORGANISM: Artificial Sequence
<220> FEATURE:
<223> OTHER INFORMATION: 146 Partial E388C

<400> SEQUENCE: 146

Ala Val Glu Trp Glu Ser Asn Gly Gln Pro Cys Asn Asn Tyr Lys Thr
1               5                   10                  15

Thr Pro Pro Val Leu
            20

<210> SEQ ID NO 147
<211> LENGTH: 21
<212> TYPE: PRT
<213> ORGANISM: Artificial Sequence
<220> FEATURE:
<223> OTHER INFORMATION: 147 Partial N390C

<400> SEQUENCE: 147

Glu Trp Glu Ser Asn Gly Gln Pro Glu Asn Cys Tyr Lys Thr Thr Pro
1               5                   10                  15

Pro Val Leu Asp Ser
            20

<210> SEQ ID NO 148
<211> LENGTH: 21
<212> TYPE: PRT
<213> ORGANISM: Artificial Sequence
<220> FEATURE:
<223> OTHER INFORMATION: 148 Partial T393C

<400> SEQUENCE: 148

Ser Asn Gly Gln Pro Glu Asn Asn Tyr Lys Cys Thr Pro Val Leu
1               5                   10                  15

Asp Ser Asp Gly Ser
            20

<210> SEQ ID NO 149
<211> LENGTH: 21
<212> TYPE: PRT
<213> ORGANISM: Artificial Sequence
<220> FEATURE:
<223> OTHER INFORMATION: 149 Partial D401C

<400> SEQUENCE: 149

Tyr Lys Thr Thr Pro Pro Val Leu Asp Ser Cys Gly Ser Phe Phe Leu
1               5                   10                  15

Tyr Ser Lys Leu Thr
            20

<210> SEQ ID NO 150
<211> LENGTH: 21
<212> TYPE: PRT
<213> ORGANISM: Artificial Sequence
<220> FEATURE:
<223> OTHER INFORMATION: 150 Partial T411C

<400> SEQUENCE: 150

Asp Gly Ser Phe Phe Leu Tyr Ser Lys Leu Cys Val Asp Lys Ser Arg
1               5                   10                  15

Trp Gln Gln Gly Asn
            20

<210> SEQ ID NO 151

```
<211> LENGTH: 21
<212> TYPE: PRT
<213> ORGANISM: Artificial Sequence
<220> FEATURE:
<223> OTHER INFORMATION: 151 Partial D413C

<400> SEQUENCE: 151

Ser Phe Phe Leu Tyr Ser Lys Leu Thr Val Cys Lys Ser Arg Trp Gln
1               5                   10                  15

Gln Gly Asn Val Phe
            20

<210> SEQ ID NO 152
<211> LENGTH: 21
<212> TYPE: PRT
<213> ORGANISM: Artificial Sequence
<220> FEATURE:
<223> OTHER INFORMATION: 152 Partial K414C

<400> SEQUENCE: 152

Phe Phe Leu Tyr Ser Lys Leu Thr Val Asp Cys Ser Arg Trp Gln Gln
1               5                   10                  15

Gly Asn Val Phe Ser
            20

<210> SEQ ID NO 153
<211> LENGTH: 21
<212> TYPE: PRT
<213> ORGANISM: Artificial Sequence
<220> FEATURE:
<223> OTHER INFORMATION: 153 Partial R416C

<400> SEQUENCE: 153

Leu Tyr Ser Lys Leu Thr Val Asp Lys Ser Cys Trp Gln Gln Gly Asn
1               5                   10                  15

Val Phe Ser Cys Ser
            20

<210> SEQ ID NO 154
<211> LENGTH: 21
<212> TYPE: PRT
<213> ORGANISM: Artificial Sequence
<220> FEATURE:
<223> OTHER INFORMATION: 154 Partial Q418C

<400> SEQUENCE: 154

Ser Lys Leu Thr Val Asp Lys Ser Arg Trp Cys Gln Gly Asn Val Phe
1               5                   10                  15

Ser Cys Ser Val Met
            20

<210> SEQ ID NO 155
<211> LENGTH: 21
<212> TYPE: PRT
<213> ORGANISM: Artificial Sequence
<220> FEATURE:
<223> OTHER INFORMATION: 155 Partial Q419C

<400> SEQUENCE: 155

Lys Leu Thr Val Asp Lys Ser Arg Trp Gln Cys Gly Asn Val Phe Ser
1               5                   10                  15

Cys Ser Val Met His
            20
```

```
<210> SEQ ID NO 156
<211> LENGTH: 21
<212> TYPE: PRT
<213> ORGANISM: Artificial Sequence
<220> FEATURE:
<223> OTHER INFORMATION: 156 Partial N421C

<400> SEQUENCE: 156

Thr Val Asp Lys Ser Arg Trp Gln Gln Gly Cys Val Phe Ser Cys Ser
1               5                   10                  15

Val Met His Glu Ala
            20

<210> SEQ ID NO 157
<211> LENGTH: 21
<212> TYPE: PRT
<213> ORGANISM: Artificial Sequence
<220> FEATURE:
<223> OTHER INFORMATION: 157 Partial M428C

<400> SEQUENCE: 157

Gln Gln Gly Asn Val Phe Ser Cys Ser Val Cys His Glu Ala Leu His
1               5                   10                  15

Asn His Tyr Thr Gln
            20

<210> SEQ ID NO 158
<211> LENGTH: 21
<212> TYPE: PRT
<213> ORGANISM: Artificial Sequence
<220> FEATURE:
<223> OTHER INFORMATION: 158 Partial A431C

<400> SEQUENCE: 158

Asn Val Phe Ser Cys Ser Val Met His Glu Cys Leu His Asn His Tyr
1               5                   10                  15

Thr Gln Lys Ser Leu
            20

<210> SEQ ID NO 159
<211> LENGTH: 21
<212> TYPE: PRT
<213> ORGANISM: Artificial Sequence
<220> FEATURE:
<223> OTHER INFORMATION: 159 Partial L432C

<400> SEQUENCE: 159

Val Phe Ser Cys Ser Val Met His Glu Ala Cys His Asn His Tyr Thr
1               5                   10                  15

Gln Lys Ser Leu Ser
            20

<210> SEQ ID NO 160
<211> LENGTH: 21
<212> TYPE: PRT
<213> ORGANISM: Artificial Sequence
<220> FEATURE:
<223> OTHER INFORMATION: 160 Partial T437C

<400> SEQUENCE: 160

Val Met His Glu Ala Leu His Asn His Tyr Cys Gln Lys Ser Leu Ser
1               5                   10                  15

Leu Ser Pro Gly Lys
            20
```

<210> SEQ ID NO 161
<211> LENGTH: 21
<212> TYPE: PRT
<213> ORGANISM: Artificial Sequence
<220> FEATURE:
<223> OTHER INFORMATION: 161 Partial Q438C

<400> SEQUENCE: 161

Val Met His Glu Ala Leu His Asn His Tyr Thr Cys Lys Ser Leu Ser
1               5                   10                  15

Leu Ser Pro Gly Lys
            20

<210> SEQ ID NO 162
<211> LENGTH: 21
<212> TYPE: PRT
<213> ORGANISM: Artificial Sequence
<220> FEATURE:
<223> OTHER INFORMATION: 162 Partial K439C

<400> SEQUENCE: 162

Val Met His Glu Ala Leu His Asn His Tyr Thr Gln Cys Ser Leu Ser
1               5                   10                  15

Leu Ser Pro Gly Lys
            20

<210> SEQ ID NO 163
<211> LENGTH: 21
<212> TYPE: PRT
<213> ORGANISM: Artificial Sequence
<220> FEATURE:
<223> OTHER INFORMATION: 163 Partial S444C

<400> SEQUENCE: 163

Val Met His Glu Ala Leu His Asn His Tyr Thr Gln Lys Ser Leu Ser
1               5                   10                  15

Leu Cys Pro Gly Lys
            20

<210> SEQ ID NO 164
<211> LENGTH: 21
<212> TYPE: PRT
<213> ORGANISM: Artificial Sequence
<220> FEATURE:
<223> OTHER INFORMATION: 164 Partial A111C

<400> SEQUENCE: 164

Thr Val Cys Ala Pro Ser Val Phe Ile Phe Pro Pro Ser Asp Glu Gln
1               5                   10                  15

Leu Lys Ser Gly Thr
            20

<210> SEQ ID NO 165
<211> LENGTH: 21
<212> TYPE: PRT
<213> ORGANISM: Artificial Sequence
<220> FEATURE:
<223> OTHER INFORMATION: 165 Partial K149C

<400> SEQUENCE: 165

Phe Tyr Pro Arg Glu Ala Lys Val Gln Trp Cys Val Asp Asn Ala Leu
1               5                   10                  15

Gln Ser Gly Asn Ser
            20

<210> SEQ ID NO 166
<211> LENGTH: 21
<212> TYPE: PRT
<213> ORGANISM: Artificial Sequence
<220> FEATURE:
<223> OTHER INFORMATION: 166 Partial K183C

<400> SEQUENCE: 166

Tyr Ser Leu Ser Ser Thr Leu Thr Leu Ser Cys Ala Asp Tyr Glu Lys
1               5                   10                  15

His Lys Val Tyr Ala
            20

<210> SEQ ID NO 167
<211> LENGTH: 21
<212> TYPE: PRT
<213> ORGANISM: Artificial Sequence
<220> FEATURE:
<223> OTHER INFORMATION: 167 Partial K188C

<400> SEQUENCE: 167

Thr Leu Thr Leu Ser Lys Ala Asp Tyr Glu Cys His Lys Val Tyr Ala
1               5                   10                  15

Cys Glu Val Thr His
            20

<210> SEQ ID NO 168
<211> LENGTH: 21
<212> TYPE: PRT
<213> ORGANISM: Artificial Sequence
<220> FEATURE:
<223> OTHER INFORMATION: 168 Partial K207C

<400> SEQUENCE: 168

Cys Glu Val Thr His Gln Gly Leu Ser Ser Pro Val Thr Cys Ser Phe
1               5                   10                  15

Asn Arg Gly Glu Cys
            20

<210> SEQ ID NO 169
<211> LENGTH: 21
<212> TYPE: PRT
<213> ORGANISM: Artificial Sequence
<220> FEATURE:
<223> OTHER INFORMATION: 169 Partial N210C

<400> SEQUENCE: 169

Cys Glu Val Thr His Gln Gly Leu Ser Ser Pro Val Thr Lys Ser Phe
1               5                   10                  15

Cys Arg Gly Glu Cys
            20

<210> SEQ ID NO 170
<211> LENGTH: 318
<212> TYPE: DNA
<213> ORGANISM: Homo sapiens

<400> SEQUENCE: 170
ggtcagccca aggctgcccc ctcggtcact ctgttcccgc cctcctctga ggagcttcaa     60
gccaacaagg ccacactggt gtgtctcata agtgacttct acccgggagc cgtgacagtg    120
gcctggaagg cagatagcag ccccgtcaag gcgggagtgg agaccaccac accctccaaa    180

```
caaagcaaca acaagtacgc ggccagcagc tatctgagcc tgacgcctga gcagtggaag    240
tcccacagaa gctacagctg ccaggtcacg catgaaggga gcaccgtgga agacagtg     300 gccctacag aatgttca                                                  318
```

<210> SEQ ID NO 171
<211> LENGTH: 106
<212> TYPE: PRT
<213> ORGANISM: Homo sapiens

<400> SEQUENCE: 171

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 172
<211> LENGTH: 106
<212> TYPE: PRT
<213> ORGANISM: Artificial Sequence
<220> FEATURE:
<223> OTHER INFORMATION: 172 K110C-huLambda

<400> SEQUENCE: 172

```
Gly Gln Pro Cys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 173
<211> LENGTH: 106
<212> TYPE: PRT
<213> ORGANISM: Artificial Sequence
<220> FEATURE:
<223> OTHER INFORMATION: 173 A111C-huLambda

<400> SEQUENCE: 173

```
Gly Gln Pro Lys Cys Ala Pro Ser Val Thr Leu Phe Pro Pro Ser Ser
1               5                   10                  15
```

```
Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
             100                 105

<210> SEQ ID NO 174
<211> LENGTH: 106
<212> TYPE: PRT
<213> ORGANISM: Artificial Sequence
<220> FEATURE:
<223> OTHER INFORMATION: 174 L125C-huLambda

<400> SEQUENCE: 174

Gly Gln Pro Lys Ala Ala Pro Ser Val Thr Leu Phe Pro Pro Ser Ser
 1               5                  10                  15

Glu Glu Cys Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
             100                 105

<210> SEQ ID NO 175
<211> LENGTH: 106
<212> TYPE: PRT
<213> ORGANISM: Artificial Sequence
<220> FEATURE:
<223> OTHER INFORMATION: K149C human lambda

<400> SEQUENCE: 175

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Cys Ala Asp Ser Ser Pro
         35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
             100                 105
```

<210> SEQ ID NO 176
<211> LENGTH: 106
<212> TYPE: PRT
<213> ORGANISM: Artificial Sequence
<220> FEATURE:
<223> OTHER INFORMATION: 176 V155C-huLambda

<400> SEQUENCE: 176

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Cys Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 177
<211> LENGTH: 106
<212> TYPE: PRT
<213> ORGANISM: Artificial Sequence
<220> FEATURE:
<223> OTHER INFORMATION: 177 G158C-huLambda

<400> SEQUENCE: 177

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Cys Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 178
<211> LENGTH: 106
<212> TYPE: PRT
<213> ORGANISM: Artificial Sequence
<220> FEATURE:
<223> OTHER INFORMATION: 178 T161C-huLambda

<400> SEQUENCE: 178

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

```
Phe Tyr Pro Gly Ala Val Thr Val Ala Trp Lys Ala Asp Ser Ser Pro
            35                  40                  45

Val Lys Ala Gly Val Glu Cys Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 179
<211> LENGTH: 106
<212> TYPE: PRT
<213> ORGANISM: Artificial Sequence
<220> FEATURE:
<223> OTHER INFORMATION: 179 Q185C-huLambda

<400> SEQUENCE: 179

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Cys Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 180
<211> LENGTH: 106
<212> TYPE: PRT
<213> ORGANISM: Artificial Sequence
<220> FEATURE:
<223> OTHER INFORMATION: 180 S188C-huLambda

<400> SEQUENCE: 180

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Cys His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 181

```
<211> LENGTH: 106
<212> TYPE: PRT
<213> ORGANISM: Artificial Sequence
<220> FEATURE:
<223> OTHER INFORMATION: 181 H189C-huLambda

<400> SEQUENCE: 181

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser Cys Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 182
<211> LENGTH: 106
<212> TYPE: PRT
<213> ORGANISM: Artificial Sequence
<220> FEATURE:
<223> OTHER INFORMATION: 182 S191C-huLambda

<400> SEQUENCE: 182

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Cys Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 183
<211> LENGTH: 106
<212> TYPE: PRT
<213> ORGANISM: Artificial Sequence
<220> FEATURE:
<223> OTHER INFORMATION: 183 T197C-huLambda

<400> SEQUENCE: 183

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45
```

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Cys His Glu Gly Ser Thr Val
                 85                  90                  95

Glu Lys Thr Val Ala Pro Thr Glu Cys Ser
            100                 105

<210> SEQ ID NO 184
<211> LENGTH: 106
<212> TYPE: PRT
<213> ORGANISM: Artificial Sequence
<220> FEATURE:
<223> OTHER INFORMATION: 184 V205C-huLambda

<400> SEQUENCE: 184

Gly Gln Pro Lys Ala Ala Pro Ser Val Thr Leu Phe Pro Pro Ser Ser
1                   5                   10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Cys
                 85                  90                  95

Glu Lys Thr Val Ala Pro Thr Glu Cys Ser
            100                 105

<210> SEQ ID NO 185
<211> LENGTH: 106
<212> TYPE: PRT
<213> ORGANISM: Artificial Sequence
<220> FEATURE:
<223> OTHER INFORMATION: 185 E206C-huLambda

<400> SEQUENCE: 185

Gly Gln Pro Lys Ala Ala Pro Ser Val Thr Leu Phe Pro Pro Ser Ser
1                   5                   10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Cys Lys Thr Val Ala Pro Thr Glu Cys Ser
            100                 105

<210> SEQ ID NO 186
<211> LENGTH: 106
<212> TYPE: PRT
<213> ORGANISM: Artificial Sequence
<220> FEATURE:
<223> OTHER INFORMATION: 186 K207C-huLambda

<400> SEQUENCE: 186

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Cys Thr Val Ala Pro Thr Glu Cys Ser
            100                 105

<210> SEQ ID NO 187
<211> LENGTH: 106
<212> TYPE: PRT
<213> ORGANISM: Artificial Sequence
<220> FEATURE:
<223> OTHER INFORMATION: 187 T208C-huLambda

<400> SEQUENCE: 187

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Cys Val Ala Pro Thr Glu Cys Ser
            100                 105

<210> SEQ ID NO 188
<211> LENGTH: 106
<212> TYPE: PRT
<213> ORGANISM: Artificial Sequence
<220> FEATURE:
<223> OTHER INFORMATION: 188 A210C -huLambda

<400> SEQUENCE: 188

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

-continued

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Cys Pro Thr Glu Cys Ser
            100                 105

<210> SEQ ID NO 189
<211> LENGTH: 14
<212> TYPE: PRT
<213> ORGANISM: Artificial Sequence
<220> FEATURE:
<223> OTHER INFORMATION: 189 Partial K110C

<400> SEQUENCE: 189

Gly Gln Pro Cys Ala Ala Pro Ser Val Thr Leu Phe Pro Pro
1               5                   10

<210> SEQ ID NO 190
<211> LENGTH: 15
<212> TYPE: PRT
<213> ORGANISM: Artificial Sequence
<220> FEATURE:
<223> OTHER INFORMATION: 190 Partial A11C

<400> SEQUENCE: 190

Gly Gln Pro Lys Cys Ala Pro Ser Val Thr Leu Phe Pro Pro Ser
1               5                   10                  15

<210> SEQ ID NO 191
<211> LENGTH: 21
<212> TYPE: PRT
<213> ORGANISM: Artificial Sequence
<220> FEATURE:
<223> OTHER INFORMATION: 191 Partial L125C

<400> SEQUENCE: 191

Val Thr Leu Phe Pro Pro Ser Ser Glu Glu Cys Gln Ala Asn Lys Ala
1               5                   10                  15

Thr Leu Val Cys Leu
            20

<210> SEQ ID NO 192
<211> LENGTH: 21
<212> TYPE: PRT
<213> ORGANISM: Artificial Sequence
<220> FEATURE:
<223> OTHER INFORMATION: VTLFPPSSEECQANKATLVCL

<400> SEQUENCE: 192

Phe Tyr Pro Gly Ala Val Thr Val Ala Trp Cys Ala Asp Ser Ser Pro
1               5                   10                  15

Val Lys Ala Gly Val
            20

<210> SEQ ID NO 193
<211> LENGTH: 21
<212> TYPE: PRT
<213> ORGANISM: Artificial Sequence
<220> FEATURE:
<223> OTHER INFORMATION: 193 Partial V155C

<400> SEQUENCE: 193

Thr Val Ala Trp Lys Ala Asp Ser Ser Pro Cys Lys Ala Gly Val Glu
1               5                   10                  15

```
Thr Thr Thr Pro Ser
            20

<210> SEQ ID NO 194
<211> LENGTH: 21
<212> TYPE: PRT
<213> ORGANISM: Artificial Sequence
<220> FEATURE:
<223> OTHER INFORMATION: 194 Partial G158C

<400> SEQUENCE: 194

Trp Lys Ala Asp Ser Ser Pro Val Lys Ala Cys Val Glu Thr Thr Thr
1               5                   10                  15

Pro Ser Lys Gln Ser
            20

<210> SEQ ID NO 195
<211> LENGTH: 21
<212> TYPE: PRT
<213> ORGANISM: Artificial Sequence
<220> FEATURE:
<223> OTHER INFORMATION: 195 Partial T161C

<400> SEQUENCE: 195

Asp Ser Ser Pro Val Lys Ala Gly Val Glu Cys Thr Thr Pro Ser Lys
1               5                   10                  15

Gln Ser Asn Asn Lys
            20

<210> SEQ ID NO 196
<211> LENGTH: 21
<212> TYPE: PRT
<213> ORGANISM: Artificial Sequence
<220> FEATURE:
<223> OTHER INFORMATION: 196 Partial Q185C

<400> SEQUENCE: 196

Ala Ser Ser Tyr Leu Ser Leu Thr Pro Glu Cys Trp Lys Ser His Arg
1               5                   10                  15

Ser Tyr Ser Cys Gln
            20

<210> SEQ ID NO 197
<211> LENGTH: 21
<212> TYPE: PRT
<213> ORGANISM: Artificial Sequence
<220> FEATURE:
<223> OTHER INFORMATION: 197 Partial S188C

<400> SEQUENCE: 197

Tyr Leu Ser Leu Thr Pro Glu Gln Trp Lys Cys His Arg Ser Tyr Ser
1               5                   10                  15

Cys Gln Val Thr His
            20

<210> SEQ ID NO 198
<211> LENGTH: 21
<212> TYPE: PRT
<213> ORGANISM: Artificial Sequence
<220> FEATURE:
<223> OTHER INFORMATION: 198 Partial H189C

<400> SEQUENCE: 198

Leu Ser Leu Thr Pro Glu Gln Trp Lys Ser Cys Arg Ser Tyr Ser Cys
```

```
1               5                   10                  15

Gln Val Thr His Glu
            20

<210> SEQ ID NO 199
<211> LENGTH: 21
<212> TYPE: PRT
<213> ORGANISM: Artificial Sequence
<220> FEATURE:
<223> OTHER INFORMATION: 199 Partial S191C

<400> SEQUENCE: 199

Leu Thr Pro Glu Gln Trp Lys Ser His Arg Cys Tyr Ser Cys Gln Val
1               5                   10                  15

Thr His Glu Gly Ser
            20

<210> SEQ ID NO 200
<211> LENGTH: 21
<212> TYPE: PRT
<213> ORGANISM: Artificial Sequence
<220> FEATURE:
<223> OTHER INFORMATION: 200 Partial T197C

<400> SEQUENCE: 200

Glu Gln Trp Lys Ser His Arg Ser Tyr Ser Cys Gln Val Cys His Glu
1               5                   10                  15

Gly Ser Thr Val Glu
            20

<210> SEQ ID NO 201
<211> LENGTH: 21
<212> TYPE: PRT
<213> ORGANISM: Artificial Sequence
<220> FEATURE:
<223> OTHER INFORMATION: EQWKSHRSYSCQVCHEGSTVE

<400> SEQUENCE: 201

Ser Cys Gln Val Thr His Glu Gly Ser Thr Cys Glu Lys Thr Val Ala
1               5                   10                  15

Pro Thr Glu Cys Ser
            20

<210> SEQ ID NO 202
<211> LENGTH: 20
<212> TYPE: PRT
<213> ORGANISM: Artificial Sequence
<220> FEATURE:
<223> OTHER INFORMATION: 202 Partial E206C

<400> SEQUENCE: 202

Cys Gln Val Thr His Glu Gly Ser Thr Val Cys Lys Thr Val Ala Pro
1               5                   10                  15

Thr Glu Cys Ser
            20

<210> SEQ ID NO 203
<211> LENGTH: 19
<212> TYPE: PRT
<213> ORGANISM: Artificial Sequence
<220> FEATURE:
<223> OTHER INFORMATION: 203 Partial K207C

<400> SEQUENCE: 203
```

```
Gln Val Thr His Glu Gly Ser Thr Val Glu Cys Thr Val Ala Pro Thr
1               5                   10                  15

Glu Cys Ser

<210> SEQ ID NO 204
<211> LENGTH: 18
<212> TYPE: PRT
<213> ORGANISM: Artificial Sequence
<220> FEATURE:
<223> OTHER INFORMATION: 204 Partial T208C

<400> SEQUENCE: 204

Val Thr His Glu Gly Ser Thr Val Glu Lys Cys Val Ala Pro Thr Glu
1               5                   10                  15

Cys Ser

<210> SEQ ID NO 205
<211> LENGTH: 16
<212> TYPE: PRT
<213> ORGANISM: Artificial Sequence
<220> FEATURE:
<223> OTHER INFORMATION: 205 Partial A210C

<400> SEQUENCE: 205

His Glu Gly Ser Thr Val Glu Lys Thr Val Cys Pro Thr Glu Cys Ser
1               5                   10                  15
```

ENGINEERED ANTIBODY CONSTANT REGIONS FOR SITE-SPECIFIC CONJUGATION AND METHODS AND USES THEREFOR

This application is a national stage application under 35 U.S.C. § 371 of International Application PCT/IB2012/057491, filed on Dec. 19, 2012, which claims priority to U.S. Provisional Patent Application No. 61/580,169, filed on Dec. 23, 2011, both of which are incorporated by reference herein in their entirety.

REFERENCE TO SEQUENCE LISTING

This application is being filed electronically via EFS-Web and includes an electronically submitted sequence listing in .txt format. The .txt file contains a sequence listing entitled "PC071868A_Sequence_Listing.txt" created on Dec. 15, 2012, and having a size of 303 KB. The sequence listing contained in this .txt file is part of the specification and is incorporated herein by reference in its entirety.

FIELD OF THE INVENTION

The present invention relates to antibodies, and fragments thereof, wherein at least one constant region is engineered to introduce an amino acid for site-specific conjugation. The invention further relates to methods and uses of the engineered antibodies and fragments for, among other things, production of antibody-drug conjugate therapeutics.

BACKGROUND OF THE INVENTION

More than 1.2 million Americans develop cancer each year. Cancer is the second leading cause of death in the United States with one in two men and one in three women diagnosed with cancer at some time during their lifetime.

Although many chemotherapeutic agents have been developed, they often demonstrate unacceptable toxicity and or lack of specificity for cancer cells over non-cancer tissues. To avoid the non-specific cytotoxic effects of chemotherapeutic agents, targeted antibody therapy has revolutionized cancer treatment, with several monoclonal antibodies (mAbs) demonstrating clinical potential. Because antibodies against tumor-specific antigens often lack therapeutic activities, they have been conjugated to cytotoxic agents in order to combine the effectiveness of chemotherapy with the targeting of antibodies. In principle, selective delivery of cytotoxic agents to specific tumor issues by antibody binding should reduce the systemic toxicity of traditional small-molecule chemotherapeutics.

Antibodies have been conjugated to a variety of cytotoxic drugs, including small molecules that alkylate DNA (e.g., duocarmycin and calicheamicin), disrupt microtubules (e.g., maytansinoids and auristatins) or bind DNA (e.g., anthracyclins). One such antibody-drug conjugate (ADC) comprising a humanized anti-CD33 antibody conjugated to calicheamicin—Mylotarg™ (gemtuzumab ozogamicin, Wyeth)—was approved in 2000 for acute myeloid leukemia. More recently, the US Food and Drug Administration approved Adcetris™ (brentuximab vedotin; Seattle Genetics), an ADC comprising a chimeric antibody to CD30 conjugated to the auristatin monomethyl auristatin E (MMAE; also referred to as N-methylvaline-valine-dolaisoleuine-dolaproine-norephedrine) for treatment of Hodgkin's lymphoma and anaplastic large cell lymphoma.

Although ADCs hold promise for cancer therapy, cytotoxic drugs are generally conjugated to the antibodides via lysine side chains or by reducing interchain disulfide bonds present in the antibodies to provide activated cysteine sulfhydryl groups. This non-specific conjugation approach, however, has numerous drawbacks. Not only is it capable of affecting protein folding by disrupting cystine bonds, non-specific conjugation creates a heterogeneous mixture of antibodies having a diverse mix of antibody-to-drug ratios (ADR) and also having a complex mixture of antibodies conjugated at a variety of positions. So, even if it was somehow possible to purify sufficient antibodies having a desired antibody:drug ratio, the fraction would still comprise a complex mix of antibodies conjugated at various positions. Each species could potentially have distinct therapeutic properties, and batch-to-batch consistency would be difficult to control, all of which present significant hurdles to success of using ADC for cancer therapy.

To attempt to avoid the drawbacks of non-specific conjugation, a number of approaches have been proposed to provide site-specific conjugation of drug to antibody. However, previous studies attempting to provide reactive conjugation sites in antibodies have shown that biotin or other small non-toxic molecules conjugated to engineered cysteines at other positions of human IgG1 did not appear to affect antibody binding to certain antigens. See, e.g., WO 2011/005481 (biotin-maleimide conjugation); WO 2010/141902 (conjugating cysteine variants with maleimide dyes); and WO 2006/034488 (biotin-maleimide conjugation was performed and all examples describing conjugation to monomethyl auristatin E (MMAE; N-methylvaline-valine-dolaisoleucine-dolaproine-norephedrine) and monomethyl auristatin F (MMAF; also referred to as "N-methylvaline-valine-dolaisoleuine-dolaproine-phenylalanine") were prophetic only). However, conjugation of a small non-toxic molecule such as biotin as was typically used in those studies is unlikely to mimic the impact on the biological properties an antibody molecule comprising a linker and cytotoxic molecule. Because a successful ADC platform antibody must successfully bind to a target antigen in order to deliver a toxic payload to a target cell without significant binding to non-target cells, it is crucial that the engineered mutant antibodies of the invention retain specific binding ability whilst conjugated to a toxic payload. It is also crucial that the ADC be able to deliver a toxic payload to a target cell, be internalized thereby, and then release the payload once inside the appropriate compartment within the cell. Each of these necessary characteristics for a successful ADC was not demonstrated by prior studies.

Despite the successes of currently available anti-cancer treatments, complete responses to these treatments or prolonged survival are infrequently observed, and the patient population refractory to these treatments is still large. Thus, there is an unmet need for the development of new therapeutic modalities, particularly those capable of augmenting or potentiating the anti-tumor activity of anti-neoplastic agents while reducing the cytotoxic side effects of current chemotherapeutics, and the present invention meets this need.

SUMMARY OF THE INVENTION

Alternate embodiments of the invention are described below including novel engineered antibody constant domains, antibodies incorporating them, novel antibody-drug conjugates comprising engineered antibody fragments and methods and uses relating thereto.

The invention includes an engineered antibody constant domain polypeptide, or a portion thereof, wherein the engineered constant domain comprises at least one amino acid substitution to introduce a cysteine residue useful for conjugation, wherein the constant domain polypeptide is:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

In one aspect, the engineered Cγ polypeptide further comprises at least one mutation selected from the group consisting of a mutation at amino acid position 284, 287, A327, N384, L398, and V422, according to the EU index of Kabat.

In another aspect, the engineered Cγ polypeptide comprises one or more of the following pairs of amino acid substitutions: a) E380 and L443; b) L398 and L443; c) V422 and L443; d) E380 and L398; e) L398 and V422; f) E380 and V422; g) K392 and L443; h) F404 and L443; and i) K392 and F404.

In yet another aspect, the engineered Cγ polypeptide comprises an amino acid sequence selected from the group consisting of (a) the amino acid sequence of SEQ ID NO:99 and the amino acid sequence of SEQ ID NO:107; (b) the amino acid sequence of SEQ ID NO:103 and the amino acid sequence of SEQ ID NO:107; (c) the amino acid sequence of SEQ ID NO:105 and the amino acid sequence of SEQ ID NO:107; (d) the amino acid sequence of SEQ ID NO:99 and the amino acid sequence of SEQ ID NO:103; (e) the amino acid sequence of SEQ ID NO:103 and the amino acid sequence of SEQ ID NO:105; (f) the amino acid sequence of SEQ ID NO:99 and the amino acid sequence of SEQ ID NO:105; (g) the amino acid sequence of SEQ ID NO:102 and the amino acid sequence of SEQ ID NO:107; (h) the amino acid sequence of SEQ ID NO:104 and the amino acid sequence of SEQ ID NO:107; and (i) the amino acid sequence of SEQ ID NO:102 and the amino acid sequence of SEQ ID NO:104.

In another aspect, the engineered Cγ polypeptide is selected from an IgG1, IgG2, IgG3, or an IgG4 subclass.

In yet another aspect, the engineered antibody constant domain polypeptide, or a portion thereof, is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, wherein the conjugation is at the substituted cysteine.

In a further aspect, the cytotoxic agent is conjugated to the polypeptide via a linker.

In an even further aspect, the linker is selected from the group consisting of mc (maleimidocaproyl), val-cit (valine-citrulline), mc-val-cit (maleimidocaproyl-valine-citrulline), mc-val-cit-PABC (maleimidocaproyl-valine-citrulline-p-aminobenzylcarbamate), Mal-PEG2C2 (maleimido-$[CH_2CH_2O]_2CH_2CH_2C(=O)$), Mal-PEG3C2 (maleimido-$[CH_2CH_2O]_3CH_2CH_2C(=O)$), and Mal-PEG6C2 (maleimido-$[CH_2CH_2O]_6CH_2CH_2C(=O)$).

In another aspect, the cytotoxic agent is selected from the group consisting of an auristatin, a maytansinoid and a calicheamicin.

In one aspect, the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCitPABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261.

In another aspect, the invention includes an antibody, or antigen-binding portion thereof, comprising an engineered Cγ polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat.

In another aspect, the antibody, or antigen-binding portion thereof, further comprises an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat.

In yet another aspect, the antibody, or antigen-binding portion thereof, further comprises an engineered human kappa light chain constant domain (Cκ) polypeptide, or portion thereof, comprising at least one amino acid substitution selected from the group consisting of A111, K183, and N210, according to the numbering of Kabat.

In one aspect, the antibody, or antigen-binding portion thereof, comprises an engineered Cγ polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat, where the antibody further comprises a Cλ polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat, and further comprises a Cκ polypeptide, or portion thereof, comprising at least one amino acid substitution selected from the group consisting of A111, K183, and N210, according to the numbering of Kabat.

In one aspect, the invention includes an antibody, or antigen-binding portion thereof, comprising an engineered Cλ polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat.

In one aspect, the invention includes an antibody, or antigen-binding portion thereof, comprising an engineered Cκ polypeptide, or portion thereof, comprising at least one amino acid substitution selected from the group consisting of A111, K183, and N210, according to the numbering of Kabat.

The invention includes an antibody, or antigen-binding portion thereof, comprising an engineered constant domain, or portion thereof, wherein the engineered constant domain comprises at least one amino acid substitution to introduce a cysteine residue useful for conjugation, and wherein the constant domain polypeptide is at least one of:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

In one aspect, the antibody, or antigen-binding portion thereof, comprises an engineered heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat; and further comprising a light chain comprising an engineered constant domain selected from the group consisting of:

(a) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat; and (b) an engineered human kappa light chain constant domain (Cκ) polypeptide, or portion thereof, comprising at least one amino acid substitution selected from the group consisting of A111, K183, and N210, according to the numbering of Kabat.

In another aspect, the antibody, or antigen-binding portion thereof, further comprises at least one of:

(a) an engineered Cκ polypeptide, or portion thereof, comprising an amino acid substitution at A111C according to the numbering of Kabat, and an engineered Cγ polypeptide, or portion thereof, comprising an amino acid substitution at Q347C according to the Eu numbering of Kabat;

(b) an engineered Cκ polypeptide, or portion thereof, comprising an amino acid substitution at A111C according to the numbering of Kabat, and an engineered Cγ polypeptide, or portion thereof, comprising an amino acid substitution at E388C according to the Eu numbering of Kabat;

(c) an engineered Cκ polypeptide, or portion thereof, comprising an amino acid substitution at A111C according to the numbering of Kabat, and an engineered Cγ polypeptide, or portion thereof, comprising an amino acid substitution at K392C according to the Eu numbering of Kabat;

(d) an engineered Cκ polypeptide, or portion thereof, comprising an amino acid substitution at A111C according to the numbering of Kabat, and an engineered Cγ polypeptide, or portion thereof, comprising an amino acid substitution at L443C according to the Eu numbering of Kabat;

(e) an engineered Cκ polypeptide, or portion thereof, comprising an amino acid substitution at K183C according to the numbering of Kabat, and an engineered Cγ polypeptide, or portion thereof, comprising an amino acid substitution at L443C according to the Eu numbering of Kabat; or (f) an engineered Cκ polypeptide, or portion thereof, comprising an amino acid substitution at K207C according to the numbering of Kabat, and an engineered Cγ polypeptide, or portion thereof, comprising an amino acid substitution at L443C according to the Eu numbering of Kabat.

In one aspect, the invention includes an Fc fusion protein comprising an engineered Cγ polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat.

In one aspect, the invention includes a pharmaceutical composition comprising an antibody, or antigen-binding portion thereof, and a pharmaceutically acceptable carrier, wherein the antibody, or antigen-binding portion thereof, comprises an engineered constant domain comprising at least one amino acid substitution to introduce a cysteine residue useful for conjugation, and wherein the constant domain polypeptide is:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

In one aspect, the invention includes a pharmaceutical composition comprising an antibody, or antigen-binding portion thereof, and a pharmaceutically acceptable carrier, wherein the antibody, or antigen-binding portion thereof, comprises an engineered heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

and further comprises a light chain comprising an engineered constant domain selected from the group consisting of:

(a) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat; and (b) an engineered human kappa light chain constant domain (Cκ) polypeptide, or portion thereof, comprising at least one amino acid substitution selected from the group consisting of A111, K183, and N210, according to the numbering of Kabat.

The invention includes a method of treating cancer, autoimmune, inflammatory, or infectious diseases or disorders in a subject in need thereof. The method comprises administering to the subject a therapeutically effective amount of an antibody, or antigen-binding portion thereof, or an Fc fusion protein, wherein the antibody, or antigen-binding portion thereof, or the Fc fusion protein, comprises an engineered constant domain polypeptide, or a portion thereof, comprising at least one amino acid substitution to introduce a cysteine residue useful for conjugation, wherein the engineered constant domain polypeptide is:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, 1336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

In one aspect, the engineered constant domain polypeptide is a Cγ polypeptide further comprising at least one mutation selected from the group consisting of a mutation at amino acid position 284, 287, 327, 359, 361, 383, 384, 398, and 422, according to the EU index of Kabat.

In yet another aspect, the antibody, or antigen-binding portion thereof, comprises an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat, and further comprises at least one light chain constant domain selected from the group consisting of an engineered Cκ polypeptide, or portion thereof, comprising at least one amino acid substitution selected from the group consisting A111C, K183C, and N210C, according to the numbering of Kabat, and an engineered Cλ polypeptide, or portion thereof, comprising at least one amino acid substitution selected from the group consisting of K110C, L125C, K149C, V155C, G158C, T161C, Q185C, S188C, H189C, S191C, T197C, V205C, E206C, and K207C, T208C, and A210C, according to the numbering of Kabat.

In yet another aspect, the engineered constant domain polypeptide, or portion thereof, is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, and wherein the conjugation is at the substituted amino acid.

In yet a further aspect, the antibody comprises an engineered constant domain polypeptide, or portion thereof, and further comprises a linker and a cytotoxic agent, wherein the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCit-PABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261.

The invention includes a nucleic acid encoding an engineered constant domain polypeptide of or a portion thereof, wherein the engineered constant domain comprises at least one amino acid substitution to introduce a cysteine residue useful for conjugation, and wherein the constant domain polypeptide is:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

The invention includes a nucleic acid encoding an engineered Fc polypeptide wherein the engineered Fc polypeptide comprises an engineered Cγ polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

In one aspect, the invention includes a host cell comprising the nucleic acid encoding the engineered Fc polypeptide.

The invention includes a nucleic acid encoding an engineered Cκ polypeptide, or portion thereof, comprising at least one amino acid substitution selected from the group consisting of A111, K183, and N210, according to the numbering of Kabat;

In one aspect, the invention includes a host cell comprising the nucleic acid encoding the engineered Cκ polypeptide, or portion thereof, The invention includes a nucleic acid encoding the engineered Cλ polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

The invention includes a nucleic acid encoding an antibody, or antigen-binding portion thereof, wherein the antibody comprises at least one engineered antibody constant domain polypeptide, or a portion thereof, wherein the engineered constant domain polypeptide comprises at least one amino acid substitution to introduce a cysteine residue useful for conjugation, and wherein the engineered constant domain polypeptide is selected from the group consisting of:

(a) an engineered human IgG heavy chain constant domain (Cγ) polypeptide, or portion thereof, comprising at least one amino acid substitution selected from the group consisting of at K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444, according to the EU index of Kabat;

(b) an engineered human lambda light chain constant domain (Cλ) polypeptide, or portion thereof, comprising at least one amino acid substitution selected from the group consisting of K110, A111, L125, K149C, V155, G158, T161, Q185, S188, H189, S191, T197, V205, E206, K207, T208 and A210, according to the numbering of Kabat;

(c) an engineered human kappa light chain constant domain (Cκ) polypeptide, or portion thereof, comprising at least one amino acid substitution selected from the group consisting of A111, K183, and N210, according to the numbering of Kabat;

(d) an engineered Cγ polypeptide, or portion thereof, comprising at least one amino acid sequence selected from the group consisting of an amino acid sequence of SEQ ID NOs:97-100, 102, 104, 107-127, and 129-163;

(e) an engineered Cκ polypeptide, or portion thereof, comprising at least one amino acid sequence selected from the group consisting of an amino acid sequence of SEQ ID NOs:90, 92, 95, 164, 166, and 169; and (f) an engineered Cλ polypeptide, or portion thereof, comprising at least one amino acid sequence selected from the group consisting of an amino acid sequence of SEQ ID NOs:172-186.

In one aspect, the invention comprises a host cell comprising the nucleic acid.

The invention includes a method of producing an engineered antibody, or antigen-binding portion thereof, comprising incubating the host cell under suitable conditions for expressing the antibody, or antigen-binding portion thereof, and isolating the antibody or antigen-binding portion.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s) which are presently preferred. It should be understood, however, that the invention is not limited to the precise arrangements and instrumentalities shown.

In the drawings:

FIGS. 2A-2B, shows the analytical SEC traces for two engineered cysteine variants conjugated to vcMMAD. FIG. 2A shows the SEC tracing for 5T4-L398C-mcMMAD (maleimidocaproyl(monomethylauristatin D) (conjugated using method SEC-A). FIG. 2B shows the SEC tracing for 5T4-V422C-vcMMAD (maleimidocaproyl-valine-citrulline-para-aminobenzyloxycarbonyl (monomethylauristatin D)) (conjugated using method SEC-B).

FIG. 3, comprising FIG. 3A shows the MS tracing and loading calculation for 5T4-E380C-mcMMAD. FIG. 3B shows the MS tracing and loading calculation for 5T4-L398C-vcMMAD.

FIG. 6A shows reverse phase HPLC traces under reducing conditions for unmodified wild type anti-5T4 antibody. FIG. 6B shows reverse phase HPLC traces under reducing conditions for 5T4-E380C-mcMMAD. FIG. 6C shows reverse phase HPLC traces under reducing conditions for 5T4-L443C-mcMMAD.

FIG. 7, comprising panels A-D, shows the tracings obtained using hydrophobic interaction chromatography (HIC) for variant 5T4-L443C both uncojugated and conjugated with vcMMAD, and for variant 5T4-E380C conjugated with vcMMAD or mcMMAD. FIG. 7A shows the tracing for HIC results for unconjugated 5T4-L443C. FIG. 7B shows the tracing for HIC results for 5T4-L443C conjugated with vcMMAD, and shows that the loading values determined using MS (2.00) and HIC (2.07) are consistent. The peaks comprising antibody loaded with one (+1), two (+2) and four (+4) vcMMAD are indicated. FIG. 7C shows the tracing for HIC results for 5T4-E380C conjugated with vcMMAD, and shows that the loading values determined using MS (1.80) and HIC (1.74) are consistent. The peaks comprising antibody loaded with none (+0), one (+1), two (+2), three (+3), and four (+4) vcMMAD are indicated. FIG. 7D shows the tracing for HIC results for 5T4-E380C conjugated with mcMMAD, and shows that the loading values determined using MS (1.78) and HIC (1.81) are consistent. The peaks comprising antibody loaded with none (+0), one (+1), two (+2), and four (+4) vcMMAD are indicated.

FIG. 8, comprising panels A-H, shows the tracings produced by conjugations using Method "A" compared with Method "B" for various cysteine variant antibodies. FIGS. 8A, 8C, 8E, and 8G show results for conjugations using "Method A" for antibodies 5T4-E380C-mcMMAD (FIG. 8A); 5T4-L398C-mcMMAD (FIG. 8C); 5T4-L443C-mcMMAD (FIG. 8E); and 5T4-K392C-mcMMAD (FIG. 8G). FIGS. 8B, 8D, 8F, 8H, show results for conjugations using "Method B" for antibodies: 5T4-E380C-mcMMAD (FIG. 8B); 5T4-L398C-mcMMAD (FIG. 8D); 5T4-L443C-mcMMAD (FIG. 8F); and 5T4-K392C-mcMMAD (FIG. 8H).

FIGS. 9A, 9C, 9E, and 9G show results for conjugations using "Method A" for antibodies 5T4-E380C+L398C-mcMMAD (FIG. 9A); 5T4-E398C+L443C-mcMMAD (FIG. 9C); 5T4-E380C+L443C-mcMMAD (FIG. 9E); and 5T4-E380C+

V422C-mcMMAD (FIG. 9G). FIGS. 9B, 9D, 9F, and 9H, show results for conjugations using "Method B" for antibodies: 5T4-E380C+L398C-mcMMAD (FIG. 9B); 5T4-E398C+L443C-mcMMAD (FIG. 9D); 5T4-E380C+L443C-mcMMAD (FIG. 9F); and 5T4-E380C+V422C-mcMMAD (FIG. 9H).

FIG. 12, comprising panels A and B, is a graph showing the binding of cysteine mutant antibodies conjugated with mcMMAD compared to binding by parental antibody comprising wild type IgG1 Fc domain.

FIG. 14, comprising panels A and B, show that engineered cysteine variant antibodies do not exhibit altered Fc effector activity compared with wild type parental antibody.

FIG. 15, comprising panels A-UUU, shows the following sequences: amino acid sequence of wild type human IgG1 heavy chain constant domain comprising the Fc region, where the Fc region begins at amino acid residue 236 (glycine, G) (FIG. 15A), an exemplary nucleic acid sequence encoding human wild type IgG1 constant domain comprising the Fc region (FIG. 15B), amino acid sequence of human IgG2 constant domain (FIG. 15C), amino acid sequence of human wild type IgG3 constant domain (FIG. 15D), amino acid sequence of human wild type IgG4 constant domain (FIG. 15E), and the amino acid sequences of engineered Fc polypeptides comprising a substitution of a cysteine at the following positions (all according to the EU numbering system of Kabat): K246 (FIG. 15F), D249 (FIG. 15G), 254 (FIG. 15H), D265 (FIG. 15I), S267 (FIG. 15J), D270 (FIG. 15K), N276 (FIG. 15L), Y278 (FIG. 15M), E283 (FIG. 15N), 284 (FIG. 15O), 287 (FIG. 15P), R292 (FIG. 15Q), E293 (FIG. 15R), E294 (FIG. 15S), Y300 (FIG. 15T), V302 (FIG. 15U), V303 (FIG. 15V), L314 (FIG. 15W), N315 (FIG. 15X), E318 (FIG. 15Y), K320 (FIG. 15Z), 327 (FIG. 15AA), 1332 (FIG. 15BB), E333 (FIG. 15CC), K334 (FIG. 15DD), 1336 (FIG. 15EE), E345 (FIG. 15FF), Q347 (FIG. 15GG), S354 (FIG. 15HH), R355 (FIG. 15II), M358 (FIG. 15JJ), T359 KK), K360 (FIG. 15LL), N361 (FIG. 15MM), Q362 (FIG. 15NN), K370 (FIG. 15OO), Y373 (FIG. 15PP), D376 (FIG. 15QQ), A378 (FIG. 15RR), E380 (FIG. 15SS), E382 (FIG. 15TT), S383 (FIG. 15UU), 384 (FIG. 15VV), Q386 (FIG. 15WW), E388 (FIG. 15XX), N390 (FIG. 15YY), K392 (FIG. 15ZZ), T393 (FIG. 15AAA), 398 (FIG. 15-BBB), D401 (FIG. 15CCC), F404 (FIG. 15DDD), T411 (FIG. 15EEE), D413 (FIG. 15FFF), K414 (FIG. 15GGG), R416 (FIG. 15HHH), Q418 (FIG. 15III), Q419 (FIG. 15JJJ), N421 (FIG. 15KKK), 422 (FIG. 15LLL), M428 (FIG. 15MMM), A431 (FIG. 15NNN), L432 (FIG. 15OOO), T437 (FIG. 15PPP), Q438 (FIG. 15QQQ), K439 (FIG. 15RRR), 440 (FIG. 15SSS), L443 (FIG. 15TTT), and S444 (FIG. 15UUU).

FIG. 16, comprising panels A-I, shows the amino acid sequences of the following IgG1 engineered Fc regions comprising two mutations as follows: E380C-L443C (FIG. 16A); L398C-L443C (FIG. 16B); V422C-L443C (FIG. 16C); E380C-L398C D); L398C-V422C (FIG. 16E); E380C-V422C (FIG. 16F); L392C-L443C (FIG. 16G); L404C-L443C (FIG. 16H); L392C-L404C (FIG. 16I).

FIG. 17, comprising panels A-F, shows the amino acid sequences of the full length heavy and light chains of various antibodies. FIG. 17A shows the amino acid sequence of the heavy chain anti-5T4 antibody where the variable domain (VH) is capitalized and the three (3) CDRs are underlined and where the sequence of the human IgG1 constant region is shown in lower case letters. FIG. 17B shows the amino acid sequence of the light chain of the anti-5T4 antibody where the variable domain (VL) is capitalized and the three (3) CDRs are underlined and where the sequence of the human Kappa constant region is shown in lower case letters. FIG. 17C shows the amino acid sequence of the heavy chain anti-Her2 antibody where the variable domain (VH) is capitalized and the three (3) CDRs are underlined and where the sequence of the human IgG1 constant region is shown in lower case letters. FIG. 17D shows the amino acid sequence of the light chain of the anti-Her2 antibody where the variable domain (VL) is capitalized and the three (3) CDRs are underlined and where the sequence of the human Kappa constant region is shown in lower case letters. FIG. 17E shows the amino acid sequence of the heavy chain anti-VEGFR2 (vascular endothelial growth factor receptor 2) antibody where the variable domain (VH) is capitalized and the three (3) CDRs are underlined and where the sequence of the human IgG1 constant region is shown in lower case letters. FIG. 17F shows the amino acid sequence of the light chain of the anti-VEGFR2 antibody where the variable domain (VL) is capitalized and the three (3) CDRs are underlined and where the sequence of the human Kappa constant region is shown in lower case letters.

FIG. 18, comprising panels A-D, shows the amino acid sequences of the wild type human kappa constant region (FIG. 18A) and the amino acid sequence of the engineered Cκ regions comprising the following mutations: A111C (FIG. 18B); K183C (FIG. 18C); and N210C (FIG. 18D).

FIG. 19, comprising panels A and B, shows the amino acid sequence alignments of human IgG1, IgG2, IgG3 and IgG4 showing the equivalent positions among the four IgG subclasses. FIG. 19A shows the amino acid sequence alignment of the Fc domains of human wild type IgG1 (hIgG1), IgG2 (hIgG2), IgG3 (hIgG3) and IgG4 (hIgG4). FIG. 19B shows the amino acid sequence alignment of the constant domain (comprising CH1, hinge, CH2 and CH3 regions) of human wild type IgG1 (human_gamma1), IgG2 (human_gamma2), IgG3 (human_gamma3) and IgG4 (human_gamma4).

FIG. 20, comprising panels A and B, shows the nucleic acid sequence encoding wild type human lambda constant region (FIG. 20A), the amino acid sequence of wild type human lambda constant region (FIG. 20B) and the amino acid sequences of the engineered Cλ regions comprising the following mutations: K110C (FIG. 20C); A111C (FIG. 20D); L125C (FIG. 20E); K149C (FIG. 20F); V155C (FIG. 20G); G158C (FIG. 20H); T161C (FIG. 20I); Q185C (FIG. 20J); S188C (FIG. 20K); H189C (FIG. 20L); S191C (FIG. 20M); T197C (FIG. 20N); V205C (FIG. 20O); E206C (FIG. 20P); K207C (FIG. 20Q); T208C (FIG. 20R); and A210C (FIG. 20S).

FIG. 21, comprising panels A and B, show graphs demonstrating the PK parameters of various engineered cysteine antibodies conjugated vi a MalPeg6C2 linker to a proprietary auristatin payload (Aur).

FIG. 22, comprising panels A-C, demonstrates the tumor reducing efficacy of anti-Her2 site-specific conjugated ADCs, where the site specific conjugation site is L443C, and using different linker and payload combinations.

DETAILED DESCRIPTION OF THE INVENTION

Figure 1:
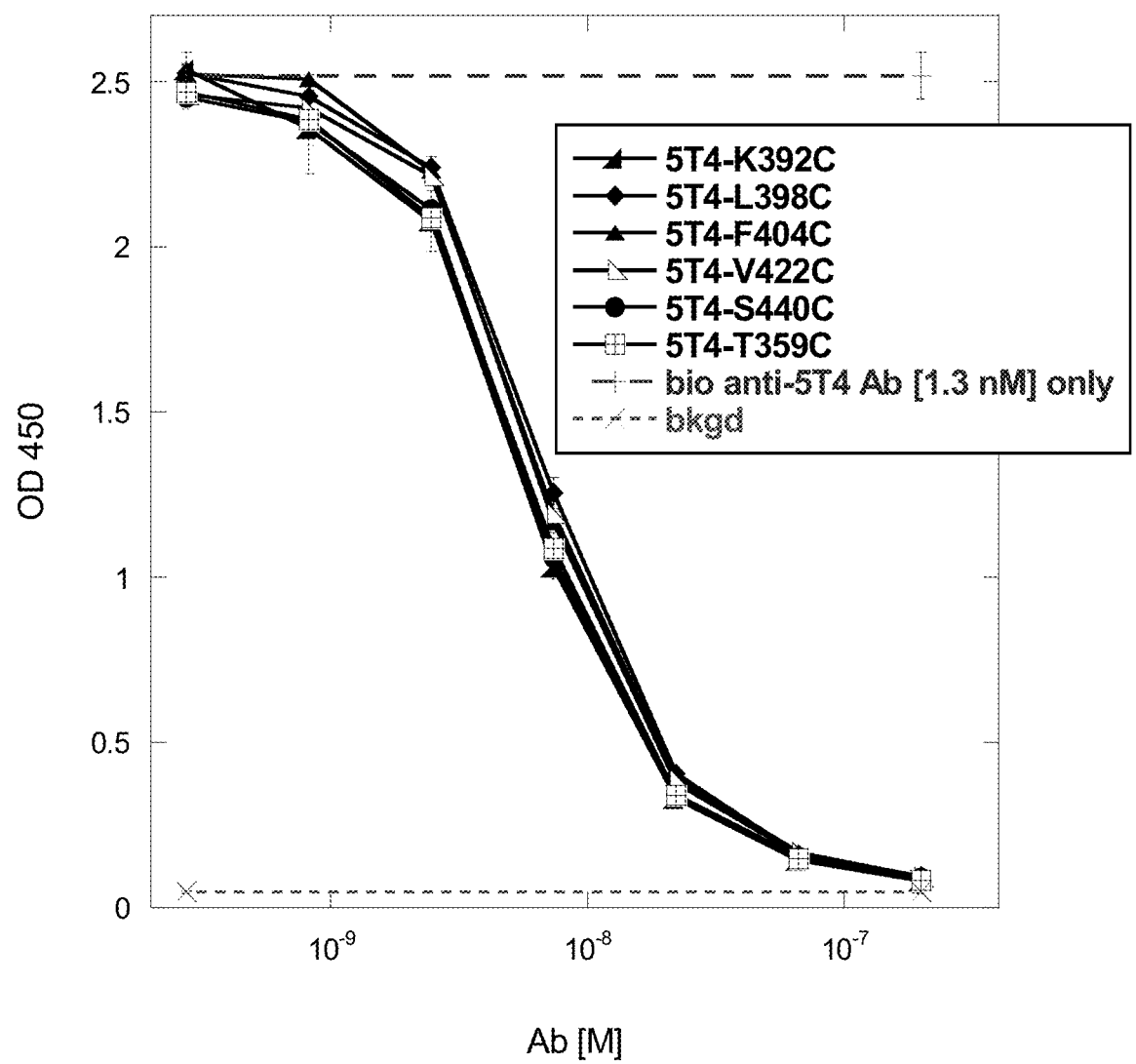
FIG. 1 shows the results of a competition binding ELISA assay demonstrating that binding to a target antigen (i.e., 5T4) is not affected in antibodies comprising an engineered Fc domain comprising a cysteine substitution. Competition binding to human truncated recombinant 5T4 protein (5T4-tm⁻_myc_his) lacking the transmembrane and intracellular domains of 5T4 (and further comprising Myc and histidine tags) was equivalent among antibodies comprising a single cysteine mutation in the Fc domain compared with the parental anti-5T4 antibody comprising a wild type IgG1 Fc domain conjugated to biotin (bio anti-5T4 Ab [1.3 nM]). The substitutions are indicated as follows: 5T4-T359C; 5T4-K392C; 5T4-L398C; 5T4-F404C; 5T4-V422C; 5T4-S440C.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, *Molecular Cloning: A Laboratory Manual*, $3^{rd}$. ed., Cold Spring Harbor Laboratory Press, Cold Spring Harbor, N.Y. (2001), Ausubel et al., *Current Protocols in Molecular Biology*, John Wiley & Sons, N.Y. (2002), Harlow and Lane *Using Antibodies: A Laboratory Manual*, Cold Spring Harbor Laboratory Press, Cold Spring Harbor, N.Y. (1998), and Coligan et al., *Short Protocols in Protein Science*, John Wiley & Sons, N.Y. (2003), which are incorporated herein by reference. Enzymatic reactions and purification techniques are performed according to manufacturers specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Throughout this specification and claims, the word "comprise," or variations such as "comprises" or "comprising," will be understood to imply the inclusion of a stated integer or group of integers but not the exclusion of any other integer or group of integers.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Reference to "about" a value or parameter herein includes (and describes) embodiments that are directed to that value or parameter per se. For example, description referring to "about X" includes a description of "X." Numeric values are inclusive of numbers defining the range.

Additionally, any reference referred to as being "incorporated herein" is to be understood as being incorporated in its entirety.

Where aspects or embodiments of the invention are described in terms of a Markush group or other grouping of alternatives, the present invention encompasses not only the entire group listed as a whole, but each member of the group individually and all possible subgroups of the main group, and also the main group absent one or more of the group members. The present invention also envisages the explicit exclusion of one or more of any of the group members in the claimed invention.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), herein incorporated by reference. A "moderately conservative" replacement is any change having a nonnegative value in the PAM250 log-likelihood matrix.

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs comprising substitutions, deletions, and/or insertions can include various muteins of a sequence other than the specified peptide sequence. For example, single or multiple amino acid substitutions (preferably conservative amino acid substitutions) may be made in the specified sequence (preferably in the portion of the polypeptide outside the domain(s) forming intermolecular contacts, e.g., outside of the CDRs). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., Nature 354:105 (1991), which are each incorporated herein by reference.

Sequence similarity for polypeptides is typically measured using sequence analysis software. Protein analysis software matches similar sequences using measures of similarity assigned to various substitutions, deletions and other modifications, including conservative amino acid substitutions. For instance, Genetics Computer Group (GCG available from Genetics Computer Group, Inc.), also referred to as the Wisconsin Package, is an integrated software package of over 130 programs for accessing, analyzing and manipulating nucleotide and protein sequences. GCG contains programs such as "Gap" and "Bestfit" which can be used with default parameters to determine sequence similarity, homology and/or sequence identity between closely related polypeptides, such as homologous polypeptides from different species of organisms or between a wild type protein and a mutein thereof. See, e.g., GCG version 6.1, version 7.0, version 9.1, and version 10.0.

Polypeptide sequences also can be compared using FASTA, a program in GCG, using default or recommended parameters. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997); herein incorporated by reference.

Conventional notation is used herein to portray polypeptide sequences: the left-hand end of a polypeptide sequence is the amino-terminus; the right-hand end of a polypeptide sequence is the carboxyl-terminus.

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extrachromasomal) or may be integrated into a host cell chromosome. In one embodiment, the vector may comprise an expression vector capable of producing a protein derived from at least part of a nucleic acid sequence inserted into the vector.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M $NaHPO_4$, 7% sodium dodecyl sulfate (SDS), at 65° C., and washing in 0.25 M $NaHPO_4$, 3.5% SDS followed by washing 0.1×SSC/0.1% SDS at a temperature ranging from room temperature to 68° C. depending on the length of the probe (see e.g. Ausubel, F. M. et al., Short Protocols in Molecular Biology, 4$^{th}$ Ed., Chapter 2, John Wiley & Sons, N.Y). For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [$\gamma$-$^{32}$P]ATP, or incorporation of radiolabeled nucleotides such as [$\alpha$-$^{32}$P]dCTP by random primer labeling. Alternatively, probes may be labeled by incorporation of biotinylated or fluorescein labeled nucleotides, and the probe detected using Streptavidin or anti-fluorescein antibodies.

The term "fusion protein" refers to a protein or polypeptide that has an amino acid sequence derived from two or more proteins. The fusion protein may also include linking regions of amino acids between amino acid portions derived from separate proteins.

The term "host cell" as used herein refers to a cell that is grown in culture according to the present invention to produce a protein or polypeptide of interest. In certain embodiments, the host cell is a mammalian cell.

By the term "hybridoma" as the term is used herein, is meant to encompass a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., 1983, Nature 537:3053).

The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. For example, a polypeptide may be glycosylated. A polypeptide to be expressed according to the present invention can be a therapeutic polypeptide. A therapeutic polypeptide is a polypeptide that has a biological effect on a region in the body on which it acts or on a region of the body on which it remotely acts via intermediates. Examples of therapeutic polypeptides are discussed in more detail below.

"Protein," as the term is used herein, refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit. A protein to be expressed according to the present invention can be a protein therapeutic. A protein therapeutic is a protein that has a biological effect on a region in the body on which it acts or on a region of the body on which it remotely acts via intermediates. Examples of protein therapeutics are discussed in more detail below.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least about 4-5, 10, 15, 20, 25, 30, 35, 40, 45, 50 or more amino acids of the full-length polypeptide.

"Recombinantly expressed polypeptide" and "recombinant polypeptide" as used herein refer to a polypeptide expressed from a host cell that has been manipulated to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

An intact "antibody" comprises at least two heavy (H) chains and two light (L) chains inter-connected by disulfide bonds. See generally, Fundamental Immunology, Ch. 7 (Paul, W., ed., 2nd ed. Raven Press, N.Y. (1989)) (incorporated by reference in its entirety for all purposes). Each heavy chain is comprised of a heavy chain variable region (HCVR or $V_H$) and a heavy chain constant region ($C_H$). The heavy chain constant region is comprised of three domains, CH1, CH2 and CH3. Each light chain is comprised of a light chain variable region (LCVR or $V_L$) and a light chain constant region. The light chain constant region is comprised of one domain, $C_L$. In humans, there are two types of light chains, kappa (κ) and lambda (λ), such that the constant regions of these two types of light chains are designated as $C_\kappa$ and $C_\lambda$, respectively. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, J. Mol. Biol. 196:901-917 (1987); Chothia et al., Nature 342:878-883 (1989).

The constant regions of the antibodies may mediate the binding of the immunoglobulin to host tissues or factors, including various cells of the immune system (e.g., effector cells) and the first component (C1q) of the classical complement system. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)).

The term "antigen-binding portion" of an antibody (or simply "antibody portion"), as used herein, refers to one or more fragments of an antibody that retain the ability to specifically bind to an antigen (e.g., a tumor-associated antigen, TAA). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), disulfide-linked Fvs (dsFv), and anti-idiotypic (anti-Id) antibodies and intrabodies. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123). Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

The terms "IgG Fc region", "Fc region", "Fc domain" and "Fc", as interchangeably used herein refer to the portion of an IgG molecule that correlates to a crystallizable fragment obtained by papain digestion of an IgG molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain. For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., 1969, Proc. Natl. Acad. Sci. USA 63(1):78-85 as described in Kabat et al., 1991. Typically, the Fc domain comprises from about amino acid residue 236 to about 447 of the human IgG1 constant domain. Exemplary human wild type IgG1, IgG2, IgG3 and IgG4 Fc domain amino acid sequences are shown in FIG. 19B. Fc polypeptide may refer to this region in isolation, or this region in the context of an antibody, or an antigen-binding portion thereof, or Fc fusion protein. Particularly preferred are engineered Fc polypeptides, which are non-naturally occurring variants of an Fc comprising at least one amino acid substitution introducing a site-specific conjugation site.

The heavy chain constant domain comprises the Fc region and further comprises the CH1 domain and hinge as well as the CH2 and CH3 (and, optionally, CH4 of IgA and IgE) domains of the IgG heavy chain. An exemplary human wild type IgG1 constant domain amino acid sequence is set forth in SEQ ID NO:1 and is shown in FIG. 15A.

By "engineered Fc polypeptide", "engineered Fc region" and "engineered Fc" as the terms are interchangeably used herein, is meant an Fc polypeptide, or portion thereof, comprising at least one mutation, e.g., an amino acid substitution, introducing a site for conjugation. Preferably, the mutation introduces a cysteine in place of the naturally-occurring amino acid residue at that position, where the mutation creates a reactive site (e.g., a reactive sulfhydryl group) for conjugation of a moiety to the Fc.

An "engineered Fc variant" refers to an engineered Fc polypeptide further comprising at least one additional modification, such as, but not limited to, an amino acid mutation, a post-translational modification (e.g., altered glycosylation), among others, in addition to the mutation creating a conjugation site.

"Hinge region" as used herein, is generally defined as stretching from Glu216 to Pro230 of human IgG1 (Burton, 1985, Molec. Immunol. 22: 161-206), and refers to the portion of an IgG molecule comprising the C-terminal portion of the CH1 domain and the N-terminal portion of the CH2 domain. Exemplary hinge regions for human IgG1, IgG2, IgG2 and IgG4 and mouse IgG1 and IgG2A are provided in U.S. Pat. No. 6,165,476, at the Table shown at column 4, line 54 to column 5, line 15, and also illustrated, for example, in Janeway et al., 1999, Immunology: The Immune System in Health and Disease, 4th ed. (Elsevier Science Ltd.); Bloom et al., 1997, Protein Science 6:407-415; Humphreys et al., 1997, J. Immunol. Methods 209: 193-202. Hinge regions of other IgG isotypes may be aligned with the IgG 1 sequence by placing the first and last cysteine residues forming inter-heavy chain S—S bonds in the same positions. An exemplary alignment of the constant domains of human IgG1, IgG2, IgG3, and IgG4 showing the alignment of the hinge region of each subclass is shown in FIG. 19B. The "lower hinge region" of an Fc region is normally defined as the stretch of residues immediately C-terminal to the hinge region, i.e. residues 233 to 239 of the Fc region The term "IgG hinge-Fc region" or "hinge-Fc fragment" as used herein refers to a hinge region (approximately residues 216-230) and an Fc region (residues 231-447) C-terminal thereto.

An "engineered Kappa light chain" as the term is used herein, refers to a Kappa light chain, or a portion thereof, comprising an engineered Kappa light chain constant region (Cκ) comprising at least one amino acid substitution to introduce a reactive group useful for conjugation at that site.

"Engineered kappa constant region", "engineered Cκ polypeptide", "engineered Cκ," and "engineered Cκ region" as used interchangeably herein, mean the constant region of a kappa light chain, or a portion thereof, comprising at least one amino acid mutation to introduce an amino acid comprising a reactive group useful for conjugation compared with a wild type kappa constant region that is not so modified. An exemplary human wild type kappa constant region amino acid sequence is as shown in FIG. 18A and set forth in SEQ ID NO:89.

"Engineered lambda constant region", "engineered Cλ polypeptide", "engineered Cλ," and "engineered Cλ region" as used interchangeably herein, mean the constant region of a lambda light chain, or a portion thereof, comprising at least one amino acid mutation to introduce an amino acid comprising a reactive group useful for conjugation compared with a wild type kappa constant region that is not so modified.

An "engineered antibody," as the term is used herein, means an antibody, or antigen binding portion thereof, comprising at least one engineered constant region, e.g., an engineered Fc region, an engineered Cκ region and/or an engineered Cλ region.

By the term "engineered antibody antigen-binding portion," or "engineered antibody portion," as used herein, is meant an antigen-binding fragment of an antibody, e.g., a Fab, a F(ab')$_2$, and the like, comprising at least one engineered constant region.

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. Human Antibodies and Hybridomas 6:93-101 (1995)) and use of a cysteine residue, a marker peptide and a C-terminal polyhistidine tag to make bivalent and biotinylated scFv molecules (Kipriyanov et al. Mol. Immunol. 31:1047-1058 (1994)). Other examples include where one or more CDRs from an antibody are incorporated into a molecule either covalently or noncovalently to make it an immunoadhesin that specifically binds to an antigen of interest, such as a tumor antigen. In such embodiments, the CDR(s) may be incorporated as part of a larger polypeptide chain, may be covalently linked to another polypeptide chain, or may be incorporated non-covalently. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Where an "antibody" is referred to herein with respect to the present invention, it should be understood that an antigen-binding portion thereof may also be used. An antigen-binding portion competes with the intact antibody for specific binding. See generally, Fundamental Immunology, Ch. 7 (Paul, W., ed., 2nd ed., Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies, single chain antibodies such as those derived from camelids or shark immunoglobulin novel antigen receptors (IgNARs), and polypeptides that contain at least a portion of an antibody that is sufficient to confer specific antigen binding to the polypeptide. In embodiments having one or more binding sites, the binding sites may be identical to one another or may be different.

The terms "monoclonal antibody" or "monoclonal antibody composition" as used herein refer to a preparation of antibody molecules of single molecular composition. A monoclonal antibody composition displays a single binding specificity and affinity for a particular epitope The terms "human antibody", or "fully human antibody", as used herein, are intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure or antigen binding portions thereof may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "human monoclonal antibody" or "fully human monoclonal antibody" refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene, where the B cell is fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

The phrases "an antibody recognizing an antigen" and "an antibody specific for an antigen" are used interchangeably herein with the term "an antibody which binds specifically to an antigen."

The term "antibody dependent cellular cytotoxicity" or "ADCC" refers to a cell-mediated reaction in which non-specific cytotoxic cells (e.g. NK cells, neutrophils, macrophages, etc.) recognize antibody bound on a target cell and subsequently cause lysis of the target cell. Such cytotoxic cells that mediate ADCC generally express Fc receptors (FcR). The primary cells for mediating ADCC (NK cells) express FcγRIII, whereas monocytes express FcγRI, FcγRII, FcγRIII, and/or FcγRIV. FcR expression on hematopoietic cells is summarized in Ravetch and Kinet, *Annu. Rev. Immunol.* 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., 1998, Proc. Natl. Acad. Sci. USA 95:652-656.

The terms "Fc receptor" or "FcR" are used to describe a receptor that binds to the Fc region of an antibody where the Fc region comprises a hinge region and the $C_H2$ and $C_H3$ domains of the heavy chain. For example, the FcR can be a native sequence human FcR. The FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, Daeron, 1997, Annu. Rev. Immunol. 15:203-234). FcRs are reviewed in Ravetch and Kinet, 1991, Annu. Rev. Immunol. 9:457-92; Capel et al., 1994, Immunomethods 4:25-34; de Haas et al., 1995, J. Lab. Clin. Med. 126:330-341; and Nimmerjahn et al., 2005, Immunity 23:2-4. Other FcRs, including those to be identified in the future, are encompassed by the term "FcR" herein. The term also includes the neonatal receptor, FcRn, which is responsible for the transfer of maternal IgGs to the fetus (Guyer et al., 1976, Immunol. 117:587) and Kim et al., 1994, J. Immunol. 24:249). The primary FcR binding site on immunoglobulin Fc fragments resides in the hinge region between the $C_H1$ and $C_H2$. This hinge region interacts with the FcR1-3 on various leukocytes and trigger these cells to attack the target. (Wines et al., 2000, J. Immunol. 164:5313-5318). The hinge region encompasses, but is not limited to, the sequences described in U.S. Pat. No. 6,165,476.

The term "capable of inducing antibody dependent cellular cytotoxicity (ADCC)" refers to the ability of an agent, such as an antibody, to demonstrate ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Such modifications are described, for example, in U.S. Patent Publication No. 2007/0092521.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide inhibitor which recognizes and binds a cognate ligand (e.g., an anti-IgE antibody that binds with its cognate antigen, IgE) in a sample, but does not substantially recognize or bind other molecules in the sample. Thus, under designated assay conditions, the specified binding moiety (e.g., an antibody or an antigen-binding portion thereof) binds preferentially to a particular target molecule, e.g., IgE, and does not bind in a significant amount to other components present in a test sample. A variety of assay formats may be used to select an antibody that specifically binds a molecule of interest. For example, solid-phase ELISA immunoassay, immunoprecipitation, BIAcore, FACS, and Western blot analysis are among many assays that may be used to identify an antibody that specifically reacts with IgE. Typically, a specific or selective reaction will be at least twice background signal or noise and more typically more than 10 times background, even more specifically, an antibody is said to "specifically bind" an antigen when the equilibrium dissociation constant ($K_D$) is ≤1 μM, preferably ≤100 nM and most preferably ≤10 nM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation, e.g. by the SPR method (Biacore). The rate constants corresponding to the association and the dissociation of a monovalent complex are referred to as the association rate constants ka (or $k_{on}$) and dissociation rate constant $k_d$ (or $k_{off}$), respectively. $K_D$ is related to ka and $k_d$ through the equation $K_D = k_d/k_a$.

Following the above definition binding affinities associated with different molecular interactions, e.g. comparison of the binding affinity of different antibodies for a given antigen, may be compared by comparison of the $K_D$ values for the individual antibody/antigen complexes.

Similarly, the specificity of an interaction may be assessed by determination and comparison of the $K_D$ value for the interaction of interest, e.g. a specific interaction between an antibody and an antigen, with the $K_D$ value of an interaction not of interest.

The term "$k_{on}$", as used herein, is intended to refer to the on-rate, or association rate of a particular antibody-antigen or receptor-ligand interaction, whereas the term "$k_{off}$" as used herein, is intended to refer to the off-rate, or dissociation rate of a particular antibody-antigen/receptor-ligand interaction. The term "$K_D$", as used herein, is intended to refer to the dissociation constant, which is obtained from the ratio of $k_{off}$ to $k_{on}$ (i.e., $k_{off}/k_{on}$) and is expressed as a molar concentration (M). $K_D$ values for antibodies or other binding partners can be determined using methods well established in the art. One method for determining the $K_D$ is by using surface plasmon resonance, typically using a biosensor system such as a Biacore® system.

The term "chimeric antibody" as used herein means an antibody that comprises regions from two or more different antibodies. In certain embodiments a "chimeric antibody" comprises variable region sequences derived from one species and constant region sequences derived from another species, such as an antibody in which the variable region sequences are derived from a mouse antibody and the constant region sequences are derived from a human antibody. In one embodiment, one or more of the CDRs are derived from a mouse anti-human tumor antigen antibody. In another embodiment, all of the CDRs are derived from a mouse anti-human tumor antigen antibody. In another embodiment, the CDRs from more than one mouse anti-human tumor antigen antibodies are combined in a chimeric human antibody. For instance, a chimeric antibody may comprise a CDR1 from the light chain of a first mouse anti-human tumor antigen antibody, a CDR2 from the light chain of a second mouse anti-human tumor antigen antibody and a CDR3 and CDR3 from the light chain of a third mouse anti-human tumor antigen antibody, and the CDRs from the heavy chain may be derived from one or more other anti-human tumor antigen antibodies. Further, the framework regions may be derived from one of the same mouse anti-human tumor antigen antibodies or from one or more different mice.

Moreover, as discussed previously herein, chimeric antibody includes an antibody comprising a portion derived from the germline sequences of more than one species.

"Glycoform" refers to a complex oligosaccharide structure comprising linkages of various carbohydrate units. Such structures are described in, e.g., *Essentials of Glycobiology* Varki et al., eds., Cold Spring Harbor Laboratory Press, Cold Spring Harbor, N.Y. (1999), which also provides a review of standard glycobiology nomenclature. Such glycoforms include, but are not limited to, G2, G1, G0, G-1, and G-2 (see, e.g., International Patent Publication No. WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

It is likely that antibodies expressed by different cell lines or in transgenic animals will have different glycoforms and/or glycosylation patterns compared with each other. However, all antibodies encoded by the nucleic acid molecules provided herein, or comprising the amino acid sequences provided herein are part of the instant invention, regardless of the glycosylation of the antibodies.

"Antibody-drug conjugate" as used herein, refer to an antibody, or a portion of an antibody, covalently linked to a cytotoxic or cytostatic drug/agent where the drug/agent is also referred to herein as a "payload." The antibody and the drug may be directly linked or they may be linked via a moiety referred to as a "linker."

By the term "effective amount", or "therapeutically effective amount," as used herein, is meant an amount that when administered to a mammal, preferably a human, mediates a detectable therapeutic response compared to the response detected in the absence of the compound. A therapeutic response, such as, but not limited to, inhibition of and/or decreased tumor growth, tumor size, metastasis, and the like, can be readily assessed by a plethora of art-recognized methods, including, e.g., such methods as disclosed herein.

The skilled artisan would understand that the effective amount of the compound or composition administered herein varies and can be readily determined based on a number of factors such as the disease or condition being treated, the stage of the disease, the age and health and physical condition of the mammal being treated, the severity of the disease, the particular compound being administered, the level of expression/availability of the target of the antibody-drug-conjugate, and the like.

By the term "compete", as used herein with regard to an antibody, is meant that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). For instance, cross-competing antibodies can bind to the epitope, or portion of the epitope, to which the antibodies used in the invention bind. Use of both competing and cross-competing antibodies is encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

"Instructional material," as that term is used herein, includes a publication, a recording, a diagram, or any other medium of expression which can be used to communicate the usefulness of the compound, combination, and/or composition of the invention in the kit for affecting, alleviating or treating the various diseases or disorders recited herein. Optionally, or alternately, the instructional material can describe one or more methods of alleviating the diseases or disorders in a cell, a tissue, or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

Except when noted, the terms "patient" or "subject" are used interchangeably and refer to mammals such as human patients and non-human primates, as well as veterinary subjects such as rabbits, rats, and mice, and other animals. Preferably, patient refers to a human.

Conventional notation is used herein to portray polypeptide sequences: the left-hand end of a polypeptide sequence is the amino-terminus; the right-hand end of a polypeptide sequence is the carboxyl-terminus.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide receptor which recognizes and binds a cognate ligand or binding partner (e.g., an anti-human tumor antigen antibody that binds a tumor antigen) in a sample, but does not substantially recognize or bind other molecules in the sample. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample. A variety of assay formats may be used to select an antibody or peptide that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) is ≤1 µM, preferably ≤100 nM and most preferably ≤10 nM.

By "ADCC" or "antibody dependent cell-mediated cytotoxicity" as used herein is meant the cell-mediated reaction wherein nonspecific cytotoxic cells that express Fc gamma Rs recognize bound antibody on a target cell and subsequently cause lysis of the target cell. ADCC activity of a molecule of interest can be assessed using an in vitro ADCC assay, such as that described in U.S. Pat. No. 5,500,362, or 5,821,337. Useful effector cells for such assays include peripheral blood mononuclear cells (PBMCs) and natural killer (NK) cells. Alternatively, or additionally, ADCC activity of the molecule of interest may be assessed in vivo, e.g., in an animal model such as that disclosed in Clynes et al., 1998, Proc. Natl. Acad. Sci. USA 95:652-656.

By "ADCP" or "antibody dependent cell-mediated phagocytosis" as used herein is meant the cell-mediated reaction wherein nonspecific cytotoxic cells that express Fc gamma Rs recognize bound antibody on a target cell and subsequently cause phagocytosis of the target cell.

"CDC" or "complement dependent cytotoxicity" refer to the lysing of a target cell in the presence of complement. The complement activation pathway is initiated by the binding of the first component of the complement system (C1q) to a molecule (e.g., an antibody) complexed with a cognate antigen. To assess complement activation, a CDC assay, such as, but not limited to, an assay described in Gazzano-Santoro et al., 1996, J. Immnol. Methods 202:163, may be performed.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22: 161-206 (1985).

The "CH3 domain" comprises the stretch of residues C-terminal to a CH2 domain in an Fc region (i.e. from about amino acid residue 341 to about amino acid residue 447 of an IgG).

The term "effector function," as the term is used herein, refers to the biological activities attributable to or mediated by the Fc region of an antibody. Exemplary "effector functions" include, but are not limited to, C1q binding; complement dependent cytotoxicity (CDC); Fc receptor binding; antibody-dependent cell-mediated cytotoxicity (ADCC); antibody dependent cell-mediated phagocytosis (ADCP); down regulation of cell surface receptors (e.g., B cell receptor; BCR), etc. See, e.g., U.S. Pat. No. 6,737,056. Such effector functions generally require the Fc region to be combined with a binding domain (e.g., an antibody variable domain) and can be assessed using various assays as herein disclosed, for example, as well as those assays known in the art, for evaluating such antibody effector functions.

By "Fc fusion" or "Fc fusion protein" as used herein is meant a protein wherein one or more polypeptides is operably linked to an Fc region or a derivative thereof. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol. 14:52-60; Ashkenazi et al., 1997, Curr. Opin. Immunol. 9:195-200). An Fc fusion combines the Fc region of an immunoglobulin with a fusion partner, which in general can be any protein or small molecule. The role of the non-Fc part of an Fc fusion, i.e. the fusion partner, is to mediate target binding, and thus it is functionally analogous to the variable regions of an antibody. Virtually any protein or small molecule may be linked to an Fc polypeptide to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic folding topology. The known Ig domains in the IgG class of antibodies are the variable heavy chain domain ($V_H$), the heavy chain constant domains—Cγ1, Cγ2, Cγ3—together comprising the Cγ domain which includes the hinge region between Cγ1 and Cγ2, the variable domain of the light chain ($V_L$), and the constant domain of the light chain ($C_L$), which in humans comprises either the kappa (Cκ) or lambda (Cλ) light chain constant domain Typically, an "Fc polypeptide," as the term is used herein, comprises a Cγ2 and a Cγ3 domain and can include at least a portion of the hinge domain, but does not usually include the entire Cγ1 domain.

By "parent polypeptide" or "precursor polypeptide" (including Fc parent or precursors) as used herein is meant a polypeptide that is subsequently modified to generate a variant or mutant. Said parent polypeptide may be a naturally occurring polypeptide, or a variant or engineered version of a naturally occurring polypeptide. Parent polypeptide may refer to the polypeptide itself, compositions that comprise the parent polypeptide, to the amino acid sequence of the polypeptide, or to the nucleic acid sequence that encodes it. Accordingly, by "parent Fc polypeptide" as used herein is meant an unmodified Fc polypeptide that is modified to generate a variant, and by "parent antibody" as used herein is meant an unmodified antibody that is modified to generate a variant antibody.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

As outlined above, certain positions of the Fc molecule can be altered. By "position" as used herein is meant a location in the sequence of a protein. Positions may be numbered sequentially, or according to an established format, for example the EU index as in Kabat. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the V kappa, V.lamda., and/or VH genes that make up the kappa, lambda, and heavy chain immunoglobulin genetic loci respectively.

By "variant polypeptide" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it. Preferably, the variant polypeptide has at least one amino acid modification compared to the parent polypeptide, e.g., from about one to about ten amino acid modifications, and preferably from about one to about five amino acid modifications compared to the parent. The variant polypeptide sequence herein will preferably possess at least about 80 percent homology with a parent polypeptide sequence, and most preferably at least about 90 percent homology, more preferably at least about 95 percent homology, even more preferably, at least about 97% homology, more preferably, at least about 98% homology, and yet more preferably, at least about 99% homology with a parent polypeptide sequence. Accordingly, by "Fc variant" as used herein is meant an Fc sequence that differs from that of a parent Fc sequence by virtue of at least one amino acid modification. An Fc variant may only encompass an Fc region, or may exist in the context of an antibody, Fc fusion, or other polypeptide that is substantially encoded by Fc. Fc variant may refer to the Fc polypeptide itself, compositions comprising the Fc variant polypeptide, the amino acid sequence of the Fc polypeptide, or the nucleic acid sequence that encodes it. In a preferred embodiment, the variant proteins of the invention comprise an Fc variant, as described herein, and as such, may comprise an antibody (and the corresponding derivatives) with the Fc variant, or an Fc fusion protein that comprises the Fc variant. In addition, in some cases, the Fc is a variant as compared to a wild-type Fc, or to a "parent" variant.

For all heavy chain constant region amino acid positions discussed in the present invention, numbering is according to the Eu index first described in Edelman et al., 1969, Proc. Natl. Acad. Sci. USA 63(1):78-85, describing the amino acid sequence of myeloma protein Eu, which is the first human IgG1 sequenced. The Eu index of Edelman et al. is also set forth in Kabat et al., 1991, Sequences of Proteins of Immunological Interest, 5th Ed., United States Public Health Service, National Institutes of Health, Bethesda. Thus, the "EU index as set forth in Kabat" or "EU index of Kabat" refers to the residue numbering system based on the human IgG1 Eu antibody of Edelman et al. as set forth in Kabat 1991.

The numbering system used for the light chain constant region amino acid sequence is that set forth in Kabat 1991.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, to "treat" means reducing the frequency with which symptoms of a disease (i.e., tumor growth and/or metastasis, or other effect mediated by the numbers and/or activity of immune cells, and the like) are experienced by a patient. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Combination therapy" embraces the administration of an antibody-drug conjugate, and another therapeutic agent as part of a specific treatment regimen optionally including a maintenance phase, intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention.

"Combination therapy" embraces administration of these therapeutic agents in a sequential manner, that is, wherein each therapeutic agent is administered at a different time, as well as administration of these therapeutic agents, or at least two of the therapeutic agents, in a substantially simultaneous manner. Sequential or substantially simultaneous administration of each therapeutic agent can be effected by any appropriate route including, but not limited to, oral routes, intravenous routes, intramuscular, subcutaneous routes, and direct absorption through mucous membrane tissues. The therapeutic agents can be administered by the same route or by different routes. For example, a first therapeutic agent (e.g., a chemotherapeutic agent) can be administered orally, and a second agent (e.g., an ADC) can be administered intravenously. Further, a first therapeutic agent of the combination selected may be administered by intravenous injection while the other therapeutic agents of the combination may be administered orally. Alternatively, for example, both the therapeutic agents may be administered by intravenous or subcutaneous injection.

In the present specification the term "sequential" means, unless otherwise specified, characterized by a regular sequence or order, e.g., if a dosage regimen includes the administration of an ADC and a chemotherapeutic agent, a sequential dosage regimen could include administration of the ADC before, simultaneously, substantially simultaneously, or after administration of the chemotherapeutic agent, but both agents will be administered in a regular sequence or order. The term "separate" means, unless otherwise specified, to keep apart one from the other. The term "simultaneously" means, unless otherwise specified, happening or done at the same time, i.e., the compounds of the invention are administered at the same time. The term "substantially simultaneously" means that the compounds are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the ADC and the chemotherapeutic agent.

"Combination therapy" also can embrace the administration of the therapeutic agents as described above in further combination with other biologically active ingredients (such as, but not limited to, a second and different antineoplastic agent, a dendritic cell vaccine or other tumor vaccine) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the protein or portion thereof, may also be included in the composition.

I. Engineered Antibodies and Antibody Fragments

The disclosure is based on the finding that certain residues presumably present on the surface of the CH2 or CH3 domain of the heavy chain of antibodies, or on the constant domain of the light chain, or otherwise accessible, are suitable for the substitution of the naturally-occurring wild type amino acid with, for example, cysteine, and are therefore useful to engineer a site capable of conjugation to various agents.

Other amino acids besides cysteine, including natural and/or non-natural amino acids, may be used in the substitution to allow, among other things, for conjugation of various agents. Such other amino acids include lysine (described in Benhar et al., (1994) Bioconjug. Chem. 55:321-326), tyrosine (described in Byers and Baldwin, (1988) Immunol. 65:329-335), histidine (described in Waibel et al. (1999) Nature Biotechnol. 17:897-901), selenocysteine, selenomethionine, and/or non-natural amino acids. Thus, where one or more cysteine substitutions are described herein, one of ordinary skill in the art may optionally employ one or more of these natural and/or non-natural amino acids instead of cysteine. One of ordinary skill in the art may also use any combination of amino acids in the substitution, such as substituting with cysteine and lysine to produce a variant antibody with cysteines substituted at some positions and lysines, tyrosines, histidines, selenocysteines, selenomethionines, and/or non-natural amino acids at others in any combination thereof.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; Kunkel, 1985, Proc. Natl. Acad. Sci USA 82:488, which are hereby incorporated by reference in their entireties).

In some embodiments, the engineered Fc polypeptide of the disclosure may be used to prepare an antibody, or antigen binding fragment thereof, such that the antibody or fragment thereof thereby comprises an engineered Fc region which can be used to conjugate, at the engineered residue (i.e., the amino acid substituted compared to wild type unmodified Fc), a wide variety of moieties.

In some embodiments, the engineered kappa light chain constant polypeptide of the disclosure may be used to prepare an antibody, or antigen binding fragment thereof, such that the antibody or fragment thereof thereby comprises an engineered $C_L$ region comprising an amino acid mutation, or portion thereof, which can be used to conjugate, at the engineered amino acid residue, a wide variety of moieties.

Engineered Antibody Constant Regions

A. Engineered Heavy Chain Constant Region

The invention encompasses an engineered Cγ, polypeptide, including, but not limited to, an Fc polypeptide, where 1, 2, 3, 4, 5, 6, 7, 8, 9, 10, 11, 12, 13, 14, 15, 16, 17, 18, 19, 20, or more amino acids chosen from positions: 246, 249, 265, 267, 270, 276, 278, 283, 292, 293, 294, 300, 302, 303, 314, 315, 318, 320, 327, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the antibody heavy chain wherein the numbering system of the constant region is that of the EU index as set forth in Kabat et al. (1991, NIH Publication 91-3242, National Technical Information Service, Springfield, Va., hereinafter "Kabat") of a parent, native, or wild type antibody, are substituted with another amino acid (including natural and non-natural/synthetic amino acids).

It should be noted that a single substitution in an Fc polypeptide, for example of a cysteine residue, normally results in the display of two corresponding residues in the resultant IgG antibody due to the homodimeric nature of IgG antibody molecules. Thus, the resultant engineered IgG antibodies of the invention may display at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more reactive groups for the purpose of conjugation to a drug or compound. In an embodiment, one or more of the substitutions is with a cysteine residue, and the resulting engineered antibodies may display at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more thiol groups for the purpose of conjugation to a drug or compound.

In another embodiment, the engineered antibody comprises one engineered Fc polypeptide comprising different substituted positions from a second engineered Fc region. That is, because of the dimeric nature of IgG antibodies and because a variety of art-recognized methods for preparing heterodimeric antibodies comprising, inter alia, two or more Fc regions that differ from each other, the present invention encompasses an antibody comprising at least one engineered Fc region comprising an amino acid substitution that is not present in the other Fc region, which may or may not also be engineered. Methods for making heterodimeric antibodies comprising Fc regions comprising different mutations are well-known in the art and include, but are not limited to, the methods discussed in U.S. Pat. No. 7,183,076 to Arathoon et al.

In some embodiments, an engineered antibody comprises a first engineered Fc polypeptide comprising at least one substitution at positions selected from 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, and further comprises a second Fc region that is not engineered, e.g., it comprises the amino acid sequence of wild type IgG1.

In some embodiments, an engineered antibody comprises a first engineered Fc polypeptide comprising at least one substitution at positions selected from 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, and further comprises a second engineered Fc polypeptide that comprises at least one substitution at positions selected from 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, wherein the substitution present in the first engineered Fc polypeptide is not a substitution present in the second engineered Fc polypeptide.

In some embodiments, the engineered Fc polypeptide of the disclosure comprises at least one substitution at positions selected from: 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, wherein the numbering system of the constant region is that of the EU index as set forth in Kabat et al. (supra).

In some embodiments, the engineered Fc polypeptide of the disclosure comprises at least two substitutions at positions selected from: 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, wherein the numbering system of the constant region is that of the EU index as set forth in Kabat et al. (supra).

In other embodiments, the engineered Fc polypeptide of the disclosure comprises at least two substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least three substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least four substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least five substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least six substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least seven substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least eight substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least nine substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprises at least ten substitutions selected from the positions 246, 249, 254, 265, 267, 270, 276, 278, 283, 284, 287, 292, 293, 294, 300, 302, 303, 314, 315, 318, 320, 327, 332, 333, 334, 336, 345, 347, 354, 355, 358, 359, 360, 361, 362, 370, 373, 376, 378, 380, 382, 383, 384, 386, 388, 390, 392, 393, 398, 401, 404, 411, 413, 414, 416, 418, 419, 421, 422, 428, 431, 432, 437, 438, 439, 440, 443, and 444, of the heavy chain of an antibody, wherein at least one substitution is selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody, and wherein the numbering system of the constant region is that of the EU index as set forth in Kabat et al. (supra).

In other embodiments, the engineered Fc polypeptide of the disclosure comprise substitutions at each of the positions 254, 359, 361, 380, 383, 384, 392, 398, 404, 422, 442, and 443 of the heavy chain of an antibody wherein the numbering system of the constant region is that of the EU index as set forth in Kabat.

In other embodiments, the engineered Fc polypeptide of the disclosure comprises at least one amino acid sequence selected from the amino acid sequence of SEQ ID NOs:97-100, 102, 104, 107-127, 129-163.

In other embodiments, the engineered Fc polypeptide of the disclosure comprises at least two amino acid sequences selected from the amino acid sequence of SEQ ID NOs:97-100, 102, 104, 107-127, and 129-163.

In some embodiments, the engineered Fc polypeptide of the disclosure comprises at least one pair of amino acid sequences selected from: (a) the amino acid sequence of SEQ ID NO:99 and the amino acid sequence of SEQ ID NO:107; (b) the amino acid sequence of SEQ ID NO:103 and the amino acid sequence of SEQ ID NO:107; (c) the amino acid sequence of SEQ ID NO:105 and the amino acid sequence of SEQ ID NO:107; (d) the amino acid sequence of SEQ ID NO:99 and the amino acid sequence of SEQ ID NO:103; (e) the amino acid sequence of SEQ ID NO:103 and the amino acid sequence of SEQ ID NO:105; (f) the amino acid sequence of SEQ ID NO:99 and the amino acid sequence of SEQ ID NO:105; (g) the amino acid sequence of SEQ ID NO:102 and the amino acid sequence of SEQ ID NO:107; (h) the amino acid sequence of SEQ ID NO:104 and the amino acid sequence of SEQ ID NO:107; and (i) the amino acid sequence of SEQ ID NO:102 and the amino acid sequence of SEQ ID NO:104.

B. Engineered Light Chain Constant Region (Cκ or Cλ) Polypeptide

In other embodiments, the engineered Cκ polypeptide of the disclosure comprises at least one amino acid sequence selected from the group consisting of the sequence of SEQ ID NOs:90-95.

In some embodiments, the engineered Cκ polypeptide of the disclosure comprises at least one amino acid sequence selected from the group consisting of the sequence of SEQ ID NOs:164-169.

One skilled in the art would appreciate once armed with the teachings provided herein that due to the dimeric nature of many antibodies (e.g., IgGs comprise two light chains and two heavy chains each heavy chain comprising an Fc region), an antibody of the invention may comprise at least one engineered Fc region and may comprise two engineered Fc regions, where each engineered Fc region may comprise the same or different mutations. More preferably, both engineered Fc regions comprise the same mutations thus providing at least one site-specific conjugation site per each Fc region.

One skilled in the art would appreciate once armed with the teachings provided herein that due to the dimeric nature of many antibodies (e.g., IgGs comprise two light chains and two heavy chains each heavy chain comprising an Fc region), an antibody of the invention may comprise at least one engineered light chain constant polypeptide (e.g., Cκ or Cλ) and may comprise two engineered light chain constant polypeptides, where each engineered light chain constant polypeptide may comprise the same or different mutations. More preferably, both engineered light chain constant polypeptides comprise the same mutations thus providing at least one site-specific conjugation site per each light chain constant region.

In other embodiments, due to the dimeric nature of many antibodies (e.g., IgGs comprise two light chains and two heavy chains each heavy chain comprising an Fc polypeptide), an antibody of the invention may comprise at least one engineered Fc polypeptide and may further comprise at least one engineered light chain constant polypeptide thereby providing at least two site-specific conjugation sites—one in the Fc polypeptide and another in the $C_L$ polypeptide.

In another embodiment, an antibody of the invention may comprise two engineered Fc polypeptides, where each engineered Fc may comprise the same or different mutations and the antibody further comprises at least one engineered light chain constant region (Cκ or Cλ) polypeptide comprising at least one mutation. In other embodiments, the antibody comprises two engineered Fc polypeptides comprising at least one mutation, and further comprises two engineered light chain constant (Cκ or Cλ) polypeptides each comprising at least one mutation thereby providing at least four site-specific conjugation sites—one per heavy chain and one per light chain. More preferably, both engineered Fc polypeptides comprise the same mutation relative to each other and both light chain constant region (Cκ or Cλ) polypeptides comprise the same mutation relative to each other.

In another embodiment, an antibody of the invention may comprise two engineered Fc polypeptides, where each engineered Fc may comprise the same or different mutations and the antibody further comprises at least one engineered light chain constant region (Cκ or Cλ) polypeptide comprising at least one mutation. In other embodiments, the antibody comprises two engineered Fc polypeptides comprising at least one mutation, and further comprises two engineered light chain constant (two Cκ, two Cλ or one Cκ and one Cλ) polypeptides each comprising at least one mutation, wherein the mutation may be the same or different between the two light chain constant domains) thereby providing at least four site-specific conjugation sites—one per heavy chain and one per light chain. That is, the invention encompasses a bispecific antibody comprising two different heavy chains and two different light chains such that the antibody binds, e.g., two different antigens or different epitopes of the same antigen, and wherein the heavy chains comprise at least one engineered Fc and/or one engineered light chain constant domain. In one aspect, the antibody comprises two different heavy chains each comprising the same or different engineered cysteine mutations and one lambda light chain and one kappa light chain wherein each light chain may comprise at least one engineered cysteine mutation.

In some embodiments, an engineered Fab may comprise at least one mutation in the light chain constant region (Cκ or Cλ) to provide at least one site-specific conjugation site thereby providing a Fab comprising at least one site-specific conjugation site.

In other embodiments, the invention encompasses an engineered F(ab')₂ wherein at least one light chain constant region (Cκ or Cλ) comprises at least one mutation thereby providing a Fab comprising at least one site-specific conjugation site. In some embodiments, the engineered F(ab')₂ of the disclosure comprises at least one mutation in each light chain constant region (Cκ or Cλ) thereby providing an engineered F(ab')₂ comprising at least two site-specific conjugation sites.

In some embodiments, the antibody comprises one engineered Fc polypeptide comprising at least one mutation and two engineered light chain Cκ polypeptides each comprising at least one mutation.

In other embodiments, an antibody of the invention may comprise two engineered Fc polypeptides and two engineered (Cκ or Cλ) polypeptides where each Fc and each $C_L$ comprises at least one mutation and where the Fc region mutation is the same in each Fc polypeptide and the mutation in one $C_L$ (Cκ or Cλ) polypeptide is different from the mutation in the other $C_L$ (Cκ or Cλ) polypeptide.

In other embodiments, where the antibody comprises at least two engineered Fc polypeptides and two engineered $C_L$ (Cκ or Cλ) polypeptides each of the mutations in the two Fc regions may be the same, each of the mutations in the $C_L$ may the same, or each Fc region and/or each $C_L$ (Cκ or Cλ) comprises a different mutation, or any permutation thereof.

In other embodiments, the engineered Fc polypeptide of the disclosure may be used to prepare an Fc fusion protein such that the Fc fusion protein comprises an engineered Fc polypeptide which can be used to conjugate a wide plethora of moieties to the Fc polypeptide.

One skilled in the art would appreciate that due to the tendency of Fc polypeptides to dimerize, the invention encompasses dimeric Fc fusion proteins comprising at least two engineered Fc polypeptides, where each engineered Fc polypeptide may comprise at least one mutation providing a site specific for conjugation.

In one embodiment, the engineered Fc polypeptide comprises one of the following pairs of substitutions at positions: a) 380 and 443; b) 398 and 443; c) 422 and 443; d) 380 and 398; e) 398 and 442; f) 380 and 422; g) 392 and 443; h) 404 and 443; and i) 392 and 404.

In another embodiment, the engineered Fc polypeptide comprises at least one of the following pairs of substitutions at positions: a) 380 and 443; b) 398 and 443; c) 422 and 443; d) 380 and 398; e) 398 and 442; f) 380 and 422; g) 392 and 443; h) 404 and 443; and i) 392 and 404.

The substitutions described above correspond to the positions in SEQ ID NO: 1 (wild type human IgG1 Fc region), and it is intended that the number with reference to the Eu index numbering system of Edelman et al., 1969, as described in Kabat 1991 throughout the disclosure may be used interchangeably with the sequential position numbering of the substitutions in reference with SEQ ID NO: 1 to describe the compositions of the disclosure.

In other embodiments, the engineered Fc polypeptide of the disclosure comprises a substitution of at least one naturally occurring amino acid chosen from: K246, D249, D265, S267, D270, N276, Y278, E283, R292, E293, E294, Y300, V302, V303, L314, N315, E318, K320, I332, E333, K334, I336, E345, Q347, S354, R355, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, L443, and S444 where the numbering is based on the heavy chain of an antibody using the numbering system of the EU index as set forth in Kabat.

In some embodiments, the engineered Fc polypeptide of the disclosure does not comprise a substitution at a position or positions selected from: 239, 254, 284, 287, 327, 361, 383, 384, 398, 422 and 440 of the heavy chain of an antibody wherein the numbering system of the constant region is that of the EU index as set forth in Kabat.

In one embodiment, the engineered Fc polypeptide of the disclosure includes an IgG1 having a naturally occurring amino acid substituted (for example, with a cysteine) at a position chosen from: 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody wherein the numbering system of the constant region is that of the EU index as set forth in Kabat. In other embodiments, the engineered Fc polypeptide of the disclosure is derived from an IgG1, IgG2, IgG3 or an IgG4 format. In yet other embodiments, the engineered Fc polypeptide of the disclosure is derived from non-IgG formats such as IgA1, IgA2 IgM, IgD, or IgE. In other embodiments, Fc polypeptide of the disclosure comprise engineering of surface residues of the CH2 and/or CH3 region of an IgG1 molecule or equivalents thereof by substitution of a naturally-occurring residue for cysteine and/or other amino acids.

The invention encompasses an engineered antibody light chain constant region ($C_L$) wherein the light chain is a kappa light chain or a lambda light chain, or a portion thereof, where 1, 2, 3, 4, 5, 6, 7, 8, 9, 10, 11, 12, 13, 14, 15, 16, 17, 18, 19, 20, or more amino acids chosen from positions 111, 149, 183, 188, 207, and 210 of the antibody light chain, wherein the numbering system of the light chain constant region is that of the Kabat numbering system as set forth in Kabat et al. (1991, NIH Publication 91-3242, National Technical Information Service, Springfield, Va., hereinafter "Kabat"), of a parent, native, or wild type antibody, are substituted with another amino acid (including natural and non-natural/synthetic amino acids).

In some embodiments, the light chain constant region is a lambda constant region (Cλ). In another embodiment, the light chain constant region is a kappa constant region (Cκ).

It should be noted that a single substitution in a light chain constant region, for example of a cysteine residue, normally results in the display of two corresponding residues in the resultant IgG antibody due to the homodimeric nature of IgG antibody molecules. Thus, the resultant engineered IgG antibodies of the invention may display at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more reactive groups for the purpose of conjugation to a drug or compound. In an embodiment, one or more of the substitutions is with a cysteine residue, and the resulting engineered antibodies may display at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more thiol groups for the purpose of conjugation to a drug or compound.

In one embodiment, the invention provides an engineered antibody comprising one engineered polypeptide comprising a kappa light chain constant domain (Cκ) comprising the same substituted position from a second engineered kappa light chain constant domain. That is, because of the dimeric bivalent nature of IgG antibodies, the antibody may comprise two Cκ polypeptides that are the same or differ from each other, and the present invention encompasses an antibody comprising at least one engineered Cκ polypeptide comprising an amino acid substitution that is present in the other Cκ polypeptide.

In another embodiment, the engineered antibody comprises one engineered polypeptide comprising a kappa light chain constant domain (Cκ) comprising different substituted positions from a second engineered kappa light chain constant domain. That is, because of the dimeric nature of IgG antibodies and because a variety of art-recognized methods for preparing heterodimeric antibodies comprising, inter alia, two or more Cκ polypeptides that differ from each other, the present invention encompasses an antibody comprising at least one engineered Cκ polypeptide comprising an amino acid substitution that is not present in the other Cκ polypeptide, which may or may not also be engineered. Methods for making heterodimeric antibodies comprising $C_L$ regions comprising different mutations are well-known in the art and include, but are not limited to, the methods discussed in U.S. Pat. No. 7,183,076 to Arathoon et al.

In some embodiments, an engineered antibody of the invention comprises a first engineered Cκ polypeptide comprising at least one substitution at positions selected from 111, 149, 183, 188, 207, and 210, and further comprises a second Cκ polypeptide that is not engineered, e.g., it comprises the amino acid sequence of wild type Cκ where an exemplary human wild type Cκ polypeptide amino acid sequence is shown in FIG. 18A and is provided in SEQ ID NO:89.

In other embodiments, an engineered Fab of the disclosure comprises an engineered Cκ polypeptide comprising at least one substitution at positions selected from 111, 183, and 210.

In some embodiments, an engineered antibody comprises a first engineered Cκ polypeptide comprising at least one substitution at positions selected from 111, 183, and 210, and further comprises a second engineered Cκ polypeptide that comprises at least one substitution at positions selected from 111, 183, and 210, wherein the substitution present in the first engineered Cκ polypeptide is not a substitution present in the second engineered Cκ polypeptide.

In some embodiments, an engineered F(ab')$_2$ of the disclosure comprises a first engineered Cκ polypeptide comprising at least one substitution at positions selected from 111, 149, 183, 188, 207, and 210, and further comprises a second engineered Cκ polypeptide that comprises at least one substitution at positions selected from 111, 183, and 210, wherein the substitution present in the first engineered Cκ polypeptide is not a substitution present in the second engineered Cκ polypeptide.

In other embodiments, an engineered F(ab')$_2$ of the disclosure comprises a first engineered Cκ polypeptide comprising at least one substitution at positions selected from 111, 149, 183, 188, 207, and 210, and further comprises a second engineered Cκ polypeptide that comprises at least one substitution at positions selected from 111, 183, and 210, wherein at least one substitution present in the first engineered Cκ polypeptide is the same substitution present in the second engineered Cκ polypeptide.

In some embodiments, the engineered Cκ polypeptide of the disclosure comprises at least one substitution at positions selected from: 111, 183, and 210 of the light chain of an antibody, wherein the numbering system of the constant region is that of the Kabat index as set forth in Kabat et al. (supra).

In some embodiments, the engineered Cκ polypeptide of the disclosure comprises at least two substitutions at positions selected from: 111, 183, and 210 of the light chain of an antibody, wherein the numbering system of the constant region is that of the Kabat index as set forth in Kabat et al. (supra).

In other embodiments, the engineered Cκ polypeptide of the disclosure comprises all three substitutions selected from the positions 111, 183, and 210, of the light chain constant region of an antibody, and wherein the numbering system of the constant region is that of the Kabat numbering index as set forth in Kabat et al. (supra).

The substitutions described above correspond to the positions in SEQ ID NO:89 (wild type human kappa light chain constant region), and it is intended that the number with reference to Kabat throughout the disclosure may be used interchangeably with the sequential position numbering of the substitutions in reference with SEQ ID NO:89 to describe the compositions of the disclosure.

In other embodiments, the engineered Cκ polypeptide of the disclosure comprises a substitution of at least one naturally occurring amino acid chosen from: A111, K183, and N210 where the numbering is based on the light chain of an antibody using the numbering system of the Kabat numbering index as set forth in Kabat.

In other embodiments, the engineered light chain constant domain is a lambda light chain constant domain (Cλ).

In one embodiment, the engineered antibody comprises one engineered polypeptide comprising a lambda light chain constant domain (Cλ) comprising the same or different substituted positions from a second engineered lambda light chain constant domain. That is, because of the dimeric nature of IgG antibodies and because a variety of art-recognized methods for preparing heterodimeric antibodies comprising, inter alia, two or more Cλ polypeptides that are the same or that differ from each other, the present invention encompasses an antibody comprising at least one engineered Cλ polypeptide comprising an amino acid substitution that is not present in the other CA polypeptide, which may or may not also be engineered. Methods for making heterodimeric antibodies comprising $C_L$ regions comprising different mutations are well-known in the art and include, but are not limited to, the methods discussed in U.S. Pat. No. 7,183,076, to Arathoon et al.

In another aspect, the engineered antibody comprises at least one engineered polypeptide comprising a lambda light chain constant domain (Cλ), wherein the antibody comprises two CA domains each comprising the same mutation or mutations.

In some embodiments, an engineered antibody of the invention comprises a first engineered CA polypeptide comprising at least one substitution at positions selected from K110C, L125C, K149C, V155C, G158C, T161C, Q185C, S188C, H189C, S191C, T197C, V205C, E206C, K207C, T208 and A210 and further comprises a second Cλ polypeptide that is not engineered, e.g., it comprises the amino acid sequence of wild type Cλ where an exemplary human wild type Cλ polypeptide amino acid sequence is shown in FIG. 20A and is provided in SEQ ID NO:170.

In other embodiments, an engineered Fab of the disclosure comprises an engineered CA polypeptide comprising at least one substitution at positions selected from K110, L125, K149, V155, G158, T161, Q185, S188, H189, S191, T197, V205, E206, K207C, T208 and A210.

In some embodiments, an engineered antibody comprises a first engineered Cλ polypeptide comprising at least one substitution at positions selected from 110, 125, 149, 155, 158, 161, 185, 188, 189, 191, 197, 205, 206, K207C, T208 and A210 and further comprises a second engineered Cλ polypeptide that comprises at least one substitution at positions selected from 110, 125, 149, 155, 158, 161, 185, 188, 189, 191, 197, 205, 206, K207C, T208 and A210, wherein the substitution present in the first engineered Cλ polypeptide is not a substitution present in the second engineered Cλ polypeptide.

In some embodiments, an engineered F(ab')$_2$ of the disclosure comprises a first engineered CA polypeptide comprising at least one substitution at positions selected from 110, 125, 149, 155, 158, 161, 185, 188, 189, 191, 197, 205, 206, 207, 208 and 210 and further comprises a second engineered Cκ polypeptide that comprises at least one substitution at positions selected from 110, 125, 149, 155, 158, 161, 185, 188, 189, 191, 197, 205, 206, 207, 208 and 210 wherein the substitution present in the first engineered Cλ polypeptide is not a substitution present in the second engineered Cλ polypeptide.

In other embodiments, an engineered F(ab')$_2$ of the disclosure comprises a first engineered CA polypeptide comprising at least one substitution at positions selected from 110, 125, 149, 155, 158, 161, 185, 188, 189, 191, 197, 205, 206, 207, 208 and 210, and further comprises a second engineered Cλ polypeptide that comprises at least one substitution at positions selected from 110, 125, 149, 155, 158, 161, 185, 188, 189, 191, 197, 205, 206, 207, 208 and 210, wherein at least one substitution present in the first engineered Cλ polypeptide is the same substitution present in the second engineered Cλ polypeptide.

In some embodiments, the engineered Cλ polypeptide of the disclosure comprises at least one substitution at positions selected from: 110, 125, 149, 155, 158, 161, 185, 188, 189, 191, 197, 205, 206, 207, 208 and 210, of the light chain of an antibody, wherein the numbering system of the constant region is that of the Kabat index as set forth in Kabat et al. (supra).

In some embodiments, the engineered Cλ polypeptide of the disclosure comprises at least two substitutions at positions selected from: 110, 125, 149, 155, 158, 161, 185, 188, 189, 191, 197, 205, 206, 20C, 208 and A210, of the light chain of an antibody, wherein the numbering system of the constant region is that of the Kabat index as set forth in Kabat et al. (supra).

In other embodiments, the engineered Cλ polypeptide of the disclosure comprises at least two substitutions selected from the positions 110, 125, 149, 155, 158, 161, 185, 188, 189, 191, 197, 205, 206, 207, 208 and 210, of the light chain constant region of an antibody, and wherein the numbering system of the constant region is that of the Kabat numbering index as set forth in Kabat et al. (supra).

In other embodiments, the engineered Cλ polypeptide of the disclosure comprises at least three substitutions selected from the positions 110, 125, 149, 155, 158, 161, 185, 188, 189, 191, 197, 205, 206, 207, 208 and 210, of the light chain constant region of an antibody, and wherein the numbering system of the constant region is that of the Kabat numbering index as set forth in Kabat et al. (supra).

In other embodiments, the engineered Cλ polypeptide of the disclosure comprises at least four substitutions selected from the positions 110, 125, 149, 155, 158, 161, 185, 188, 189, 191, 197, 205, 206, 207C, 208 and 210, of the light chain constant region of an antibody, wherein at least one substitution is selected from the positions 110, 125, 149, 155, 158, 161, 185, 188, 189, 191, 197, 205, 206, 207, 208 and 210 of the light chain constant domain of an antibody, and wherein the numbering system of the constant region is that of the Kabat numbering index as set forth in Kabat et al. (supra).

In other embodiments, the engineered Cλ polypeptide of the disclosure comprises at least five substitutions selected from the positions 110, 125, 149, 155, 158, 161, 185, 188, 189, 191, 197, 205, 206, 207, 208 and 210, of the light chain constant region of an antibody, and wherein the numbering system of the constant region is that of the Kabat numbering index as set forth in Kabat et al. (supra).

In other embodiments, the engineered Cλ polypeptide of the disclosure comprises at least six substitutions selected from the positions 110, 125, 149, 155, 158, 161, 185, 188, 189, 191, 197, 205, 206, 207, 208 and 210, of the light chain of an antibody, and wherein the numbering system of the constant region is that of the Kabat numbering index as set forth in Kabat et al. (supra).

In other embodiments, the engineered Cλ polypeptide of the disclosure comprises at least seven substitutions selected from the positions 110, 125, 149, 155, 158, 161, 185, 188, 189, 191, 197, 205, 206, 207, 208 and 210, of the light chain of an antibody, and wherein the numbering system of the constant region is that of the Kabat numbering index as set forth in Kabat et al. (supra).

In other embodiments, the engineered Cλ polypeptide of the disclosure comprises at least eight substitutions selected from the positions 110, 125, 149, 155, 158, 161, 185, 188, 189, 191, 197, 205, 206, 207, 208 and 210, of the light chain of an antibody, and wherein the numbering system of the constant region is that of the Kabat numbering index as set forth in Kabat et al. (supra).

In other embodiments, the engineered Cλ polypeptide of the disclosure comprises at least nine substitutions selected from the positions 110, 125, 149, 155, 158, 161, 185, 188, 189, 191, 197, 205, 206, 207C, 208 and 210, of the light chain of an antibody, and wherein the numbering system of the constant region is that of the Kabat numbering index as set forth in Kabat et al. (supra).

In other embodiments, the engineered Cλ polypeptide of the disclosure comprises at least ten substitutions selected from the positions 110, 125, 149, 155, 158, 161, 185, 188, 189, 191, 197, 205, 206, 207, 208 and 210, of the light chain of an antibody, and wherein the numbering system of the constant region is that of the Kabat numbering index as set forth in Kabat et al. (supra).

In other embodiments, the engineered Cλ polypeptide of the disclosure comprises substitutions at each of the positions 110, 125, 149, 155, 158, 161, 185, 188, 189, 191, 197, 205, 206, 207, 208 and 210, of the light chain of an antibody wherein the numbering system of the constant region is that of the Kabat numbering index as set forth in Kabat.

The substitutions described above correspond to the positions in SEQ ID NO:170 (wild type human lambda light chain constant region), and it is intended that the number with reference to Kabat throughout the disclosure may be used interchangeably with the sequential position numbering of the substitutions in reference with SEQ ID NO:170 to describe the compositions of the disclosure.

In other embodiments, the engineered Cλ polypeptide of the disclosure comprises a substitution of at least one naturally occurring amino acid chosen from: 110, 125, 149, 155, 158, 161, 185, 188, 189, 191, 197, 205, 206, 207, 208 and 210 where the numbering is based on the light chain of an antibody using the numbering system of the Kabat numbering index as set forth in Kabat.

C. Engineered Antibody, or Antigen-Binding Portion Thereof, Comprising and Engineered Constant Domain (Heavy and/or Light)

One skilled in the art would appreciate once armed with the teachings provided herein that due to the dimeric nature of many antibodies (e.g., IgGs comprise two light chains each comprising a constant region (CL) and two heavy chains each heavy chain comprising an Fc region), an antibody of the invention may comprise at least one engineered constant region (e.g., a heavy chain constant region, an IgG Cγ region, a Cκ region, and/or a Cλ region) and may comprise two engineered $C_L$ regions, where each engineered $C_L$ region may comprise the same or different mutations. More preferably, both engineered $C_L$ (Cκ or Cλ) regions comprise the same mutations thus providing at least one site-specific conjugation site per each $C_L$ (Cκ or Cλ) region.

In another embodiment, the engineered antibody of the invention comprises at least one engineered Fc polypeptide and may comprise two engineered Fc polypeptides, where each engineered Fc polypeptide may comprise the same or different mutations. More preferably, both engineered Fc polypeptides comprise the same mutations thus providing at least one site-specific conjugation site per each Fc polypeptide. The antibody may further comprise at least one engineered Cκ polypeptide and may comprise two engineered Cκ polypeptides wherein each engineered Cκ polypeptide may comprise the same or different mutations. More preferably, both engineered Fc polypeptides comprise the same mutations and both engineered Cκ polypeptides comprise the same mutations thus providing at least one site-specific conjugation site per each Fc polypeptide and at least one site-specific conjugation site per Cκ polypeptide thereby providing an antibody comprising at least four potential conjugation sites.

In some embodiments, the engineered antibody of the invention comprises at least one engineered Fc polypeptide and may comprise two engineered Fc polypeptides, where each engineered Fc polypeptide may comprise the same or different mutations. More preferably, both engineered Fc polypeptides comprise the same mutations thus providing at least one site-specific conjugation site per each Fc polypeptide. The antibody may further comprise at least one engineered CA polypeptide and may comprise two engineered Cλ polypeptides wherein each engineered CA polypeptide may comprise the same or different mutations. More preferably, both engineered Fc polypeptides comprise the same mutations and both engineered Cλ polypeptides comprise the same mutations thus providing at least one site-specific conjugation site per each Fc polypeptide and at least one site-specific conjugation site per Cλ polypeptide thereby providing an antibody comprising at least four potential conjugation sites.

In one embodiment, the engineered antibody of the invention comprises at least one engineered Fc polypeptide and may comprise two engineered Fc polypeptides, where each engineered Fc polypeptide may comprise the same or different mutations. More preferably, both engineered Fc polypeptides comprise the same mutations thus providing at least one site-specific conjugation site per each Fc polypeptide. The antibody may further comprise at least one engineered Cλ polypeptide and may comprise two engineered Cλ polypeptides wherein each engineered Cλ polypeptide may comprise the same or different mutations. More preferably, both engineered Fc polypeptides comprise the same mutations and both engineered Cλ polypeptides comprise the same mutations thus providing at least one site-specific conjugation site per each Fc polypeptide and at least one site-specific conjugation site per Cλ polypeptide thereby providing an antibody comprising at least four potential conjugation sites.

In other embodiments, the engineered antibody of the invention comprises at least one engineered Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one engineered Cκ polypeptide comprising at least one substitution selected from the positions 111, 149, 183, 188, 207, and 210, of the light chain of an antibody, and wherein the numbering system of the light chain constant polypeptide is that of the Kabat numbering index as set forth in Kabat et al. (supra). That is, where the engineered antibody comprises at least one engineered heavy chain constant domain (Cγ) comprising at least one amino acid substitution selected from a substitution at position 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, according to the Eu numbering of Kabat, and/or where the antibody comprises at least one engineered Cλ domain comprising at least one amino acid substitution selected from the group consisting of K110C, L125C, K149C, V155C, G158C, T161C, Q185C, S188C, H189C, S191C, T197C, V205C, E206C, K207C, T208 and A210, the antibody can further comprise at least one engineered Cκ comprising at least one substitution selected from the group consisting of A111, K183, and N210, and/or at least one substitution known in the art, including, but not limited to, an amino acid substitution in a Cκ as disclosed in International Patent Publication No. WO 2011/156382, published Dec. 15, 2011, such as, K149 (SEQ ID NO:91), K188 (SEQ ID NO:93) and K207 (SEQ ID NO:94).

In one embodiment, the engineered antibody of the invention comprises at least one engineered Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In some embodiments, the engineered antibody of the invention comprises at least one engineered Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one: (a) engineered Cκ polypeptide comprising at least one substitution selected from the positions 111, 183, and 210, of the light chain of an antibody, and/or (b) at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In other embodiments, the engineered antibody of the invention comprises at least one engineered Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one: (a) engineered Cκ polypeptide comprising at least one substitution selected from the positions 111, 149, 183, 188, 207, and 210, of the light chain of an antibody, and/or (b) at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In other embodiments, the engineered antibody of the invention comprises at least one engineered Cκ polypeptide comprising at least one substitution selected from the positions 111, 149, 183, 188, 207, and 210, of the light chain of an antibody, and comprises at least one: (a) Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and/or (b) at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In some embodiments, the engineered antibody of the invention comprises at least one engineered Cκ polypeptide comprising at least one substitution selected from the positions 111, 149, 183, 188, 207, and 210, of the light chain of an antibody wherein the numbering is according to Kabat, and an Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, In one aspect, the engineered antibody of the invention comprises two engineered Cκ polypeptides each comprising a substitution at A111 according to the numbering of Kabat, and two engineered Fc polypeptides each comprising a substitution at Q347 using the numbering system of the EU index as set forth in Kabat, In one aspect, the engineered antibody of the invention comprises two engineered Cκ polypeptides each comprising a substitution at A111 according to the numbering of Kabat, and two engineered Fc polypeptides each comprising a substitution at E388 using the numbering system of the EU index as set forth in Kabat, In another aspect, the engineered antibody of the invention comprises two engineered Cκ polypeptides each comprising a substitution at A111 according to the numbering of Kabat, and two engineered Fc polypeptides each comprising a substitution at K392 using the numbering system of the EU index as set forth in Kabat, In yet another aspect, the engineered antibody of the invention comprises two engineered Cκ polypeptides each comprising a substitution at A111 according to the numbering of Kabat, and two engineered Fc polypeptides each comprising a substitution at L443 using the numbering system of the EU index as set forth in Kabat, In a further aspect, the engineered antibody of the invention comprises two engineered Cκ polypeptides each comprising a substitution at K183 according to the numbering of Kabat, and two engineered Fc polypeptides each comprising a substitution at L443 using the numbering system of the EU index as set forth in Kabat, In another aspect, the engineered antibody of the invention comprises two engineered Cκ polypeptides each comprising a substitution at K207 according to the numbering of Kabat, and two engineered Fc polypeptides each comprising a substitution at L443 using the numbering system of the EU index as set forth in Kabat, Further, the present invention is not limited to these or any other particular combinations of substitutions among the constant domains, but includes any combination or permutation of the novel amino acid substitutions and combinations thereof disclosed herein.

In other embodiments, the engineered antibody of the invention comprises at least one engineered Cλ polypeptide comprising at least one substitution selected from the positions 110, 111, 125, 149, 155, 158, 161, 185, 188, 189, 191, 197, 205, 206 and 207, wherein the numbering system of the light chain constant polypeptide is that of the Kabat numbering index as set forth in Kabat et al., and comprises at least one: (a) Fc polypeptide comprising at least one substitution selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and/or (b) an engineered Cκ polypeptide comprising at least one substitution selected from the positions 111, 149, 183, 188, 207, and 210, of the light chain of an antibody wherein the numbering system of the light chain constant polypeptide is that of the Kabat numbering index (supra).

In other embodiments, the engineered antibody of the invention comprises at least one engineered Fc polypeptide comprising at least two substitutions selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one engineered Cκ polypeptide comprising at least two substitutions selected from the positions 111, 149, 183, 188, 207, and 210, of the light chain of an antibody, and wherein the numbering system of the light chain constant polypeptide is that of the Kabat numbering index as set forth in Kabat et al. (supra) and/or comprises at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In other embodiments, the engineered antibody of the invention comprises at least one engineered Fc polypeptide comprising at least three substitutions selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one engineered Cκ polypeptide comprising at least three substitutions selected from the positions 111, 149, 183, 188, 207, and 210, of the light chain of an antibody, and wherein the numbering system of the light chain constant polypeptide is that of the Kabat numbering index as set forth in Kabat et al. (supra) and/or comprises at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In other embodiments, the engineered antibody of the invention comprises at least one engineered Fc polypeptide comprising at least five substitutions selected from the positions 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, of the heavy chain using the numbering system of the EU index as set forth in Kabat, and comprises at least one engineered Cκ polypeptide comprising at least five substitutions selected from the positions 111, 149, 183, 188, 207, and 210, of the light chain of an antibody, and wherein the numbering system of the light chain constant polypeptide is that of the Kabat numbering index as set forth in Kabat et al. (supra) and/or comprises at least one engineered Cλ polypeptide comprising at least one substitution selected from the positions 110, 111, 125, 149, 155, 158, 161, 185, 188, 189, 191, 197, 205, 206 and 207, of the light chain of an antibody, and wherein the numbering system of the light chain constant polypeptide is that of the Kabat numbering index as set forth in Kabat et al. (supra).

In other embodiments, where the antibody comprises at least two engineered Fc polypeptides and two engineered light chain constant polypeptides (Cκ-Cκ, Cλ-Cλ or Cκ-Cλ) wherein each of the mutations in the two Fc polypeptides may be the same, each of the mutations in the $C_\kappa$ or $C_\lambda$ may the same, or each Fc polypeptide and/or each $C_\kappa$ or $C_\lambda$ comprises a different mutation, or no mutation, and any combination of the foregoing.

One of ordinary skill in the art can readily select a suitable amino acid to use in the substitution. It may be desirable to select a residue that is similar to the non-naturally occurring residue (e.g., a conservative substitution) in order to minimize changes to the protein structure. For example, for cysteine substitutions, it can be desirable, but not necessary, to substitute cysteine for a naturally occurring alanine or serine.

In the case of substitutions in IgG2, IgG3, and IgG4, one of ordinary skill in the art can use sequence alignment of the Ig type of interest with IgG1 to determine the relative residues of the desired isoform corresponding with the above-described positions of positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the heavy chain of an antibody wherein the numbering system of the constant region is that of the EU index as set forth in Kabat. The amino acid sequences of human wild type heavy chain constant domains (HC Fc) of IgG2, IgG3, and IgG4 are disclosed herein as SEQ ID NOs: 2, 3, and 4, and shown in FIGS. 15C, 15D, and 15E, respectively.

An exemplary alignment, showing the corresponding positions for each amino acid of the Fc domains of human IgG1, IgG2, IgG3 and IgG4, is provided in FIG. 19A. The Fc region for human IgG1 begins at amino acid residue 236 glycine ($^{236}$G) using the Eu index as described in Kabat. Thus, the sequences shown in FIG. 15 show the CH1 region and the complete hinge region of human IgG1 where the human Fc region more preferably begins at $^{236}$G.

In other embodiments, the invention encompasses expression of an isolated Fc polypeptide comprising engineered residues. Such isolated Fc polypeptides may be useful as scaffolds for display purposes or as dimerization domains alone or when combined with another agent. In one aspect, the invention comprises a fusion protein comprising an engineered Fc polypeptide and a binding domain comprising a binding site of a receptor, cytokine, ligand, and the like, such that the binding domain provides binding specificity for the engineered Fc polypeptide such that any moiety conjugated to the engineered Fc polypeptide is targeted to the cognate binding molecule that specifically binds with the binding domain. An exemplary Fc fusion protein encompassed by the invention comprises a tumor necrosis factor receptor 2 (TNFR2), or a TNFα-binding portion thereof, fused with an engineered Fc polypeptide of the invention, similar, but not identical to, etanercept (ENBREL™), comprising TNFR2 fused with a wild type IgG1 Fc polypeptide. Thus, one of ordinary skill in the art would appreciate once armed with the teachings provided herein, that the invention is not limited to engineered antibodies, but rather, the invention encompasses an engineered Fc polypeptide fused with any binding domain providing specificity for a target of interest.

In other embodiments, the disclosure provides fusion proteins comprising an engineered Fc polypeptide that comprises at least one or more substitutions at positions selected from: 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444, wherein the numbering system of the constant region is that of the EU index as set forth in Kabat, fused to another protein.

Antibody Affinity

Typically, the $K_D$ for the antibody with respect to the target will be 2-fold, preferably 5-fold, more preferably 10-fold less than the $K_D$ with respect to another, non-target molecule such as, but not limited to, unrelated material or accompanying material in the environment. More preferably, the $K_D$ will be 50-fold less, such as 100-fold less, or 200-fold less; even more preferably 500-fold less, such as 1,000-fold less, or 10,000-fold less than the $K_D$ with respect the non-target molecule.

The value of this dissociation constant can be determined directly by well-known methods, and can be computed even for complex mixtures by methods such as those, for example, set forth in Caceci et al., 1984, Byte 9: 340-362. For example, the $K_D$ may be established using a double-filter nitrocellulose filter binding assay such as that disclosed by Wong and Lohman, 1993, Proc. Natl. Acad. Sci. USA 90: 5428-5432. Other standard assays to evaluate the binding ability of ligands such as antibodies towards targets are known in the art, including for example, ELISAs, Western blots, RIAs, and flow cytometry analysis. The binding kinetics and binding affinity of the antibody also can be assessed by standard assays known in the art, such as Surface Plasmon Resonance (SPR), e.g. by using a Biacore™ system.

A competitive binding assay can be conducted in which the binding of the antibody to the target is compared to the binding of the target by another ligand of that target, such as another antibody. The concentration at which 50 percent binding inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

An antibody of the invention may have a $K_D$ for its target of $1 \times 10^{-7}$ M or less, $1 \times 10^{-8}$ M or less, or $1 \times 10^{-9}$ M or less, or $1 \times 10^{-10}$ M or less, $1 \times 10^{-11}$ M or less, or $1 \times 10^{-12}$ M or less.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-target molecule.

In one embodiment, an antibody comprising an engineered Fc polypeptide of the disclosure may have an affinity rate constant or $K_a$ ($k_{on}/k_{off}$) of at least $10^2$ M$^{-1}$, at least $5 \times 10^2$ M$^{-1}$, at least $10^3$ M$^{-1}$, at least $5 \times 10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$ at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $_{10}14$ M$^{-1}$, at least $5 \times 10^{14}$ M$^{-1}$, at least $10^{15}$ M$^{-1}$, or at least $5 \times 10^{15}$ M$^{-1}$.

In another embodiment, an antibody comprising engineered Fc polypeptides of the disclosure may have a dissociation rate constant or $K_d$ ($k_{off}/k_{on}$) of less than $5 \times 10^{-2}$ M, less than $10^{-2}$ M, less than $5 \times 10^{-3}$ M, less than $10^{-3}$ M, less than $5 \times 10^{-4}$ M, less than $10^{-4}$ M, less than $5 \times 10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M.

An antibody comprising an engineered Fc polypeptide used in accordance with a method described herein may have a dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using a method described herein or known to one of skill in the art (e.g., a BIAcore Assay™, ELISA) (Biacore International AB, Uppsala, Sweden).

Antibodies comprising engineered Fc polypeptides of the disclosure retain the antigen binding capability of their native counterparts. In one embodiment, the antibodies comprising an engineered Fc polypeptide of the disclosure exhibit essentially the same affinity as compared to an antibody prior to engineering. In another embodiment, antibodies comprising an engineered Fc polypeptide of the disclosure exhibit a reduced affinity as compared to an antibody prior to engineering. In another embodiment, antibodies comprising an engineered Fc polypeptide of the disclosure exhibit an enhanced affinity as compared to an antibody prior to engineering.

In one embodiment, an antibody comprising an engineered Fc polypeptide of the disclosure may have a dissociation constant ($K_d$) about equal to the $K_d$ of the antibody prior to engineering.

In one embodiment, an antibody comprising an engineered Fc polypeptide of the disclosure may have a dissociation constant ($K_d$) about 1-fold, more preferably about 2-fold, even more preferably, about 3-fold, more preferably, about 4-fold, yet more preferably, about 5-fold, even more preferably, about 10-fold, more preferably, about 20-fold, even more preferably, about 50-fold, more preferably, about 100-fold, even more preferably, about 150-fold, more preferably, about 200-fold, yet more preferably, about 250-fold, even more preferably, about 300-fold, more preferably, about 400-fold, even more preferably, about 500-fold, more preferably, about 600-fold, even more preferably, about 700-fold, more preferably, about 800-fold, even more preferably 900-fold, and yet more preferably, about 1000-fold greater for its cognate antigen compared with the $K_d$ of the antibody prior to engineering.

In yet another embodiment, an antibody comprising an engineered Fc polypeptide of the disclosure may have a $K_d$ about 1-fold, more preferably about 2-fold, even more preferably, about 3-fold, more preferably, about 4-fold, yet more preferably, about 5-fold, even more preferably, about 10-fold, more preferably, about 20-fold, even more preferably, about 50-fold, more preferably, about 100-fold, even more preferably, about 150-fold, more preferably, about 200-fold, yet more preferably, about 250-fold, even more preferably, about 300-fold, more preferably, about 400-fold, even more preferably, about 500-fold, more preferably, about 600-fold, even more preferably, about 700-fold, more preferably, about 800-fold, even more preferably 900-fold, and yet more preferably, about 1000-fold lower for its cognate antigen compared with the $K_d$ of the antibody prior to engineering.

Antibody Specificity

In some embodiments, engineered antibody, Fab, and F(ab')$_2$ of the disclosure comprises an antibody, Fab, and F(ab')$_2$ that comprises an epitope binding domain (for example, but not limited to, an antibody variable region having all 6 CDRs, or an equivalent region that is at least 90 percent identical to an antibody variable region) chosen from: abagovomab, abatacept (ORENCIA®), abciximab (REOPRO®, c7E3 Fab), adalimumab (HUMIRA®), adecatumumab, alemtuzumab (CAMPATH®, MabCampath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (SIMULECT®), bavituximab, bectumomab (LYMPHOSCAN®), belimumab (LYMPHOSTAT-B®), bertilimumab, besilesomab, betacept (EN-BREL®), bevacizumab (AVASTIN®), biciromab brallobarbital, bivatuzumab mertansine, brentuximab vedotin (ADCETRIS®), canakinumab (ACZ885), cantuzumab mertansine, capromab (PROSTASCINT®), catumaxomab (REMOVAB®), cedelizumab (CIMZIA®), certolizumab pegol, cetuximab (ERBITUX®), clenoliximab, dacetuzumab, dacliximab, daclizumab (ZENAP AX®, denosumab (AMG 162), detumomab, dorlimomab aritox, dorlixizumab, duntumumab, durimulumab, durmulumab, ecromeximab, eculizumab (SOLIRIS®), edobacomab, edrecolomab (Mabl7-1A, PANOREX®), efalizumab (RAPTIVA®), efungumab (MYCOGRAB®), elsilimomab, enlimomab pegol, epitumomab cituxetan, efalizumab, epitumomab, epratuzumab, erlizumab, ertumaxomab (REXOMUN®), etaracizumab (etaratuzumab, VITAXIN®, ABEGRIN™), exbivirumab, fanolesomab (NEUTROSPEC®), faralimomab, felvizumab, fontolizumab (HUZAF®), galiximab, gantenerumab, gavilimomab (ABX-CBL®), gemtuzumab ozogamicin (MYLOTARG®), golimumab (ONTO 148), gomiliximab, ibalizumab (TNX-355), ibritumomab tiuxetan (ZEVALIN®), igovomab, imciromab, infliximab (REMICAD E®), inolimomab, inotuzumab ozogamicin, ipilimumab (YERVOY®, MDX-010), iratumumab, keliximab, labetuzumab, lemalesomab, lebrilizumab, lerdelimumab, lexatumumab (HGS-ETR2, ETR2-ST01), lexitumumab, libivirumab, lintuzumab, lucatumumab, lumiliximab, mapatumumab (HGS-ETRI, TRM-I), maslimomab, matuzumab (EMD72000), mepolizumab (BOSATRIA®), metelimumab, milatuzumab, minretumomab, mitumomab, morolimumab, motavizumab (NUMAX™), muromonab (OKT3), nacolomab tafenatox, naptumomab estafenatox, natalizumab (TYSABRI®, ANTEGREN®), nebacumab, nerelimomab, nimotuzumab (THERACIM hR3®, THERA-CIM-hR3®, THER-ALOC®), nofetumomab merpentan (VERLUMA®), ocrelizumab, odulimomab, ofatumumab, omalizumab (XOLAIR®), oregovomab (OVAREX®), otelixizumab, pagibaximab, palivizumab (SYNAGIS®), panitumumab (ABX-EGF, VECTIBIX®), pascolizumab, pemtumomab (THERAGYN®), pertuzumab (2C4, OMNITARG®), pexelizumab, pintumomab, ponezumab, priliximab, pritumumab, ranibizumab (LUCENTIS®), raxibacumab, regavirumab, reslizumab, rituximab (RITUXAN®, MabTHERA®), rovelizumab, ruplizumab, satumomab, sevirumab, sibrotuzumab, siplizumab (MEDI-507), sontuzumab, stamulumab (Myo-029), sulesomab (LEUKOSCAN®), tacatuzumab tetraxetan, tadocizumab, talizumab, taplitumomab paptox, tefibazumab (AUREXIS®), telimomab aritox, teneliximab, teplizumab, ticilimumab, tocilizumab (ACTEMRA®), toralizumab, tositumomab, trastuzumab (HERCEPTIN®), tremelimumab (CP-675, 206), tucotuzumab celmoleukin, tuvirumab, urtoxazumab, ustekinumab (ONTO 1275), vapaliximab, veltuzumab, vepalimomab, visilizumab (NUVION®), volociximab (M200), votumumab (HUMASPECT®), zalutumumab, zanolimumab (HuMAX-CD4), ziralimumab, or zolimomab aritox.

In other embodiments, an engineered antibody, Fab, and F(ab')$_2$ of the disclosure comprise a heavy and light chain variable domain having six CDRs, and/or compete for binding with an antibody selected from the preceding list. In other embodiments, an antibody, Fab, and F(ab')$_2$ comprising an engineered Fc polypeptide and/or an engineered Cκ or Cλ polypeptide of the disclosure bind the same epitope as the antibodies in the preceeding list. In other embodiments, an antibody, Fab, and F(ab')$_2$ comprising an engineered Fc polypeptide and/or an engineered Cκ or Cλ polypeptide of the disclosure comprises a heavy and light chain variable domain having six total CDRs, and binds to the same antigen as the antibodies in the proceeding list.

In other embodiments, an antibody, Fab, and F(ab')$_2$ comprising an engineered Fc polypeptide and/or an engineered C$_\kappa$ or C$_\lambda$ polypeptide of the disclosure comprises a heavy and light chain variable domain having six (6) total CDRs, and specifically binds to an antigen selected from: PDGFRalpha, PDGFRbeta, PDGF, VEGF, VEGF-A, VEGF-B, VEGF-C, VEGF-D, VEGF-E, VEGF-F, VEGFR1, VEGFR2, VEGFR3, FGF, FGF2, HGF, KDR, flt-1, FLK-1, Ang-2, Ang-1, PLGF, CEA, CXCL13, Baff, IL-21, CCL21, TNF-alpha, CXCL12, SDF-I, bFGF, MAC-I, IL23pl9, FPR, IGFBP4, CXCR3, TLR4, CXCR2, EphA2, EphA4, EphrinB2, EGFR (ErbBI), HER2 (ErbB2 or p85neu), HER3 (ErbB3), HER4 ErbB4 or tyro2), SCI, LRP5, LRP6, RAGE, s100A8, s100A9, Nav1.7, GLPI, RSV, RSV F protein, Influenza HA protein, Influenza NA protein, HMGBI, CD16, CD19, CD20, CD21, CD28, CD32, CD32b, CD64, CD79, CD22, ICAM-1, FGFRI, FGFR2, HDGF, EphB4, GITR, beta-amyloid, hMPV, PIV-I, PIV-2, OX40L, IGFBP3, cMet, PD-I, PLGF, Neprolysin, CTD, IL-18, IL-6, CXCL-13, ILIRI, IL-15, IL-4R, IgE, PAI-I, NGF, EphA2, uPARt, DLL-4, αvβ5, αvβ6, α5β1, α3β1, interferon receptor type I and type II, CD 19, ICOS, IL-17, Factor 11, Hsp90, IGF, IGF-I, IGF-II, CD 19, GM-CSFR, PIV-3, CMV, IL-13, IL-9, and EBV.

In other embodiments, an antibody, or antigen-binding portion thereof, e.g., Fab, and F(ab')$_2$ fragment, comprising an engineered Fc polypeptide and/or an engineered C$_\kappa$ or C$_\lambda$ polypeptide of the disclosure specifically binds to a member (receptor or ligand) of the TNF superfamily. Various molecules include, but are not limited to Tumor Necrosis Factor-alpha ("TNF-alpha"), Tumor Necrosis Factor-beta ("TNF-beta"), Lymphotoxin-alpha ("LT-alpha"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-1 (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CARI, HVEM (also known as ATAR or TR2), GITR, ZTNFR-5, NTR-I, TNFLI, CD30, LTBr, 4-1BB receptor and TR9.

In another embodiment, the antibody, or antigen-binding portion thereof, e.g., Fab, and F(ab')$_2$ fragment, comprising an engineered Fc polypeptide and/or an engineered Cκ or Cλ polypeptide of the disclosure is capable of binding one or more targets chosen from 5T4, ABL, ABCB5, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAGI, BAII, BCR, BCL2, BCL6, BDNF, BLNK, BLRI (MDR15), BlyS, BMP1, BMP2, BMP3B (GDFIO), BMP4, BMP6, BMP7, BMP8, BMP9, BMP11, BMP12, BMPR1A, BMPR1B, BMPR2, BPAGI (plectin), BRCAI, C19orf10 (IL27w), C3, C4A, C5, C5R1, CANTI, CASPI, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CCL3 (MIP-Ia), CCL4 (MIP-Ib), CCL5 (RANTES), CCL7 (MCP-3), CCL8 (mcp-2), CCNAI, CCNA2, CCNDI, CCNEI, CCNE2, CCRI (CKRI/HM145), CCR2 (mcp-IRB/RA), CCR3 (CKR3/CMKBR3), CCR4, CCR5 (CMKBR5/ChemR13), CCR6 (CMKBR6/Cκ R-L3/STRL22/DRY6), CCR7 (CKR7/EBI1), CCR8 (CMKBR8/TERI/Cκ R-LI), CCR9 (GPR-9-6), CCRLI (VSHKI), CCRL2 (L-CCR), CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18, CDH19, CDH20, CDH5, CDH7, CDH8, CDH9, CDK2, CDK3, CDK4, CDK5, CDK6, CDK7, CDK9, CDKNIA (p21WapI/CipI), CDKNIB (p27KipI), CDKNIC, CDKN2A (pl6INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8A1, COL1A1.COL4A3, COL6A1, CR2, Cripto, CRP, CSFI (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI (GROI), CXCLIO (IP-IO), CXCLII (1-TAC/IP-9), CXCL12 (SDFI), CXCL13, CXCL 14, CXCL 16, CXCL2 (GR02), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB2IP, DES, DKFZp451J0118, DNCLI, DPP4, E2F1, ECGFI5EDGI, EFNAI, EFNA3, EFNB2, EGF, EGFR, ELAC2, ENG, endoglin, ENOI, ENO2, ENO3, EPHAI, EPHA2, EPHA3, EPHA4, EPHA5, EPHA6, EPHA7, EPHA8, EPHA9, EPHAIO, EPHBI, EPHB2, EPHB3, EPHB4, EPHB5, EPHB6, EPHRIN-AI, EPHRIN-A2, EPH-RIN-A3, EPHRIN-A4, EPHRIN-A5, EPHRIN-A6, EPH-RIN-BI, EPHRIN-B2, EPHRTN-B3, EPHB4, EPG, ERBB2 (Her-2), EREG, ERK8, Estrogen receptor, ESRI, ESR2, F3 (TF), FADD, farnesyltransferase, FasL, FASNf, FCER1A, FCER2, FCGR3A, FGF, FGFI (aFGF), FGFIO, FGFI 1, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FILI (EPSI-LON), FBLI (ZETA), FLJ12584, FLJ25530, FLRTI (fibronectin), FLTI, FLT-3, FOS, FOSLI (FRA-I), FY (DARC), GABRP (GABAa), GAGEBI, GAGECI, GALNAC4S-65T, GATA3, GD2, GD3, GDF5, GDF8, GFII, GGTI, GM-CSF, GNASI, GNRHI, GPR2 (CCRIO), GPR31, GPR44, GPR81 (FKSG80), GRCCIO (C10), gremlin, GRP, GSN (Gelsolin), GSTPI, HAVCR2, HDAC, HDAC4, HDAC5, HDAC7A, HDAC9, Hedgehog, HGF, HIFIA, HIPI, histamine and histamine receptors, HLA-A, HLA-DRA, HM74, HMOXI, HSP90, HUMCYT2A, ICE-BERG, ICOSL, ID2, IFN-a, IFNAI, IFNA2, IFNA4, IFNA5, EFNA6, BFNA7, IFNBI, IFNgamma, IFNWI, IGBPI, IGFI, IGFIR, IGF2, IGFBP2, IGFBP3, IGFBP6, DL-I, ILIO, ILIORA, ILIORB, IL-1, ILIRI (CD121a), ILIR2 (CD121b), IL-IRA, IL-2, IL2RA (CD25), IL2RB (CD122), IL2RG (CD132), IL-4, IL-4R(CD123), IL-5, IL5RA (CD125), IL3RB (CD131), IL-6, IL6RA (CD126), IR6RB (CD130), IL-7, IL7RA (CD127), IL-8, CXCRI (IL8RA), CXCR2 (IL8RB/CD128), IL-9, IL9R (CD129), IL-10, IL10RA (CD210), IL10RB (CDW210B), IL-11, ILI IRA, IL-12, IL-12A, IL-12B, IL-12RB1, IL-12RB2, IL-13, IL13RA1, IL13RA2, 1L14, 1L15, IL15RA, IL16, 1L17, IL17A, IL17B, IL170, IL17R, IL18, IL18BP, IL18R1, IL18RAP, IL19, ILIA, ILIB, ILIFIO, IL1F5, IL1F6, IL1F7, IL1F8, DL1F9, ILIHYI, ILIRI, IL1R2, ILIRAP, ILIRAPLI, IL1RAPL2, ILIRLI, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4R, IL6ST (glycoprotein 130), ILK, INHA, INHBA, INSL3, INSL4, IRAKI, IRAK2, ITGA1, ITGA2, ITGA3, ITGA6 (alpha 6 integrin), ITGAV, ITGB3, ITGB4 (beta 4 integrin), JAGI, JAKI, JAK3, JTB, JUN, K6HF, KAII, KDR, KIM-1, KITLG, KLF5 (GC Box BP), KLF6, KLKIO, KLK12, KLK13, KLK14, KLK15, KLK3, KLK4, KLK5, KLK6, KLK9, KRTI, KRT19 (Keratin 19), KRT2A, KRTHB6 (hair-specific type II keratin), LAMAS, LEP (leptin), Lingo-p75, Lingo-Troy, LPS, LRP5, LRP6, LTA (TNF-b), LTB, LTB4R (GPR16), LTB4R2, LTBR, MACMARCKS, MAG or Omgp, MAP2K7 (c-Jun), MCP-1, MDK, MIBI, midkine, MIF, MISRII, MJP-2, MK, MK167 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCH, NOX5, NPPB, NROBI, NROB2, NRIDI, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, peg-asparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-beta, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARB, RGSI, RGS13, RGS3, RNFI10 (ZNF144), Ron, R0B02, RXR, selectin, S100A2, S100A8, S100A9, SCGB 1D2 (lipophilin B), SCGB2A1 (mammaglobin 2), SCGB2A2 (mammaglobin 1), SCYEI (endothelial Monocyte-activating cytokine), SDF2, SERPENA1, SERPINA3, SERPINB5 (maspin), SERPINEI (PAI-I), SERPINFI, SHIP-1, SHIP-2, SHBI, SHB2, SHBG, SfcAZ, SLC2A2, SLC33A1, SLC43A1, SLIT2, SPPI, SPRRIB (SprI), ST6GAL1, STABI, STAT6, STEAP, STEAP2, SULF-1, Sulf-2, TB4R2, TBX21, TCPIO, TDGFI, TEK, TGFA, TGFBI, TGFBIII, TGFB2, TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-a, TNFAIP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (AP03L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, T0P2A (topoisomerase lia), TP53, TPMI, TPM2, TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

Engineered Fc Fusion Protein

In another embodiment, the engineered Fc polypeptide of the disclosure may be fused/covalently linked with a portion of any of the proteins in the preceding list or the Fc polypeptide may be fused/covalently linked with any receptor or ligand that specifically binds a protein in the preceding list. In one aspect, the invention encompasses an Fc polypeptide fusion protein comprising an engineered Fc polypeptide fused with a protein listed above, or a portion of the protein that binds its cognate ligand or receptor. For example, abatacept and betanercept are Fc fusion proteins comprising a portion of CTLA4 and TNFR2, respectively. The present invention therefore encompasses a fusion protein comprising a CTLA4-Fc fusion protein (abatacept; ORENCIA™) where the Fc is an engineered Fc polypeptide of the invention and CTLR4 is an extracellular domain of CTLA4 which is capable of binding its cognate antigens, e.g., CD80 (B7-1) and CD86 (B7-2). Likewise, the invention encompasses a fusion protein comprising a TNFR2-Fc fusion protein that binds TNFalpha (etanercept; ENBREL™) wherein the Fc is an engineered Fc polypeptide of the invention; an Fc fusion protein comprising the extracellular domain (ECD) of LFA3 (alefacept; AMEVIVE™) which binds CD2 wherein the Fc is an engineered Fc polypeptide of the invention; and an Fc fusion protein comprising a thrombopoietin receptor-binding peptide which binds thrombopoietin receptor (romiplostim) wherein the Fc is an engineered Fc polypeptide of the invention. The invention is in no way limited to these particular embodiments, but rather, encompasses a wide variety of Fc fusion proteins comprising any protein of interest fused with an engineered Fc polypeptide of the invention.

In one embodiment, the invention encompasses a fusion protein comprising an engineered Fc polypeptide fused with any of the following proteins, or a binding portion thereof: PDGFRalpha, PDGFRbeta, PDGF, VEGF, VEGF-A, VEGF-B, VEGF-C, VEGF-D, VEGF-E, VEGF-F, VEGFR-I, VEGFR-2, VEGFR-3, FGF, FGF2, HGF, KDR, flt-1, FLK-1, Ang-2, Ang-1, PLGF, CEA, CXCL13, Baff, IL-21, CCL21, TNF-alpha, CXCL12, SDF-I, bFGF, MAC-I, IL23pl9, FPR, IGFBP4, CXCR3, TLR4, CXCR2, EphA2, EphA4, EphrinB2, EGFR (ErbBI), HER2 (ErbB2 or pl85neu), HER3 (ErbB3), HER4 ErbB4 or tyro2), SCI, LRP5, LRP6, RAGE, Nav1.7, GLPI, RSV, RSV F protein, Influenza HA protein, Influenza NA protein, HMGBI, CD16, CD19, CD20, CD21, CD28, CD32, CD32b, CD64, CD79, CD22, ICAM-1, FGFR1, FGFR2, HDGF, EphB4, GITR, beta-amyloid, hMPV, PIV-1, PIV-2, OX40L, IGFBP3, cMet, PD-1, PLGF, Neprolysin, CTD, IL-18, IL-6, CXCL-13, IL-1R1, IL-15, IL-4R, IgE, PAI-I, NGF, EphA2, uPARt, DLL-4, αvβ5, αvβ6, α5β1, α3β1, interferon receptor type I and type II, CD 19, ICOS, IL-17, Factor II, Hsp90, IGF, IGF-I, IGF-II, CD 19, GM-CSFR, PIV-3, CMV, IL-13, IL-9, and EBV, TNF-alpha, TNF-beta, LT-alpha, CD30L, CD27L, CD40L, 4-1 BBL, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANKL (also referred to as TRANCE), TALL-1 (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CARI, HVEM (also known as ATAR or TR2), GITR, ZTNFR-5, NTR-1, TNFL1, CD30, LTBr, 4-1BB receptor and TR9.

In another embodiment, the Fc fusion comprising an engineered Fc polypeptide of the disclosure is capable of binding one or more proteins chosen from 5T4, ABL, ABCB5, ABCFI, ACVRI, ACVRIB, ACVR2, ACVR2B, ACVRLI, AD0RA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAGI, BAII, BCR, BCL2, BCL6, BDNF, BLNK, BLRI (MDR15), BlyS, BMPI, BMP2, BMP3B (GDFIO), BMP4, BMP6, BMP8, BMPRIA, BMPRIB, BMPR2, BPAGI (plectin), BRCAI, C19orflO (IL27w), C3, C4A, C5, C5R1, CANT1, CASP1I, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CCL3 (MIP-Ia), CCL4 (MIP-Ib), CCL5 (RANTES), CCL7 (MCP-3), CCL8 (mcp-2), CCNAI, CCNA2, CCNDI, CCNEI, CCNE2, CCR1 (CKR1/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TERI/Cκ R-L1), CCR9 (GPR-9-6), CCRLI (VSHKI), CCRL2 (L-CCR), CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18, CDH19, CDH20, CDH5, CDH7, CDH8, CDH9, CDK2, CDK3, CDK4, CDK5, CDK6, CDK7, CDK9, CDKNIA (p21WapI/CipI), CDKNIB (p27KipI), CDKNIC, CDKN2A (pI6INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8A1, COL1A1.COL4A3, COL6A1, CR2, Cripto, CRP, CSFI (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI (GROI), CXCLIO (IP-IO), CXCLII (1-TAC/IP-9), CXCL12 (SDFI), CXCL13, CXCL 14, CXCL 16, CXCL2 (GR02), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB2IP, DES, DKFZp451J0118, DNCLI, DPP4, E2F1, ECGFI5EDGI, EFNAI, EFNA3, EFNB2, EGF, EGFR, ELAC2, ENG, endoglin, ENOI, ENO2, ENO3, EPHAI, EPHA2, EPHA3, EPHA4, EPHA5, EPHA6, EPHA7, EPHA8, EPHA9, EPHA10, EPHBI, EPHB2, EPHB3, EPHB4, EPHB5, EPHB6, EPHRIN-A1, EPHRIN-A2, EPHRIN-A3, EPHRIN-A4, EPHRIN-A5, EPHRIN-A6, EPHRIN-B1, EPHRIN-B2, EPHRTN-B3, EPHB4, EPG, ERBB2 (Her-2), EREG, ERK8, Estrogen receptor, ESRI, ESR2, F3 (TF), FADD, farnesyltransferase, FasL, FASNf, FCER1A, FCER2, FCGR3A, FGF, FGFI (aFGF), FGFIO, FGFI 1, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FILI (EPSILON), FBLI (ZETA), FLJ12584, FLJ25530, FLRTI (fibronectin), FLTI, FLT-3, FOS, FOSLI (FRA-1), FY (DARC), GABRP (GABAa), GAGEBI, GAGECI, GALNAC4S-6ST, GATA3, GD2, GD3, GDF5, GFII, GGTI, GM-CSF, GNASI, GNRHI, GPR2 (CCRIO), GPR31, GPR44, GPR81 (FKSG80), GRCC10 (010), GRP, GSN (Gelsolin), GSTPI, HAVCR2, HDAC, HDAC4, HDAC5, HDAC7A, HDAC9, Hedgehog, HGF, HIFIA, HIPI, histamine and histamine receptors, HLA-A, HLA-DRA, HM74, HMOXI, HSP90, HUMCYT2A, ICEBERG, ICOSL, 1D2, IFN-a, IFNAI, IFNA2, IFNA4, IFNA5, EFNA6, BFNA7, IFNBI, IFNgamma, IFNWI, IGBPI, IGFI, IGFIR, IGF2, IGFBP2, IGFBP3, IGFBP6, DL-I, ILIO, ILIORA, ILIORB, IL-1, ILIRI (CD121a), ILIR2 (CD121b), IL-IRA, IL-2, IL2RA (CD25), IL2RB (CD122), IL2RG (CD132), IL-4, IL-4R(CD123), IL-5, IL5RA (CD125), IL3RB (CD131), IL-6, IL6RA (CD126), IR6RB (CD130), IL-7, IL7RA (CD127), IL-8, CXCRI (IL8RA), CXCR2 (IL8RB/CD128), IL-9, IL9R (CD129), IL-10, IL10RA (CD210), IL10RB (CDW210B), IL-11, ILI IRA, IL-12, IL-12A, IL-12B, IL-12RB1, IL-12RB2, IL-13, IL13RA1, IL13RA2, 1L14, 1L15, IL15RA, IL16, 1L17, IL17A, IL17B, IL17C, IL17R, IL18, IL18BP, IL18R1, IL18RAP, IL19, ILIA, ILIB, ILI-FIO, IL1F5, IL1F6, IL1F7, IL1F8, DL1F9, ILIHYI, ILIRI, IL1R2, ILIRAP, ILIRAPLI, IL1RAPL2, ILIRLI, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4R, IL6ST (glycoprotein 130), ILK, INHA, INHBA, INSL3, INSL4, IRAKI, IRAK2, ITGAI, ITGA2, ITGA3, ITGA6 (<x6 integrin), ITGAV, ITGB3, ITGB4 (beta 4 integrin), JAGI, JAKI, JAK3, JTB, JUN, K6HF, KAII, KDR, KIM-1, KITLG, KLF5 (GC Box BP), KLF6, KLKIO, KLK12, KLK13, KLK14, KLK15, KLK3, KLK4, KLK5, KLK6, KLK9, KRTI, KRT19 (Keratin 19), KRT2A, KRTHB6 (hair-specific type II keratin), LAMAS, LEP (leptin), Lingo-p75, Lingo-Troy, LPS, LRP5, LRP6, LTA (TNF-b), LTB, LTB4R (GPR16), LTB4R2, LTBR, MACMARCKS, MAG or Omgp, MAP2K7 (c-Jun), MCP-1, MDK, MIBI, midkine, MIF, MISRII, MJP-2, MK, MKI67 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCH, NOX5, NPPB, NROBI, NROB2, NRIDI, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, peg-asparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-beta, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARB, RGSI, RGS13, RGS3, RNFI10 (ZNF144), Ron, R0B02, RXR, selectin, S100A2, S100A8, S100A9, SCGB 1D2 (lipophilin B), SCGB2A1 (mammaglobin 2), SCGB2A2 (mammaglobin 1), SCYEI (endothelial Monocyte-activating cytokine), SDF2, SERPENA1, SERPINA3, SERPINB5 (maspin), SERPINEI (PAI-I), SERPINFI, SHIP-1, SHIP-2, SHBI, SHB2, SHBG, SfcAZ, SLC2A2, SLC33A1, SLC43A1, SLIT2, SPPI, SPRRIB (SprI), ST6GAL1, STABI, STATE, STEAP, STEAP2, SULF-1, Sulf-2, TB4R2, TBX21, TCPIO, TDGFI, TEK, TGFA, TGFBI, TGFBIII, TGFB2, TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-a, TNFAIP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (AP03L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, T0P2A (topoisomerase lia), TP53, TPMI, TPM2, TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

Further Modification of the Fc Region

The disclosure also provides an engineered Fc polypeptide that may be further modified. It is known that variants of the Fc region, e.g., amino acid substitutions, insertions, and/or additions and/or deletions, enhance or diminish effector function. See, e.g., Presta et al, 2002, Biochem. Soc. Trans. 30:487-490; Strohl, 2009, Curr. Opin. Biotechnol. 20(6):685-691; U.S. Pat. Nos. 5,624,821, 5,648,260, 5,885,573, 6,737,056, 7,317,091; PCT publication Nos. WO 99/58572, WO 00/42072, WO 04/029207, WO 2006/105338, WO 2008/022152, WO 2008/150494, WO 2010/033736; U.S. Patent Application Publication Nos. 2004/0132101, 2006/0024298, 2006/0121032, 2006/0235208, 2007/0148170; Armour et al., 1999, Eur. J. Immunol. 29(8): 2613-2624 (reduced ADCC and CDC); Shields et al., 2001, J. Biol. Chem. 276(9):6591-6604 (reduced ADCC and CDC); Idusogie et al., 2000, J. Immunol. 164(8):4178-4184 (increased ADCC and CDC); Steurer et al., 1995, J. Immunol. 155(3):1165-1174 (reduced ADCC and CDC); Idusogie et al., 2001, J. Immunol. 166(4):2571-2575 (increased ADCC and CDC); Lazar et al., 2006, Proc. Natl. Acad. Sci. USA 103(11): 4005-4010 (increased ADCC); Ryan et al., 2007, Mol. Cancer. Ther., 6: 3009-3018 (increased ADCC); Richards et al., 2008, Mol. Cancer Ther. 7(8):2517-2527.

In one embodiment, the engineered Fc polypeptide exhibits a similar level of inducing effector function as compared to the native wild-type Fc polypeptide. In another embodiment, the engineered Fc polypeptide exhibits a higher induction of effector function as compared to the native Fc. In another embodiment, the engineered Fc polypeptide exhibits lower induction of effector function as compared to the native Fc. In another embodiment, the engineered Fc polypeptide exhibits higher induction of ADCC as compared to the native Fc. In another embodiment, the engineered Fc polypeptide exhibits lower induction of ADCC as compared to the native Fc. In another embodiment, the engineered Fc polypeptide exhibits higher induction of CDC as compared to the native Fc. In another embodiment, the engineered Fc polypeptide exhibits lower induction of CDC as compared to the native Fc. Specific embodiments of engineered Fc polypeptides further modified to affect effector function are detailed infra.

The present disclosure encompasses engineered Fc proteins which further comprise altered binding properties for an Fc ligand (e.g., an Fc receptor, Clq, and the like) relative to a reference molecule (e.g., a protein having the same amino acid sequence except having a native wild type Fc polypeptide). Examples of binding properties include but are not limited to, binding specificity, equilibrium dissociation constant ($K_D$), dissociation and association rates ($k_{off}$ and $k_{on}$, respectively), binding affinity and/or avidity. It is generally understood that a binding molecule (e.g., a Fc variant protein such as an antibody) with a low $K_D$ may be preferable to a binding molecule with a high $K_D$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc polypeptide for its ligand may be determined by a variety of in vitro assay methods (biochemical or immunological based assays) known in the art for determining Fc-FcγR interactions, i.e., specific binding of an Fc polypeptide to an FcγR including but not limited to, equilibrium methods (e.g., enzyme-linked immunoabsorbent assay (ELISA), or radioimmunoassay (RIA)), or kinetics (e.g., BIACORE® analysis, OCTET®, FortéBio, Menlo Park, Calif.), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th ed. (Lippincott-Raven, Philadelphia, 1999), which focuses on antibody-immunogen interactions.

In one embodiment, the engineered Fc polypeptide comprises an additional mutation and exhibits enhanced binding to one or more Fc ligands relative to a comparable molecule engineered Fc without the additional mutation compared with wild type unmodified Fc. In another embodiment, the engineered Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than a comparable engineered Fc without the additional mutation. In a specific embodiment, the engineered Fc variant protein has enhanced binding to an Fc receptor. In another specific embodiment, the Fc variant protein has enhanced binding to the Fc receptor FcγRIIIA. In a further specific embodiment, the Fc variant protein has enhanced binding to the Fc receptor FcγRIIB. In still another specific embodiment, the Fc variant protein has enhanced binding to the Fc receptor FcRn. In yet another specific embodiment, the Fc variant protein has enhanced binding to Clq relative to a comparable Fc molecule lacking the mutations (e.g., wild type parental Fc).

The ability of any particular engineered Fc variant protein to mediate lysis of the target cell by ADCC can be assayed. To assess ADCC activity an engineered Fc variant protein of interest is added to target cells in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, J. Immunol. Methods 79(2):277-282; Bruggemann et al., 1987, J. Exp. Med. 166:1351-1361; Wilkinson et al., 2001, J. Immunol Methods 258:183-191; Patel et al., 1995, J. Immunol. Methods 184:29-38. ADCC activity of the engineered Fc variant protein of interest may also be assessed in vivo, e.g., in an animal model such as that disclosed in Clynes et al., 1998, Proc. Natl. Acad. Sci. USA 95:652-656.

In one embodiment, an engineered Fc variant protein has enhanced ADCC activity relative to a comparable molecule (e.g., a wild type natural Fc without any mutations and/or an engineered Fc without any additional modifications). In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

In one embodiment, an engineered Fc variant protein has reduced ADCC activity relative to a comparable molecule (e.g., a wild type natural Fc without any mutations and/or an engineered Fc without any additional modifications). In a specific embodiment, an engineered Fc variant protein has ADCC activity that is at least 2 fold, or at least 3 fold, or at least 5 fold or at least 10 fold or at least 50 fold or at least 100 fold lower than that of a comparable molecule. In another specific embodiment, an engineered Fc variant protein has reduced binding to the Fc receptor FcγRIIIA and has reduced ADCC activity relative to a comparable molecule. In other embodiments, the engineered Fc variant protein has both reduced ADCC activity and enhanced serum half life relative to a comparable molecule.

In one embodiment, an engineered Fc variant protein has enhanced CDC activity relative to a comparable molecule (e.g., a wild type natural Fc without any mutations and/or an engineered Fc without any additional modifications). In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the engineered Fc variant protein has both enhanced CDC activity and enhanced serum half life relative to a comparable molecule. In one embodiment, the engineered Fc variant protein has reduced binding to one or more Fc ligand relative to a comparable molecule. In another embodiment, the engineered Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold lower than that of a comparable molecule. In a specific embodiment, the engineered Fc variant protein has reduced binding to an Fc receptor. In another specific embodiment, the engineered Fc variant protein has reduced binding to the Fc receptor FcγRIIIA. In a further specific embodiment, an engineered Fc variant described herein has an affinity for the Fc receptor FcγRIIIA that is at least about 5 fold lower than that of a comparable molecule, wherein said engineered Fc variant has an affinity for the Fc receptor FcγRIIB that is within about 2 fold of that of a comparable molecule. In still another specific embodiment, the engineered Fc variant protein has reduced binding to the Fc receptor FcRn. In yet another specific embodiment, the engineered Fc variant protein has reduced binding to C1q relative to a comparable molecule.

In addition to modification of the amino acid sequence, it is also known that the glycosylation of an Fc polypeptide can be modified to increase or decrease effector function (see for examples, Umaña et al., 1999, Nat. Biotechnol. 17:176-180; Davies et al., 2001, Biotechnol. Bioeng. 74:288-294; Shields et al., 2002, J. Biol. Chem. 277:26733-26740; Shinkawa et al., 2003, J. Biol. Chem. 278:3466-3473; U.S. Pat. No. 6,602,684; U.S. Patent Application Publication No. 2003/0157108; U.S. Patent Application Publication No. 2003/0003097; International Patent Publication Nos. WO 00/61739A1; WO 01/292246A1; WO 02/311140A1; and WO 02/30954A1; Potillegent™ technology (Biowa, Inc. Princeton, N.J.); GlycoMAb™ glycosylation engineering technology (GLYCART biotechnology AG, Zurich, Switzerland).

Accordingly, in one embodiment, the engineered Fc polypeptides of antibodies and fusion proteins of the disclosure may comprise altered glycosylation of amino acid residues. In another embodiment, the altered glycosylation of the amino acid residues results in decreased effector function. In another embodiment, the altered glycosylation of the amino acid residues results in increased effector function. In a specific embodiment, the engineered Fc polypeptide has reduced fucosylation. In another embodiment, the engineered Fc polypeptide is afucosylated (see, e.g., U.S. Patent Application Publication No. 2005/0226867).

In other embodiments, where the engineered Fc polypeptide comprises a C-terminal lysine (K) amino acid residue (e.g., human IgG1 heavy chain comprises a terminal lysine), one skilled in the art would understand that the lysine residue may be clipped resulting in a fusion protein lacking the C-terminal lysine residue. Thus, in some embodiments, the antibody or the Fc fusion protein comprising an engineered Fc polypeptide comprises a polypeptide where the terminal lysine otherwise present is not present.

In other embodiments, the engineered Fc polypeptide of the disclosure comprises a substitution of the naturally occurring amino acid at position 297 wherein said substitution detectably reduces and/or abrogates glycosylation at position 297. In specific embodiments, the engineered Fc polypeptide of the disclosure comprises a substitution of cysteine for asparagine at position 297 of the heavy chain of the antibody. In yet other embodiments, the disclosure provides antibodies lacking glycosylation at position 297 of the heavy chain of the antibody. In each of these, the numbering system of the constant region is that of the EU index as set forth in Kabat.

Addition of sialic acid to the oligosaccharides on IgG molecules enhances their anti-inflammatory activity and alters their cytotoxicity (Keneko et al., 2006, Science 313: 670-673, Scallon et al., 2007, Mol. Immunol. 44(7):1524-1534). Thus, the efficacy of antibody therapeutics may be optimized by selection of a glycoform that is suited to the intended application. The two oligosaccharide chains interposed between the two CH2 domains of antibodies are involved in the binding of the Fc polypeptide to its receptors. The studies referenced above demonstrate that IgG molecules with increased sialylation have anti-inflammatory properties whereas IgG molecules with reduced sialylation have increased immunostimulatory properties. Therefore, an antibody therapeutic comprising an engineered Fc polypeptide of the disclosure can be modified with an appropriate sialylation profile for a particular application. Methods for modulating the sialylation state of antibodies are presented in WO2007/005786 and WO2007/117505, each of which is incorporated by reference herein in its entirety for all purposes.

It is also known in the art that the Fc region can be modified to increase the half-lives of proteins. The increase in half-life allows for the reduction in amount of drug given to a patient as well as reducing the frequency of administration. Accordingly, antibodies of the disclosure with increased half-lives may be generated by modifying (for example, substituting, deleting, or adding) amino acid residues identified as involved in the interaction between the Fc and the FcRn receptor (see, for examples, PCT publication Nos. WO 97/34631 and WO 02/060919, Hinton et al., 2004, J. Biol. Chem. 279(8):6213-6216, Vaccaro et al., 2005, Nat. Biotechnol. 23(10):1283-1288, each of which are incorporated by reference in their entireties).

In addition, the half-life of antibodies and fusion proteins of the disclosure may be increase by conjugation to a biopolymer (e.g., polyethylene glycol (PEG), albumin, hydroxyethyl starch (HES), hydroxyalkyl starch, XTEN (Amunix, Inc.), by techniques widely utilized in the art. In some embodiments the engineered Fc polypeptides of antibodies of the disclosure comprise an increase in half-life of about 5 percent, about 10 percent, about 15 percent, about 20 percent, about 25 percent, about 30 percent, about 35 percent, about 40 percent, about 45 percent, about 50 percent, about 55 percent, about 60 percent, about 65 percent, about 70 percent, about 75 percent, about 80 percent, about 85 percent, about 90 percent, about 95 percent, about 100 percent, about 125 percent, about 150 percent or more as compared to a reference wild type unmodified Fc polypeptide. In some embodiments, the engineered Fc polypeptides of antibodies of the disclosure comprise an increase in half-life of about 2 fold, about 3 fold, about 4 fold, about 5 fold, about 10 fold, about 20 fold, about 50 fold or more as compared to an unmodified reference Fc polypeptide.

In an alternate embodiment, the engineered Fc polypeptides of antibodies and Fc fusion proteins of the disclosure comprise a decrease in half-life. In some embodiments the engineered Fc polypeptides of antibodies of the disclosure comprise a decrease in half-life of about 5 percent, about 10 percent, about 15 percent, about 20 percent, about 25 percent, about 30 percent, about 35 percent, about 40 percent, about 45 percent, about 50 percent, about 55 percent, about 60 percent, about 65 percent, about 70 percent, about 75 percent, about 80 percent, about 85 percent, about 90 percent, about 95 percent, about 100 percent, about 125 percent, about 150 percent or more as compared to a reference unmodified Fc polypeptide. In some embodiments, the engineered Fc polypeptides of antibodies of the disclosure comprise a decrease in half-life of about 2 fold, about 3 fold, about 4 fold, about 5 fold, about 10 fold, about 20 fold, about 50 fold or more as compared to an unmodified reference Fc polypeptide.

In one embodiment, the present disclosure provides Fc variants, wherein the engineered Fc polypeptide further comprises a non naturally occurring amino acid residue in addition to or other than, the substitutions disclosed above at one or more positions chosen from 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the engineered Fc polypeptide may comprise an additional non-naturally occurring amino acid residue at additional and/or alternative positions known to one skilled in the art (see, e.g., U.S. Pat. Nos. 5,624,821, 6,277,375, 6,737,056, 7,217,797, U.S. Patent Publication No. US2007/0135620; PCT Patent Publication Nos. WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114, each of which is incorporated by reference herein in its entirety).

In a specific embodiment, the present disclosure provides an engineered Fc variant antibody, wherein the engineered Fc polypeptide comprises at least one modification e.g., amino acid substitutions, amino acid insertions, amino acid deletions, amino acid additions) at one or more positions chosen from 234, 235, 237, and 331. In one embodiment, the non-naturally occurring amino acids are chosen from 234F, 235F, 235Y, and 331S. In one embodiment, the non-naturally occurring amino acids are chosen from 234A, 235A, and 237A. In another specific embodiment, the present disclosure provides an engineered Fc variant, wherein the Fc polypeptide comprises at least one non-naturally occurring amino acid at one or more positions chosen from 239, 330 and 332. In one embodiment, the non-naturally occurring amino acids are selected from the group chosen from 239D, 330L and 332E.

In a specific embodiment, the present disclosure provides an engineered Fc variant antibody, wherein the Fc polypeptide comprises at least one non-naturally occurring amino acid at one or more positions chosen from 252, 254, and 256. In one embodiment, the non-naturally occurring amino acids are selected from the group chosen from 252Y, 254T and 256E (referred to as the "YTE modification"), as described in Dall'Acqua et al., 2006, J. Biol. Chem. 281:23514-23524, and in U.S. Pat. No. 7,083,784, both of which are incorporated herein by reference in their entireties.

In other embodiments, the engineered Fc variant comprises an engineered Fc polypeptide comprising at least one amino acid substitution selected from a substitution at position 246, 249, 254, 265, 267, 270, 276, 278, 283, 284, 287, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 using the EU index as set forth in Kabat (supra), and further comprising at least one non-naturally occurring amino acid at one or more positions chosen from 428 and 434. In one embodiment, the additional amino acid substitutions comprise 428L and 434S as described in International Patent Publication No. WO 2009/086320.

In other embodiments, engineered variant antibodies of the disclosure may further comprise at least one or more non-naturally occurring cysteine amino acids in the 131-139 region of the CH1 domain of an antibody. In some embodiments, the engineered antibodies of the disclosure comprise at least one substitution at positions selected from: 131, 132, 133, 134, 135, 136, 137, 138, and 139 of the CH1 domain of an antibody, wherein the numbering system of the constant region is that of the EU index as set forth in Kabat.

Methods of Producing Antibodies

The engineered constant domain (Fc, Cκ, and Cλ) polypeptide of the disclosure and an antibody, Fab, and F(ab')₂ comprising the engineered polypeptide may be produced by any method known in the art for the synthesis of antibodies, Fab and F(ab')₂, in particular, by chemical synthesis or preferably, by recombinant expression techniques.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a target antigen (either the full length protein or a domain thereof, e.g., the extracellular domain or the ligand binding domain) and once an immune response is detected, e.g., antibodies specific for the target antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Hybridoma clones are then assayed by methods known in the art for cells that secrete antibodies capable of binding a polypeptide of the disclosure. Ascites fluid, which generally contains high levels of antibodies, can be generated by immunizing mice with positive hybridoma clones.

Accordingly, monoclonal antibodies can be generated by culturing a hybridoma cell secreting an antibody of the disclosure wherein, preferably, the hybridoma is generated by fusing splenocytes isolated from a mouse immunized with a target antigen with myeloma cells and then screening the hybridomas resulting from the fusion for hybridoma clones that secrete an antibody able to bind to a specific target antigen.

Antibody fragments which recognize specific target antigen epitopes may be generated by any technique known to those of skill in the art. For example, Fab and F(ab')2 fragments of the disclosure may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present disclosure can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., pCANTAB6 or pComb3 HSS). The vector is electroporated in E. coli and the E. coli is infected with helper phage. Phage used in these methods are typically filamentous phage including fd and M 13 and the VH and VL domains are usually recombinantly fused to either the phage gene III or gene VIII. Phage expressing an antigen binding domain that binds to an epitope of interest can be selected or identified with antigen, e.g., using labeled antigen or antigen bound or captured to a solid surface or bead. Examples of phage display methods that can be used to make the antibodies of the present disclosure include those disclosed in Brinkman et al., 1995, J. Immunol. Methods 182:41-50; Ames et al., 1995, J. Immunol. Methods 184:177; Kettleborough et al., 1994, Eur. J. Immunol. 24:952-958; Persic et al., 1997, Gene 187:9; Burton et al., 1994, Advances in Immunology 57:191-280; International Publication Nos. WO 92/01047, WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al, 1992, BioTechniques 12:864; Sawai et al., 1995, AJRI 34-.26; and Better et al., 1988, Science 240:1041 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 1 constant region, and the PCR amplified VL domains can be cloned into vectors expressing a VL constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the disclosure. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, Science 229:1202; Oi et al, 1986, BioTechniques 4:214; Gillies et al., 1989, J. Immunol. Methods 125:191-202; and U.S. Pat. Nos. 6,311,415, 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 0 239 400; International Publication No. WO 91/09967; and U.S. Pat. Nos. 5,225,539, 5,530,101, and 5,585,089), veneering or resurfacing (EP 0 592 106; EP 0 519 596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

Framework residues in the framework regions are typically substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, Nature 332:323, which are incorporated herein by reference in their entireties).

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 (for IgA and IgM isotypes) regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically human IgG1. Where such cytotoxic activity is not desirable, the constant domain may be of the human IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75 percent of the humanized antibody residues will correspond to those of the parental framework region (FR) and CDR sequences, more often 90 percent, or even greater than 95 percent.

Humanized antibodies can be produced using variety of techniques known in the art, including but not limited to, CDR-grafting (European Patent No. EP 0 239 400; International Publication No. WO 91/09967; and U.S. Pat. Nos. 5,225,539, 5,530,101, and 5,585,089), veneering or resurfacing (European Patent Nos. EP 0 592 106 and EP 0 519 596; Padlan, 1991, Molecular Immunology 28(4/5):489-498; Studnicka et al., 1994, Protein Engineering 7(6):805-814; and Roguska et al., 1994, Proc. Natl. Acad. Sci. USA 91:969-973), chain shuffling (U.S. Pat. No. 5,565,332), and techniques disclosed in, e.g., U.S. Pat. Nos. 6,407,213, 5,766,886, 5,585,089, International Publication No. WO 93/7105, Tan et al., 2002, J. Immunol. 169: 1119-25, Caldas et al., 2000, Protein Eng. 13:353-360, Morea et al., 2000, Methods 20:267-279, Baca et al., 1997, J. Biol. Chem. 272:10678-10684, Roguska et al., 1996, Protein Eng. 9:895-904, Couto et al., 1995, Cancer Res. 55(23 Supp):5973s-5977s, Couto et al., 1995, Cancer Res. 55:1717-1722, Sandhu, 1994, Gene 150:409-410, Pedersen et al., 1994, J. Mol. Biol. 235:959-973, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.).

Further, the antibodies of the disclosure can, in turn, be utilized to generate anti-idiotype antibodies using techniques well known to those skilled in the art. (See, e.g., Greenspan and Bona, 1989, FASEB J. 7:437-444; and Nissinoff, 1991, J. Immunol. 147:2429-2438). The disclosure provides methods employing the use of polynucleotides comprising a nucleotide sequence encoding an antibody of the disclosure or a fragment thereof.

Additionally, various publications describe methods for obtaining physiologically active molecules whose half-lives are modified either by introducing an FcRn-binding polypeptide into the molecules (WO 97/43316; U.S. Pat. Nos. 5,869,046; 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039). Specific techniques and methods of increasing half-life of physiologically active molecules can also be found in U.S. Pat. No. 7,083,784, which is hereby incorporated by reference for all purposes. Specifically, it is contemplated that the antibodies of the disclosure comprise an Fc polypeptide comprising amino acid residue mutations (as numbered by the EU index as set forth in Kabat): M252Y/S254T/T256E or H433K/N434F/Y436H.

Polynucleotides Encoding an Antibody

The polynucleotides may be obtained, and the nucleotide sequence of the polynucleotides determined, by any method known in the art. Since the amino acid sequences of the antibodies are known, nucleotide sequences encoding these antibodies can be determined using methods well known in the art, i.e., nucleotide codons known to encode particular amino acids are assembled in such a way to generate a nucleic acid that encodes the antibody or fragment thereof of the disclosure. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al, 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley and Sons, N.Y., which are both incorporated by reference herein in their entireties), to generate antibodies having a different amino acid sequence, for example to create amino acid substitutions, deletions, and/or insertions.

In one embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to 5T4, Her2 or VEGF. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibodies lacking one or more intrachain disulfide bonds. Other alterations to the polynucleotide are encompassed by the present disclosure and are within the skill of the art.

Recombinant Expression of Engineered Constant Domain (Fc, Cκ and Cλ) Polypeptides, and Antibodies Comprising the Polypeptides Recombinant expression of an engineered antibody, including Fab and F(ab')$_2$, comprising an engineered constant domain polypeptide of the disclosure, or a derivative, analog or fragment thereof, requires construction of an expression vector containing a polynucleotide that encodes the polypeptide. Once a polynucleotide encoding an engineered antibody or an engineered heavy or light chain of an antibody, or portion thereof, of the disclosure has been obtained, the vector for the production of the antibody or engineered polypeptide comprising the same may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

The disclosure, thus, provides replicable vectors comprising a nucleotide sequence encoding an antibody of the disclosure, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains, wherein the heavy chain comprises an engineered Fc region and/or the light chain comprises an engineered Cκ region of the invention.

The expression vector is transferred to a host cell by conventional techniques (transfection and transduction) and the host cells are then cultured by conventional techniques to produce an antibody of the disclosure. Thus, the disclosure includes host cells containing a polynucleotide encoding an engineered Fc polypeptide, an engineered Cκ or Cλ polypeptide, or an antibody, Fab and F(ab')$_2$ comprising the same, or fragments thereof, or a heavy or light chain thereof, or portion thereof, or a single chain antibody of the disclosure, or a fusion protein comprising an engineered Fc polypeptide of the disclosure operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies and engineered polypeptides of the disclosure (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody of the disclosure in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody, are used for the expression of engineered polypeptides and/or a recombinant antibody comprising the same.

For example, mammalian cells such as Chinese hamster ovary cells (CHO), in conjunction with a vector comprising the major intermediate early gene promoter element from human cytomegalovirus is an effective expression system for antibodies (Foecking et al., 1986, Gene 45: 101; and Cockett et al., 1990, BioTechnology 8:2).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pFN vectors (Inouye and Inouye, 1985, Nucleic Acids Res. 13:3101-3109; Van Heeke and Schuster, 1989, J. Biol. Chem. 24:5503-5509); and the like. PGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into nonessential regions of the virus and placed under control of an AcNPV promoter.

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing the antibody in infected hosts (e.g., see Logan and Shenk, 1984, Proc. Natl. Acad. Sci. USA 81:6355-6359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT2O, NS1 and T47D, NS0 (a murine myeloma cell line that does not endogenously produce any immunoglobulin chains), CRL7030 and HsS78Bst cells.

In one embodiment the antibodies and fusion proteins comprising an engineered Fc polypeptide of the disclosure and/or an engineered Cκ or Cλ polypeptide of the disclosure are produced according to the methods disclosed in U.S. Pat. No. 7,521,541 and U.S. Patent Application Publication No. 2009/0175865, which are incorporated by reference in their entireties.

For long-term, high-yield production of recombinant proteins, stable expression is preferred. For example, cell lines which stably express the antibody may be engineered.

Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody. Such engineered cell lines may be particularly useful in screening and evaluation of compositions that interact directly or indirectly with the antibody.

A number of selection systems may be used, including but not limited to, the herpes simplex virus thymidine kinase (Wigler et al, 1977, Cell 11:223), glutamine synthetase, hypoxanthine guanine phosphoribosyltransferase (Szybalska and Szybalski, 1992, Proc. Natl. Acad. Sci. USA 48:202), and adenine phosphoribosyltransferase (Lowy et al., 1980, Cell 22:8-17) genes can be employed in tk−, gs−, hgprt− or aprt− cells, respectively. Also, antimetabolite resistance can be used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan and Berg, 1981, PNAS 78:2072); neo, which confers resistance to the aminoglycoside G-418 (Wu and Wu, 1991, Biotherapy 3:87; Tolstoshev, 1993, Ann. Rev. Pharmacol. Toxicol. 32:573; Mulligan, 1993, Science 260:926; and Morgan and Anderson, 1993, Ann. Rev. Biochem. 62:191; May, 1993, TIB TECH 11:155); and hygro, which confers resistance to hygromycin (Santerre et al., 1984, Gene 30: 147), may be used for selection purposes. Methods commonly known in the art of recombinant DNA technology may be routinely applied to select the desired recombinant clone, and such methods are described, for example, in Ausubel et al. (eds.), Current Protocols in Molecular Biology, John Wiley and Sons, N.Y. (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley and Sons, N.Y. (1994); Colberre-Garapin et al., 1981, J Mol. Biol. 150: 1, which are incorporated by reference herein in their entireties.

The host cell may be co-transfected with two expression vectors of the disclosure, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, PNAS 77:2197). The coding sequences for the heavy and light chains may comprise cDNA or genomic DNA.

Once an engineered Fc polypeptide, or antibody, or antigen-binding portion thereof, or Fc fusion protein comprising the engineered Fc polypeptide, or an engineered Cκ or Cλ polypeptide has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the proteins of the present disclosure or fragments thereof may be fused to heterologous polypeptide sequences described herein or otherwise known in the art to facilitate purification.

Antibody Conjugates and Fusion Proteins

The present disclosure encompasses the use of engineered antibody constant regions, e.g., Fc and/or Cγ, Cκ, or CA, and antibodies comprising the same (i.e., "engineered antibody"), which are recombinantly fused or chemically conjugated (including both covalent and non-covalent conjugations) to a heterologous agent. The disclosure also encompasses engineered Fab and F(ab')2 comprising an engineered constant domain region, e.g., Fc and/or Cγ, Cκ, or Cλ. Antibody immunoconjugates are described in, among many others, Francisco et al., 2003, Blood 102:1458-1465, Doronina et al., 2008, Bioconjugate Chem. 19:1960-1963, and Dosio et al., 2011, Toxins 3:848-883. Suitable substances for attachment to the engineered antibodies of the disclosure include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semisolid matrixes and combinations thereof.

Methods for conjugation or covalently attaching another substance to an antibody are well known in the art. The fusion or conjugation does not necessarily need to be direct, but may occur through linker sequences. Engineered antibodies fused or conjugated to heterologous agents may be used in vivo to detect, treat, manage, or monitor the progression of a disorder using methods known in the art. See, e.g., International Publication WO 93/21232; EP 0 439 095; Naramura et al, 1994, Immunol. Lett. 39:91-99; U.S. Pat. No. 5,474,981; Gillies et al., 1992, Proc. Natl. Acad. Sci. USA 89:1428-1432; and Fell et al., 1991, J. Immunol. 146:2446-2452, which are incorporated by reference in their entireties. In some embodiments, the disorder to be detected, treated, managed, or monitored is an autoimmune, inflammatory, infectious disease or cancer related disorder. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 0 307 434; EP 0 367 166; International Publication Nos. WO 96/04388 and WO 91/06570; Ashkenazi et al., 1991, Proc. Natl. Acad. Sci. USA 88:10535-10539; Zheng et al., 1995, J. Immunol. 154:5590-5600; and Vil et al., 1992, Proc. Natl. Acad. Sci. USA 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of engineered antibodies of the disclosure (e.g., antibodies with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16:76; Hansson, et al., 1999, J. Mol. Biol. 287:265; and Lorenzo and Blasco, 1998, BioTechniques 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment may be recombined with one or more components, motifs, sections, parts, domains, fragments, etc. of one or more heterologous agents.

In certain embodiments, the engineered Fc regions, Cκ regions, and Cλ regions, or the antibodies of the disclosure comprising them, are conjugated to a solid support. Antibodies may be conjugated to a solid support as part of the screening and/or purification and/or manufacturing process. Alternatively antibodies of the disclosure may be conjugated to a solid support as part of a diagnostic method or composition. A solid support suitable for use in the present disclosure is typically substantially insoluble in liquid phases. A large number of supports are available and are known to one of ordinary skill in the art. Thus, solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports In some embodiments, the solid support may include a reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the engineered antibodies of the disclosure.

In one embodiment, engineered antibodies of the present disclosure or fragments or variants thereof are conjugated or fused to a marker sequence, such as a peptide, to facilitate purification. In certain embodiments, the marker amino acid sequence is a hexa-histidine peptide, such as the tag provided in a pQE vector (QIAGEN, Inc., Chatsworth, Calif.), among others, many of which are commercially available. As described in Gentz et al, 1989, Proc. Natl. Acad. Sci. USA 86:821, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, engineered antibodies of the present disclosure thereof are conjugated or fused to a diagnostic or detectable agent. Such engineered antibodies can be useful for monitoring or prognosing the development or progression of a disorder (such as, but not limited to cancer) as part of a clinical testing procedure, such as determining the efficacy of a particular therapy.

Such diagnosis and detection can accomplished by fusing or site-specifically conjugating the engineered antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, bioluminescent materials, such as but not limited to, luciferase, luciferin, and aequorin; radioactive materials, such as but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho). indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{173}$Yb), yttrium ($^{90}$Y), zinc ($^{65}$Zn); positron emitting metals using various positron emission tomographies, and nonradioactive paramagnetic metal ions.

In other embodiments, engineered antibodies of the present disclosure are conjugated to a therapeutic agent such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics {e.g., dactinomycin (formerly actinomycin), bleomycin, mithramycin, and anthramycin (AMC)), and anti-mitotic agents (e.g., vincristine and vinblastine). Chemical toxins can also be taken from the group chosen from duocarmycin (U.S. Pat. Nos. 5,703,080; 4,923, 990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (U.S. Pat. No. 4,675,187), Melphalan, and other related nitrogen mustards.

In one embodiment, the cytotoxic agent is chosen from an enediyne, a lexitropsin, a duocarmycin, a taxane, a puromycin, a dolastatin, a maytansinoid, and a vinca alkaloid. In other embodiments, the cytotoxic agent is paclitaxel, docetaxel, CC-1065, SN-38, topotecan, morpholino-doxorubicin, rhizoxin, cyanomorpholino-doxorubicin, dolastatin-10, echinomycin, combretastatin, calicheamicin, maytansine, drug maytansinoid 1 (DM-1), an auristatin or other dolastatin derivatives, such as auristatin E or auristatin F, AEB, AEVB, AEFP, MMAD (monomethylauristatin D), MMAE (monomethylauristatin E), MMAF (monomethylauristatin F), eleutherobin or netropsin. The synthesis and structure of auristatin E, also known in the art as dolastatin-10, and its derivatives are described in U.S. Patent Application Publ. Nos. 2003/0083263 and 2005/0009751; International Patent Application No.: PCT/US02/13435, U.S. Pat. Nos. 6,323, 315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, all of which are incorporated by reference in their entireties herein.

In some embodiments, the cytotoxic agent is a novel cytotoxin disclosed in International Patent Application No. PCT/IB2012/056224 filed Nov. 7, 2012, which is incorporated by reference as if set forth in its entirety herein, Such novel cytotoxic agents include, but are not limited to, 0101 (#54), 3377 (#115), and 8261 (#69) as described in the application which further discloses their synthesis.

In certain embodiments, the cytoxic agent is maytansine or maytansinoids, and derivatives thereof, wherein antibodies (full length or fragments) of the disclosure comprising an engineered constant region (Cγ, Cλ, Cκ, including an Fc), are site-specifically conjugated at the engineered amino acid substitution to one or more maytansinoid molecules. Maytansinoids are mitotic inhibitors which act by inhibiting tubulin polymerization. Maytansine was first isolated from the east African shrub *Maytenus serrata* (U.S. Pat. No. 3,896,111), and additional maytansinoids were later isolated from other certain microbes, e.g., maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Immunoconjugates comprising maytansinoids non-specifically conjugated to an antibody and their therapeutic use are disclosed, for example, in U.S. Pat. Nos. 5,208,020, 5,416,064 and European Patent EP 0 425 235; Liu et al., 1996, Proc. Natl. Acad. Sci. USA 93:8618-8623 (immunoconjugates comprising DM1 non-specifically conjugated to mAb C242 targeting human colorectal cancer); Chari et al., 1992, Cancer Research 52: 127-131 (maytansinoid non-specifically conjugated to murine anti-colon cancer cell mAb A7 or murine mAb TA.1 anti-HER-2). Thus, the present disclosure contemplates engineered antibodies site-specifically conjugated to maytansinoid agents for therapeutic treatment of certain cancers.

In a specific embodiment, the drug is a maytansinoid. In a more specific embodiment, the drug is maytansine. Further, in a specific embodiment, the cytotoxic or cytostatic agent is DM-1 (ImmunoGen, Inc.; see also Chari et al., 1992, Cancer Res 52:127-131).

In other embodiments, the cytotoxic agent of an engineered antibody conjugate of the disclosure is an anti-tubulin agent. Anti-tubulin agents are a well established class of cancer therapy compounds. Examples of anti-tubulin agents include, but are not limited to, taxanes (e.g., Taxol® (paclitaxel), docetaxel), T67 (Tularik), vincas, and auristatins (e.g., auristatin E, AEB, AEVB, AEFP, MMAD, MMAE, MMAF, among others). Antitubulin agents included in this class are also: vinca alkaloids, including vincristine and vinblastine, vindesine and vinorelbine; taxanes such as paclitaxel and docetaxel and baccatin derivatives, epithilone A and B, nocodazole, 5-Fluorouracil and colcimid, estramustine, cryptophysins, cemadotin, maytansinoids, combretastatins, dolastatins, discodermolide and eleutherobin In more specific embodiments, the cytotoxic agent is chosen from a vinca alkaloid, a podophyllotoxin, a taxane, a baccatin derivative, a cryptophysin, a maytansinoid, a combretastatin, and a dolastatin.

In more specific embodiments, the cytotoxic agent is vincristine, vinblastine, vindesine, vinorelbine, VP-16, camptothecin, paclitaxel, docetaxel, epithilone A, epithilone B, nocodazole, colchicine, colcimid, estramustine, cemadotin, discodermolide, maytansine, DM-1, an auristatin or other dolastatin derivatives, such as auristatin E or auristatin F, AEB, AEVB, AEFP, MMAD (monomethylauristatin D), MMAE (monomethylauristatin E), MMAF (monomethylauristatin F), eleutherobin or netropsin.

In some embodiments, the antibodies of the disclosure comprising an engineered Fc region may be conjugated or fused to other small molecule or protein toxins, such as, but not limited to, abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, afla toxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

Further examples of toxins, spacers, linkers, stretchers and the like, and their structures can be found in U.S. Patent Application Publication Nos. 2006/0074008, 2005/0238649, 2005/0123536, 2005/0180972, 2005/0113308, 2004/0157782, U.S. Pat. Nos. 6,884,869, 5,635,483, all of which are hereby incorporated by reference herein in their entirety.

As discussed previously herein, the compounds used for conjugation to the antibody conjugates of the present disclosure can include conventional chemotherapeutics, such as doxorubicin, paclitaxel, carboplatin, melphalan, vinca alkaloids, methotrexate, mitomycin C, etoposide, and others. In addition, potent agents such CC-1065 analogues, calichiamicin, maytansine, analogues of dolastatin 10, rhizoxin, and palytoxin can be linked to the antibodies at the engineered conjugation site provided in the Fc region to provide potent immunoconjugates.

In certain embodiments, the cytotoxic or cytostatic agent is a dolastatin. In more specific embodiments, the dolastatin is of the auristatin class. In a specific embodiment of the disclosure, the cytotoxic or cytostatic agent is MMAD. In another specific embodiment of the disclosure, the cytotoxic or cytostatic agent is MMAE. In yet another specific embodiment of the disclosure, the cytotoxic or cytostatic agent is MMAF.

In other embodiments, antibodies of the present disclosure or an engineered constant domain, or portion thereof, are conjugated or fused to a therapeutic agent or drug moiety that modifies a given biological response.

Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, e.g., TNF-a, TNF-beta, AIM I (see, International Publication No. WO 97/33899), AIM II (see, International Publication No. WO 97/34911), Fas Ligand (Takahashi et al., 1994, J. Immunol, 6:1567), and VEGF (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-4 ("IL-4"), interleukin-6 ("IL-6"), interleukin-7 ("IL-7"), interleukin-9 ("IL- 9"), interleukin-10 ("IL-10"), interleukin-15 ("IL-15"), interleukin-12 ("IL-12"), granulocyte macrophage colony stimulating factor ("GM-CSF"), and granulocyte colony stimulating factor ("G-CSF")), or a growth factor (e.g., growth hormone ("GH")), and a receptor, or ligand binding portion thereof, of any of the preceding molecules.

In other embodiments, engineered antibodies of the present disclosure are specifically conjugated to a polypeptide that comprises poly-arginine or poly-lysine residues. In some embodiments, said polypeptide comprises 5, 6, 7, 8, 9, 10, 11, 12, 13, 14, 15, or more amino acid residues. In some embodiments, the poly-arginine polypeptide may comprise at least 5, 6, 7, 8, 9, 10, 11, 12, 13, 14, 15, or more arginine residues. In other embodiments, the poly-lysine polypeptide may comprise at least 5, 6, 7, 8, 9, 10, 11, 12, 13, 14, 15, or more lysine residues. In other embodiments, the polypeptide may comprise any combination of arginine and lysine residues.

In other embodiments, engineered antibodies of the present disclosure are conjugated to a therapeutic agent such as radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"'-tetraacetic acid (DOTA) which can be attached to the antibody via a linker molecule. Such linker molecules, further discussed herein below, are commonly known in the art and described in Denardo et al., 1998, Clin Cancer Res. 4:2483-90; Peterson et al, 1999, Bioconjug. Chem. 10:553; and Zimmerman et al., 1999, Nucl. Med. Biol. 26:943-50, each of which is incorporated by reference herein in its entirety.

In other embodiments, engineered antibodies of the present disclosure are conjugated to a nucleic acid. The nucleic acid may be selected from DNA, RNA, short interfering RNA (siRNA), microRNA, hairpin or nucleic acid mimetics such as peptide nucleic acid. In some embodiments the conjugated nucleic acid is at least 10, at least 20, at least 30, at least 40, at least 50, at least 60 at least 100, at least 200, at least 500, at least 1000, at least 5000 or more base pairs. In some embodiments, the conjugated nucleic acid is single stranded. In alternative embodiments, the conjugated nucleic acid is double stranded.

Techniques for delivery of nucleic acids to cells may be found at Song et al., 2005, Nat. Biotechnol. 23(6):709-717 and also U.S. Pat. No. 6,333,396, which is incorporated by reference in its entirety.

Conjugation Methods

Techniques for conjugating therapeutic moieties to antibodies are well known. Moieties can be conjugated to antibodies by any method known in the art, including, but not limited to aldehyde/Schiff linkage, sulfhydryl linkage, acid-labile linkage, cis-aconityl linkage, hydrazone linkage, enzymatically degradable linkage (see generally Garnett, 2002, Adv. Drug Deliv. Rev. 53:171-216). Additional techniques for conjugating therapeutic moieties to antibodies are well known, see, e.g., Arnon et al., in Monoclonal Antibodies And Cancer Therapy, Reisfeld et al. (eds.), pp. 243-56 (Alan R. Liss, Inc. 1985); Hellstrom et al., in Controlled Drug Delivery (2nd ed.), Robinson et al. (Eds.), pp. 623-53 (Marcel Dekker, Inc. 1987); Thorpe, in Monoclonal Antibodies '84: Biological And Clinical Applications, Pinchera et al. (Eds.), pp. 475-506 (1985); Baldwin et al. (eds.) in Monoclonal Antibodies For Cancer Detection And Therapy, pp. 303-316 (Academic Press 1985), and Thorpe et al., 1982, Immunol. Rev. 62:119-158.

Methods for fusing or conjugating antibodies to polypeptide moieties are known in the art. See, e.g., U.S. Pat. Nos. 5,336,603, 5,622,929, 5,359,046, 5,349,053, 5,447,851, and 5,112,946; EP 0,307,434; EP 0,367,166; International Publication Nos. WO 96/04388 and WO 91/06570; Ashkenazi et al, 1991, Proc. Nat. Acad. Sci. USA 88:10535-10539; Zheng et al, 1995, J. Immunol. 154:5590-5600; and Vil et al., 1992, Proc. Nat. Acad. Sci. USA 89: 11337-11341. The fusion of an antibody to a moiety does not necessarily need to be direct, but may occur through linker sequences. Such linker molecules are commonly known in the art and described in Denardo et al., 1998, Clin Cancer Res. 4:2483-90; Peterson et al., 1999, Bioconjug. Chem. 10:553; Zimmerman et al., 1999, Nucl. Med. Biol 26:943-50; Garnett, 2002, Adv. Drug Deliv. Rev. 53: 171-216; Francisco et al., 2003, Blood 102:1458-1465; Doronina et al., 2008, Bioconjugate Chem. 19:1960-1963; and Dosio et al., 2011, Toxins 3:848-883, each of which is incorporated herein by reference in its entirety.

Two exemplary approaches may be taken to minimize drug activity outside the cells that are targeted by the antibody conjugates of the disclosure: first, an antibody that binds to a cell membrane receptor but not soluble receptor may be used, so that the drug, including drug produced by the actions of the prodrug converting enzyme, is concentrated at the cell surface of the cells, such as an activated lymphocyte; second, the drugs are conjugated in a manner that would reduce their activity unless they are hydrolyzed or cleaved off the antibody. Such methods would employ attaching the drug to the antibodies with linkers that are sensitive to the environment at the cell surface of the activated lymphocyte (e.g., the activity of a protease that is present at the cell surface of the activated lymphocyte) or to the environment inside the activated lymphocyte the conjugate encounters when it is taken up by the activated lymphocyte (e.g., in the endosomal or, for example by virtue of pH sensitivity or protease sensitivity, in the lysosomal environment). Examples of linkers that can be used in the present disclosure are disclosed in U.S. Patent Application Publication Nos. 2005/0123536, 2005/0180972, 2005/0113308, 2004/0157782, and U.S. Pat. No. 6,884,869, all of which are hereby incorporated by reference herein in their entirety.

In one embodiment, the linker is an acid-labile hydrazone or hydrazide group that is hydrolyzed in the lysosome (see, e.g., U.S. Pat. No. 5,622,929). In alternative embodiments, drugs can be conjugated to antibodies through other acid-labile linkers, such as cis-aconitic amides, orthoesters, acetals and ketals (Dubowchik and Walker, 1999, Pharm. Therapeutics 83:67-123; Neville et al., 1989, Biol. Chem. 264: 14653-14661). Such linkers are relatively stable under neutral pH conditions, such as those in the blood, but are unstable at below pH 5, the approximate pH of the lysosome.

In other embodiments, drugs are attached to the antibodies of the disclosure at an engineered reactive site using peptide spacers that are cleaved by intracellular proteases. Target enzymes include cathepsins B and D and plasmin, all of which are known to hydrolyze dipeptide drug derivatives resulting in the release of active drug inside target cells (Dubowchik and Walker, 1999, Pharm. Therapeutics 83:67-123). The advantage of using intracellular proteolytic drug release is that the drug is highly attenuated when conjugated and the serum stabilities of the conjugates can be extraordinarily high.

In one embodiment, the cathepsin B sensitive dipeptide linker is valine-citrulline (referred to herein as "val-cit" or "ValCit") as described in, e.g., Gerber et al., 2009, Blood 113(18):4352-4361), which is incorporated by referenced herein in its entirety for all purposes.

In one embodiment, the engineered Fc polypeptide and/or the engineered Cκ polypeptide of an engineered antibody is site-specifically conjugated to a cleavable linker, e.g., val-cit, which is conjugated to an auristatin, such as, but not limited to, val-cit-MMAD, val-cit-MMAE, and val-cit-MMAF, among many others.

In one embodiment, the engineered Fc polypeptide and/or the engineered Cκ polypeptide of the disclosure, or an engineered antibody comprising the polypeptide, is site-specifically conjugated to a noncleavable linker, e.g., maleimidocaproyl (mc or mal-c), which is conjugated to an auristatin, such as, but not limited to, mc-MMAD, mc-MMAE, and mc-MMAF, among many others. As used here, "maleimido" can be represented by "mal".

In other embodiments, noncleavable linkers may be used to site-specifically conjugate a cytotoxic or cytostatic agent to an engineered Fc polypeptide and/or an engineered Cκ polypeptide or an engineered antibody comprising an engineered polypeptide of the disclosure. Noncleavable linkers include, but are not limited to, maleimidocaproyl (mc) linkers such as those described in Lee et al., 2009, J. Natl. Cancer Inst. 2009 101:1193-1205 (conjugating MMAF with an anti-EphA2 antibody using a maleimidocaproyl linker).

In yet other embodiments, the linker is a malonate linker (Johnson et al., 1995, Anticancer Res. 15:1387-1393), a maleimidobeiizoyl linker (Lau et al., 1995, Bioorg. Med. Chem. 3(10):1299-1304), or a 3'-N-amide analog (Lau et al, 1995, Bioorg. Med. Chem. 3(10):1305-1312).

Linking chemistry employing a maleimide group and a spacer (such as polyethylene glycol (PEG) or the like) is suitable for cysteine, lysine, selenocysteine, and selenomethaionine substitutions. For histidine substitutions, one may use a spacer coupled with a metal (such as copper, zinc, iron, nickel, etc.) for conjugation. For tyrosine, one may conjugate to a functional group present in a sugar or other hydroxyl compound. Details of these and other suitable conjugation techniques are known those of ordinary skill in the art and can be found in, for example, Bioconjugate Techniques, 2nd ed., by Greg T. Hermanson, Academic Press (2008).

In some embodiments, an engineered Fc polypeptide and/or an engineered Cκ polypeptide or an engineered antibody of the disclosure is site-specifically conjugated to a cytoxic or cytostatic agent via a cleavable or noncleavable linker further comprising a spacer such as, but not limited to, —[CH$_2$CH$_2$O]$_2$CH$_2$CH$_2$C(=O)— (PEG2-C2), —[CH$_2$CH$_2$O]$_3$CH$_2$CH$_2$C(=O)— (PEGS-C2) and —[CH$_2$CH$_2$O]$_6$CH$_2$CH$_2$C(=O)— (PEG6-C2), among others. In other embodiments, the noncleavable linker is maleimidocaproyl linked to a spacer such as, but not limited to, PEG2-C2, PEG3-C2 and PEG6-C2 to form a linker-spacer moiety mc-PEG2-C2, mc-PEG3-C2, and mc-PEG6-C2, among others. In other embodiments, the linker is a cleavable linker such as, but not limited to, valine-citrulline which is susceptible to cathepsin B cleavage, which is conjugated to a spacer moiety such as, but not limited to, PEG2-C2, PEG3-C2, and PEG6-C2 to form a linker-spacer moiety including val-cit-PEG2-C2, val-cit-PEG3-C2 and val-cit-PEG6-C2, among others.

In some embodiments, the cleavable linker-spacer moiety is conjugated to an auristatin, including, but not limited to, MMAD, MMAE, MMAF, 0101, 3377, and 8261. In some embodiments, the linker-spacer-auristatin encompasses mc-val-cit-PABC-MMAD (vc-MMAD), mc-val-cit-PABC-MMAE (vc-MMAE) and mc-val-cit-PABC-MMAF (vc-MMAF). As used here, "para-aminobenzyloxycarbonyl" is represented by "PABC." In some embodiments, the linker-spacer-auristatin encompasses mc-val-cit-PABC-PEG2-C2-MMAD (vc-PEG-C2-MMAD), mc-val-cit-PABC-PEG3-C2-MMAD (vc-PEG3-C2-MMAD), mc-val-cit-PABC-PEG6-C2-MMAD (vc-PEG6-C2-MMAD), mc-val-cit-PABC-PEG2-C2-MMAE (vc-PEG2-C2-MMAE), mc-val-cit-PABC-PEG3-C2-MMAE (vc-PEG3-C2-MMAE), mc-val-cit-PABC-PEG6-C2-MMAE (vc-PEG6-C2-MMAE), mc-val-cit-PABC-PEG2-C2-MMAF (vc-PEG2-C2-MMAF), mc-val-cit-PABC-PEG3-C2-MMAF (vc-PEG3-C2-MMAF), and mc-val-cit-PABC-PEG6-C2-MMAF (vc-PEG6-C2-MMAF), among others.

In other embodiments, the noncleavable linker-spacer moiety is further conjugated to an auristatin, including, but not limited to, MMAD, MMAE, MMAF, 0101, 3377, and 8261. In some embodiments, the linker-spacer-auristatin encompasses mc-PEG2-C2-MMAD, mc-PEG3-C2-MMAD, mc-PEG6-C2-MMAD, mc-PEG2-C2-MMAE, mc-PEG3-C2-MMAE, mc-PEG6-C2-MMAE, mc-PEG2-C2-MMAF, mc-PEG3-C2-MMAF, and mc-PEG6-C2-MMAF, among others.

In some embodiments, a cytotoxic agent is conjugated to an engineered Fc polypeptide via a linker. In other embodiments, the linker may be mc (maleimidocaproyl), val-cit (valine-citrulline), mc-val-cit (maleimidocaproyl-valine-citrulline), mc-val-cit-PABC (maleimidocaproyl-valine-citrulline-p-aminobenzylcarbamate), Mal-PEG3C2 (maleimido-[CH$_2$CH$_2$O]$_3$CH$_2$CH$_2$C(=O)), and Mal-PEG6C2 (maleimido-[CH$_2$CH$_2$O]$_6$CH$_2$CH$_2$C(=O)).

In another embodiment, a cytotoxic agent is conjugated to an engineered antibody constant domain polypeptide, or portion thereof, via a linker such as, but not limited to, the linkers described herein or known in the art, and the cytotoxic agent is an auristatin, a maytansinoid and a calicheamicin, among others.

In some embodiments, an engineered antibody constant domain polypeptide, or portion thereof, comprising an introduced cysteine, is conjugated via a linker and cytotoxic agent combination including, but not limited to, maleimidocaproyl-monomethyl auristatin D (mcMMAD), maleimidocaproyl-monomethyl auristatin E (mcMMAE), maleimidocaproyl-monomethyl auristatin F (mcMMAF), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-monomethyl auristatin E (vcMMAE), valine-citrulline-monomethyl auristatin F (vcMMAF), valine-citrulline-0101 (vc0101), valine-citrulline-3377 (vc3377), valine-citrulline-8261 (vc8261), mcValCitPABCMMAD (maleimidocaproyl-valine-citrulline-monomethyl auristatin D), mcValCitMMAE (maleimidocaproyl-valine-citrulline-monomethyl auristatin E), mcValCitMMAF (maleimidocaproyl-valine-citrulline-monomethyl auristatin F), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, and Mal-PEG6C2-

MMAD, Mal-PEG2C2-MMAE, Mal-PEG3C2-MMAE, and Mal-PEG6C2-MMAE, Mal-PEG2C2-MMAF, Mal-PEG3C2-MMAF, and Mal-PEG6C2-MMAF, PEG2C2-0101, Mal-PEG3C2-0101, and Mal-PEG6C2-0101, PEG2C2-3377, Mal-PEG3C2-3377, and Mal-PEG6C2-3377, PEG2C2-8261, Mal-PEG3C2-8261, and Mal-PEG6C2-8261.

In some embodiments, a cytotoxic agent is conjugated to an engineered Cκ polypeptide via a linker. In other embodiments, the linker may be mc (maleimidocaproyl), val-cit (valine-citrulline), mc-val-cit (maleimidocaproyl-valine-citrulline), mc-val-cit-PABC (maleimidocaproyl-valine-citrulline-p-aminobenzylcarbamate), Mal-PEG3C2 (maleimido-[$CH_2CH_2O$]$_2CH_2CH_2C$(=O)), and Mal-PEG6C2 (maleimido⁻[$CH_2CH_2O$]$_6CH_2CH_2C$(=O)).

In some embodiments, a cytotoxic agent is conjugated to an engineered antibody constant domain (e.g., Cγ, Cκ, and Cλ) polypeptide, or portion thereof, via a linker, to a cytotoxic agent, wherein the linker and the cytotoxic agent are selected from the group consisting of maleimidocaproyl-monomethyl auristatin D (mcMMAD), maleimidocaproyl-monomethyl auristatin E (mcMMAE), maleimidocaproyl-monomethyl auristatin F (mcMMAF), maleimidocaproyl-0101 (mc0101), maleimidocaproyl-3377 (mc3377) maleimidocaproyl-8261 (mc8261), valine-citrulline-monomethyl auristatin D (vcMMAD), valine-citrulline-monomethyl auristatin E (vcMMAE), valine-citrulline-monomethyl auristatin F (vcMMAF), valine-citrulline-0101 (vc0101), valine-citrulline-3377 (vc3377), valine-citrulline-8261, (vc8261), mcValCitPABCMMAD (maleimido-caproyl-valine-citrulline-monomethyl auristatin D), mcVal-CitMMAE (maleimidocaproyl-valine-citrulline-monomethyl auristatin E), mcValCitMMAF (maleimidocaproyl-valine-citrulline-monomethyl auristatin F), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, and Mal-PEG6C2-MMAD, Mal-PEG2C2-MMAE, Mal-PEG3C2-MMAE, and Mal-PEG6C2-MMAE, Mal-PEG2C2-MMAF, Mal-PEG3C2-MMAF, and Mal-PEG6C2-MMAF, Mal-PEG2C2-0101, Mal-PEG3C2-0101, and Mal-PEG6C2-0101, Mal-PEG2C2-3377, Mal-PEG3C2-3377, and Mal-PEG6C2-3377, Mal-PEG2C2-8261, Mal-PEG3C2-8261, Mal-PEG6C2-8261.

In another embodiment, a cytotoxic agent is conjugated to an engineered Cκ polypeptide via a linker such as, but not limited to, the linkers described herein or known in the art, and the cytotoxic agent is an auristatin, a maytansinoid and a calicheamicin, among others.

In some embodiments, an engineered Cκ or Cλ polypeptide comprising an introduced cysteine, is conjugated via a linker and cytotoxic agent combination including, but not limited to, maleimidocaproyl-monomethyl auristatin D (mcMMAD), maleimidocaproyl-monomethyl auristatin E (mcMMAE), maleimidocaproyl-monomethyl auristatin F (mcMMAF), maleimidocaproyl-0101 (mc0101), maleimidocaproyl-3377 (mc3377), maleimidocaproyl-8261 (mc8261) valine-citrulline-monomethyl auristatin D (vcMMAD), valine-citrulline-monomethyl auristatin E (vcMMAE), valine-citrulline-monomethyl auristatin F (vcMMAF), valine-citrulline-0101 (vc0101), valine-citrulline-3377 (vc3377), valine-citrulline-8261 (vc8261) mcValCitPABCMMAD (maleimidocaproyl-valine-citrulline-monomethyl auristatin D), mcValCitMMAE (maleimidocaproyl-valine-citrulline-monomethyl auristatin E), mcValCitMMAF (maleimidocaproyl-valine-citrulline-monomethyl auristatin F), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, and Mal-PEG6C2-MMAD, Mal-PEG2C2-MMAE, Mal-PEG3C2-MMAE, and Mal-PEG6C2-MMAE, Mal-PEG2C2-MMAF, Mal-PEG3C2-MMAF, and Mal-PEG6C2-MMAF, Mal-PEG2C2-0101, Mal-PEG3C2-0101, and Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261, among many other linker/cytotoxic agent combinations known in the art or disclosed herein.

As discussed above, engineered antibody conjugates are generally made by conjugating a compound or a drug to an engineered antibody, or an engineered Fc polypeptide and/or engineered Cκ polypeptide, through a linker. Any linker that is known in the art may be used in the conjugates of the present disclosure, e.g., bifunctional agents (such as dialdehydes or imidoesters) or branched hydrazone linkers (see, e.g., U.S. Pat. No. 5,824,805, which is incorporated by reference herein in its entirety).

In certain, non-limiting, embodiments of the disclosure, the linker region between the conjugate moiety and the engineered antibody/engineered Fc/Cκ polypeptide moiety is cleavable under certain conditions, wherein cleavage or hydrolysis of the linker releases the drug moiety from the antibody/engineered Fc/Cκ moiety. In some embodiments, the linker is sensitive to cleavage or hydrolysis under intracellular conditions.

In one embodiment, the linker region between the conjugate moiety and the engineered antibody moiety is cleavable if the pH changes by a certain value or exceeds a certain value. In another embodiment of the disclosure, the linker is cleavable in the milieu of the lysosome, e.g., under acidic conditions (i.e., a pH of around 5-5.5 or less). In other embodiments, the linker is a peptidyl linker that is cleaved by a peptidase or protease enzyme, including but not limited to a lysosomal protease enzyme, a membrane-associated protease, an intracellular protease, or an endosomal protease. Typically, the linker is at least two amino acids long, more typically at least three amino acids long. For example, a peptidyl linker that is cleavable by cathepsin-B (e.g., a Val-Cit linker, a Gly-Phe-Leu-Gly linker, among others), a thiol-dependent protease that is highly expressed in cancerous tissue, can be used. Other such linkers are described, e.g., in U.S. Pat. No. 6,214,345, which is incorporated by reference in its entirety herein.

In other, non-mutually exclusive embodiments of the disclosure, the linker by which the engineered antibody and compound of an antibody conjugate of the disclosure are conjugated promotes cellular internalization. In certain embodiments, the linker-drug moiety promotes cellular internalization. In certain embodiments, the linker is chosen such that the structure of the entire antibody conjugate promotes cellular internalization. In one embodiment, the linker is a thioether linker (see, e.g., U.S. Pat. No. 5,622,929, which is incorporated by reference herein in its entirety). In another embodiment, the linker is a hydrazone linker (see, e.g., U.S. Pat. Nos. 5,122,368, and 5,824,805, which are incorporated by reference herein in their entireties).

In yet other embodiments, the linker is a disulfide linker. A variety of disulfide linkers are known in the art, including but not limited to those that can be formed using SATA (N-succinimidyl-S-acetylthioacetate), SPDP (N-succinimidyl-3-(2-pyridyldi-thio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene). SPDB and SMPT (see, e.g., Thorpe et al., 1987, Cancer Res., 47:5924-5931; Wawrzynczak et al., 1987, In Immunoconjugates: Antibody Conjugates in Radioimagery and Therapy of Cancer, ed. C. W. Vogel, Oxford U. Press, pp. 28-55; see also U.S. Pat. No. 4,880,935, which is incorporated by reference herein in its entirety).

A variety of linkers that can be used with the compositions and methods of the present disclosure are described in U.S. Patent Application Publication No. US 2004/0018194 A1, which is incorporated by reference in its entirety herein.

Elimination of amine-containing drugs that are substituted at the a-position of glycine (Kingsbury, et al., J. Med. Chem., 1984, 27, 1447) are also examples of self-immolative spacer strategies that can be applied to the antibody-linker-drug conjugates of the disclosure.

In yet other embodiments of the present disclosure, the linker unit of an antibody conjugate links the cytotoxic or cytostatic agent (drug; -D) and the antibody (-Ab). In certain embodiments, the linker unit has the general formula:

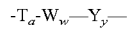

wherein:
i. -T- is a stretcher unit;
ii. a is 0 or 1;
iii. each —W— is independently an amino acid unit;
iv. w is independently an integer ranging from 2 to 12;
v. —Y— is a spacer unit; and
vi. y is 0, 1 or 2.

The stretcher unit (-T-), when present, links the antibody unit to an amino acid unit (—W—). Useful functional groups that can be present on an antibody, either naturally or via chemical manipulation include, but are not limited to, sulfhydryl, amino, hydroxyl, the anomeric hydroxyl group of a carbohydrate, and carboxyl. Engineered antibodies of the disclosure wherein a cysteine has been introduced present at least one sulfhydryl group for conjugation. Other methods of introducing sulfhydryl groups involve the reduction of the intramolecular disulfide bonds of an antibody. Alternatively, sulfhydryl groups can be generated by reaction of an amino group of an engineered lysine moiety of an antibody (which has been introduced) with 2-iminothiolane (Traut's reagent) or other sulfhydryl generating reagents.

The amino acid unit (—W—) links the stretcher unit (-T-) to the Spacer unit (—Y—) if the Spacer unit is present, and links the stretcher unit to the cytotoxic or cytostatic agent (drug; D) if the spacer unit is absent.

In some embodiments, —$W_W$— is a dipeptide, tripeptide, tetrapeptide, pentapeptide, hexapeptide, heptapeptide, octapeptide, nonapeptide, decapeptide, undecapeptide or dodecapeptide unit. The amino acid unit of the linker unit can be enzymatically cleaved by an enzyme including, but not limited to, a tumor-associated protease, cathepsin B, cathepsin D, plasmin, and the like, to liberate the drug (-D) which is protonated in vivo upon release to provide a cytotoxic drug (D).

In a one embodiment, the amino acid unit is a phenylalanine-lysine dipeptide (phe-lys or FK linker). In another embodiment, the amino acid unit is a valine-citrulline dipeptide (val-cit).

The spacer unit (—Y—), when present, links an amino acid unit to the drug unit. Spacer units are of two general types: self-immolative and non self-immolative. A non self-immolative spacer unit is one in which part or all of the spacer unit remains bound to the drug unit after enzymatic cleavage of an amino acid unit from the antibody-linker-drug conjugate or the drug-linker compound. Examples of a non self-immolative spacer unit include, but are not limited to a (glycine-glycine) spacer unit and a glycine spacer unit. When an antibody-linker-drug conjugate of the disclosure containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from Ab-T-$W_W$—. To liberate the drug, an independent hydrolysis reaction should take place within the target cell to cleave the glycine-drug unit bond.

Other examples of self-immolative spacers include, but are not limited to, para-aminobenzyloxycarbonyl (PABC) and aromatic compounds that are electronically equivalent to the PABC group such a 2-aminoimidazol-5-methanol derivatives (see Hay et al., 1999, Bioorg. Med. Chem. Lett. 9:2237 for examples) and ortho- or para-aminobenzylacetals. Spacers can be used that undergo facile cyclization upon amide bond hydrolysis, such as substituted and unsubstituted 4-aminobutyric acid amides (Rodrigues et al., Chemistry, Biology, 1995, 2, 223), appropriately substituted ring systems (Storm, et al., J. Amer. Chem. Soc, 1972, 94, 5815) and 2-aminophenylpropionic acid amides (Amsberry, et al., J. Org. Chem., 1990, 55, 5867).

Methods of Conjugating a Heterologous Molecule to an Engineered Constant Domain

Heterologous molecules, such as those described herein may be efficiently conjugated to engineered antibodies comprising an engineered Fc region and/or an engineered Cκ region and/or an engineered Cλ region of the disclosure through the reactive groups the engineered amino acid residues provide. In one aspect, the disclosure provides methods for efficiently conjugating heterologous molecules to cysteine engineered antibodies. In one embodiment, the conjugation of a heterologous molecule may occur at a reactive group provided by at least one engineered residue selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the Fc region or antibody comprising the Fc polypeptide, wherein the numbering system of the constant region is that of the EU index as set forth in Kabat. In a further aspect, the reactive group is a thiol, and the conjugation of a heterologous molecule may occur at a thiol group provided by at least one engineered cysteine residue selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the Fc polypeptide or an antibody comprising the Fc polypeptide, wherein the numbering system of the constant region is that of the EU index as set forth in Kabat.

In one embodiment, the conjugation of a heterologous molecule may occur at a reactive group provided by at least one engineered residue selected from the positions 111, 149, 183, 188, 207, and 210, of the engineered Cκ polypeptide or an engineered antibody comprising the engineered Cκ polypeptide, wherein the numbering system of the constant region is that of the Kabat numbering index as set forth in Kabat. In a further aspect, the reactive group is a thiol, and the conjugation of a heterologous molecule may occur at a thiol group provided by at least one engineered cysteine residue selected from the positions 111, 149, 183, 188, 207, and 210, of the engineered Cκ polypeptide or an engineered antibody comprising the engineered Cκ polypeptide, wherein the numbering system of the constant region is that of the Kabat numbering index as set forth in Kabat.

The engineering of non-naturally occurring cysteine residues into antibodies may alter the disulfide pairing of the heavy and light chains such that a naturally occurring cysteine residue which was part of a disulfide bond is liberated and presents a thiol group capable of conjugation. In another embodiment, the method comprises the efficient conjugation of a heterologous molecule to a cysteine engineered antibody at a thiol group provided by at least one engineered cysteine residue selected from the positions 246, 249, 265, 267, 270, 276, 278, 283, 292, 293, 294, 300, 302, 303, 314, 315, 318, 320, 332, 333, 334, 336, 345, 347, 354, 355, 358, 360, 362, 370, 373, 376, 378, 380, 382, 386, 388, 390, 392, 393, 401, 404, 411, 413, 414, 416, 418, 419, 421, 428, 431, 432, 437, 438, 439, 443, and 444 of the Fc region of an antibody.

The engineering of non-naturally occurring cysteine residues into antibodies may alter the disulfide pairing of the heavy and light chains such that a naturally occurring cysteine residue which was part of a disulfide bond is liberated and presents a thiol group capable of conjugation. In another embodiment, the method comprises the efficient conjugation of a heterologous molecule to a cysteine engineered antibody at a thiol group provided by at least one engineered cysteine residue selected from the positions 111, 149, 183, 188, 207, and 210, of the Cκ region of an antibody.

The presence of free thiol groups in antibodies may be determined by various art accepted techniques, such as those described herein infra. The efficiency of conjugation of a heterologous molecule to an antibody may be determined by assessing the presence of free thiols remaining after the conjugation reaction. In one embodiment, the disclosure provides a method of efficiently conjugating a heterologous molecule to a cysteine engineered antibody. In one embodiment, the conjugation efficiency is at least 5 percent, at least 20 percent, at least 50 percent, at least 80 percent, at least 90 percent, at least 95 percent, at least 98 percent, at least 99 percent, or more as measured by the level of free thiol groups remaining after the conjugation reaction.

In another embodiment, the disclosure provides a method of conjugating a heterologous molecule to an engineered antibody, including a Fab or F(ab')2, or engineered Fc region and/or Cκ region or Cλ of the antibody wherein the antibody or Fc, Cκ and/or Cλ region comprises at least one amino acid substitution, such that 2 or more reactive groups are formed. In another embodiment, the method comprises an engineered Fc polypeptide, an engineered Cκ polypeptide, an engineered Cλ polypeptide, or engineered antibody comprising at least one amino acid substitution, such that at least 2, at least 4, at least 6, at least 8, at least 10, at least 12, at least 14, at least 16, at least 18, at least 20, or more newly-introduced reactive groups are formed. In a further embodiment, at least one of the substitutions is with a cysteine, and the reactive groups are thiol groups.

Engineered constant regions (Fc, Cκ, and Cλ), and antibodies comprising them of the disclosure capable of conjugation may contain cysteine residues that comprise sulfhydryl groups that are blocked or capped. Such caps include proteins, peptides, ions and other materials that interact with the sulfhydryl group and prevent or inhibit conjugate formation. In some embodiments, antibodies of the disclosure may require uncapping prior to a conjugation reaction. In specific embodiments, engineered constant regions (Fc, Cκ, and Cλ), and engineered antibodies of the disclosure comprising the polypeptides are uncapped and display a sulfhydryl group capable of conjugation. In other specific embodiments, antibodies of the disclosure are subjected to an uncapping reaction that results in minimal disruption or rearrangement of the naturally occurring disulfide bonds. In some embodiments, the level of naturally occurring disulfide bond disruption may range from about 30% to an undetectable level compared with the level of disruption in the untreated polypeptide. In other embodiments, antibodies of the disclosure are subjected to an uncapping reaction as presented in International Patent Publication Nos. WO 2008/141044, WO 2009/092011, and WO 2010/1411902.

In some embodiments, engineered antibodies of the disclosure may be subjected to conjugation reactions wherein the antibody to be conjugated is present at a concentration of at least 1 mg/ml, at least 2 mg/ml, at least 3 mg/ml, at least 4 mg/ml, at least 5 mg/ml, at least 8 mg/ml, at least 10 mg/ml, at least 13 mg/ml, at least 14 mg/ml, at least 15 mg/ml, at least 16 mg/ml or higher.

Methods of Using Engineered Antibody Conjugates

A. Use of Engineered Antibody Conjugates for Diagnosis

The engineered antibody conjugates can be used for diagnostic imaging. For example, the engineered antibody conjugate can be a radiolabeled monoclonal antibody. See, for example, Srivastava (ed.), Radiolabeled Monoclonal Antibodies For Imaging And Therapy, Plenum Press (1988); Chase, "Medical Applications of Radioisotopes," in Remington's Pharmaceutical Sciences, 18th Edition, Gennaro et al. (eds.), Mack Publishing Co., pp. 624-652 (1990); and Brown, "Clinical Use of Monoclonal Antibodies," in Biotechnology and Pharmacy, Pezzuto et al. (eds.), Chapman and Hall, pp. 227-249 (1993). This technique, also known as immunoscintigraphy, uses a gamma camera to detect the location of gamma-emitting radioisotopes conjugated to monoclonal antibodies. Diagnostic imaging can be used to diagnose cancer, autoimmune disease, infectious disease and/or cardiovascular disease. (See, e.g., Brown, supra.)

In one embodiment, the engineered antibody conjugates can be used to diagnose cardiovascular disease. For example, engineered antibody conjugates comprising anti-myosin antibody fragments can be used for imaging myocardial necrosis associated with acute myocardial infarction. engineered antibody conjugates comprising antibody fragments that bind to platelets or fibrin can be used for imaging deep-vein thrombosis. Moreover, engineered antibody conjugates comprising antibody fragments that bind to activated platelets can be used for imaging atherosclerotic plaque.

Engineered antibody conjugates can also be used in the diagnosis of infectious diseases. For example, engineered antibody conjugates comprising antibody fragments that bind specific bacterial antigens can be used to localize abscesses. In addition, engineered antibody conjugates comprising antibody fragments that bind granulocytes and inflammatory leukocytes can be used to localize sites of bacterial infection.

Numerous studies have evaluated the use of monoclonal antibodies for scintigraphic detection of cancer. See, for example, Brown, supra. Investigations have covered the major types of solid tumors such as melanoma, colorectal carcinoma, ovarian carcinoma, breast carcinoma, sarcoma, and lung carcinoma. Thus, the present invention also contemplates the detection of cancer using engineered antibody conjugates comprising antibody fragments that bind tumor markers to detect cancer. Examples of such tumor markers include carcinoembryonic antigen, alpha-fetoprotein, oncogene products, tumor-associated cell surface antigens, and necrosis-associated intracellular antigens, as well as the tumor-associated antigens and tumor-specific antigens discussed infra.

In addition to diagnosis, monoclonal antibody imaging can be used to monitor therapeutic responses, detect recurrences of a disease, and guide subsequent clinical decisions.

For diagnostic and monitoring purposes, radioisotopes may be bound to antibody fragments either directly or indirectly by using an intermediary functional group. Such intermediary functional groups include, for example, DTPA (diethylenetriaminepentaacetic acid) and EDTA (ethylene diamine tetraacetic acid). The radiation dose delivered to the patient is typically maintained at as low a level as possible. This may be accomplished through the choice of isotope for the best combination of minimum half-life, minimum retention in the body, and minimum quantity of isotope which will permit detection and accurate measurement. Examples of radioisotopes which can be bound to antibodies and are appropriate for diagnostic imaging include $^{99}$mTc and $^{111}$In.

Studies indicate that antibody fragments, particularly Fab and Fab', provide suitable tumor/background ratios. (See, e.g., Brown, supra.)

The engineered antibody conjugates also can be labeled with paramagnetic ions for purposes of in vivo diagnosis. Elements which are particularly useful for Magnetic Resonance Imaging include Gd, Mn, Dy, and Fe ions.

The engineered antibody conjugates can also detect the presence of particular antigens in vitro. In such immunoassays, the engineered antibody conjugates may be utilized in liquid phase or bound to a solid-phase carrier. For example, an intact antibody, or antigen-binding fragment thereof, can be attached to a polymer, such as aminodextran, in order to link the antibody component to an insoluble support such as a polymer-coated bead, plate, or tube.

Alternatively, the engineered antibody conjugates can be used to detect the presence of particular antigens in tissue sections prepared from a histological specimen. Such in situ detection can be accomplished, for example, by applying a detectably-labeled immunoconjugate to the tissue sections. In situ detection can be used to determine the presence of a particular antigen and to determine the distribution of the antigen in the examined tissue. General techniques of in situ detection are well known to those of ordinary skill. (See, e.g., Ponder, "Cell Marking Techniques and Their Application," in Mammalian Development: A Practical Approach, Monk (ed.), IRL Press, pp. 115-138 (1987); Coligan et al., supra.)

Detectable labels such as enzymes, fluorescent compounds, electron transfer agents, and the like can be linked to a carrier by conventional methods well known to the art. These labeled carriers and the engineered antibody conjugates prepared from them can be used for in vitro immunoassays and for in situ detection, much as an antibody conjugate can be prepared by direct attachment of the labels to antibody. The loading of the engineered antibody conjugates with a plurality of labels can increase the sensitivity of immunoassays or histological procedures, where only a low extent of binding of the antibody, or antibody fragment, to target antigen is achieved.

B. Use of Engineered Antibody Conjugates for Therapy

Engineered antibody conjugates can be used to treat viral and bacterial infectious diseases, cardiovascular disease, autoimmune disease, and cancer. The objective of such therapy is to deliver cytotoxic or cytostatic doses of an active agent (e.g., radioactivity, a toxin, or a drug) to target cells, while minimizing exposure to non-target tissues.

A radioisotope can be attached to an intact antibody, or antigen-binding fragment thereof, directly or indirectly, via a chelating agent. For example, $^{67}$Cu can be conjugated to an antibody component using the chelating agent, p-bromo-acetamidobenzyl-tetraethylaminetetraacetic acid (TETA). (See, e.g., Chase, supra.)

Moreover, engineered antibody conjugates can be prepared in which the therapeutic agent is a toxin or drug. Useful toxins for the preparation of such engineered antibody conjugates include ricin, abrin, pokeweed antiviral protein, gelonin, diphtherin toxin, and *Pseudomonas* endotoxin. Useful chemotherapeutic drugs for the preparation of immunoconjugates include auristatin, dolastatin, MMAE, MMAF, AFP, AEB, doxorubicin, daunorubicin, methotrexate, melphalan, chlorambucil, vinca alkaloids, 5-fluorouridine, mitomycin-C, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbazine, topotecan, nitrogen mustards, cytoxan, etoposide, BCNU, irinotecan, camptothecins, bleomycin, idarubicin, dactinomycin, plicamycin, mitoxantrone, asparaginase, vinblastine, vincristine, vinorelbine, paclitaxel, and docetaxel and salts, solvents and derivatives thereof. Other suitable agents include chelators, such as DTPA, to which detectable labels such as fluorescent molecules or cytotoxic agents such as heavy metals or radionuclides can be complexed; and toxins such as *Pseudomonas* exotoxin, and the like.

In some embodiments, the diagnostic, preventative or therapeutic agent is auristatin E (also known in the art as dolastatin-10) or a derivative thereof as well as pharmaceutically salts or solvates thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives, as well as linkers, are described in U.S. patent application Ser. No. 09/845,786 (U.S. Patent Application Publication No. 20030083263), U.S. Patent Application Publication No. 2005-0238629; International Patent Publication No. WO 2004/010957; International Patent Publication No. WO 2002/088172; International Patent Publication No. WO 04/073656; and U.S. Pat. Nos. 6,884,869; 6,323,315; 6,239,104; 6,214,345; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414 (all of which are incorporated by reference herein in their entirety).

In some embodiments, the anti-cancer agent includes, but is not limited to, a drug listed in below: methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, L-asparaginase, topotecan, nitrogen mustards, cytoxan, etoposide, BCNU, vinca alkaloids, platinum compounds, mitomycin, gemcitabine, hexamethylmelamine, temsirolimus (CCI-779); lapatinib (GW 572016); RAD-001 (everolimus); XRP-9881; ixabepilone (BMS-247550); pertuzumab (OMNITARG, 2C4); topotecan, tyrosine kinase inhibitors, tyrphostins, imatinib mesylate (GLEEVEC), herbimycin A, genistein, erbstatin, and lavendustin A.

In other embodiments, suitable chemotherapeutics include, but are not limited to, alkylating agents: nitrogen mustards (e.g., cyclophosphamide, ifosfamide, trofosfamide, chlorambucil); nitrosoureas (e.g., carmustine (BCNU), lomustine (CCNU)); alkylsulphonates (e.g., busulfan, treosulfan); triazenes (e.g., dacarbazine); Platinum containing compounds (e.g., cisplatin, carboplatin, aroplatin, oxaliplatin); Plant Alkaloids: Vinca alkaloids (e.g., vincristine, vinblastine, vindesine, vinorelbine); Taxoids (e.g., paclitaxel, docetaxel; DNA Topoisomerase Inhibitors: epipodophyllins (e.g., etoposide, teniposide, topotecan, 9-aminocamptothecin, camptothecin, crisnatol); mitomycins (e.g., mitomycin C, anti-metabolites); anti-folates: DHFR inhibitors (e.g., methotrexate, trimetrexate) IMP dehydrogenase Inhibitors (e.g., mycophenolic acid, tiazofurin, ribavirin, EICAR); Ribonuclotide reductase Inhibitors (e.g., hydroxyurea, deferoxamine); pyrimidine analogs: uracil analogs (e.g., 5-fluorouracil, floxuridine, doxifluridine, ratitrexed); cytosine analogs (e.g., cytarabine (ara C), cytosine arabinoside, fludarabine); purine analogs (e.g., mercaptopurine, thioguanine); DNA antimetabolites (e.g., 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, pyrazoloimidazole); Hormonal therapies: Receptor antagonists: Anti-estrogen (e.g., tamoxifen, raloxifene, megestrol); aromatase inhibitors (e.g., exemestane, anastrozole, letrozole); GnRH antagonists (e.g., abarelix, histrelin); selective estrogen receptor modulators (SERMs) (e.g., lasofoxifene); LH-RH agonists (e.g., goserelin, tryptorelin, buserelin, leuprolide acetate); Anti-androgens (e.g., flutamide, bicalutamide, nilutamide, megestrol, cyproterone); Retinoids/Deltoids cis-retinoic acid; vitamin A derivative (e.g., all-trans retinoic acid (ATRA-IV)); vitamin D3 analogs (e.g., EB 1089, CB 1093, KH 1060); Photodynamic therapies (e.g., vertoporfin (BPD-MA), phthalocyanine, photosensitizer Pc4, demethoxy-hypocrellin A (2BA-2-DMHA); Cytokines, e.g., IL-1α, IL-1β, IL-2, IL-3, IL-4, IL-5, IL-6, IL-7, IL-8, IL-9, IL-10, IL-11, IL-12, IL-15, IL-18, IFNα, IFNβ, IFNγ, TNFα, TNFβ, G-CSF, GM-CSF, TGF-β, SLC, EMAP2, MIP-3α, MIP-3β, HLA-B7, other members of the TNF family (e.g., TRAIL, TRANCE, TWEAK, CD40L, LT-α, LT-β, OX40L, CD40L, FasL, CD27L, CD30L, 4-1BBL, APRIL, LIGHT, TL1, TNFSF16, TNFSF17, and AITR-L, or a functional portion thereof); Angiogenesis Inhibitors: angiostatin (plasminogen fragment), antiangiogenic antithrombin III, angiozyme, ABT-627, Bay 12-9566, benefin, bevacizumab, BMS-275291, cartilage-derived inhibitor (CD), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon alpha/beta/gamma, interferon inducible protein (IP-10), interleukin-12, Kringle 5 (plasminogen fragment), marimastat, metalloproteinase inhibitors (TIMPs), 2-methoxyestradiol, MMI 270 (CGS 27023A), MoAb IMC-1C11, neovastat (Aeterna), NM-3, panzem, PI-88, placental ribonuclease inhibitor, plasminogen activator inhibitor, platelet factor-4 (PF4), prinomastat, prolactin 16kD fragment, proliferin-related protein (PRP), PTK 787/ZK 222594, retinoids, solimastat, squalamine, SS 3304, SU 5416, SU6668, SU11248, SU12662, SU14813, BAY 43-9006, AG-013736, tetrahydrocortisol-S, tetrathiomolybdate, thalidomide, thrombospondin-1 (TSP-1), TNP-470, transforming growth factor-beta (TGF-b), vasculostatin, vasostatin (calreticulin fragment), ZD6126, ZD 6474, farnesyl transferase inhibitors (FTI), bisphosphonates; Antimitotic agents (e.g., allocolchicine, halichondrin B, colchicine, colchicine derivative, dolstatin 10, maytansine, rhizoxin, thiocolchicine, trityl Cysteine); Other agents: isoprenylation inhibitors; dopaminergic neurotoxins (e.g., 1-methyl-4-phenylpyridinium ion); cell cycle inhibitors (e.g., staurosporine): actinomycins (e.g., actinomycin D, dactinomycin); bleomycins (e.g., bleomycin A2, bleomycin B2, peplomycin); anthracyclines (e.g., daunorubicin, doxorubicin (adriamycin), idarubicin, epirubicin, pirarubicin, zorubicin, mitoxantrone); mTOR inhibitors (e.g., temsirolimus, everolimus); MDR inhibitors (e.g., verapamil); $Ca^{2+}$ ATPase inhibitors (e.g., thapsigargin); toll-like receptor agonists (e.g., CpG-7909, also known as PF03512676 or PROMUNE; Coley Pharm); costimulatory molecules (e.g., CD4, CD25, PD-1, B7-H3, 4-1BB, OX40, ICOS, CD30, HLA-DR, MHCII, and LFA, and agonist antibodies thereto); among many other agents known in the art.

Additional anti-cancer agents that may be used in the methods of the present invention include, but are not limited to: acivicin; aclarubicin; acodazole hydrochloride; acronine; adozelesin; aldesleukin; altretamine; ambomycin; ametantrone acetate; amifostine trihydrate; aminoglutethimide; amsacrine; anastrozole; anthramycin; arsenic trioxide; asparaginase; asperlin; azacitidine; azetepa; azotomycin; *Bacillus* Calmette-Guerin; batimastat; benzodepa; bevacizumab; bicalutamide; bisantrene hydrochloride; bisnafide dimesylate; bizelesin; bleomycin sulfate; bortezomib; brequinar sodium; bropirimine; busulfan; cactinomycin; calusterone; capecitabine; caracemide; carbetimer; carboplatin; carmustine; carubicin hydrochloride; carzelesin; cedefingol; chlorambucil; cirolemycin; cisplatin; chlorambucil; cladribine; clodronate; crisnatol mesylate; cyclophosphamide; cytarabine; dacarbazine; dactinomycin; darbepoietin; daunorubicin hydrochloride; decitabine; dexormaplatin; dexrazoxane; dezaguanine; dezaguanine mesylate; diaziquone; diethylstilbestrol; docetaxel; doxorubicin; doxorubicin hydrochloride; droloxifene; droloxifene citrate; dromostanolone propionate; duazomycin; farmorubicin; edatrexate; eflornithine hydrochloride; elsamitrucin; enloplatin; enpromate; epipropidine; epirubicin hydrochloride; erbulozole; erlotinib; erythropoietin; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgastrim (G-CSF); floxuridine; fludarabine phosphate; fludrocortisone; fluorouracil; fluoxymesterone; flurocitabine; fosquidone; fostriecin sodium; fulvestrant; gefitinib; gemcitabine; gemcitabine hydrochloride; gemtuzumab; goserelin; hydroxyurea; ibritumomab tiuxetan; idarubicin hydrochloride; ifosfamide; ilmofosine; imatinib; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; ixabepilone; ketoconazole; lanreotide acetate; lapatinib; letrozole; leucovorin; leuprolide acetate; levamisole; liarozole hydrochloride; lometrexol sodium; lomustine; losoxantrone hydrochloride; masoprocol; maytansine; mechlorethamine hydrochloride; medroxyprogesterone; megestrol acetate; melengestrol acetate; melphalan; menogaril; mercaptopurine; mesna; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; octreotide; ormaplatin; oxaliplatin; oxisuran; paclitaxel; pamidronate; pegaspargase; PEG-L-asparaginase; PEG-filgastrim; peliomycin; pentamustine; pentostatin; peplomycin sulfate; perfosfamide; pertuzumab; pipobroman; piposulfan; piroxantrone hydrochloride; plicamycin; plomestane; porfimer sodium; porfimer; porfiromycin; prednimustine; pemetrexed; procarbazine hydrochloride; puromycin; puromycin hydrochloride; pyrazofurin; raltitrexed; riboprine; rituximab; rogletimide; safingol; safingol hydrochloride; semustine; simtrazene; somavert (PEGVISOMANT); sparfosate sodium; sparsomycin; spirogermanium hydrochloride; spiromustine; spiroplatin; streptonigrin; streptozocin; sulofenur; sunitinib; streptozocin; talisomycin; tecogalan sodium; tegafur; teloxantrone hydrochloride; temoporfin; temozolomide; temsirolimus; teniposide; teroxirone; testolactone; thalidomide; thiamiprine; thioguanine; thiotepa; tiazofurin; tirapazamine; topotecan; toremifene citrate; trastuzumab; tretinoin; trestolone acetate; triciribine phosphate; trimetrexate; trimetrexate glucuronate; triptorelin; topotecan; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zolendronate; zorubicin hydrochloride.

Other anti-cancer drugs that can be used include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the diagnostic, preventative or therapeutic agent is not a radioisotope.

In some embodiments, an engineered antibody conjugate can be used to treat one of the following particular types of cancer: It is contemplated that the engineered antibody conjugates of the present disclosure may be used to treat various diseases or disorders, e.g. those characterized by the overexpression of a tumor antigen. Exemplary conditions or hyperproliferative disorders include benign or malignant tumors, leukemia and lymphoid malignancies. Others include neuronal, glial, astrocytal, hypothalamic, glandular, macrophagal, epithelial, endothelial, and stromal malignancies. Other cancers or hyperproliferative disorders include: cancers of the head, neck, eye, mouth, throat, esophagus, chest, skin, bone, lung, colon, rectum, colorectal, stomach, spleen, kidney, skeletal muscle, subcutaneous tissue, metastatic melanoma, endometrial, prostate, breast, ovaries, testicles, thyroid, blood, lymph nodes, kidney, liver, pancreas, brain, or central nervous system. Examples of cancers that can be prevented, managed, treated or ameliorated in accordance with the methods of the disclosure include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblasts, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al, 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., inc., United States of America). It is also contemplated that cancers caused by aberrations in apoptosis can also be treated by the methods and compositions of the disclosure. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

The engineered antibody conjugates of the disclosure, and the engineered Fc polypeptides and engineered Cκ polypeptides, and compositions comprising the same are useful for many purposes, for example, as therapeutics against a wide range of chronic and acute diseases and disorders including, but not limited to, autoimmune and/or inflammatory disorders, which include Sjogren's syndrome, rheumatoid arthritis, lupus psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. Other Examples of autoimmune and/or inflammatory disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, *pemphigus vulgaris*, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. The compositions and methods of the disclosure can be used with one or more conventional therapies that are used to prevent, manage or treat the above diseases.

The disclosure also provides methods of using the engineered antibody conjugates of the disclosure, and the engineered Fc polypeptides and engineered Cκ polypeptides of the disclosure, to inactivate various infectious agents such as viruses, fungi, eukaryotic microbes, and bacteria. In some embodiments the compositions of the disclosure may be used to inactivate RSV, hMPV, PIV, or influenza viruses. In other embodiments, compositions of the disclosure may be used to inactivate fungal pathogens, such as, but not limited to members *Naegleria, Aspergillus, Blastomyces, Histoplasma, Candida* or *Tinea* genera. In other embodiments, the compositions of the disclosure may be used to inactivate eukaryotic microbes, such as, but not limited to members of *Giardia, Toxoplasma, Plasmodium, Trypanosoma,* and *Entamoeba* genera. In other embodiments, compositions of the disclosure may be used to inactivate bacterial pathogens, such as but not limited to members of *Staphylococcus, Streptococcus, Pseudomonas, Clostridium, Borrelia, Vibro* and *Neiserria* genera.

The compositions of the disclosure are useful for many purposes, for example, as therapeutics against a wide range of chronic and acute diseases and disorders including, but not limited to, infectious disease, including viral, bacterial and fungal diseases. Examples of viral pathogens include but are not limited to: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae {e.g., levivirus, enterobacteria phase MS2, allolevirus), poxviridae (e.g., chordopoxvirinae, parapoxvirus, avipoxvirus, capripoxvirus, leporiipoxvirus, suipoxvirus, molluscipoxvirus, and entomopoxvirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus T, spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). Examples of bacterial pathogens include but are not limited to: but not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *Clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*), Vampirovibr Helicobacter family, and Vampirovibrio family. Examples of fungal pathogens include, but are not limited to: *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kerr, Candida krusei, Candida par apsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunning hamella* species, *dermatophytes, Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes.

The disclosure also provides methods of using engineered antibody conjugates to deplete a cell population. In one embodiment, methods of the disclosure are useful in the depletion of the following cell types: eosinophil, basophil, neutrophil, T cell, B cell, mast cell, monocytes, endothelial cell and tumor cell. In some embodiments, antibodies of the disclosure deplete a respective cell population by at least 5 percent, 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, or more as compared to a control non-engineered antibody or a conjugate thereof.

The engineered antibodies of the disclosure and conjugates thereof may also be useful in the diagnosis and detection of diseases of symptoms thereof. In another embodiment, the compositions of the disclosure may be useful in the monitoring of disease progression. In another embodiment, the compositions of the disclosure may be useful in the monitoring of treatment regimens. In another embodiment, the compositions of the disclosure are useful for diagnosis in an ex vivo application, such as a diagnostic kit.

The compositions of the disclosure may be useful in the visualization of target antigens. In some embodiments, the target antigens are cell surface receptors that internalize. In other embodiments, the target antigen is an intracellular antigen. In other embodiments the target is an intranuclear antigen.

In one embodiment, the engineered antibodies or antibody-drug conjugates of the disclosure once bound, internalize into cells wherein internalization is at least about 10 percent, at least about 20 percent, at least about 30 percent, at least about 40 percent, at least about 50 percent, at least about 60 percent, at least about 70 percent, at least about 80 percent, or at least about 90 percent, at least about 100 percent, at least about 110 percent, at least about 130 percent, at least about 140 percent, at least about 150 percent, at least about 160 percent, or at least about 170 percent more than control antibodies as described herein.

The use of engineered antibody conjugates of the disclosure, and the engineered Fc polypeptides, engineered Cκ polypeptides, and engineered Cλ polypeptides for the treatment of other cancers or autoimmune disorders is also contemplated and within the scope of the present invention.

Pharmaceutical Compositions

In another aspect, the present disclosure provides a composition, for example, but not limited to, a pharmaceutical composition, containing an engineered antibody or engineered antibody conjugate, an engineered Fc polypeptide or conjugate thereof, an engineered Fc fusion protein comprising an engineered Fc region or a conjugate thereof, an engineered Cκ polypeptide or a conjugate thereof, and engineered Cλ polypeptide or a conjugate thereof, formulated together with a pharmaceutically acceptable carrier.

In another aspect, the composition is a pharmaceutical composition comprising one or a combination of engineered antibodies, or engineered antibody conjugates of the present disclosure, formulated together with a pharmaceutically acceptable carrier.

Such compositions may include one or a combination of, for example, but not limited to two or more different engineered antibodies of the disclosure. For example, a pharmaceutical composition of the disclosure may comprise a combination of engineered antibodies that bind to different epitopes on the target antigen or that have complementary activities.

Pharmaceutical compositions of the disclosure also can be administered in combination therapy, such as, combined with other agents. For example, the combination therapy can include an engineered antibody or conjugate thereof of the present disclosure combined with at least one other therapy wherein the therapy may be surgery, immunotherapy, chemotherapy, radiation treatment, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in *Remington's Pharmaceutical Sciences*, Genaro, ed., Mack Publishing Co., Easton, Pa. (1985), which is incorporated herein by reference.

In one embodiment, the engineered antibody or engineered antibody conjugate is administered in an intravenous formulation as a sterile aqueous solution containing 5 mg/m, or more preferably, about 10 mg/ml, or yet more preferably, about 15 mg/ml, or even more preferably, about 20 mg/ml of antibody, with sodium acetate, polysorbate 80, and sodium chloride at a pH ranging from about 5 to 6. Preferably, the intravenous formulation is a sterile aqueous solution containing 5 or 10 mg/ml of antibody, with 20 mM sodium acetate, 0.2 mg/ml polysorbate 80, and 140 mM sodium chloride at pH 5.5. Further, a solution comprising an engineered antibody or engineered antibody conjugate can comprise, among many other compounds, histidine, mannitol, sucrose, trehalose, glycine, poly(ethylene) glycol, EDTA, methionine, and any combination thereof, and many other compounds known in the relevant art.

In one embodiment, part of the dose is administered by an intraveneous bolus and the rest by infusion of the engineered antibody or engineered antibody conjugate formulation. For example, a 0.01 mg/kg intravenous injection of the engineered antibody or engineered antibody conjugate may be given as a bolus, and the rest of a predetermined engineered antibody or engineered antibody conjugate dose may be administered by intravenous injection. A predetermined dose of the engineered antibody may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg. In another embodiment, endotoxin and pyrogen levels in the composition are less then about 10 EU/mg, or less then about 5 EU/mg, or less then about 1 EU/mg, or less then about 0.1 EU/mg, or less then about 0.01 EU/mg, or less then about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

Dosing/Administration

To prepare pharmaceutical or sterile compositions including an engineered antibody or engineered antibody conjugate of the disclosure, the antibody/antibody conjugate is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, N.Y., N.Y.; Avis, et al. (eds.) (1993) Pharmaceutical Dosage Forms: Parenteral Medications, Marcel Dekker, N.Y.; Lieberman, et al. (eds.) (1990) Pharmaceutical Dosage Forms: Tablets, Marcel Dekker, N.Y.; Lieberman, et al. (eds.) (1990) Pharmaceutical Dosage Forms: Disperse Systems, Marcel Dekker, N.Y.; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, N.Y., N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising engineered antibodies or engineered antibody conjugates of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 micro g/kg body weight, at least 0.2 micro g/kg, at least 0.5 micro g/kg, at least 1 micro g/kg, at least 10 micro g/kg, at least 100 micro g/kg, at least 0.2 mg/kg, at least 1.0 mg/kg, at least 2.0 mg/kg, at least 10 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 micro g, at least 20 micro g, at least 25 micro g, at least 30 micro g, at least 35 micro g, at least 40 micro g, at least 45 micro g, at least 50 micro g, at least 55 micro g, at least 60 micro g, at least 65 micro g, at least 70 micro g, at least 75 micro g, at least 80 micro g, at least 85 micro g, at least 90 micro g, at least 95 micro g, or at least 100 micro g. The doses administered to a subject may number at least 1, 2, 3, 4, 5, 6, 7, 8, 9, 10, 11, or 12, or more.

For engineered antibodies or engineered antibody conjugates of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the engineered antibodies or engineered antibody conjugates of the disclosure may be calculated using the patient's weight in kilograms (kg) multiplied by the dose to be administered in mg/kg. The dosage of the antibodies of the disclosure may be 150 micro g/kg or less, 125 micro g/kg or less, 100 micro g/kg or less, 95 micro g/kg or less, 90 micro g/kg or less, 85 micro g/kg or less, 80 micro g/kg or less, 75 micro g/kg or less, 70 micro g/kg or less, 65 micro g/kg or less, 60 micro g/kg or less, 55 micro g/kg or less, 50 micro g/kg or less, 45 micro g/kg or less, 40 micro g/kg or less, 35 micro g/kg or less, 30 micro g/kg or less, 25 micro g/kg or less, 20 micro g/kg or less, 15 micro g/kg or less, 10 micro g/kg or less, 5 micro g/kg or less, 2.5 micro g/kg or less, 2 micro g/kg or less, 1.5 micro g/kg or less, 1 micro g/kg or less, 0.5 micro g/kg or less, or 0.5 micro g/kg or less of a patient's body weight.

Unit dose of the engineered antibodies or engineered antibody conjugates of the disclosure may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the engineered antibodies or engineered antibody conjugates of the disclosure may achieve a serum titer of at least 0.1 micro g/ml, at least 0.5 micro g/ml, at least 1 micro g/ml, at least 2 micro g/ml, at least 5 micro g/ml, at least 6 micro g/ml, at least 10 micro g/ml, at least 15 micro g/ml, at least 20 micro g/ml, at least 25 micro g/ml, at least 50 micro g/ml, at least 100 micro g/ml, at least 125 micro g/ml, at least 150 micro g/ml, at least 175 micro g/ml, at least 200 micro g/ml, at least 225 micro g/ml, at least 250 micro g/ml, at least 275 micro g/ml, at least 300 micro g/ml, at least 325 micro g/ml, at least 350 micro g/ml, at least 375 micro g/ml, or at least 400 micro g/ml in a subject. Alternatively, the dosage of the antibodies of the disclosure may achieve a serum titer of at least 0.1 micro g/ml, at least 0.5 micro g/ml, at least 1 micro g/ml, at least, 2 micro g/ml, at least 5 micro g/ml, at least 6 micro g/ml, at least 10 micro g/ml, at least 15 micro g/ml, at least 20 micro g/ml, at least 25 micro g/ml, at least 50 micro g/ml, at least 100 micro g/ml, at least 125 micro g/ml, at least 150 micro g/ml, at least 175 micro g/ml, at least 200 micro g/ml, at least 225 micro g/ml, at least 250 micro g/ml, at least 275 micro g/ml, at least 300 micro g/ml, at least 325 micro g/ml, at least 350 micro g/ml, at least 375 micro g/ml, or at least 400 micro g/ml in the subject.

Doses of engineered antibodies or engineered antibody conjugates of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an engineered antibody or engineered antibody conjugate, combination therapy, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the engineered antibodies or engineered antibody conjugates of the disclosure are administered in a controlled release or sustained release system, a pump may be used to achieve controlled or sustained release (see Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984);

Ranger and Peppas, 1983, J., Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 7 1: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), polyvinyl alcohol), polyacrylamide, polyethylene glycol), polylactides (PLA), polyoeactide-co-glycol ides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. MI. Symp. Control. Rel. Bioact. Mater. 24:853-854, and Lam et al., 1997, "Microencapsulation of Recombinant Humanized Monoclonal Antibody for Local Delivery," Proc. MI. Symp. Control Rel. Bioact. Mater. 24:759-160, each of which is incorporated herein by reference in their entirety.

If the engineered antibody or engineered antibody conjugate of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising engineered antibodies or engineered antibody conjugates are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10 th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with the engineered antibodies or engineered antibody conjugates of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

The engineered antibodies or engineered antibody conjugates of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the engineered antibodies or engineered antibody conjugates of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); p120 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising engineered antibodies or engineered antibody conjugates of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising engineered antibodies or engineered antibody conjugates of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Equivalents

The foregoing written specification is considered to be sufficient to enable one skilled in the art to practice the disclosure. The foregoing description and Examples detail certain exemplary embodiments of the disclosure. It will be appreciated, however, that no matter how detailed the foregoing may appear in text, the disclosure may be practiced in many ways and the disclosure should be construed in accordance with the appended claims and any equivalents thereof.

All references cited herein, including patents, patent applications, papers, text books, and the like, and the references cited therein, to the extent that they are not already, are hereby incorporated herein by reference in their entirety.

Exemplary Embodiments

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Engineering Reactive Cysteines into Human Antibody IgG1-Fc Region for Site-Specific Conjugation Conventional conjugation strategies for antibody drug conjugates (ADCs) rely on randomly conjugating the payload to the antibody through lysines or cysteines. The methods exemplified herein produce a homogeneous population of ADCs comprised of species with a defined molar drug:antibody ratio (DAR). The data disclosed herein demonstrate that site-specific conjugation of toxic payloads to antibodies using reactive amino acid residues at these novel positions yields homogeneous ADC preparations with uniform stoichiometry resulting in improved pharmacokinetics, biodistribution and safety profile of the conjugate. The data disclosed herein demonstrate an approach whereby reactive cysteine residues were engineered into the antibody constant regions (e.g., heavy and light chain constant regions) to facilitate generation of homogeneous ADCs with drug:antibody ratio of either 2 or 4 and the successful use of these novel antibodies as a useful platform for site-specific conjugation for various therapeutic targeting moieties.

In essence, the crystal structure of human IgG1 (publicly available at Sondermann et al., 2000, Nature 406:267-273; PDB code 3D03, 10.2210/pdb3do3/pdb) was used to predict, using structural modeling the positions, where the reactive cysteines should be introduced for optimal conjugation with a sulfhydryl reactive agent. The twelve positions set forth in Table 1, below, were identified in the CH2 and CH3 domains of human IgG1 based on the following criteria: about 30 to 50% solvent accessibility, retention of protein structure/stability, and lack of interference of the introduction of reactive cysteines at each position with functional properties of the antibody such as, but not limited to, binding to antigen, FcγR binding, binding to FcRn and/or binding to Protein A. The amino acid sequence of wild type IgG1 without mutations and with numbering in sequential order (starting at alanine 1 and ending in lysine 330) is as follows, and is designated as SEQ ID NO:1:

```
ASTKGPSVFP LAPSSKSTSG GTAALGCLVK DYFPEPVTVS WNSGALTSGV      50

HTFPAVLQSS GLYSLSSVVT VPSSSLGTQT YICNVNHKPS NTKVDKKVEP     100

KSCDKTHTCP PCPAPELLGG PSVFLFPPKP KDTLMISRTP EVTCVVVDVS     150

HEDPEVKFNW YVDGVEVHNA KTKPREEQYN STYRVVSVLT VLHQDWLNGK     200

EYKCKVSNKA LPAPIEKTIS KAKGQPREPQ VYTLPPSREE MTKNQVSLTC     250

LVKGFYPSDI AVEWESNGQP ENNYKTTPPV LDSDGSFFLY SKLTVDKSRW     300

QQGNVFSCSV MHEALHNHYT QKSLSLSPGK                           330
```

Table 2 sets forth the location of the mutations relative to wild type endogenous human IgG1 wherein the amino acid residue was mutated to cysteine for thiol reactive site-specific conjugation. Table 2 indicates the positions where human IgG1 residues were replaced with reactive cysteines. Positions are identified using the EU index numbering system as set forth in Kabat et al. (1991, NIH Publication 91-3242, National Technical Information Service, Springfield, Va.) and also according to sequential numbering relative to the sequence of SEQ ID NO:1.

chain variable domains specifically binding human 5T4 and a human IgG1 Fc-region (the antibody referred to herein as anti-5T4 or simply "5T4"). The reactive cysteine residues were introduced into the IgG1 Fc at the twelve positions listed in Table 2 using an over-lapping PCR mutagenesis method. The amino acid sequence of wild type human IgG1, without mutations, is set forth in SEQ ID NO:1.

PCR mutagenesis was performed as follows. Sense and anti-sense mutagenic oligonucleotides harboring the individual cysteine mutations as well as forward and reverse human IgG1 constant region flanking primers were synthesized at Integrated DNA Technologies, Inc (ParkCoralville, Iowa). PCR reaction 1 contained one hundred nanograms (ng) of anti-5T4 antibody encoding plasmid DNA, 100 pmoles forward flanking primer oligonucleotide, 100 pmoles anti-sense mutagenic oligonucleotide, 1 µl Vent® polymerase (New England Biolabs Inc., Ipswich, Mass.), 25 µl 2×HN PCR buffer (EPICENTRE® Biotechnologies, Madison, Wis.) and H$_2$O to bring the volume of the reaction to 50 µl. Similarly, PCR reaction 2 was made by mixing 100 ng A1 anti-5T4 antibody encoding plasmid DNA, 100

TABLE 2

| Position ID of Engineered Cysteine (Kabat EU) | Position of engineered Cys (Sequential No.) | Sequence ID of full-length Fc comprising Cys mutant | Amino acids flanking the engineered cysteine which is underlined | SEQ ID NO of amino acids flanking engineered cysteine |
|---|---|---|---|---|
| S254C | S137 | SEQ ID NO. 8 | PPKPKDTLMICRTPEVTCVVV | 96 |
| T359C | T242 | SEQ ID NO. 37 | YTLPPSREEMCKNQVSLTCLV | 97 |
| N361C | N244 | SEQ ID NO. 39 | LPPSREEMTKCQVSLTCLVKG | 98 |
| E380C | E263 | SEQ ID NO. 45 | KGFYPSDIAVCWESNGQPENN | 99 |
| S383C | S266 | SEQ ID NO. 47 | YPSDIAVEWECNGQPENNYKT | 100 |
| N384C | N267 | SEQ ID NO. 48 | PSDIAVEWESCGQPENNYKTT | 101 |
| K392C | K275 | SEQ ID NO. 52 | ESNGQPENNYCTTPPVLDSDG | 102 |
| L398C | L281 | SEQ ID NO. 54 | ENNYKTTPPVCDSDGSFFLYS | 103 |
| F404C | F287 | SEQ ID NO. 56 | TPPVLDSDGSCFLYSKLTVDK | 104 |
| V422C | V305 | SEQ ID NO. 64 | VDKSRWQQGNCFSCSVMHEAL | 105 |
| S440C | S323 | SEQ ID NO. 71 | VMHEALHNHYTQKCLSLSPGK | 106 |
| L443C | L326 | SEQ ID NO. 72 | VMHEALHNHYTQKSLSCSPGK | 107 |

Materials and Methods
Generation of Single Cysteine Engineered Antibody Human IgG1

Single reactive cysteine residues were introduced into a humanized antibody comprising humanized heavy and light chain variable domains specifically binding human 5T4 and pmoles sense mutagenic oligonucleotide, 100 pmoles reverse flanking primer oligonucleotide, 1 µl Vent® polymerase, 25 µl 2×HN PCR buffer and adding H$_2$O to bring the volume of the reaction to 50 µl. The PCR parameters for reactions 1 and 2 were 95° C. for 1 minute, 63° C. for 1 minute, 72° C. for 1 minute for 25 cycles and then 10 minutes at 72° C. The final PCR reaction was done by mixing 1 µl each of PCR reactions 1 and 2, 100 pmoles each of the forward and reverse flanking primer oligonucleotides, 1 µl Vent® polymerase, 25 µl 2×HN PCR buffer and H₂O to bring the volume of the reaction to 50 µl. The final PCR reaction parameters were the same as used for reactions 1 and 2. The human IgG1 variants harboring the individual engineered cysteine residues were joined to the A1 heavy chain variable region using T4 DNA Ligase (New England Biolabs Inc., Ipswich, Mass.) and the nucleic acid was sequence confirmed.

Evaluation of Transient Expression of Single Cysteine Engineered Anti-5T4 Antibody Variants To confirm that the humanized anti-5T4 antibody comprising the engineered single cysteine could be efficiently expressed, COS-1 cells were transiently co-transfected with plasmid DNA encoding the cysteine variants and the parental anti-5T4 antibody, i.e., the wild type IgG1 Fc region that did not comprise any mutations, using standard methods. After a period of 48 hours, the cell culture medium was harvested and the resultant conditioned medium containing the 5T4-cysteine antibody variants was quantitated by total human IgG sandwich ELISA. Briefly, a flat bottom ELISA plate (Costar catalog #3590) was coated overnight at room temperature with 100 µl each well of 1 µ/ml goat anti-human IgG in PBS (Thermo/Pierce catalog #31125). Plates were blocked with 100 µl/well of a 0.02% Casein Solution in PBS for a minimum of 3 hours or up to 24 hours at room temperature. Standards and samples were serially diluted in assay buffer (0.5% BSA+0.02% Tween-20 in PBS) and 100 µl was added to the coated/blocked ELISA plate and incubated for 3 to 24 hours at room temperature. The contents of the plate were discarded and the plate was washed 4-times with 0.03% Tween-20 in PBS, 200 µl per well. Goat anti-human IgG (Thermo/Pierce catalog #31413) was diluted 1:5000 in assay buffer, 100 µl was added to well and allowed to incubate for 15 minutes at room temperature. The plate was washed as previously described and developed in 100 µl per well BioFX TMB (3,3',5,5' tetramethylbenzidine; Cat. No. TMBW-0100-01, BioFX Labs., Inc., Owings Mills, Md.). The reaction was stopped in 100 µl per well 0.18 N H₂SO₄ and the plate was read at 450 nM on Molecular Devices vMax plate reader. The concentration of antibody in the unknowns was calculated from the linear range of the curve from the dilution series of the standard. As shown in Table 3, all single cysteine engineered anti-5T4 antibody variants expressed at a comparable level to the parental anti-5T4 antibody comprising the wild-type human IgG1 constant region lacking mutations. Therefore, these data demonstrate that transient expression level of single cysteine engineered antibody variants was not affected by the introduction of reactive cysteines at these positions.

TABLE 3

| Anti-5T4 Variant (position of mutation indicated using Kabat EU numbering) | Human IgG in the cell culture medium [µg/ml] |
|---|---|
| Parental anti-5T4 Ab | 39.8 |
| 5T4-S254C | 38.6 |
| 5T4-T359C | 39.9 |
| 5T4-E380C | 50.1 |
| 5T4-K392C | 47.0 |
| 5T4-F404C | 47.3 |

TABLE 3-continued

| Anti-5T4 Variant (position of mutation indicated using Kabat EU numbering) | Human IgG in the cell culture medium [µg/ml] |
|---|---|
| 5T4-V422C | 35.6 |
| 5T4-S440C | 44.4 |
| 5T4-L443C | 43.3 |

Production of Stably Transfected Cells Expressing Anti-5T4 Single-Cysteine Variants To determine that the single engineered antibody variants could be stably expressed in cells and large-scale produced, CHO cells were co-transfected with heavy and light chain DNA encoding eight (S254C, T359C, E380C, K392C, L398C, V422C, S440C and L443C) anti-5T4 antibody single cysteine variants and stable high production pools were isolated using standard procedures well-known in the art. DNA was co-transfected into the CHO cells since the heavy and light chain expression constructs were on separate expression plasmids. The CHO pool for the parental anti-5T4 antibody was also generated by co-transfecting heavy and light chain expression constructs into CHO cells. For all Fc-engineered cysteine mutants, they share a common light chain DNA sequence with the parental anti-5T4 antibody but have different heavy chain sequences due to cysteine incorporation into the heavy chain constant region. The titer and cellular productivity of these single-engineered cysteine antibody variants expressed in stable CHO pools was acceptable and was comparable to the parental anti-5T4 antibody comprising the wild-type human IgG1 Fc-region (Table 4).

A standard two step purification strategy, i.e., Protein-A affinity capture followed by size exclusion chromatography (SEC), was used to isolate these cysteine variants from the concentrated CHO pool starting material. The ability to isolate the antibodies using this two-step process demonstrated that the Fc region Protein A binding site was not altered by the presence of the engineered cysteine and that the mutated IgG1 Fc region bound Protein A similarly to wild type IgG1 Fc. Minimal high molecular weight aggregated species were detected following elution from Protein A resin for 6 of the 8 single-cysteine variants and this species is reported as percent peak of interest (% POI) in Table 4. Unexpectedly, 2 of the 8 eight mutants (S254C and S440C) were prone to aggregation (Table 4). These data demonstrate that production of antibody comprising engineered single cysteine variants at these positions using stable mammalian cell pools was not affected compared with wild type IgG1.

TABLE 4

| Anti-5T4 Single Cysteine Variant | % POI after ProA | % POI after Superdex 200 | Yield [mg/Liter] |
|---|---|---|---|
| S254C | 84% | 88.9% | 21.5 |
| T359C | 97% | >99% | 31.1 |
| E380C | 97% | >99% | 39.6 |
| K392C | 95% | >99% | 25.3 |
| L398C | 98% | >99% | 41.3 |
| V422C | 96.4% | >99% | 18.4 |
| S440C | 95% | 96.5% | 24.4 |
| L443C | 98% | >99% | 42.8 |
| Parental anti-5T4 Ab | 98% | >99% | 58.8 |

Evaluation of 5T4 Antigen Binding Properties of Single-Cysteine Anti-5T4 Antibody Variants 5T4 binding properties were assessed for the anti-5T4 antibody variants comprising single-cysteine variants using a competition ELISA assay with biotinylated wild type anti-5T4 antibody comprising the wild-type human IgG1 constant region as the reporter antibody to determine if the 5T4 cysteine variants could effectively compete with this wild type 5T4 antibody for binding to 5T4 antigen. For this competition ELISA assay, the parental anti-5T4 reporter antibody (comprising wild type IgG1 Fc without mutations) was biotinylated using EZ-link Sulfo-NHS-Biotin Sulfosuccinimidobiotin (Thermo/Pierce, catalog number 21217) at a molar coupling ratio of 20:1 according to the manufacturer's protocols. Protein for this assay was generated by transiently transfecting DNA encoding the anti-5T4 single-cysteine variants and the wild type anti-5T4 antibody into COS-1 cells. That is, both the variants and the control wild type antibodies comprised human IgG1 Fc regions. The resultant conditioned medium containing the anti-5T4 single-cysteine variants and the anti-5T4 wild type gG1 antibody was assayed using a total human IgG sandwich ELISA as previously described. For this competition ELISA assay procedure, a 96-well plate (Costar catalog #3590) was coated with human truncated recombinant 5T4 protein (5T4-tm⁻_myc_his) lacking the transmembrane and intracellular domains of 5T4 (see Boghaert et al., 2008, Int. J. Oncol. 32:221-234) and further comprising Myc and histidine tags. The 5T4-tm⁻_myc_his construct was diluted to 1 µg/ml in PBS-CMF pH 7.2, 100 µl was added to each well of the plate, and the plate was incubated overnight at 4° C. The contents of the plate were discarded and then the plate was blocked with PBS-CMF pH7.2+0.02% casein for 3 hours at room temperature. Biotinylated anti-5T4 antibody at 20 ng/ml in PBS+0.5% BSA+0.02% tween-20 was mixed with varying concentrations of the anti-5T4 single-cysteine variants or wild type anti-5T4 antibody as the positive control, the samples were added to the 5T4 coated-blocked plate and incubated at room temperature for 2 hours. More specifically, each of the antibodies used in this assay comprise the identical humanized anti-5T4 $V_L$ and $V_H$ domains, but the biotinylated reporter antibody comprises a wild type IgG Fc region without an engineered cysteine while the competitor antibodies comprise either the wild type IgG1 Fc region or mutated IgG1 Fc regions comprising a single-cysteine mutation.

The wells were washed four times with PBS-CMF pH7.2+0.03% tween-20. Streptavidin-HRP (catalog #7100-05, Southern Biotech, (Birmingham, Ala.) diluted 1:10,000 was added and incubated for 30 minutes at room temperature. The wells were washed four times with PBS-CMF pH 7.2+0.03% tween-20 and TMB (BioFx) was added. The reaction developed for 5 to 10 minutes and was then quenched with 0.18 N $H_2SO_4$. The absorbance at 450 nm was determined and the results are shown in FIG. 1. These data demonstrate that reactive cysteine incorporation into the anti-5T4 antibody IgG1 Fc-region at the positions indicated in the graph does not alter the 5T4 binding properties of the antibody. That is, each 5T4 single-cysteine variant equally competed with the biotinylated reporter anti-5T4 antibody for binding to 5T4.

Detection of Free Sulfhydryl for the Anti-5T4 Single Cysteine Variants

As discussed previously, antibodies contain inter and intra-chain disulfide bonds that link the four peptide chains and all of these canonical disulfide bonds should be formed for proper antibody folding. The presence of free sulfhydryl (—SH) groups may result in a molecule that is partially unfolded or improperly folded, leading to a heterogeneous population of antibody and decreased protein stability. The fluorescent reagent ThioGlo®1 (EMD Millipore), a dye that binds using maleimide chemistry, was used to detect free sulfhydryl groups for the anti-5T4 single-cysteine variants.

All antibodies were evaluated with and without dithiothreitol DTT reduction (see, e.g., Antioxidants & Redox Signaling, Volume 4, Number 5 (2002) Mary Ann Liebert, Inc.). Briefly, partial reduction with dithiothreitol (DTT; 2 mM) exposes the unpaired cysteine from cysteine or glutathione adducts presumably formed during CHO cell culturing process, while leaving remaining paired cysteine formed disulfide bonds intact. After DTT partial reduction, the antibodies were treated with guanidine hydrochloride (6.7 M) to expose buried —SH groups and to increase solvent accessibility prior to the addition of ThioGlo®1 fluorescent reagent (20 M). N-acetyl-L-cysteine was used as a standard to quantify the amount of free sulfhydryl present for each antibody. Bovine serum albumin (BSA; OmniPur BSA Fraction V, Catalog No. 2910, EMD Chemicals) was additionally included as a positive control since it contains one single unpaired cysteine. As shown in Table 5, the results disclosed herein indicate that free sulfhydryl was detected for the anti-5T4 single-cysteine variants and not for the parental anti-5T4 antibody. In the absence of DTT, increased levels of free —SH was not observed for the six cysteine variants assessed compared with the wild type anti-5T4 protein. Unpredictably, the 5T4-S254C variant exhibited aggregation and was unstable following reduction with DTT.

TABLE 5

| Antibody | µM -SH/µM protein | |
|---|---|---|
| | No DTT | DTT (2 mM) |
| Parental 5T4 | 0.24 | 0.30 |
| 5T4-S254C | 0.19 | 0.03 < LOQ |
| 5T4-E380C | 0.16 | 0.82 |
| 5T4-L398C | 0.26 | 0.90 |
| 5T4-V422C | 0.20 | 1.02 |

Evaluation of Anti-5T4 Engineered Single Cysteine Variants Binding to Human FcRn It is believed in the art that FcRn interacts with IgG regardless of subtype in a pH dependent manner and protects the antibody from degradation by preventing it from entering the lysosomal compartment where it is degraded. Therefore, a consideration for selecting positions for introduction of reactive cysteines into the wild type IgG1-Fc region was to avoid altering the FcRn binding properties and half-life of the antibody comprising the engineered cysteine.

BIAcore® analysis was performed to determine the steady-state affinity (KD) for anti-5T4 engineered single cysteine variants for binding human FcRn. BIAcore® technology utilizes changes in the refractive index at the surface layer of a sensor upon binding of the anti-5T4 single engineered cysteine variants to human FcRn protein immobilized on the layer. Binding is detected by surface plasmon resonance (SPR) of laser light refracting from the surface. Human FcRn was specifically biotinylated through an engineered Avi-tag using the BirA reagent (Catalog #: BIRA500, Avidity, LLC, Aurora, Colo.) and immobilized onto a streptavidin (SA) sensor chip to enable uniform orientation of the FcRn protein on the sensor. Next, various concentrations of the anti-5T4 single-cysteine variants in 20 mM MES (2-(N-morpholino)ethanesulfonic acid pH 6.0, with 150 mM NaCl, 3 mM EDTA (ethylenediaminetetraacetic acid), 0.5% Surfactant P20 (MES-EP) were injected over the chip surface. The surface was regenerated using HBS-EP+0.05%

Surfactant P20 (GE Healthcare, Piscataway, N.J., Piscataway, N.J.), pH 7.4, between injection cycles. The steady-state binding affinities were determined for the anti-5T4 engineered single-cysteine variants and these were compared with the parental wild type anti-5T4 (comprising no cysteine mutations in the IgG1 Fc region). The results are set forth at Table 6, and these data demonstrate that incorporation of engineered cysteine residues into the IgG-Fc region at the novel positions of the invention did not alter affinity to FcRn.

TABLE 6

| Antibody | Steady-state KD [nM] |
| --- | --- |
| Parental anti-5T4 Ab | 412.1 |
| 5T4-E380C | 390.1 |
| 5T4-K392C | 383.5 |
| 5T4-L398C | 513.4 |
| 5T4-V422C | 443.3 |
| 5T4-S440C | 608.4 |

Evaluation of Single-Cysteine Anti-5T4 Variant ADCs Binding to Human FcRn

BIAcore® analysis was performed to determine the steady-state affinity (KD) for anti-5T4 ADCs binding to human FcRn where the ADCs were site-specifically conjugated through the engineered cysteines thereby linking a toxin to the antibody. Briefly, ADCs were prepared by conjugating mcMMAD, as more fully disclosed below, to the engineered cysteine for the variants 5T4-E380C, 5T4-L398C, 5T4-V422C and 5T4-L443C. Using the same Biacore SPR method described previously, various concentrations of the site-specifically conjugated 5T4-mcMMAD ADCs, the single-cysteine variants not conjugated to mcMMAD (described previously and results shown in Table 6), and the parental "naked" (i.e., not conjugated to mcMMAD) wild type anti-5T4 antibody in MES-EP+0.5% Surfactant P20 pH 6.0 were injected, separately, over the human FcRn surface and steady-state affinities were determined and the results are shown in Table 7.

TABLE 7

| ADC or Naked Antibody | Steady-state KD [nM] |
| --- | --- |
| Parental anti-5T4 antibody | 493.3 |
| 5T4-E380C-mcMMAD | 408.7 |
| 5T4-L398C-mcMMAD | 703.9 |
| 5T4-V422C-mcMMAD | 401.8 |
| 5T4-L443C-mcMMAD (1) | 697.0 |
| 5T4-L443C-mcMMAD (2) | 518.5 |

The results shown in Table 7 demonstrate that the 5T4-mcMMAD ADCs site-specifically conjugated using the novel cysteine positions of the invention have similar affinities to human FcRn compared with each other and that these affinities for FcRn are comparable to those of the naked un-conjugated single cysteine variants (compare with Table 6 above), as well as for the un-conjugated parental 5T4 antibody. Thus, these data demonstrate that conjugation of a toxin moiety to the engineered reactive cysteines introduced into the IgG1 Fc region did not affect Fc binding to FcRn.

Example 2

Generation of Double-Cysteine Engineered Anti-5T4 Antibodies

Nine combinations of two reactive cysteine residues were introduced into the anti-5T4 antibody comprising human IgG1. The amino acid sequence of the wild type full-length heavy chain of this antibody is set forth in FIG. 17A (SEQ ID NO:83) and the amino acid sequence of the full-length kappa light chain of this antibody is set forth in FIG. 17B (SEQ ID NO:84). The mutations to substitute the relevant wild type amino acid to the novel engineered cysteine in the heavy chain constant region were introduced using the same over-lapping PCR mutagenesis method as described previously in Example 1. Introduction of two reactive cysteines into each IgG1 Fc region thus provided four novel cysteine conjugation sites that would yield ADCs with a drug:antibody ratio (DAR) of 4 for each antibody (i.e., 2 reactive novel cysteines×2 heavy chain Fc regions per antibody molecule). The relative positions of the engineered reactive cysteines for each double-mutant are shown below in Table 8 which shows the ten (10) amino acids both before and after the mutation except where the mutation is less than 10 amino acid residues from the C-terminus of the Fc region. The full length amino acid sequence for each Fc region is provided in the SEQ ID NO indicated in the table.

TABLE 8

| IgG1 Double Cysteine Positions | Sequence ID | Amino Acid Sequence |
| --- | --- | --- |
| E380C + L443C | SEQ ID NO: 74 | -KGFYPSDIAVCWESNGQPENN- + -VMHEALHNHYTQKSLSCSPGK |
| L398C + L443C | SEQ ID NO: 75 | -ENNYKTTPPVCDSDGSFFLYS- + -VMHEALHNHYTQKSLSCSPGK |
| V422C + L443C | SEQ ID NO: 76 | -VDKSRWQQGNCFSCSVMHEAL- + -VMHEALHNHYTQKSLSCSPGK |
| E380C + L398C | SEQ ID NO: 77 | -KGFYPSDIAVCWESNGQPENN- + -ENNYKTTPPVCDSDGSFFLYS- |
| L398C + V422C | SEQ ID NO: 78 | -ENNYKTTPPVCDSDGSFFLYS- + -VDKSRWQQGNCFSCSVMHEAL- |
| E380C + V422C | SEQ ID NO: 79 | -KGFYPSDIAVCWESNGQPENN- + -VDKSRWQQGNCFSCSVMHEAL- |
| K392C + L443C | SEQ ID NO: 80 | -ESNGQPENNYCTTPPVLDSDG- + -VMHEALHNHYTQKSLSCSPGK |
| F404C + L443C | SEQ ID NO: 81 | -TPPVLDSDGSCFLYSKLTVDK- + -VMHEALHNHYTQKSLSCSPGK |
| K392C + F404C | SEQ ID NO: 82 | -ESNGQPENNYCTTPPVLDSDG- + TPPVLDSDGSCFLYSKLTVDK |

Transient Expression of Double Cysteine Engineered Anti-5T4 Antibodies

To confirm that the anti-5T4 antibodies comprising the engineered double cysteines could be expressed, COS-1 cells were transiently co-transfected with heavy and light chain DNA encoding the 5T4 double cysteine variants and the parental 5T4 antibody. After a period of 48 hours, each cell culture medium was assayed to determine the level of human IgG1 antibody expressed for each construct using the total human IgG sandwich ELISA described previously. As shown in Table 9, each double cysteine engineered anti-5T4 antibody variant expressed at a comparable level compared with the parental anti-5T4 antibody not comprising any additional cysteines.

TABLE 9

| 5T4 antibody | Amount of human IgG1 in the cell culture medium [µg/ml] |
|---|---|
| Wild type 5T4 | 41.2 |
| 5T4-E380C+L443C | 32.6 |
| 5T4-E380C+L398C | 45.4 |
| 5T4-L398C+L443C | 52.0 |
| 5T4-E380C+V422C | 39.6 |
| 5T4-V422C+L443C | 42.2 |
| 5T4-L398C+V422C | 44.0 |

Production of 5T4 Double Cysteine Variants from Transient HEK-293 Expression System To produce sufficient material for conjugation studies, HEK-293 cells were transiently co-transfected with heavy and light chain DNA encoding the six 5T4 double-cysteine engineered antibody variants using standard methods. Next, the double-cysteine variant antibodies were purified using a standard two step purification strategy, Protein-A affinity capture followed by size exclusion chromatography (SEC). These results shown in Table 10 demonstrate that acceptable levels of high molecular weight (HMW) aggregated species were detected following elution from Protein A resin for all six 5T4 double cysteine variants and that this undesirable HMW species could be removed using size exclusion chromatography. Additionally, the data disclosed herein demonstrate that the Protein A binding site in the human IgG1 constant region was not altered by the presence of the engineered double cysteine residues.

TABLE 10

| 5T4 Double Cysteine Variant | % POI after ProA | % POI after Superdex 200 | Yield [mg/Liter] |
|---|---|---|---|
| 5T4-E380C+L443C | 91.0% | >99% | 22.4 |
| 5T4-E380C+L398C | 97.3% | >99% | 24.0 |
| 5T4-L398C+L443C | 90.9% | >99% | 29.0 |
| 5T4-E380C+V422C | 89.5% | >99% | 16.0 |
| 5T4-V422C+L443C | 94.3% | >99% | 8.2 |
| 5T4-L398C+V422C | 92.7% | >99% | 10.5 |

Example 3

Generation of Anti-Her2 Single and Double Cysteine Engineered Antibody Variants

To demonstrate that these selected positions for engineering reactive cysteines can be applied to other antibodies regardless of antigen-binding specificity, four (4) single and nine (9) double cysteine residues were engineered into the IgG1 Fc region of an anti-human Her2 antibody. The amino acid sequence of the full-length heavy chain of the anti-Her2 antibody is show in FIG. 17C (SEQ ID NO:85) showing the wild type IgG1 Fc region without mutations (lower case letters). The amino acid sequence of the full-length light chain of the anti-Her2 antibody is show in FIG. 17D (SEQ ID NO:86) showing the wild type Cκ region without mutations (lower case letters). The positions of the cysteine mutations introduced are set forth Table 11. The nucleic acid encoding the anti-Her2 antibody human IgG1 constant region was removed from the vector by restriction enzyme digestion and replaced with a nucleic acid encoding human heavy chain constant IgG1 Fc regions comprising the single and double engineered cysteine residues using T4 DNA Ligase (New England Biolabs Inc., Ipswich, Mass.). The resulting nucleic acid was sequence confirmed for each construct.

TABLE 11

| Anti-Her2 Engineered Cysteine Variant | Sequence of IgG1 Fc portion of the antibody SEQ ID NO: |
|---|---|
| Her2-E380C | SEQ ID NO: 45 |
| Her2-L398C | SEQ ID NO: 54 |
| Her2-V422C | SEQ ID NO: 64 |
| Her2-L443C | SEQ ID NO: 72 |
| Her2-E380C+L443C | SEQ ID NO: 74 |
| Her2-L398C+L443C | SEQ ID NO: 75 |
| Her2-V422C+L443C | SEQ ID NO: 76 |
| Her2-E380C+L398C | SEQ ID NO: 77 |
| Her2-L398C+V422C | SEQ ID NO: 78 |
| Her2-E380C+V422C | SEQ ID NO: 79 |
| Her2-K392C+L443C | SEQ ID NO: 80 |
| Her2-F404C+L443C | SEQ ID NO: 81 |
| Her2-K392C+F404C | SEQ ID NO: 82 |

Production of Anti-Her2 Engineered Cysteine Variants

Antibodies were successfully produced for use in conjugation studies by transiently co-transfecting COS-1 cells with heavy and light chain DNA encoding the anti-Her2 single and double cysteine engineered antibody variants demonstrating that the antibodies could be transiently expressed in cells. Further, the antibodies were purified using a standard two step purification strategy, Protein-A affinity capture followed by size exclusion chromatography (SEC). The data disclosed herein (Table 12) demonstrate that low levels of high molecular weight (HMW) aggregated species were detected following elution from Protein A resin for all 6 anti-Her2 double cysteine variants and that this HMW species could be removed using size exclusion chromatography. These data demonstrate that the Fc binding to Protein A for these variants was not affected by introduction of the reactive cysteines at the novel positions.

TABLE 12

| Anti-Her2 Cysteine Variant | % POI after ProA | % POI after Superdex 200 | Yield [mg/Liter] |
|---|---|---|---|
| E380C | 98.8% | 100% | 7 |
| L443C | 95.0% | 98.9% | 12 |
| E380C+L443C | 94.2% | 99.3% | 11 |

Example 4

Production of Anti-VEGFR2 Single Cysteine Engineered Antibody Variant

To further demonstrate that the novel positions for engineering reactive cysteines could be applied to antibodies targeting vascular endothelium, a single cysteine residue was engineered into an anti-human VEGFR2 antibody. The amino acid sequence of the full-length heavy chain of the anti-VEGFR2 antibody is show in FIG. 17E (SEQ ID NO:87) showing the wild type IgG1 Fc region without mutations (lower case letters). The amino acid sequence of the full-length light chain of the anti-VEGFR2 antibody is show in FIG. 17F (SEQ ID NO:88) showing the wild type Cκ region without mutations (lower case letters). The nucleic acid sequence encoding the wild type human IgG1 Fc constant region of an anti-human VEGFR2 antibody was removed by restriction enzyme digestion and replaced with a nucleic acid sequence encoding the heavy chain constant region comprising a single cysteine residue at position L443C (SEQ ID NO:72) using T4 DNA Ligase (New England Biolabs Inc., Ipswich, Mass.) and the resulting nucleic acid was sequence confirmed.

The antibody is produced by transfecting COS-1 with the nucleic acid encoding the antibody and the protein is purified using a two-step (Protein A followed by SEC chromatographies) process. This demonstrates that the anti-human VEGFR2 antibody comprising the single reactive cysteine can be expressed and that the Protein A binding of the Fc region is not affected.

In summary, as disclosed previously herein, twelve residue positions were identified for introduction of reactive cysteines into human IgG1 Fc regions. Of these twelve novel positions, nine antibody single-cysteine variants were produced for conjugation and characterization. Of these nine, only two single mutations unexpectedly demonstrated apparent protein aggregation S254C and S440C (by EU numbering), and the other seven single cysteine variants showed nominal aggregation similar to the parental antibody comprising the wild-type IgG1 constant region. Further, of the seven variants that did not demonstrate apparent aggregation, two—T359C and F404C (by EU numbering)—exhibited marginal conjugation efficiency with different linker and payload combinations. Engineered cysteines at 5 positions, E380C, L398C, K392C, V422C and L443C (numbering using the Eu index of Kabat), demonstrated acceptable conjugation efficiencies across a number of conditions. Furthermore, this difference in conjugation efficiency was not detected if only the ability to conjugate with biotin was assessed. That is, the difference in conjugation efficiency was only detected when a more rigorous standard was applied, i.e., where larger toxic payloads were conjugated to the antibody. Under this more rigorous demand, the novel cysteines of the present invention were demonstrated to provide efficient novel conjugation platforms for production of potentially therapeutically effective ADCs.

Example 5

Additional Positions in Human IgG1 Fc Region for Introduction of Reactive Cysteine for Site-Specific Conjugation In addition to the novel twelve positions in human IgG1 disclosed previously herein for successful production of engineered Fc regions comprising reactive cysteines, additional positions for incorporation of reactive cysteines were identified as follows. Briefly, the crystal complex of the Fc domain of human IgG1 (PDB code 3D03, 10.2210/pdb3do3/pdb) was obtained from the RCSB protein databank and prepared for visualization and modeling in Discovery Studio (Accelrys Inc., San Diego, Calif.). The individual side chains were mutated to cysteine and minimized using the Mutate Residue feature in Discovery Studios according to manufacturer's instructions. The side chain solvent accessibility of the mutated residue was calculated, as was the residue pKa, using the method of Spassov and Yan (2008, Protein Sci. 17(11):1955-1970).

More specifically, and without wishing to be bound by any particular theory, viewing the data disclosed herein for the first time for the novel twelve Fc positions disclosed previously, suggested that a low pKa or a high side chain accessibility may lead to inefficient drug loading, protein aggregation or other issues. Additional sites consistent with these side chain solvent accessibility and pKa ranges were identified based on calculations using Discovery Studio.

The data disclosed herein suggest that cysteine residues with either an optimal predicted pKa range between 9.5 and 11.5, and/or a predicted side chain solvent accessibility between 15 and 60, may mimic the properties of the conjugated cysteine mutants disclosed previously herein, including, but not limited to E380C, K392C, L398C, V422C and L443C. Since these properties (pKa and predicted side chain solvent accessibility) are correlated, it is difficult to establish which criteria are associated with the desired biological outcomes, including, but not limited to, low propensity to aggregate and facile conjugation to linkers and payloads. The additional positions selected by our novel in silico design method for introducing reactive cysteines based on the surprising data obtained for the novel twelve mutants disclosed herein are listed in Table 13 with their corresponding EU numbering position.

TABLE 13

| Sequential Position | Position (EU Numbering) | SEQ ID NO full engineered IgG1 | Amino Acid Sequence (w/ amino acids flanking the engineered cysteine) | SEQ ID NO portion showing engineered Cys |
|---|---|---|---|---|
| 129 | K246C | 6 | GGPSVFLFPPCPKDTLMISRT | 108 |
| 132 | D249C | 7 | SVFLFPPKPKCTLMISRTPEV | 109 |
| 148 | D265C | 9 | RTPEVTCVVVCVSHEDPEVKF | 110 |
| 150 | S267C | 10 | PEVTCVVVDVCHEDPEVKFNW | 111 |
| 153 | D270C | 11 | TCVVVDVSHECPEVKFNWYVD | 112 |
| 159 | N276C | 12 | VSHEDPEVKFCWYVDGVEVHN | 113 |
| 161 | Y278C | 13 | HEDPEVKFNWCVDGVEVHNAK | 114 |
| 166 | E283C | 14 | VKFNWYVDGVCVHNAKTKPRE | 115 |
| 167 | V284C | 15 | KFNWYVDGVECHNAKTKPREE | 116 |
| 170 | A287C | 16 | WYVDGVEVHNCKTKPREEQYN | 117 |
| 175 | R292C | 17 | VEVHNAKTKPCEEQYNSTYRV | 118 |
| 176 | E293C | 18 | EVHNAKTKPRCEQYNSTYRVV | 119 |
| 177 | E294C | 19 | VHNAKTKPRECQYNSTYRVVS | 120 |

TABLE 13-continued

| Sequential Position | Position (EU Numbering) | SEQ ID NO full engineered (w/ IgG1 | Amino Acid Sequence amino acids flanking the engineered cysteine) | SEQ ID NO portion showing engineered Cys |
|---|---|---|---|---|
| 183 | Y300C | 20 | KPREEQYNSTCRVVSVLTVLH | 121 |
| 185 | V302C | 21 | REEQYNSTYRCVSVLTVLHQD | 122 |
| 186 | V303C | 22 | EEQYNSTYRVCSVLTVLHQDW | 123 |
| 197 | L314C | 23 | SVLTVLHQDWCNGKEYKCKVS | 124 |
| 198 | N315C | 24 | VLTVLHQDWLCGKEYKCKVSN | 125 |
| 201 | E318C | 25 | VLHQDWLNGKCYKCKVSNKAL | 126 |
| 203 | K320C | 26 | HQDWLNGKEYCCKVSNKALPA | 127 |
| 210 | A327C | 27 | KEYKCKVSNKCLPAPIEKTIS | 128 |
| 215 | I332C | 28 | KVSNKALPAPCEKTISKAKGQ | 129 |
| 216 | E333C | 29 | VSNKALPAPICKTISKAKGQP | 130 |
| 217 | K334C | 30 | SNKALPAPIECTISKAKGQPR | 131 |
| 219 | I336C | 31 | KALPAPIEKTCSKAKGQPREP | 132 |
| 228 | E345C | 32 | TISKAKGQPRCPQVYTLPPSR | 133 |
| 230 | Q347C | 33 | SKAKGQPREPCVYTLPPSREE | 134 |
| 237 | S354C | 34 | REPQVYTLPPCREEMTKNQVS | 135 |
| 238 | R355C | 35 | EPQVYTLPPSCEEMTKNQVSL | 136 |
| 241 | M358C | 36 | VYTLPPSREECTKNQVSLTCL | 137 |
| 243 | K360C | 38 | TLPPSREEMTCNQVSLTCLVK | 138 |
| 245 | Q362C | 40 | PPSREEMTKNCVSLTCLVKGF | 139 |
| 253 | K370C | 41 | KNQVSLTCLVCGFYPSDIAVE | 140 |
| 256 | Y373C | 42 | VSLTCLVKGFCPSDIAVEWES | 141 |
| 259 | D376C | 43 | TCLVKGFYPSCIAVEWESNGQ | 142 |
| 261 | A378C | 44 | LVKGFYPSDICVEWESNGQPE | 143 |
| 265 | E382C | 46 | FYPSDIAVEWCSNGQPENNYK | 144 |
| 269 | Q386C | 49 | DIAVEWESNGCPENNYKTTPP | 145 |
| 271 | E388C | 50 | AVEWESNGQPCNNYKTTPPVL | 146 |
| 273 | N390C | 51 | EWESNGQPENCYKTTPPVLDS | 147 |
| 276 | T393C | 53 | SNGQPENNYKCTPPVLDSDGS | 148 |
| 284 | D401C | 55 | YKTTPPVLDSCGSFFLYSKLT | 149 |
| 294 | T411C | 57 | DGSFFLYSKLCVDKSRWQQGN | 150 |
| 296 | D413C | 58 | SFFLYSKLTVCKSRWQQGNVF | 151 |
| 297 | K414C | 59 | FFLYSKLTVDCSRWQQGNVFS | 152 |
| 299 | R416C | 60 | LYSKLTVDKSCWQQGNVFSCS | 153 |
| 301 | Q418C | 61 | SKLTVDKSRWCQGNVFSCSVM | 154 |
| 302 | Q419C | 62 | KLTVDKSRWQCGNVFSCSVMH | 155 |
| 304 | N421C | 63 | TVDKSRWQQGCVFSCSVMHEA | 156 |
| 311 | M428C | 65 | QQGNVFSCSVCHEALHNHYTQ | 157 |

TABLE 13-continued

| Sequential Position | Position (EU Numbering) | SEQ ID NO full engineered IgG1 | Amino Acid Sequence (w/ amino acids flanking the engineered cysteine) | SEQ ID NO portion showing engineered Cys |
|---|---|---|---|---|
| 314 | A431C | 66 | NVFSCSVMHECLHNHYTQKSL | 158 |
| 315 | L432C | 67 | VFSCSVMHEACHNHYTQKSLS | 159 |
| 320 | T437C | 68 | VMHEALHNHYCQKSLSLSPGK | 160 |
| 321 | Q438C | 69 | VMHEALHNHYCQKSLSLSPGK | 161 |
| 322 | K439C | 70 | VMHEALHNHYCQKSLSLSPGK | 162 |
| 327 | S444C | 73 | VMHEALHNHYCQKSLSLSPGK | 163 |

Example 6

Generation of Additional Single Cysteine Engineered Anti-Her2 Antibody Variants Certain reactive cysteines positions shown in Table 13 were selected with optimal side chain solvent accessibility and pKa ranges and these are shown in Table 14. Human IgG1 Fc regions comprising engineered single cysteines at these eleven (11) novel positions were incorporated into an anti-Her2 antibody (see above) for further evaluation.

TABLE 14

| Variant | SEQ ID NO full length Fc | Amino Acid Sequence | SEQ ID NO of portion showing position of engineered amino acid |
|---|---|---|---|
| K246C | SEQ ID NO: 6 | GGPSVFLFPPCPKDTLMISRT | 108 |
| Q347C | SEQ ID NO: 33 | SKAKGQPREPCVYTLPPSREE | 134 |
| M358C | SEQ ID NO: 36 | VYTLPPSREECTKNQVSLTCL | 137 |
| Y373C | SEQ ID NO: 42 | VSLTCLVKGFCPSDIAVEWES | 141 |
| E388C | SEQ ID NO: 50 | AVEWESNGQPCNNYKTTPPVL | 146 |
| N390C | SEQ ID NO: 51 | EWESNGQPENCYKTTPPVLDS | 147 |
| D413C | SEQ ID NO: 58 | SFFLYSKLTVCKSRWQQGNVF | 151 |
| Q418C | SEQ ID NO: 61 | SKLTVDKSRWCQGNVFSCSVM | 154 |
| N421C | SEQ ID NO: 63 | TVDKSRWQQGCVFSCSVMHEA | 156 |
| A431C | SEQ ID NO: 66 | NVFSCSVMHECLHNHYTQKSL | 158 |
| Q438C | SEQ ID NO: 69 | VMHEALHNHYTCKSLSLSPGK | 161 |

Example 7

Conjugation and Characterization of ADCs Using Single-Cysteine Variant Antibodies Conjugation of Single-Cysteine Variant Antibodies with Linkers and Payloads:

The novel ADCs disclosed previously demonstrating successful conjugation of the antibodies comprising novel IgG1 Fc regions comprising engineered reactive cysteines were prepared as now described herein below.

Condition A: (Condition B is described below at Example 8) Conjugation reactions were performed in the upper portion of a centrifugal ultrafiltration device such as Amicon Ultra 50 k Ultracel filters (part #UFC805096, GE). A 132 mM stock solution of L-cysteine was prepared in PBS containing 50 mM EDTA. This solution (50 uL) was added to a mixture of the respective mutant antibody (5 mg) in 950 uL of PBS containing 50 mM EDTA. The final cysteine concentration in the reaction mixture was 6.6 mM. After allowing the reaction to stand at rt (about 23 degrees C.) for 1.5 hour the reaction tube was centrifuged to concentrate the material to approximately 100 uL. The mixture was diluted to 1 mL with PBS containing 50 mM EDTA. This process was repeated 4 times in order to remove all the cysteine reductant.

The resulting material was diluted to 1 mL in PBS containing 50 mM EDTA and treated with 16 uL of a 5 mM solution of mcMMAD in dimethyl acetamide (DMA) (approximately 5 equivalents). After standing at room temperature (about 23 degrees C.) for 1.5 hour the reaction tube was centrifuged to concentrate the material to approximately 100 µL. The mixture was diluted to 1 mL with PBS. This process was repeated 2 times in order to remove the excess maleimide reactant (e.g., mcMMAD).

The antibody conjugates were generally purified and characterized using size-exclusion chromatography (SEC)

as described below. The loading of the drug onto the intended site of conjugation was determined using a variety of methods including mass spectrometry (MS), reverse phase HPLC, and hydrophobic interaction chromatography (HIC), as more fully described below. The combination of these three analytical methods provides a variety of ways to verify and quantitate the loading of the small-molecule onto the protein thereby providing an accurate determination of the DAR for each conjugate.

Characterization of Cysteine Mutant Antibody ADCs by Size-Exclusion Chromatography (SEC):

Preparative SEC:

Antibody-drug conjugates (Ab-linker-payload, e.g., Ab-mcMMAD and Ab-vcMMAD) were generally purified using SEC chromatography using a Waters Superdex200 10/300GL column on an Akta Explorer FPLC system in order to remove protein aggregate and to remove traces of payload-linker left in the reaction mixture. On occasion, ADCs were free of aggregate and small molecule prior to SEC purification and were therefore not subjected to preparative SEC. The eluent used was PBS at 1 mL/min flow. Under these conditions, aggregated material (eluting at about 10 minutes at room temperature) was easily separated from non-aggregated material (eluting at about 15 minutes at room temperature). Hydrophobic payload-linker combinations frequently resulted in a "right-shift" of the SEC peaks. Without wishing to be bound by any particular theory, this SEC peak shift may be due to hydrophobic interactions of the linker-payload with the stationary phase. In some cases, this right-shift allowed for conjugated protein to be partially resolved from non-conjugated protein.

Analytical Size-Exclusion Chromatography (SEC):

Analytical SEC was carried out on an Agilent 1100 HPLC using PBS as eluent. The eluent was monitored at 220 and 280 nM. The methods utilized are as follows:

Method SEC-A: The column was a TSKGel G3000SW column (7.8×300 mm, catalog number R874803P). The mobile phase used was PBS with a flow rate of 0.9 mL/min for 30 minutes.

Method SEC-B: The column was a BiosepSEC3000 column (7.8×300 mm) with PBS as the mobile phase using a flow rate of 1.0 mL/min for 25 minutes.

The results of the methods above are now discussed.

Table 15 below sets forth the results for various antibody-drug conjugates purified and characterized using the above methods. The loading analysis and MS characterizations are discussed below.

Figure 2:
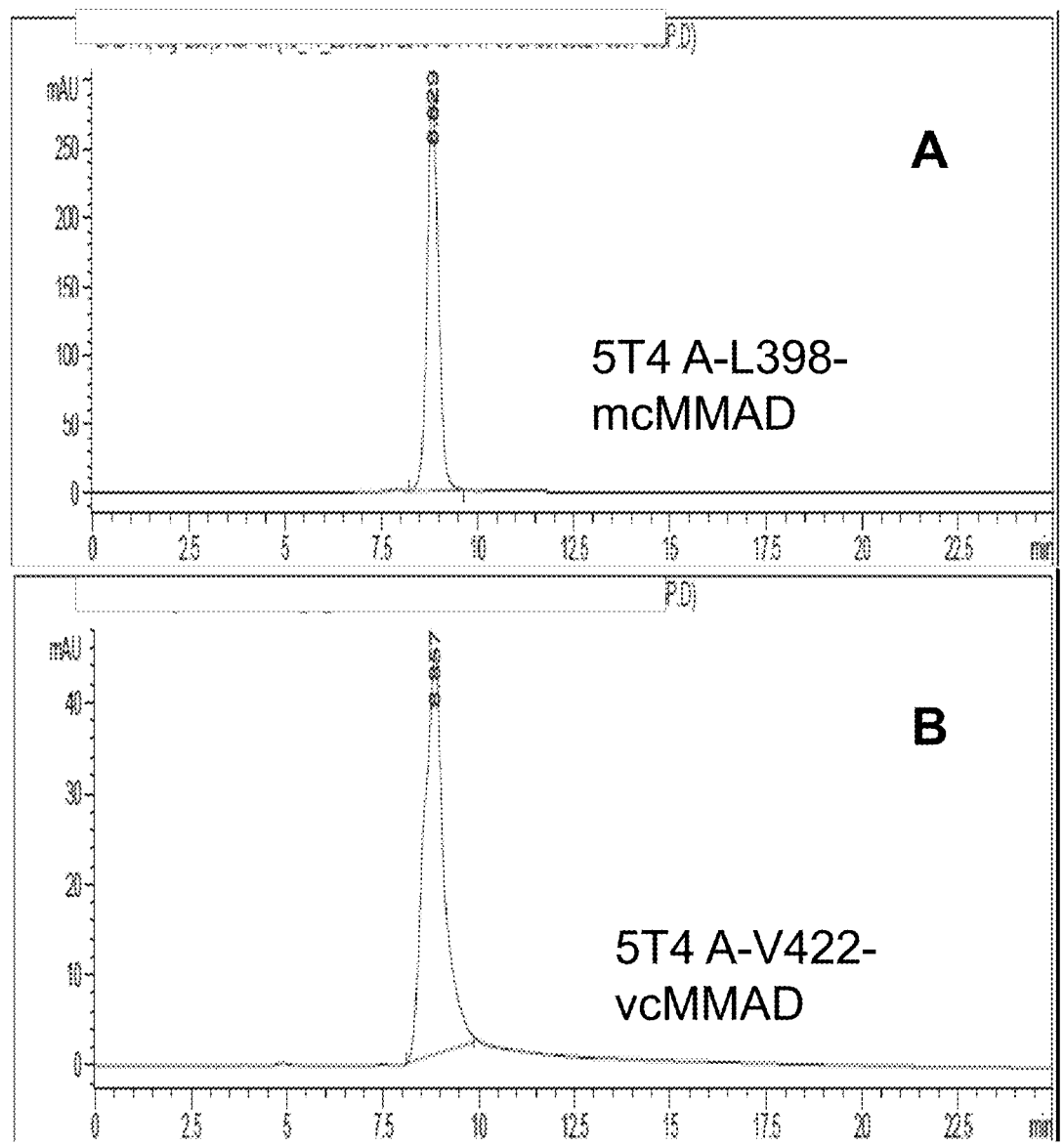
FIG. 2, comprising

The conjugates were analyzed by analytical SEC in order to establish the integrity of the purified protein conjugate and to ensure that minimal aggregation occurred during the conjugation. The two methods described above give approximately equivalent retention times and were used in different circumstances simply for practical purposes such as column availability and reliability. Generally it was observed that aggregated material induced a leftward shift of the retention time of approximately one minute. Examples of two analytical SEC traces are illustrated in FIG. 2. FIG. 2A shows the SEC tracing for 5T4-L398C-mcMMAD (using method SEC-A); FIG. 2B shows the SEC trace for 5T4-V422C-vcMMAD (using method SEC-B). These tracings show that the material is non-aggregated and contains no measurable small molecule contaminant. It was generally observed that more hydrophobic payloads such as vcMMAD resulted in ADCs with modestly broader and less uniform SEC peaks. In some cases the conjugation of a hydrophobic payload (such as vcMMAD) resulted in a significant rightward shift in the retention time. (For example, see 5T4-L443C-vcMMAD in Table 15.) However, the major peak could always be easily distinguished from the aggregate peak which typically eluted at about 7.5 mins. The analytical SEC data for a variety of 5T4 ADCs (all prepared by Method A) are outlined in Table 15.

TABLE 15

| Antibody | Linker-payload | Isolated yield (mg) | SEC rt (min) | SEC method |
|---|---|---|---|---|
| 5T4-A1 | None | NA | 9.12 | SEC-B |
| 5T4-E380C | mcMMAD | 2.5 mg | 9.13 | SEC-A |
| 5T4-L398C | mcMMAD | 2.5 mg | 8.92 | SEC-A |
| 5T4-V422C | mcMMAD | 4.0 mg | 9.23 | SEC-A |
| 5T4-L443C | mcMMAD | 4.0 mg | 9.73 | SEC-A |
| 5T4-K392C | mcMMAD | 2.7 mg | 8.89 | SEC-A |
| 5T4-E380C | vcMMAD | 2.6 mg | 9.36 | SEC-A |
| 5T4-L398C | vcMMAD | 3.3 mg | 8.46 | SEC-B |
| 5T4-V422C | vcMMAD | 2.9 mg | 8.86 | SEC-B |
| 5T4-L443C | vcMMAD | 2.6 mg | 10.68 | SEC-A |

Mass Spectroscopy Characterization and Analysis of the Antibody-Conjugates

MS Analysis and Sample Prep:

Samples were prepped for LCMS analysis by combining approximately 20 uL of sample (approximately 1 mg/mL ADC in PBS) with 20 uL of 20 mM dithiothreitol (DTT). After allowing the mixture to stand at room temperature for 5 minutes, the samples were injected into an Agilent 1100 HPLC system fitted with a Agilent Poroshell 300SB-C8 (2.1×75 mm) column. The system temperature was set to 60° C. A 5 minute gradient from 20% to 45% acetonitrile in water (with 0.1% formic acid modifier) was utilized. The eluent was monitored by UV (220 nM) and by a Waters MicromassZQ mass spectrometer (ESI ionization; cone voltage: 20V; Source temp: 120° C.; Desolvation temp: 350° C.). The crude spectrum containing the multiple-charged species was deconvoluted using MaxEnt1 within MassLynx 4.1 software package according to the manufacturer's instructions.

MS Determination of Loading Per Antibody:

The spectra for the entire elution window (usually 5 minutes) are combined into a single summed spectra (i.e., a mass spectrum that represents the MS of the entire sample). MS results for ADC samples were compared directly to the corresponding MS of the identical non-loaded control antibody. This allows for the identification of loaded/nonloaded heavy chain (HC) peaks and loaded/nonloaded light chain (LC) peaks. The ratio of the various peaks can be used to establish loading based on the equation below (Equation 1). Calculations are based on the assumption that loaded and non-loaded chains ionize equally which has been determined to be a generally valid assumption. Further, to cross-check these loading calculations, a subset of ADCs was also assessed for loading using alternative methods (reverse phase high performance liquid chromatography [rpHPLC]-based and hydrophobic interaction chromatography [HIC]-based methods) as more fully described in the sections below.

The following calculation was performed in order to establish the total loading (also referred to as "Drug Antibody Ratio" or "DAR") of the conjugate:

Equation 1:
$$\text{Loading} = 2*[LC1/(LC1+LC0)] + 2*[HC1/(HC0+HC1+HC2)] + 4*[HC2/(HC0+HC1+HC2)]$$

Where the indicated variables are the relative abundance of: LC0=unloaded light chain, LC1=single loaded light chain, HC0=unloaded heavy chain, HC1=single loaded heavy chain, and HC2=double loaded heavy chain. One of ordinary skill in the art would appreciate that the invention encompasses expansion of this calculation to encompass higher loaded species such as LC2, LC3, HC3, HC4, HC5, and the like.

Equation 2, below, is used to estimate the amount of loading onto non-engineered cysteine residues For engineered Fc mutants, loading onto the light chain (LC) was considered, by definition, to be nonspecific loading. Moreover, it was assumed that loading only the LC was the result of inadvertent reduction of the HC-LC disulfide bridge (i.e., the antibody was "over-reduced"). Given that a large excess of maleimide electrophile was used for the conjugation reactions (generally approximately 5 equivalents for single mutants and 10 equivalents for double mutants), it was assumed that any nonspecific loading onto the light chain was accompanied by a corresponding amount of non-specific loading onto the heavy chain (i.e., the other "half" of the broken HC-LC disulfide). With these assumptions in mind, the following equation (Equation 2) was used to estimate the amount of non-specific loading onto the protein:

$$\text{Nonspecific loading} = 4*[LC1/(LC1+LC0)] \quad \text{Equation 2:}$$

Where the indicated variables are the relative abundance of: LC0=unloaded light chain, LC1=single loaded light chain.

Figure 3A:
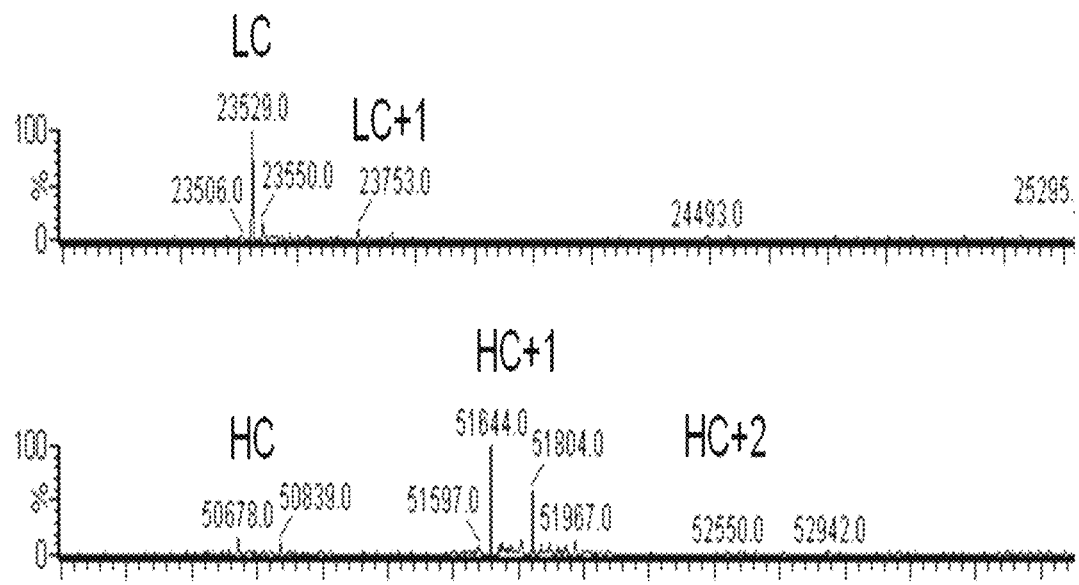
FIGS. 3A-3B, shows the MS tracing and loading calculations for two exemplary ADCs.
Figure 3B:
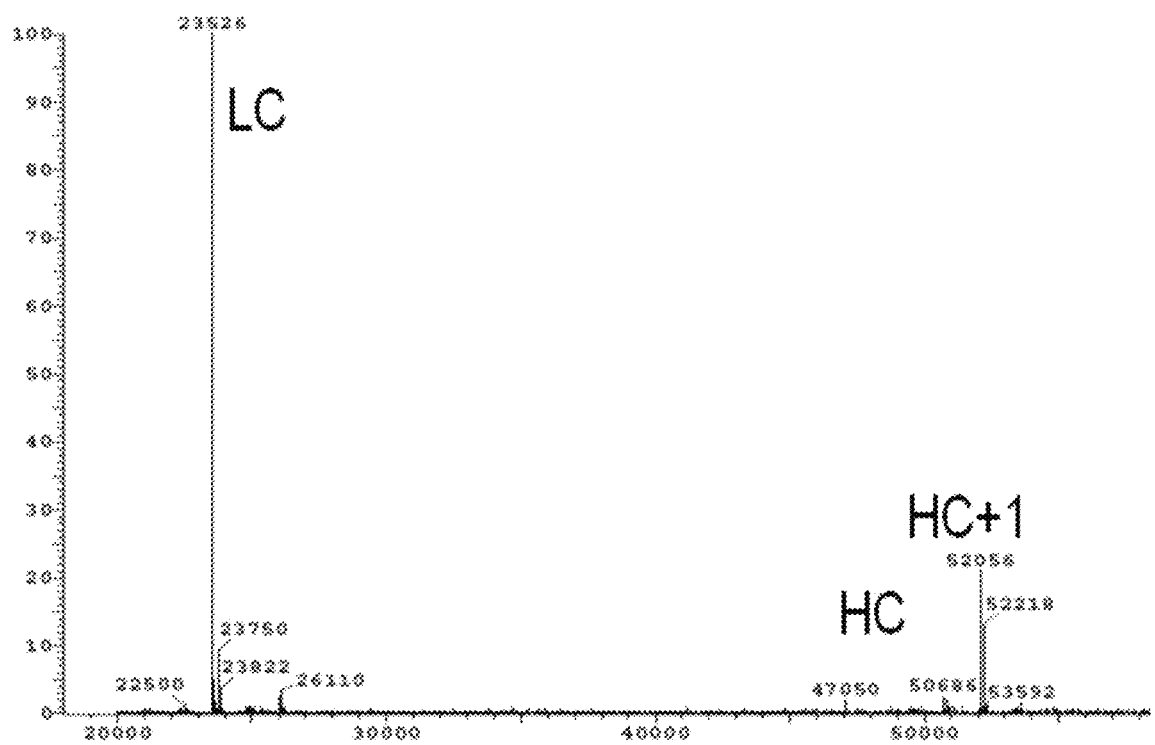

Loading calculations using this MS analysis for two exemplary ADCs (5T4-E380C-mcMMAD and 5T4-L398C-vcMMAD) are shown in FIGS. 3A and 3B, respectively.

Table 16 sets forth Mass spectrometry results and loading calculations for the ADCs assayed.

TABLE 16

| Antibody | Linker-payload | MW of non-loaded HC (lowest MW glycoform) | Theoretical MW of HC | Observed MW of HC (loaded) | Estimated non-specific loading per Ab (non-specific) (DAR) | Total loading per Ab DAR |
|---|---|---|---|---|---|---|
| 5T4-E380C | mcMMAD | 50678 | 51642 | 51644 | 0.15 | 1.78 |
| 5T4-L398C | mcMMAD | 50828 | 51792 | 51793 | 0.18 | 1.82 |
| 5T4-V422C | mcMMAD | 50707 | 51671 | 51673 | 0.08 | 1.37 |
| 5T4-L443C | mcMMAD | 50693 | 51657 | 51659 | 0.23 | 2.10 |
| 5T4-K392C | mcMMAD | 50827 | 51791 | 51792 | 0.24 | 1.74 |
| 5T4-E380C | vcMMAD | 50668 | 52037 | 52038 | 0.0 | 1.80 |
| 5T4-L398C | vcMMAD | 50686 | 52055 | 52056 | 0.0 | 1.76 |
| 5T4-V422C | vcMMAD | 50700 | 52069 | 52070 | 0.08 | 1.76 |
| 5T4-L443C | vcMMAD | 50686 | 52055 | 52053 | 0.0 | 2.00 |

Figure 4:
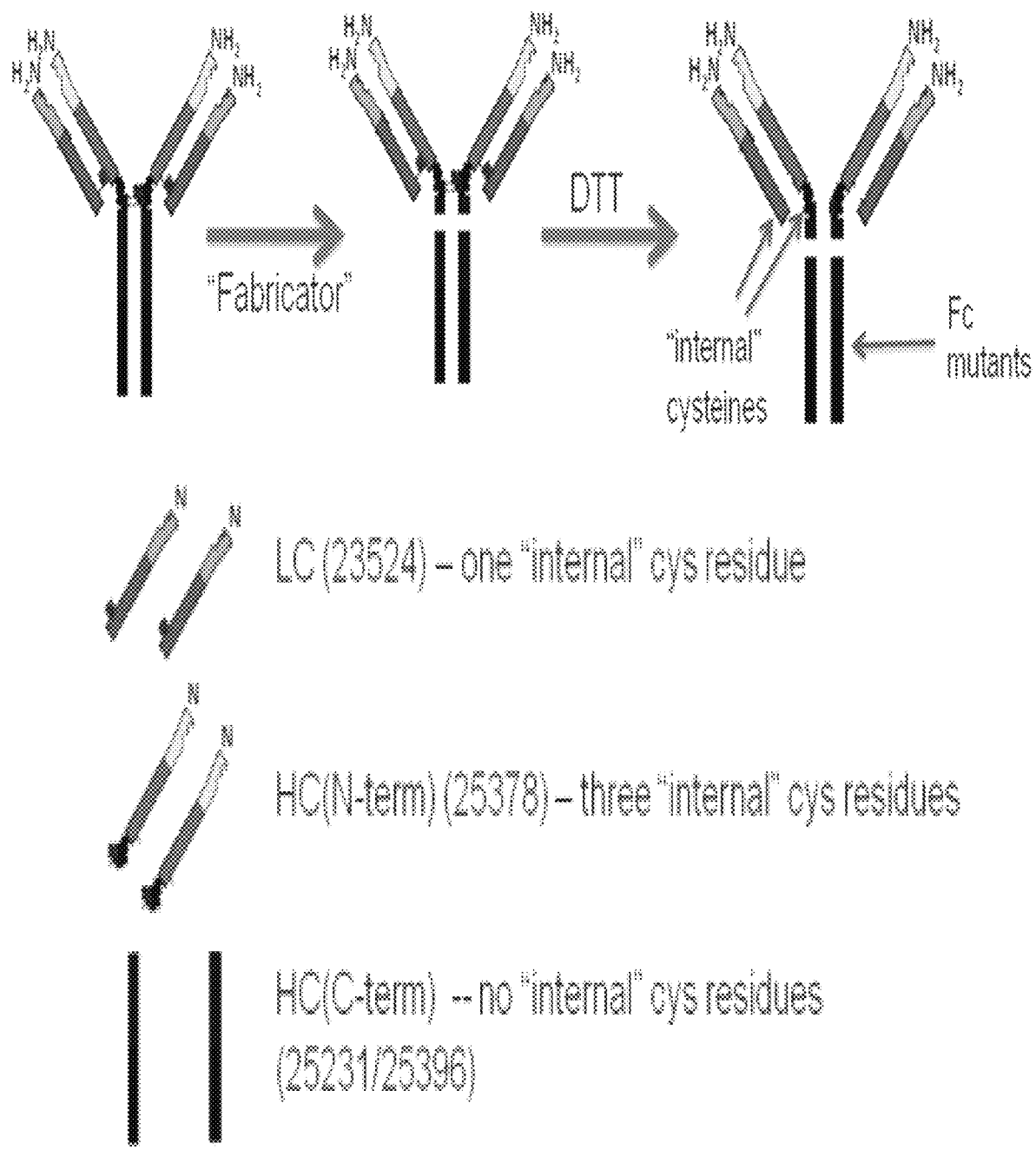
FIG. 4 is a diagram depicting the fragments generated by treatment of an intact antibody with FabRICATOR® followed by reduction of disulfide bonds by dithiothreitol (DTT). The cysteine residues are indicated by small black boxes and the interchain S—S bonds are indicated by lines.

Proteolysis with FabRICATOR® to Establish the Site of Loading:

The cysteine mutants disclosed in Tables 14-16 are located in the CH2 and CH3 domains within the Fc domain of the IgG1 heavy chain. Any nonspecific loading of the electrophillic payload onto the antibody is presumed to occur at the "interchain" also referred to as the "internal" cysteine residues (i.e., those that are typically part of the HC—HC or HC-LC disulfide bridges). In order to distinguish loading of electrophile onto the engineered cysteines in the Fc domain versus loading onto the internal cysteine residues (otherwise typically forming the S—S bonds between HC—HC or HC-LC), the conjugates were treated with a protease known to cleave between the Fab domains and the Fc domain of the antibody. One such protease is the cysteine protease IdeS, marketed as "FabRICATOR®" by Genovis, and described in von Pawel-Rammingen et al., 2002, EMBO J. 21:1607. FIG. 4 depicts a diagram illustrating the cleavage by this protease of an intact antibody molecule showing the positions (dark squares) of the internal cystine bonds.

Figure 5:
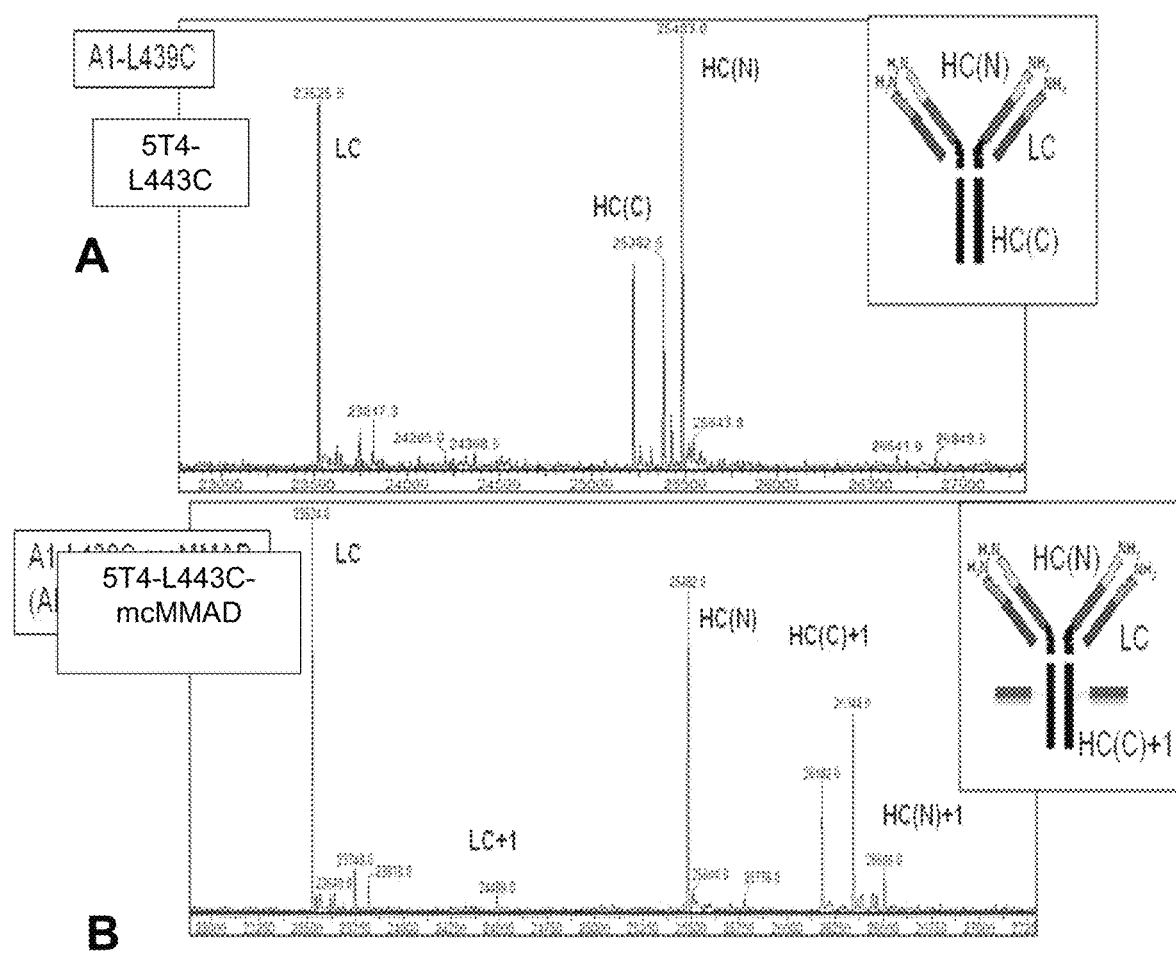
FIG. 5, comprising panels A and B, depicts a MS tracing of the FabRICATOR® fragments generated by digestion of an unconjugated cysteine variant antibody (5T4-L443C) in FIG. 5A compared with the same antibody conjugated with mcMMAD (5T4-L443-McMMAD) in FIG. 5B. The fragments generated are heavy chain C-terminus (HC(C)), heavy chain N-terminus (HC(N)), light chain (LC), heavy chain C-terminus conjugated with one mcMMAD (HC(C)+1), and a small amount of heavy chain N-terminus conjugated with one mcMMAD (HC(N)+1), which was detected at 26505.1 on the tracing shown in FIG. 5B.

Briefly, following the manufacturer's suggested conditions, the ADC was treated with FabRICATOR® protease and the sample was incubated at 37° C. for 30 minutes. Samples were prepped for LCMS analysis by combining approximately 20 µL of sample (approximately 1 mg/mL in PBS) with 20 µL of 20 mM dithiothreitol (DTT) and allowing the mixture to stand at room temperature for 5 minutes. This treatment of human IgG1 resulted in three antibody fragments, all ranging from about 23 to 26 kD in size as illustrated in the diagram depicted in FIG. 4 which illustrates the fragments resulting from FabRICATOR treatment: the LC fragment comprising an internal cysteine which typically forms an LC-HC interchain disulfide bond; the N-terminal HC fragment comprising three internal cysteines (where one typically forms an LC-HC disulfide bond and the other two cysteines found in the hinge region of the antibody and which typically form HC—HC disulfide bonds between the two heavy chains of the antibody); and the C-terminal HC fragment which contains no reactive cysteines other than those introduced by mutation in the novel constructs disclosed herein. The samples were analyzed by MS as described above. Loading calculations were performed in the same manner as previously described (above) in order to quantitate the loading of the LC, the N-terminal HC, and the C-terminal HC. Loading on the C-terminal HC is considered "specific" loading while loading onto the LC and the N-terminal HC is considered "nonspecific" loading. FIG. 5A shows the MS tracing results for 5T4-L443C variant that is not loaded after FabRICATOR® protease treatment. The insert depicts a diagram illustrating the proteolytic cleavage fragments generated by FabRICATOR® treatment. FIG. 5B is a graph showing the MS tracings results for FabRICATOR® treatment of ADC 5T4-L443C-mcMMAD. The insert shows a diagram illustrating the fragments resulting from proteolytic cleavage and illustrating that the linker and payload are associated with the C-terminal HC fragment indicating that loading is located at the reactive cysteine introduced by mutation. The results for the analysis of a subset of the ADCs are set forth in Table 17.

TABLE 17

| Antibody | Linker-payload | HC(C-term) loading per Ab (specific loading) | HC(N-term) loading per Ab (nonspecific loading) | LC loading per Ab (nonspecific loading) | Total loading per Ab |
|---|---|---|---|---|---|
| 5T4-E380C | mcMMAD | 1.9 | 0.0 | 0.1 | 2.0 |
| 5T4-L398C | mcMMAD | 1.9 | 0.0 | 0.0 | 1.9 |
| 5T4-V422C | mcMMAD | 1.4 | 0.0 | 0.0 | 1.4 |
| 5T4-L443C | mcMMAD | 2.0 | 0.1 | 0.1 | 2.2 |
| 5T4-E380C | vcMMAD | 1.8 | 0.1 | 0.0 | 1.8 |

TABLE 17-continued

| Antibody | Linker-payload | HC(C-term) loading per Ab (specific loading) | HC(N-term) loading per Ab (nonspecific loading) | LC loading per Ab (nonspecific loading) | Total loading per Ab |
|---|---|---|---|---|---|
| 5T4-L398C | vcMMAD | 1.7 | 0.0 | 0.0 | 1.7 |
| 5T4-V422C | vcMMAD | 1.6 | 0.0 | 0.0 | 1.6 |
| 5T4-L443C | vcMMAD | 1.8 | 0.1 | 0.0 | 1.9 |

Results of the FabRICATOR® cleavage of the novel ADCs of the invention demonstrate that there is very little, if any, detectable non-specific loading of the antibodies. Further, the data demonstrate that loading of the antibody is at the reactive cysteine introduced into the IgG1 Fc region and that the expected stoichiometry of 2:1 (DAR=2) is achieved for most if not all of the novel ADCs. These data demonstrate that the novel cysteine mutants can be successfully and specifically conjugated to produce potentially therapeutic ADCs having controlled and specific stoichiometry for successful drug delivery.

Reverse Phase HPLC Analysis of ADCs:

Samples were prepped for reverse-phase HPLC analysis by combining approximately 20 uL of sample (approximately 1 mg/mL in PBS) with 20 uL of 20 mM dithiothreitol (DTT). After allowing the mixture to stand at room temperature for 5 minutes, the samples were injected into an Agilent 1100 HPLC system fitted with an Agilent Poroshell 300SB-C8 (2.1×75 mm) column. The system temperature was set to 60° C. and the eluent was monitored by UV (220 nM and 280 nM). A 20-minute gradient from 20% to 45% acetonitrile in water (with 0.1% TFA modifier) was utilized:

T=0 min: 25% acetonitrile; T=2 min: 25% acetonitrile; T=19 min: 45% acetonitrile; and T=20 min: 25% acetonitrile.

Figure 6:
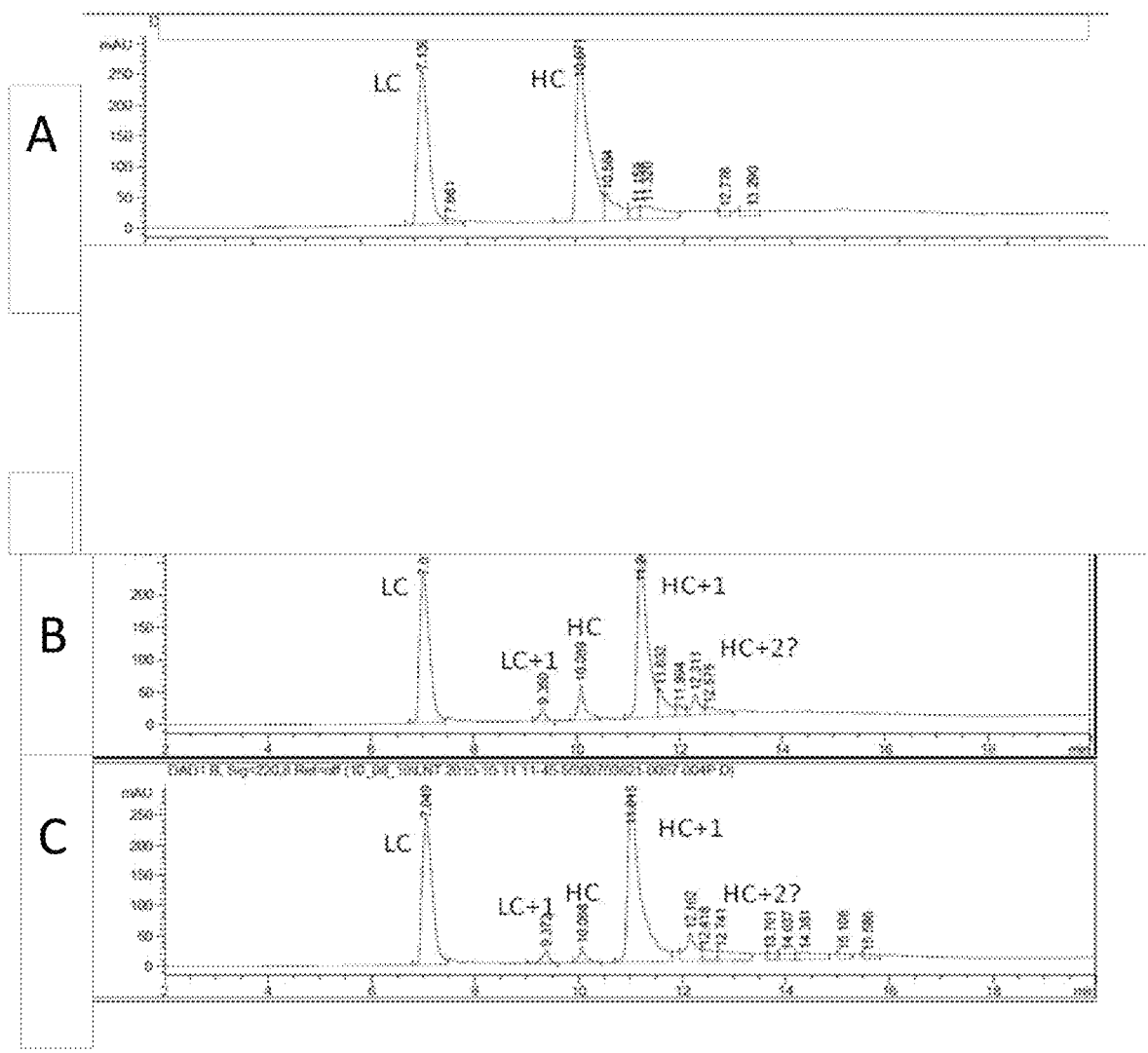
FIG. 6, comprising panels A-C, shows tracings resulting from reverse phase HPLC analysis under reducing conditions demonstrating that the light chain (LC) remains largely unmodified while the heavy chain (HC) is modified.

Using these conditions, the HC and LC of the antibody could be baseline separated. As illustrated in FIG. 6, the results of this analysis indicate that the LC remains largely unmodified while the HC is modified. More specifically, FIG. 6 shows reverse phase HPLC traces under reducing conditions for (A) unmodified wild type anti-5T4 antibody; (B) 5T4-E380C-mcMMAD; and (C) 5T4-L443C-mcMMAD. The results obtained with reverse phase HPLC are consistent with those obtained using MS analysis as disclosed previously herein. Using the equations previous described to determine loading, the specific loading and non-specific loading were calculated for each sample using the AUC for each indicated peak in FIG. 6. The loading values thus obtained are consistent with the previous loading calculations.

Hydrophobic Interaction Chromatography (HIC)

Compounds were prepared for HIC analysis by diluting a 30 uL sample (at approximately 1 mg/mL ADC) with 30 uL of 2M K$_2$HPO$_4$ (pH 8.5). The samples were analyzed using an Agilent 1200 HPLC with a TSK-GEL Butyl NPR column (4.5×35 mm, 2.5 μm). About 60 uL of sample was injected and a gradient method was run as follows:

Mobile phase A: 1M K$_2$HPO$_4$ (pH 8.5); Mobile phase B: water; T=0 min. 90% A; T=40 min., 0% A; and T=50 min, 0% A.

The peaks generally eluted from the column from lowest-loaded species to highest-loaded species although this could not be verified for every example. FIG. 7 shows HIC traces produced for several variants illustrating the distribution of variously loaded antibody species. FIG. 7 depicts traces for (A) control anti-5T4-L443C non-loaded antibody; (B) 5T4-L443C-vcMMAD; (C) 5T4-E380C-vcMMAD; and (D) 5T4-E380C-mcMMAD. As can be seen, the loaded antibody can easily be baseline separated from nonloaded antibody using the described method. Moreover, differentially loaded species can typically (but not always) be resolved. The AUC for the various peaks shown in FIG. 7 was used to calculate loading values based on HIC and to complement and further verify the loading values determined by other methods previously described. The loadings thus calculated are set forth in Table 18 which compares the loading estimations produced using HIC methodology and MS methodology. As can be seen, there is a very tight correlation between loading values calculated using the two different methods.

TABLE 18

| Antibody | Linker-payload | Loading as determined by MS method | Loading as determined by HIC method |
|---|---|---|---|
| 5T4-E380C | mcMMAD | 1.78 | 1.81 |
| 5T4-L398C | mcMMAD | 1.82 | 1.84 |
| 5T4-V422C | mcMMAD | 1.37 | 1.42 |
| 5T4-L443C | mcMMAD | 2.10 | 1.89 |
| 5T4-E380C | vcMMAD | 1.80 | 1.74 |
| 5T4-L443C | vcMMAD | 2.00 | 2.07 |

The above methodology provides several independent methods for establishing the loading of electrophilic payload-linkers onto the engineered Cys residues. These methods are complementary, consistent, and independent of one another. The combination of these methods allows the loading estimates to be determined even in the face of complicating factors such as payloads that may contain functionality that results in unusual MS ionization or high UV absorption. These data demonstrate that the ADCs comprising a reactive cysteine at a novel position in the IgG1 Fc region provide a useful platform for production of potentially therapeutically effective ADCs demonstrating a precise DAR which can be carefully controlled and measured.

Example 8

Reduction/Reoxidation Method for the Conjugation of Maleimide Payloads to Single and Double Cys-Mutants Using an Alternative Conjugation Method ("Method B")

While the conjugation methodology described above gave acceptable results for the conjugation of single-cys mutants, HIC chromatography showed that there was significant heterogeneity in the case of double-cys mutants conjugated using the method (Method A) described in Example 7. This was expected since a variety of partially loaded double mutants may theoretically be obtained where there are four reactive cysteines and each HC comprises two thereby providing for a heterogeneous mix of 1-, 2-, 3-, or 4-loaded antibodies. In addition, each of the loaded ADCs may have partial nonspecific loading onto internal cysteine residues, as shown in Example 7. The net result is an exponential increase in the heterogeneity of double mutants as compared to the single mutants.

Figure 9:
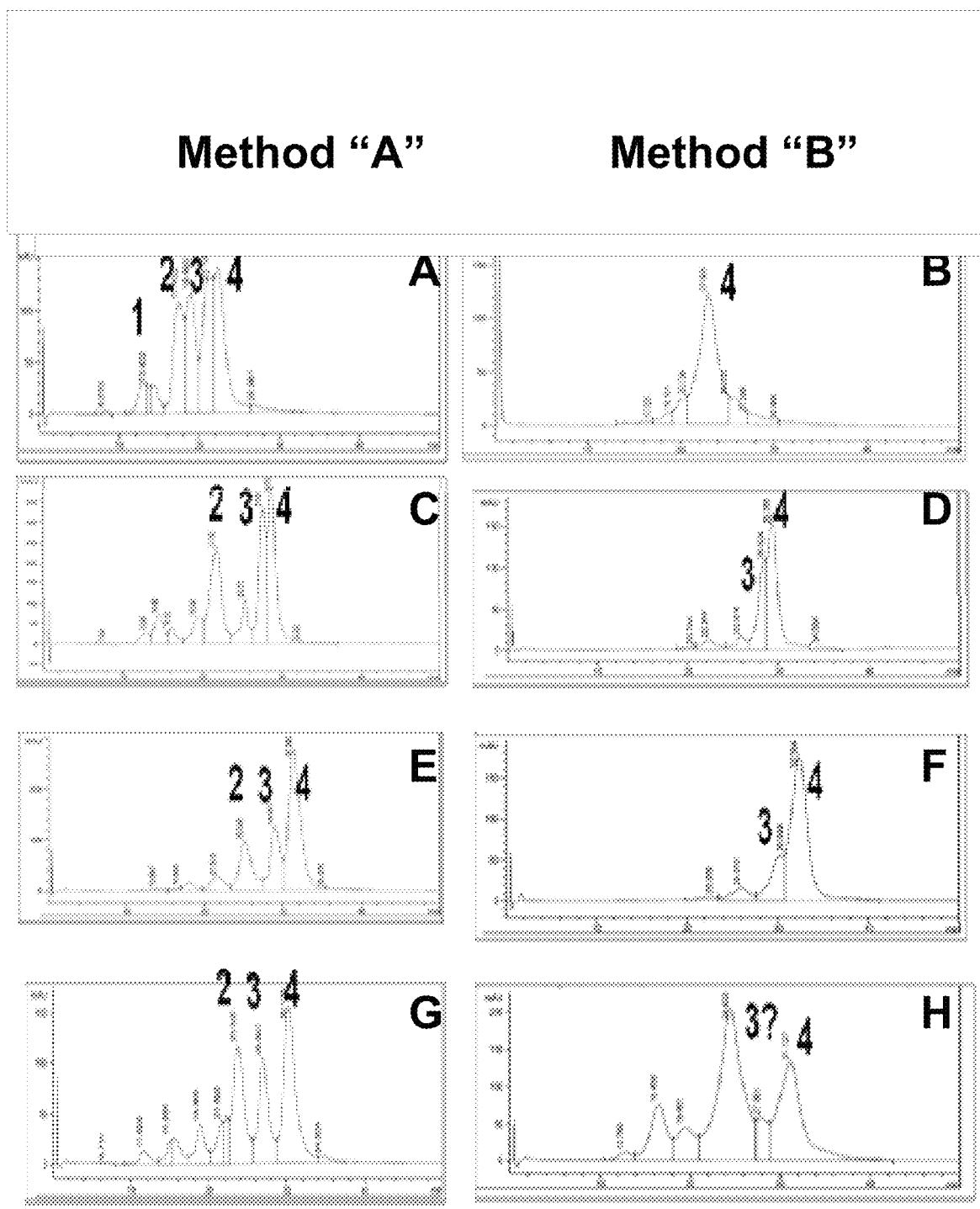
FIG. 9, comprising panels A-H, shows the tracings produced by conjugations using Method "A" compared with Method "B" for various cysteine variant antibodies.

In order to improve homogeneity of loading, an alternative procedure ("Method B") involving complete reduction of the engineered antibody with TCEP (tris2-carboxyethyl) phosphine) followed by re-oxidation of the internal disulfides with DHA (dehydroascorbic acid) was used which allowed for a conjugation with maleimides that resulted in a more homogeneous ADC (as measured by MS and by HIC). FIGS. 8 and 9 show the tracings produced by conjugations using Method "A" (FIGS. 8A, 8C, 8E, 8G, 9A, 9C, 9E and 9G) and conjugations using "Method B" (FIGS. 8B, 8D, 8F, 8H, 9B, 9D, 9F, and 9H). Descriptions of the 8 conjugates are as follows: 8A and 8B, 5T4-E380C-mcMMAD; 8C and 8D, 5T4-L398C-mcMMAD; 8E and 8F, 5T4-L443C-mcMMAD; 8G and 8H, 5T4-K388C-mcMMAD; 9A and 9B, 5T4-E380C+L398C-mcMMAD; 9C and 9D, 5T4-E398C+L443C-mcMMAD; 9E and 9F, 5T4-E380C+L443C-mcMMAD; and 9G and 9H, 5T4-E380C+V422C-mcMMAD.

A summary of the results of various conjugations using "Method A" and "Method B" is presented in Table 19. The data disclosed in Table 19 and in FIGS. 8 and 9 demonstrate that conjugates generated using "Method B" showed improved specific loading and improved homogeneity as compared to the same conjugates prepared by "Method A".

Conjugation "Method B"

Conjugation "Method B" was performed as follows. A 20 mM TCEP solution (50 to 100 molar equivalents) was added to the antibody (5 mg) such that the final antibody concentration was 5 mg/mL in PBS containing 50 mM EDTA. After allowing the reaction to stand at 37° C. for 1.5 hour, the antibody was buffer exchanged into PBS containing 50 mM EDTA using a 50 kD MW cutoff spin concentration device (3×3 mL wash, 10× concentration per cycle). The resulting antibody was re-suspended in 1 mL of PBS containing 50 mM EDTA and treated with a freshly prepared 50 mM solution of DHA in 1:1 PBS/EtOH (final DHA concentration=1 mM–4 mM) and allowed to stand at 4° C. overnight.

Figure 10:
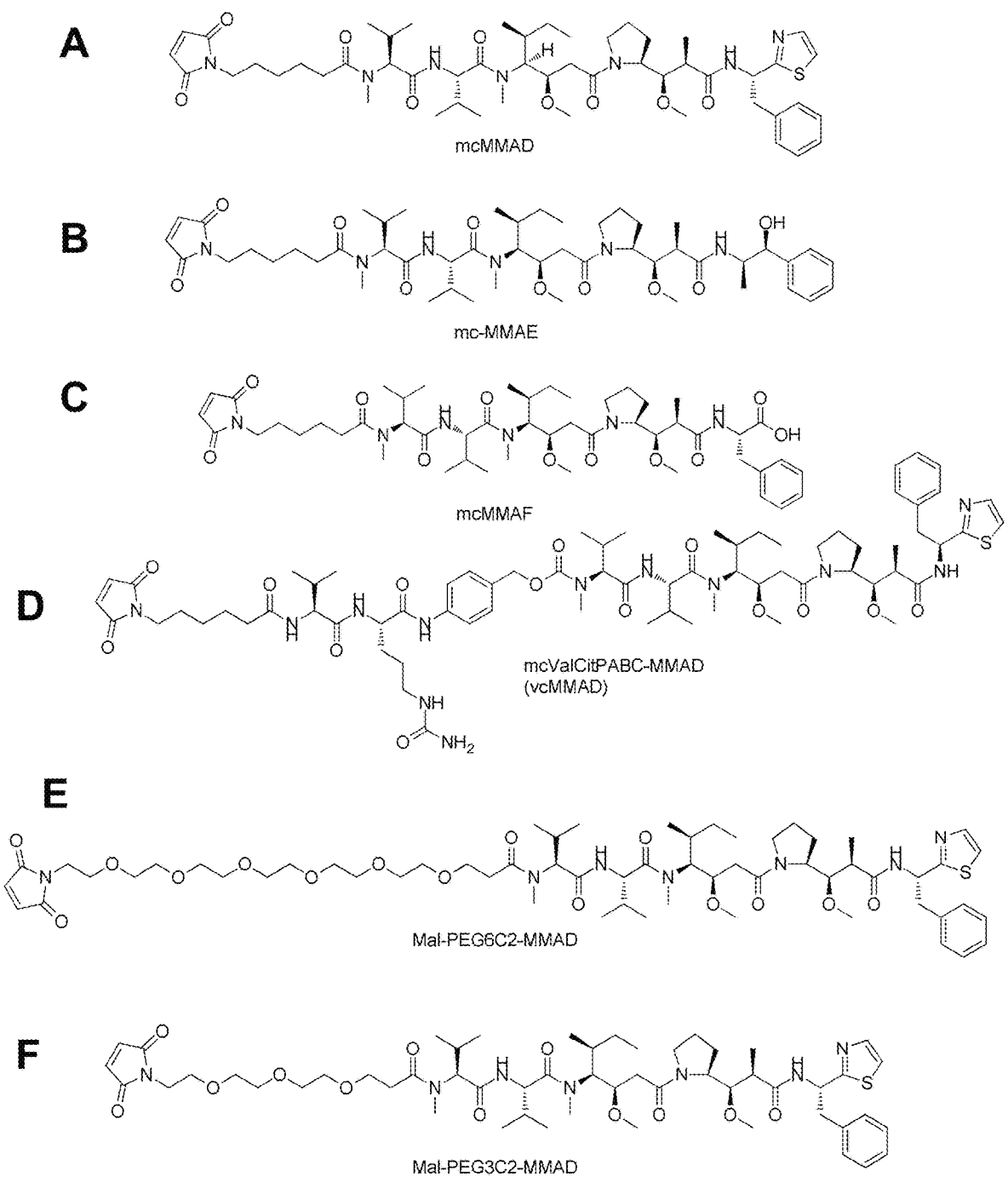
FIG. 10, comprising panels A-F, depict the structures of the following linker-payload combinations: mcMMAD (FIG. 10A); mcMMAE (FIG. 10B); mcMMAF (FIG. 10C); mcValCitPABC-MMAD, also referred to herein as "vcM-MAD" (FIG. 10D); Mal-PEG6C2-MMAD (FIG. 10E) and Mal-PEG3C2-MMAD (FIG. 10F).

The antibody/DHA mixture was buffer exchanged into PBS containing 50 mM EDTA using a 50 kD MW cutoff spin concentration device (3×3 mL wash, 10× concentration per cycle). The resulting antibody was re-suspended in 1 mL of PBS containing 50 mM EDTA and treated with 33 uL of 10 mM maleimide payload (mcMMAD) in DMA. After standing for 1.5 hours, the material was buffer exchanged (as above) into 1 mL of PBS (3×3 mL washes, 10× concentration per cycle). Purification by SEC was performed (as needed) to remove any aggregated material. The structures of the mcMMAD, vcMMAD, and mcMMAF linker-payload used to produce the results in Tables 15-19 are shown in FIG. 10 which also includes Mal-PEG6C2-MMAD and Mal-PEG3C2-MMAD.

The loading results of a variety of conjugations of double-cysteine mutants, comprising engineered cysteines in the Fc and/or Kappa (Table 24; Example 10) constant domains, using both Method A and Method B, are provided in Table 19 below.

TABLE 19

| Antibody | Linker-payload | Loading (using Method B)* | Loading (using Method A)* |
|---|---|---|---|
| 5T4-E380C | mcMMAD | 2.0 (0) | 1.8 (0.2) |
| 5T4-L398C | mcMMAD | 1.8 (0) | 1.8 (0.2) |
| 5T4-L443C | mcMMAD | 2.0 (0) | 2.1 (0.2) |

TABLE 19-continued

| Antibody | Linker-payload | Loading (using Method B)* | Loading (using Method A)* |
|---|---|---|---|
| 5T4-V422C | mcMMAD | 1.6 (0) | 1.4 (0.1) |
| 5T4-K392C | mcMMAD | 2.0 (0) | 1.7 (0.24) |
| 5T4-E380C-L398C | mcMMAD | 4.0 (0.2) | 3.2 (0) |
| 5T4-L398C-L443C | mcMMAD | 3.8 (0) | 3.2 (0) |
| 5T4-E380C-L443C | mcMMAD | 4.0 (0.2) | 3.6 (0) |
| 5T4-E380C-V422C | mcMMAD | 4.0 (0.2) | 3.3 (0) |
| Her2-E380C-L443C | mcMMAD | 4.3 (0.6) | NA |
| Her2-L443C | mcMMAD | 2.0 (0.08) | NA |
| Her2-E380C | mcMMAD | 1.9 (0.12) | NA |
| 5T4-L398C-L443C | mcMMAD | 3.8 (0) | NA |
| 5T4-L398C-V422C | mcMMAD | 3.7 (0) | NA |
| 5T4-K392C-L443C | mcMMAD | 3.5 (0) | NA |
| Her2-Q347C | MalPeg6C2-MMAD | 2 | NA |
| Her2-Q347C | mcMMAD | 2 | NA |
| Her2-Y373C | MalPeg6C2-MMAD | 1.6 | NA |
| Her2-Y373C | mcMMAD | 1.9 | NA |
| Her2-E380C | MalPeg3C2-MMAD | 2 | NA |
| Her2-E380C+L443C | MalPeg3C2-MMAD | 3.8 | NA |
| Her2-K392C | MalPeg6C2-MMAD | 2 | NA |
| Her2-K392C | mcMMAD | 2 | NA |
| Her2-K392C+L443C | mcMMAD | 4 | NA |
| Her2-L398C+L443C | mcMMAD | 4 | NA |
| Her2-N421C | MalPeg6C2-MMAD | 1.98 | NA |
| Her2-N421C | mcMMAD | 2.1 | NA |
| Her2-L443C | MalPeg3C2-MMAD | 2 | NA |
| Her2-L443C | MalPeg6C2-MMAD | 2 | NA |
| Her2-kappa-A111C | mcMMAD | 1.8 | NA |
| Her2-kappa-A111C+Q347C | mcMMAD | 3.5 | NA |
| Her2-kappa-A111C+K392C | mcMMAD | 3.6 | NA |
| Her2-kappa-A111C+L443C | mcMMAD | 3.5 | NA |
| Her2-kappa-K149C | mcMMAD | 1.7 | NA |
| Her2-kappa-K183C | mcMMAD | 1.9 | NA |
| Her2-kappa-K183C+L443C | mcMMAD | 3.8 | NA |
| Her2-kappa-K207C | mcMMAD | 1.8 | NA |
| Her2-kappa-K207C+L443C | mcMMAD | 3.5 | NA |

*The reported loading was measured using the MS method described in example 3. The number in parentheses is the estimated nonspecific loading, as determined by the observed loading onto light chain.

The combination of the loading/specificity data from Table 19 and the HIC data from FIGS. 8 and 9 demonstrate the heterogeneity of drug loading when double-cysteine mutants were conjugated using Method A described previously compared with the much more homogeneous loading achieved using the conjugation Method B.

These data demonstrate that potential heterogeneity in loading of the novel cysteine mutants of the invention can be readily reduced using art recognized conjugation methods. Therefore, the data disclosed herein demonstrate that the novel double-cys mutants of the invention can be readily conjugated using a variety of linkers to produce nearly homogeneous ADCs comprising a predictable and desirable number of payload moieties per antibody (i.e., DAR), as well as homogeneity as to the sites of conjugation on the antibodies.

Example 9

Characterization of 5T4 Engineered Cysteine Mutants

The Materials and Methods in this Example are as follows.

Cell Lines:

MDAMB435/5T4 transfected cells expressing human 5T4 antigen and control MDAMB435/neo cell that were not transfected were prepared as described previously (Boghaert et al., 2008, Int. J. Oncol. 32:221-234). Raji (CCL-86) cell line was obtained from the American Type Culture Collection (ATCC, Manassas, Va.). The cell lines were determined to be mycoplasma free as determined by a polymerase chain reaction mycoplasma detection assay (ATCC, Manassas, Va.).

The cell line MDAMB453/5T4, was maintained in MEM medium with Earl's salts supplemented with 10% fetal bovine serum (FBS), 1% MEM non essential amino acids and 1% MEM vitamins, 1 mM sodium pyruvate, penicillin G sodium 100 U/ml, streptomycin sulfate 100 µg/ml and 2 mM L-Glutamine plus 1.5 mg/mL of selection antibiotic G418.

Raji cell line was maintained in RPMI 1640 medium supplemented with 10% fetal bovine serum (FBS), 10 mM HEPES (N-2-hydroxyethylpiperazine-N'-2-ethanesulfonic acid), 1 mM sodium pyruvate, 0.2% glucose, penicillin G sodium 100 U/ml, streptomycin sulfate 100 µg/ml and 2 mM L-Glutamine. Before using Raji, viable cells were isolated by density-gradient centrifugation (30 min at 1000×g) using Lymphoprep (Nycomed, Oslo, Norway).

Mice:

Female nu/nu (nude) mice (18-23 g) were obtained from Charles River Laboratories, Wilmington, Mass. All procedures using mice were approved by the Wyeth Animal Care and Use Committee according to established guidelines.

Binding Studies:

Cells expressing 5T4, and the negative control Raji cells, were plated at a density of 500,000 cells/well on non-tissue culture treated 96 well plates and kept on ice. Dilutions of the primary antibody were made in 3% BSA in dPBS (Dulbecco's phosphate buffered saline, 100 mM phosphate, pH 7.4) and added to the plate at a final concentration of 10 µg/mL. The plates were then incubated on ice for 1 hour followed by 2 washes with 1×DPBS. The secondary antibody, PE conjugated Goat Anti-Human IgG Fc (Jackson ImmunoResearch Labs #109-115-098), was added to the wells at 1:100 dilution. After 30 minutes of incubation at 4° C., the plates were washed twice with 1×DPBS and the mean fluorescence intensity was then measured using a FACSort flow cytometer (Becton Dickinson Immunocytometry Systems, Sunnyvale, Calif.).

Modulation Studies:

The modulation of surface bound anti-5T4 antibody as defined by the loss of surface display of the bound antibody was evaluated by flow cytometry. MDAMB435/5T4 cells were plated at 10,000 cells in black 96 well plates. The primary antibody was added at a final concentration of 1 µg/mL. The plates were then incubated on ice for 1 hour, washed twice with 1×DPBS and then incubated at 4° C. in cold media for another hour (this is referred to herein as the "binding plate"). For internalization studies, internalization plates were incubated at 37° C. for either 1, 4, or 20 hours. The plates were washed once with 1×DPBS. The secondary antibody, peroxidase-conjugated Affinity Pure Goat Anti-Human IgG Fc (Jackson ImmunoResearch Labs #109-035-008), was added to the wells at 1:4000 dilution. After one hour incubation at 4° C. with the secondary antibody, the plates were washed thrice and the substrate, LumiGLO® (Cat. No. #54-61-01, Kirkegaard & Perry Labs., Gaithersburg, Md.) was added. The difference in average relative fluorescence between the binding plate and the internalization plate was expressed as percentage of binding to estimate the internalization of the antibody.

Conjugation of Anti-5T4 Antibodies (Mutants and Parental Wild Type) to Toxins

Conjugation to mcMMAD and vcMMAD to both wild type parental anti-5T4 antibody (human wild type IgG1 without mutations) and novel variants comprising a mutation introducing a single reactive cysteine into the IgG1 Fc region was described previously elsewhere herein (Example 7).

Growth Inhibition Studies:

The effect of the ADCs on cell lines was assessed using a cellular viability indicator assay, CellTiter 96® AQ$_{ueous}$ Non-Radioactive Cell Proliferation Assay (MTS) (Promega, Madison, Wis.), to determine the number of surviving cells following exposure to various ADC treatments. Cells were seeded in 96-well microtiter plates at a density of 5,000 to 10,000 cells per well and exposed to various concentrations of antibody or ADC. Following determination of the number of viable cells surviving 96 hours of drug exposure (or 240 hours for 37622a primary cells), the $IC_{50}$ of each treatment was calculated based on the logistic regression parameters derived from the dose-response curves. $IC_{50}$s were calculated by logistic non-linear regression and are reported as the concentration (nM) from each treatment group that causes 50% loss of cell viability.

Antibody Dependent Cellular Cytotoxicity (ADCC) Assay:

Blood from a healthy volunteer was collected into a BD Vacutainer CPT cell preparation tube with sodium heparin. Human peripheral blood mononucleocytes (PBMC) were harvested and resuspended in assay buffer (RPMI 1640 supplemented with 10 mM HEPES) at $2.5 \times 10^7$ cells/ml. Target cells MDAMB435/5T4 or MDAMB435/neo control cells were seeded at a density of $1 \times 10^4$ cells/well in a 96 well assay plate. Antibody or ADCs were added, then human PBMC effector cells ($5 \times 10^5$) were dispensed into the wells for an effector:target cell ratio (E:T) of 50:1. The assay plate was incubated at 37° C. for 4 hours for ADCC activity. The plate was harvested by adding equal volume of CytoTox-One reagent (Promega). Stop solution (Promega; 50 µl) was added to each well and lactate dehydrogenase release was quantified by measuring fluorescence intensity. As a positive control, 2 µl of lysis buffer per well was added to generate a maximum LDH release (100% cytotoxicity) in control wells. Percent specific cytotoxicity was calculated using the following equation:

$$\% \text{ Specific Cytotoxicity} = \frac{\text{experimental} - \text{effector spontaneous} - \text{target spontaneous}}{\text{target maximum} - \text{target spontaneous}} \times 100$$

Where "experimental" corresponds to the signal measured in one of the experimental conditions, "effector spontaneous" corresponds to the signal measured in the presence of PBMC alone, "target spontaneous" corresponds to the signal measured in the presence of target cells alone, and "target maximum" corresponds to the signal measured in the presence of detergent-lysed target cells alone.

The experimental results were as follows.

Figure 11:
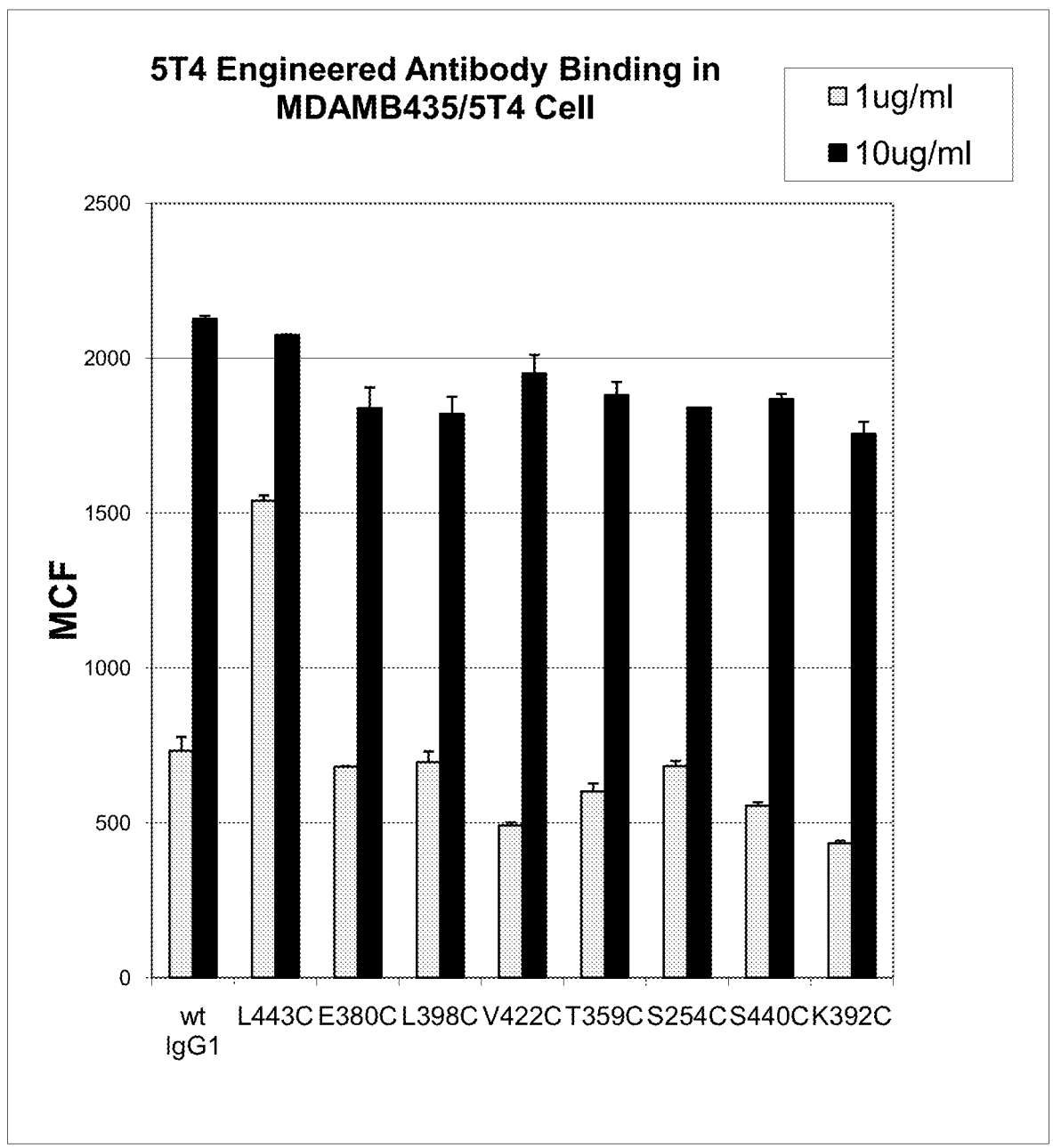
FIG. 11 is a graph showing the binding of unconjugated cysteine mutant anti-5T4 antibodies to MDAMB435 cells expressing 5T4 antigen (MDAMB435/5T4) expressed as mean calculated fluorescence, compared with binding of parental anti-5T4 antibody comprising a wild type IgG1 Fc domain. The results demonstrate that the cysteine variant antibodides L443C, E380C, L398C, V422C, T359C, S254C, S440C and K392C, at both 1 µg (gray bars) and 10 µg/ml (black bars), demonstrate binding to MDAMB435/5T4 cells comparable to the wild type parental antibody (indicated as "wt IgG1").

Binding to 5T4 on Cells by Non-Conjugated Anti-5T4 Variants is Equivalent to Binding by Non-Conjugated Wild Type Anti-5T4 Parental Antibody:

Binding of the anti-5T4 IgG1 single-cysteine mutant antibodies (L443C, E380C, L398C, V422C, T359C, S254C, S440C, and K392C), all non-conjugated "naked" antibodies, to 5T4 expressed on the membrane of 5T4+cell line MDAMB435/5T4 was demonstrated as shown in FIG. 11. Binding of each of the non-conjugated cys mutant 5T4 Abs was similar to the wild type non-conjugated 5T4 IgG1 Ab (labeled as "wtIgG1") at both concentrations tested (1 µg/ml and 10 µg/ml). These data demonstrate that introduction of an engineered cysteine into these novel positions of human IgG1 did not significantly affect the binding of the antibodies to the antigen expressing tumor cells.

Binding to Cells Expressing 5T4 Antigen was not Affected by Conjugation of Novel Mutant Cysteine Variant ADCs Conjugated to Toxic Payloads The data disclosed previously herein demonstrate that introduction of engineered cysteines at novel positions of human IgG1 did not affect antibody binding to cells when compared to binding of the wild type antibody comprising human wild type IgG1 Fc region without mutations. Previous studies have shown that biotin or other small molecules conjugated to engineered cysteines at other positions of human IgG1 did not appear to affect antibody binding to their antigens. See, e.g., WO 2011/005481 (biotin-maleimide conjugation); WO 2010/141902 (conjugating cysteine variants with maleimide dyes); and WO 2006/034488 (biotin-maleimide conjugation was performed and all examples describing conjugation to MMAE and MMAF were prophetic only). However, conjugation of a small non-toxic molecule such as biotin, as was typically used in those studies, is unlikely to mimic the impact on the biological properties an antibody molecule mediated by conjugation of a much larger moiety such as a linker and toxin molecule. Because a successful ADC platform antibody must effectively bind to a target antigen in order to deliver a toxic payload to the target cell, without significant binding to non-target cells, it is crucial that the engineered mutant antibodies of the invention retain specific binding ability whilst conjugated to a toxic payload. Accordingly, the ability of the novel engineered mutant antibodies of the present invention to bind to target cells expressing 5T4 antigen, and not to bind to 5T4 negative cells, was assessed. As demonstrated below, the novel cysteine mutant antibodies when conjugated to a toxin retained the specific binding characteristics of the unconjugated parental antibody and do not exhibit non-specific binding.

Antibody drug conjugates were prepared using four (4) of the 5T4 cysteine mutants: E380C, L398C, L443C, and V4220. In each instance, the ADC was prepared by conjugating the mutated antibodies to mcMMAD and vcMMAD as previously disclosed herein (see Example 7).

Figure 12A:
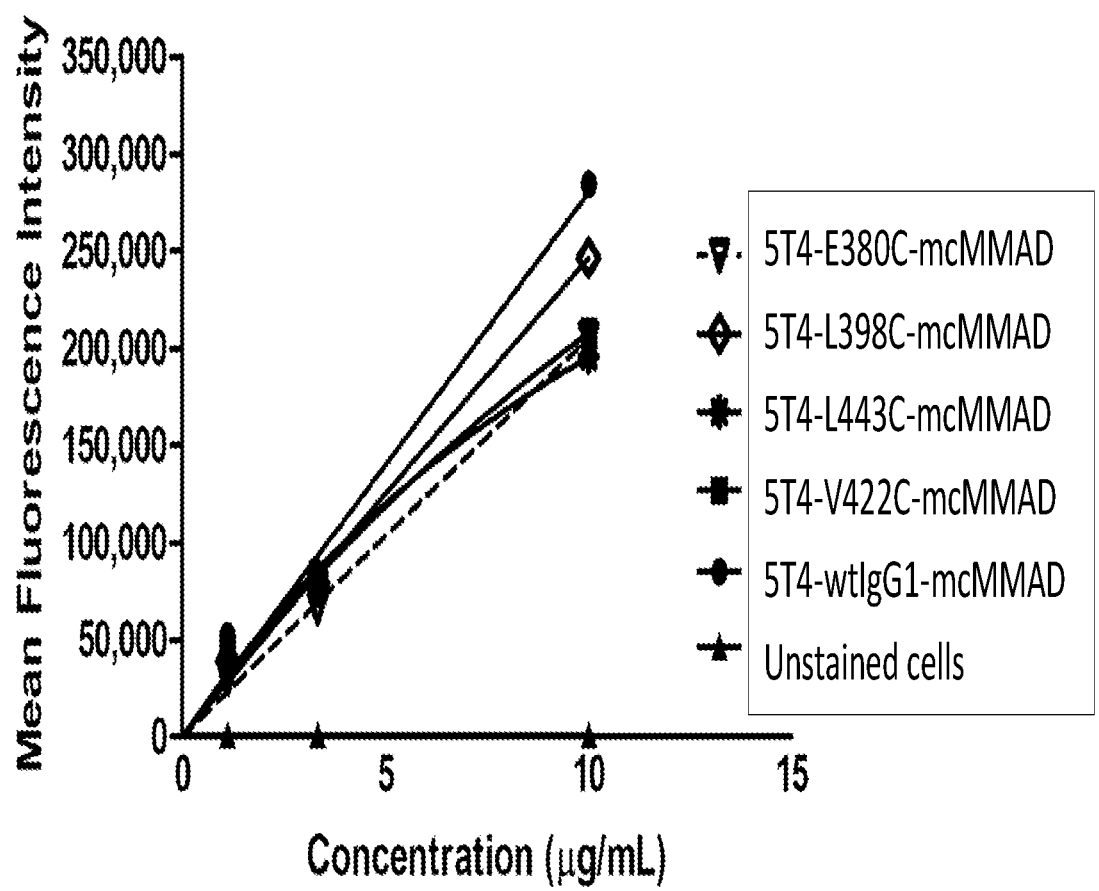
FIG. 12A is a graph showing binding of cysteine variant antibodies conjugated to mcMMAD to cells expressing 5T4 antigen (MDAMB435/5T4 cells) compared with wild type parental anti-5T4 antibody. Binding of antibodies 5T4-E380C-mcMMAD, 5T4-L398C-mcMMAD, 5T4-L443C-mcMMAD, and 5T4-V422C-mcMMAD antibodies was compared with binding by parental antibody 5T4 (wt IgG1).
Figure 12B:
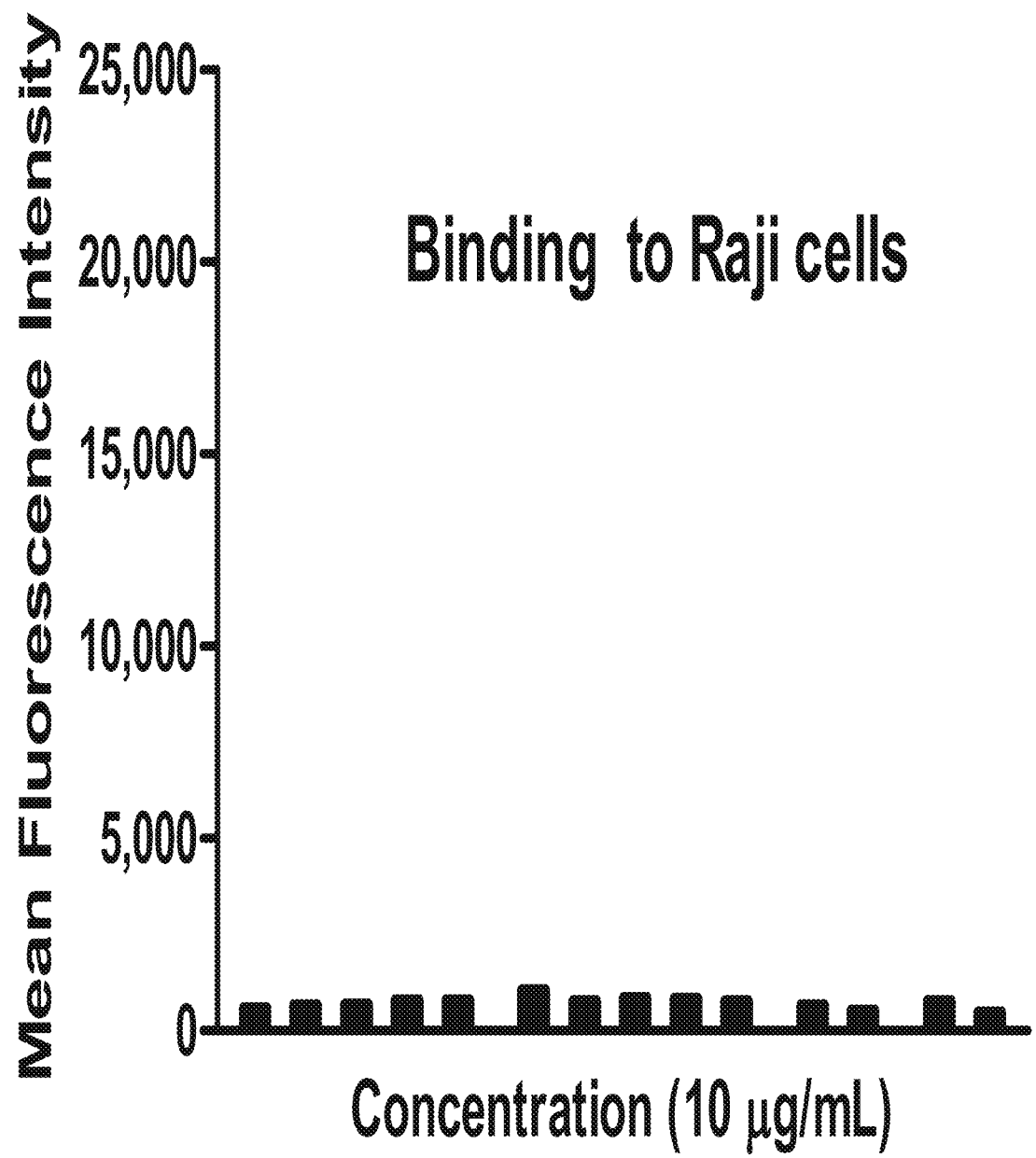
FIG. 12B is a graph showing the lack of binding of cysteine variant antibodies conjugated to mcMMAD compared with similar lack of binding of wild type parental antibody in Raji cells which do not express the target antigen 5T4.

Binding of 5T4 ADCs specifically conjugated with mcMMAD via engineered cysteines was compared with native non-conjugated 5T4 wild-type IgG1 parental antibody on the 5T4-positive MDAMB435/5T4 cell line and on the 5T4-negative Raji cell line. The results are shown in FIG. 11. FIG. 12A depicts a graph demonstrating that for 5T4-L398C-mcMMAD, 5T4-443C-mcMMAD and 5T4-V422C-mcMMAD, binding of the ADC to the 5T4-positive cell lines, on average for the three (3) ADC concentrations tested (1, 3 and 10 µg/kg), was similar to that of the native, unconjugated 5T4 antibody. These data demonstrate that conjugating a linker and payload to each of these novel 5T4 cysteine mutant antibodies did not significantly affect its ability to bind to 5T4 antigen on cells. The data shown in FIG. 12B demonstrate that each of the ADCs showed negligible binding to the 5T4-negative Raji cell line thereby demonstrating that conjugating a linker and payload to the cysteine mutated antibodies does not affect 5T4 binding properties relative to the parental wild-type IgG1 antibody.

Internalization of Cys Mutant ADCs is Comparable to Parental Wild Type-IgG1 Antibody:

Another critical property for an ADC activity is to be rapidly internalized whilst conjugated to a toxin in order to deliver the toxic payload to the intracellular lysosomal compartment. Again, prior studies have shown the ability of purported novel ADCs to be internalized while conjugated to the small vitamin molecule biotin. The novel cysteine mutant ADCs of the present invention were subjected to more rigorous and appropriate tests to determine whether they would be internalized whilst conjugated to a true representative linker and cytotoxic payload combination (e.g., mcMMAD) with comparable efficiency when compared to internalization of the parental antibody comprising wild type-IgG1 conventionally conjugated to the same linker-payload combination. The results disclosed herein demonstrate that the novel Cys mutant ADCs were internalized with comparable efficiency to the parental control ADC.

Figure 13:
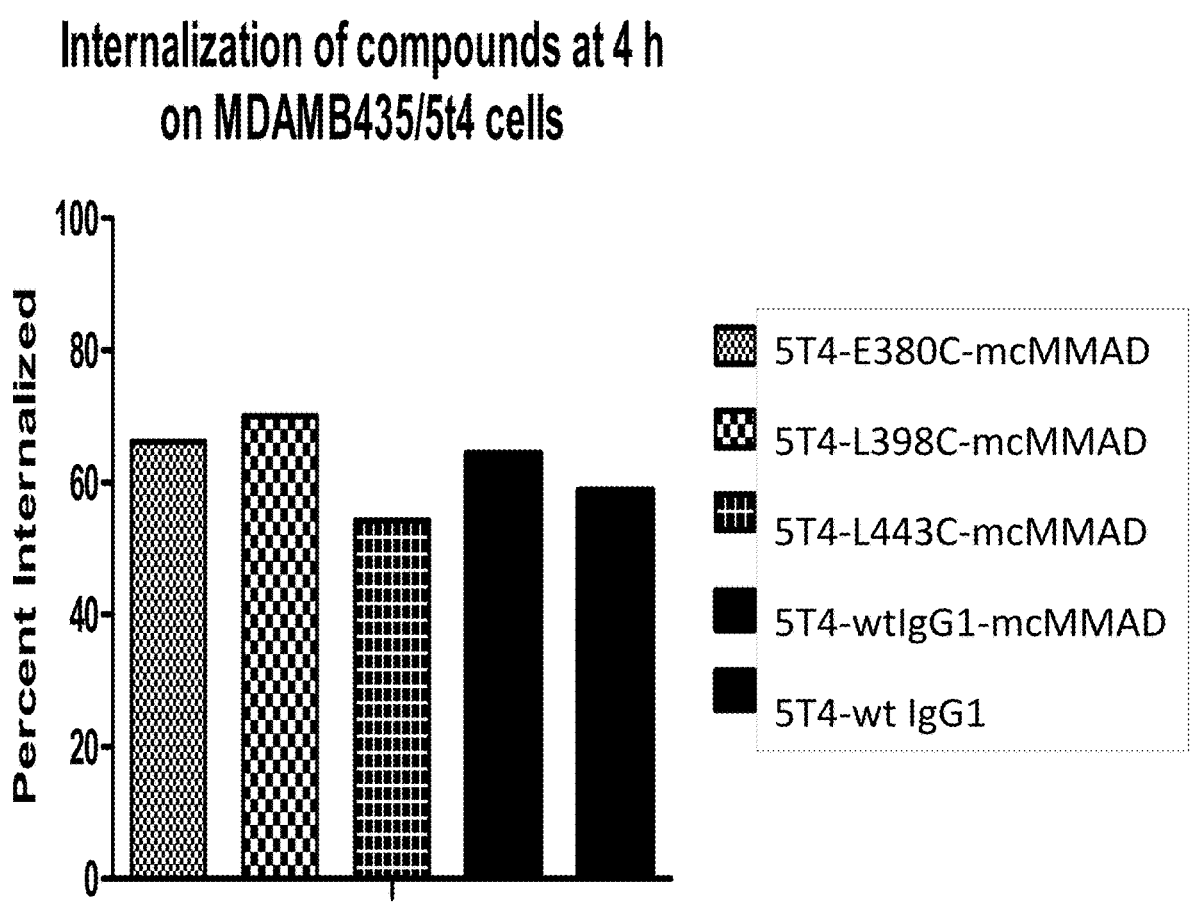
FIG. 13 is a graph showing the internalization of cysteine variant antibodies conjugated with mcMMAD compared with the internalization of wild type antibody conjugated with mcMMAD (5T4-IgG1-mcMMAD) and wild type antibody which was not conjugated (wt IgG1). The data show that cysteine mutant antibody drug conjugates 5T4-E380C-mcMMAD, 5T4-L398C-mcMMAD, and 5T4-L443C-mcMMAD, were internalized by MDAMB435/5T4 cells substantially the same as wild type parental antibody drug conjugate 5T4-IgG1-mcMMAD and wild type parental antibody 5T4 not conjugated (wt IgG1).

When non-conjugated 5T4-IgG1 parental antibody or Cys mutant ADC (E380C, L398C, L443C, and the IgG1 parental antibody, each conjugated to mcMMAD) was incubated with MDAMB435/5T4 cells at 37° C. for 4 hours at a concentration of 2.25 µg/ml, the ADC was modulated (i.e., internalized in that it was no longer detected at the cell membrane) in a time-dependent manner as demonstrated by the results shown in FIG. 13. At 4 hours, approximately 65% of the non-conjugated parental anti-5T4 antibody or ADC was internalized (range was a high of 70% for L3980 to a low of 54% for L4430). These results demonstrate that 5T4 antibody binding to the 5T4 antigen internalizes in a relatively fast manner, that conjugating the 4 mutated anti-5T4 Abs to a linker and toxin payload does not significantly affect their internalization relative to the unconjugated 5T4 Ab, and that the mutated anti-5T4 ADCs internalize to an extent equivalent to the non-mutated (native) 5T4-mcMMAD ADC (designated as "A1-IgG1mcMMAD"). Thus, these data demonstrate that conjugation to a cytotoxic payload and linker, not just biotin, does not affect the ability of the cys mutant ADCs to be internalized compared to the non-conjugated anti-5T4 cys mutant antibody or the parental antibody comprising a wild type-IgG1 Fc region conjugated to the MMAD payload by conventional methods.

Cytotoxicity of the Cys Mutant ADCs was Comparable to Parental Wild Type ADC:

The ADC platform was also tested to determine whether it can mediate a cytotoxic effect on the target cells while not significantly affecting non-target cells. That is, the ADC, whilst carrying a cytotoxic payload, must still specifically bind to target cells while not significantly binding to non-target cells, then it must internalize and deliver the payload to a compartment where it will then mediate a cytotoxic effect to the target cells while sparing non-target cells which may be in close proximity. The novel ADCs of the present invention were subjected to this test and, as shown below, were able to bind to target cells while carrying a true linker and payload (not just the non-toxic vitamin biotin), be internalized, and mediate a cytotoxic effect to target cells, while not affecting non-target cells. This effect was comparable to the parental antibody comprising a wild type-IgG1 Fc region.

The results set forth in Table 20 demonstrate that the 5T4 Cys-mutated mcMMAD and vcMMAD ADCs were each able to inhibit the growth of the 5T4 expressing cell lines MDAMB435/5T4 (a high 5T4 expressor) and MDAMB-468 (a HER2 resistant cell line with moderate 5T4 expression). The same ADCs were observed to be largely inactive on 5T4 negative Raji cells. The increased loading of drug onto the double Cys-mutants is reflected in a detectable increase in potency of the inhibition of growth of the MDAMB435 and MDAMB-468 cells lines. The vcMMAD conjugated Cys mutant Abs were approximately 10-fold more potent than the mcMMAD ADCs in inhibiting the growth in the 5T4+ cells. The vcMMAD ADCs are linked with a more labile cathepsin sensitive vc linker and thus are more active in inhibiting cell growth than the more stably linked mcM-MAD ADCs. Being more labile, the vc-linked ADCs also tend to be more toxic in animals. Both linker types have been tested in the clinic as ADCs. These data demonstrate that the novel cys mutants of the invention provide an effective platform for production of effective homogenous ADCs which can deliver a cytotoxic payload with precise stoichiometry of DAR and thereby provide a therapeutic effect. The cytotoxcity observed for these ADCs is dependent upon antigen expression and antibody loading (DAR).

TABLE 20

| Mutant antibody | Payload | Loading (method of preparation) | IC-50 (ng ADC/ml) MDAMB435/5T4 (5T4+) (5T4 expression 3+) | IC50 MDA-MB-468 (ng/mL) (5T4 expression 2+) | IC-50 (ng Ab/ml) Raji (5T4−) (5T4 expression−) |
|---|---|---|---|---|---|
| 5T4-E380C | mcMMAD | 2.0 (B) | 170 | 8100 | 29000 |
| 5T4-K392C | mcMMAD | 2.0 (B) | 160 | 32000 | >75000 |
| 5T4-L398C | mcMMAD | 1.8 (B) | 160 | 13000 | >83000 |
| 5T4-L443C | mcMMAD | 2.0 (B) | 120 | 20000 | >75000 |
| 5T4-V422C | mcMMAD | 1.6 (B) | 270 | 36000 | 84000 |
| 5T4-K392C+L443C | mcMMAD | 3.5 (B) | 98 | 30000 | >43000 |
| 5T4-L398C+L443C | mcMMAD | 3.8 (B) | 81 | 5500 | >39000 |
| 5T4-L398C+V422C | mcMMAD | 3.7 (B) | 100 | 17000 | >41000 |
| 5T4-E380C+L398C | mcMMAD | 4.0 (B) | 79 | 5100 | 19000 |
| 5T4-E380C+L443C | mcMMAD | 4.0 (B) | 79 | 3300 | 36000 |
| 5T4-E380C+V422C | mcMMAD | 4.0 (B) | 100 | 5000 | 21000 |
| 5T4-L398C+L443C | mcMMAD | 3.8 (B) | 79 | 7100 | >29000 |
| 5T4-E380C | vcMMAD | 1.8 (A) | 15 | NA | 25000 |
| 5T4-L398C | vcMMAD | 1.8 (A) | 14 | NA | >45000 |
| 5T4-L443C | vcMMAD | 2.0 (A) | 40 | 1400 | 16000 |
| 5T4-V422C | vcMMAD | 1.8 (A) | 15 | NA | NA |

Table 21 illustrates the cytotoxicity of anti-Her2 mutants conjugated to the payload mcMMAD. The data disclosed further demonstrate the cytotoxicity of anti-Her2 Fc mutants and Fc and kappa chain double-mutants conjugated to MMAD via mc, MalPeg6C2 and MalPeg3C2 linkers. Again, the increased loading of the double mutants is reflected by an increase in potency against Her2 expressing cell lines, BT474 and N87 (both considered to be high-expressers of Her2). The ADCs were between 100 and 1000-fold less active against a non-Her2 expressing cell line (MDA-MB468). These data indicate that the disclosed sites of mutation can be effectively transferred between different antibody platforms (antibodies binding 5T4 and Her2) and using various linkers and payloads. Therefore, these data demonstrate that the novel cys mutants of the invention are of wide utility and is generally applicable across antibody platforms and linkers and payloads and are not limited to those antibodies, linkers and payloads exemplified herein.

TABLE 21

| Mutant antibody | Payload | Loading | BT474 (nM) | N87 (nM) | MDA-MB-468 (nM) |
|---|---|---|---|---|---|
| Her2 Q347C | MalPeg6C2-MMAD | 2.0 | 0.65 | 1.9 | 850 |
| Her2 Q347C | mcMMAD | 2.0 | 1.1 | 38 | >750 |
| Her2 Y373C | MalPeg6C2-MMAD | 1.6 | 0.35 | 4.42 | >1,000.00 |
| Her2 Y373C | mcMMAD | 1.9 | 1.1 | >710 | >930 |
| Her2 S375C | mcMMAD | 1.8 | 1.1 | 570570 | >770 |
| Her2 E380C | MalPeg3C2-MMAD | 2.0 | 0.87 | NA | 320 |
| Her2 E380C+L443C | MalPeg3C2-MMAD | 3.8 | 0.81 | 3.3 | 620 |
| Her2 E392C | MalPeg6C2-MMAD | 2.0 | 0.87 | 4.9 | 720 |
| Her2 E392C | mcMMAD | 2.0 | 0.61 | >520 > 520 | >810 |
| Her2 K392C+L443C | mcMMAD | 4.0 | 0.77 | 9.3 | >1,000.00 |
| Her2 L398C+L443C | mcMMAD | 4.0 | 0.76 | 11 | 460 |
| Her2 N421C | MalPeg6C2-MMAD | 2.0 | 1.0 | 3.7 | 770 |
| Her2 N421C | mcMMAD | 2.1 | 0.78 | 30 | 430 |
| Her2 L443C | MalPeg3C2-MMAD | 2.0 | 0.82 | 2.8 | 520 |
| Her2 L443C | MalPeg6C2-MMAD | 2.0 | 0.39 | 2.3 | >890 |
| Her2 kappa-A111C | mcMMAD | 1.8 | 0.51 | 4433 | >1,000 |
| Her2 Q347C+kappa-A111C | mcMMAD | 3.5 | 0.50 | 8.9 | >1,000 |
| Her2 E392C+kappa-A111C | mcMMAD | 3.6 | 0.58 | 7.4 | >1,000 |
| Her2 L443C+kappa A111C | mcMMAD | 3.5 | 0.66 | 6.4 | >1,000 |
| Her2 kappa K183C | mcMMAD | 1.9 | 0.48 | 19 | 560 |
| Her2 L443C+kappa K183C | mcMMAD | 3.8 | 0.65 | 9.2 | 740 |
| Her2 L443C+kappa-K207C | mcMMAD | 3.5 | 0.66 | 7.1 | >1,000 |
| Her2 E380C | mcMMAD | 1.9 | 0.91 | NA | 120 |
| Her2 E380C+L443C | mcMMAD | 4.3 | 1.8 | 8.7 | 310 |
| Her2 L443C | mcMMAD | 2.0 | 0.69 | NA | 410 |

Effector Function (ADCC) is not Affected by Novel Cys Mutations in Human IgG1 Fc Region:

The Fc region of IgG1 may mediate desirable effector functions, such as ADCC, which may provide additional therapeutic effects to the antibody. Accordingly, the effector function, e.g., ability to mediate ADCC, of the cys mutant antibodies of the present invention was assessed as follows.

Figure 14A:
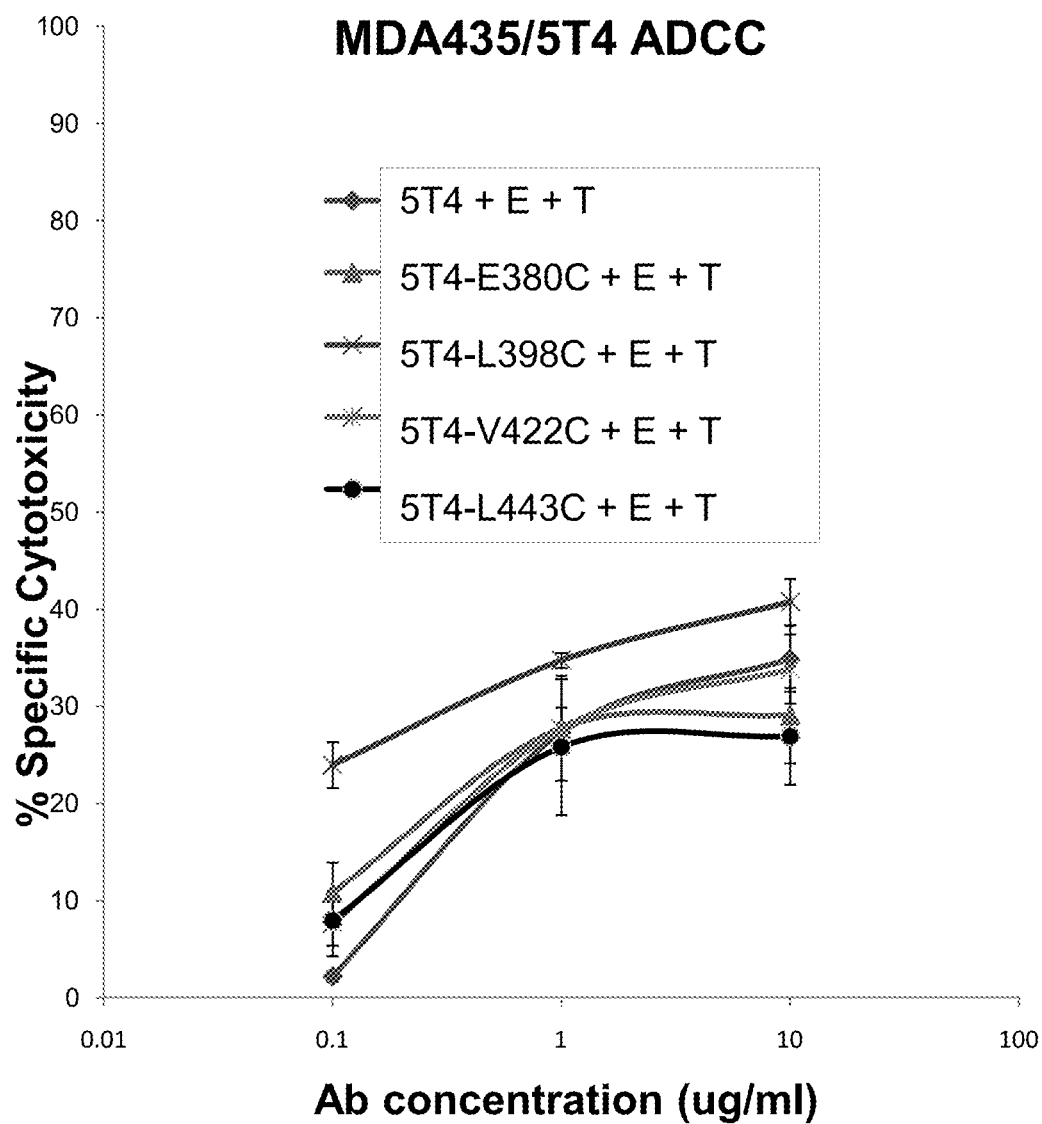
FIG. 14A shows a graph showing that cysteine variants 5-T4-E380C, 5T4-L398C, 5T4-V422C, and 5T4-L443C demonstrate the same ADCC activity as wild type parental antibody (5T4) in cells expressing 5T4 (MDA435/5T4).
Figure 14B:
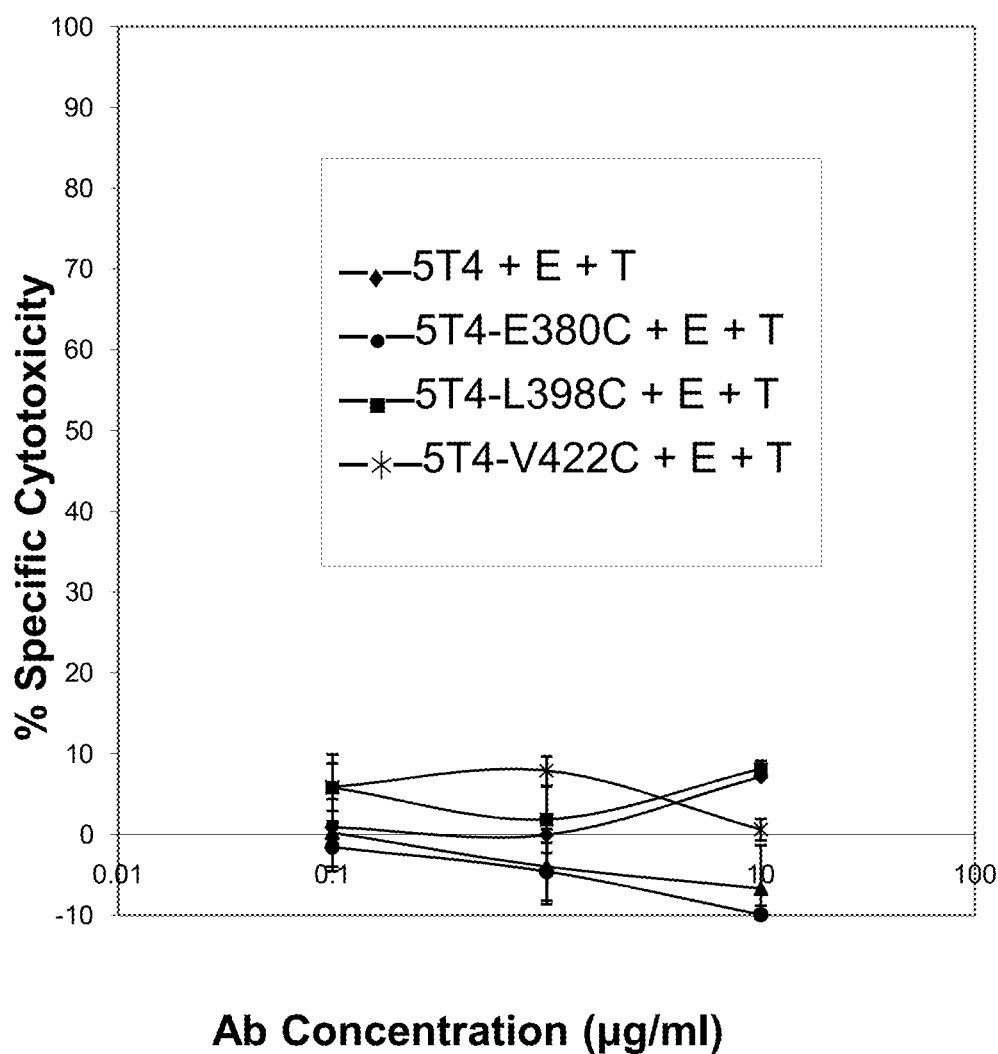
FIG. 14B shows a graph showing that cysteine variants 5T4-E380C, 5T4-L398C, 5T4-V422C, and 5T4-L443C demonstrate the same ADCC activity (none) compared with wild type parental antibody (5T4) in cells that do not express 5T4 antigen (MDA435/Neo).

The data disclosed herein demonstrate that the Cys mutant 5T4 antibodies (E380C, L398C, V422C, L4430) and the native 5T4 antibody comprising a wild type-IgG1 each mediated dose-dependent ADCC activity against 5T4 positive MDAMB435/5T4 target cells (T) using human effector cells (E) from a healthy volunteer (FIG. 14A). Against MDAMB435 neo cells (5T4+/−), no activity was observed with any of the Abs demonstrating the targeting requirement of the 5T4 antigen for mediating ADCC activity (FIG. 14B). These data demonstrate that introduction of reactive cysteines at the novel positions disclosed herein does not affect the effector function, e.g., ability to mediate ADCC, of the human IgG1 Fc region. Effector functions are known to provide therapeutic benefits thereby further emphasizing the potential therapeutic usefulness of the mutants of the present invention.

Pharmacokinetics of the Cys Mutant ADCs is Comparable to the Parental Wild Type-IgG1 Antibody:

A study was conducted to determine the pharmacokinetic parameters of human anti-5T4 antibody comprising a wild type IgG1 Fc region and human cys mutant anti-5T4 antibody site specifically conjugated to a payload (ADC) in female nu/nu mice (non tumor bearing) given a single 3 mg/kg IV dose of either 5T4 antibody alone, 5T4-mcMMAD ADC (conventional cys-conjugation) or various 5T4 cys-mutant mcMMAD ADCs. Blood samples from individual animals were collected at various time points up to 336 hours after dosing and analyzed for 5T4 antibody and conjugate concentrations using an ELISA-based assay.

In this study, the systemic clearance of the 5T4 non-conjugated antibody (Table 22) and site-specifically conjugated ADC (Table 23) was slower compared to the clearance of conventional cysteine conjugation ADC. The exposure (AUC) values for the 5T4 antibody were approximately 85%, 74%, 61% and 43% higher in mice given 5T4-L398C-mcMMAD, 5T4-V422C-mcMMAD, 5T4-L443C-mcM-MAD and 5T4-E376-CmcMMAD, respectively, compared to those dosed with the 5T4-mcMMAD (conventional cys conjugation) ADC as shown in Table 22.

TABLE 22

| Compound | Cmax (µg/mL) | T½ (days) | AUC$_{0-\infty}$ (µg · h/mL) | CL (mL/h/kg) | Vss (mL/kg) |
|---|---|---|---|---|---|
| 5T4-mcMMAD | 49.3 ± 2.8 | 4.2 ± 1.6 | 3870 ± 755 | 0.80 ± 0.15 | 106 ± 17 |
| 5T4-L398C-mcMMAD | 58.2 ± 9.8 | 6.4 ± 1.7 | 7160 ± 1640 | 0.44 ± 0.11 | 92 ± 13 |
| 5T4-V422C-mcMMAD | 70.2 ± 9.7 | 4.3 ± 0.8 | 6740 ± 1390 | 0.46 ± 0.08 | 71 ± 9 |
| 5T4-L443C-mcMMAD | 61.3 ± 3.8 | 4.6 ± 1.1 | 6220 ± 1960 | 0.52 ± 0.14 | 73 ± 7 |
| 5T4-E380C-mcMMAD | 58.4 ± 8.5 | 5.2 ± 0.9 | 5550 ± 938 | 0.55 ± 0.09 | 90 ± 8 |
| 5T4-IgG1 | 63.1 ± 4.4 | 5.1 ± 2.6 | 6410 ± 3030 | 0.55 ± 0.23 | 85 ± 5 |

When evaluating conjugate (ADC) concentrations, the exposure values were approximately 58%, 61% and 55% higher in mice given 5T4-L398C-mcMMAD, 5T4-V422C-mcMMAD and 5T4-L443C-mcMMAD, respectively, compared to those dosed with the 5T4-mcMMAD (conventional cysteine conjugation) ADC as shown in Table 23. The ADC exposure of 5T4-E380C-mcMMAD was lower (−9%) than the conventional ADC (5T4-mcMMAD).

TABLE 23

| Compound | Cmax (µg/mL) | T½ (days) | AUC$_{0-\infty}$ (µg · h/mL) | CL (mL/h/kg) | Vss (mL/kg) |
|---|---|---|---|---|---|
| 5T4-L398C-mcMMAD | 56.1 ± 3.2 | 5.2 ± 1.2 | 5320 ± 1090 | 0.58 ± 0.13 | 94 ± 6 |
| 5T4-V422C-mcMMAD | 78.5 ± 8.3 | 4.2 ± 0.6 | 5440 ± 824 | 0.56 ± 0.08 | 72 ± 5 |
| 5T4-L443C-mcMMAD | 55.8 ± 4.2 | 3.8 ± 1.0 | 5220 ± 1430 | 0.61 ± 0.15 | 73 ± 7 |
| 5T4-E380C-mcMMAD | 71.7 ± 9.0 | 4.3 ± 0.6 | 3030 ± 326 | 1.00 ± 0.10 | 97 ± 9 |
| 5T4-mcMMAD | 48.0 ± 4.8 | 4.1 ± 0.8 | 3370 ± 386 | 0.90 ± 0.10 | 105 ± 10 |

The higher exposure of particular cysteine-mutant ADCs (e.g. 5T4-L443C-mcMMAD) compared to the conventional ADC indicate that improvement of PK parameters depend on the site of payload conjugation determined by position of engineered cysteine. Therefore, the administration of ADCs produced using the novel site specific conjugation methodology via particular engineered cysteine positions of this invention, can result in more efficient delivery of the cytotoxic payload to the target tumor site compared to conventional ADCs.

Example 10

Engineered Kappa Constant Region Comprising Reactive Cysteines for Site-Specific Conjugation Sites to engineer reactive cysteines were selected in the Kappa light chain constant region to expand diversity of positions for site-specific conjugation and to enable conjugation of 4 toxic payloads per antibody by combining engineered Kappa regions with select single Fc-region cysteine mutants. Preferred positions for engineered cysteines in the Kappa constant region have predicted pKa values of 9.5-11.5 and predicted side chain solvent accessibility of 15-60 Å$^2$, properties which are predicted to mimic the most successful conjugated cysteine mutants disclosed previously herein, including, but not limited to Q347C, E380C, K392C, and L443C.

Property predictions were performed on several Kappa domain crystal structures, and positions giving optimal property predictions on multiple structures (2R8S and 1N8Z; Ye et al., 2008, Proc. Natl. Acad. Sci. USA 105:82-87 and Cho et al., 2003, Nature 421:756-760, respectively) were preferred. Each position was examined in each crystal structure by first mutating the position to cysteine and predicting the rotamer with SCWRL4 (Krivov et al., 2009, Proteins 77(4):778-795), then by predicting the cysteine side chain pKa using methods such as those described in, inter alia, Spassov and Yan, 2008, Protein Sci. 17:1955-1970) and side chain solvent accessibility using Discovery Studio 3.0 (Accelrys, Inc., San Diego, Calif.). Table 24 sets forth the location of the mutations relative to wild type endogenous human Kappa constant region wherein the amino acid residue was mutated to cysteine for thiol reactive site-specific conjugation. Table 24 indicates the positions where human Kappa residues were replaced with reactive cysteines. Positions were defined by the Kabat numbering system as set forth in Kabat et al. (1991, NIH Publication 91-3242, National Technical Information Service, Springfield, Va.), so all positions are numbered according to the Kabat system.

TABLE 24

| Position (Kabat Numbering) | SEQ ID NO of full Cκ region | Amino Acids Flanking Engineered Cysteine | SEQ ID NO of portion showing engineered amino acid |
|---|---|---|---|
| Wild type human Cκ | 89 | Not applicable | Not applicable |
| A111C | 90 | TVCAPSVFIFPPSDEQLKSGT | 164 |
| K183C | 92 | YSLSSTLTLSCADYEKHKVYA | 166 |
| N210C | 95 | CEVTHQGLSSPVTKSFCRGEC | 169 |

Example 11

Generation of Single Cysteine Engineered Human Kappa Constant Region Anti-Her2 Antibodies Human Kappa constant regions comprising engineered single cysteines at these novel positions shown in Table 24 were incorporated into an anti-Her2 antibody (amino acid sequences of the VH and VL domains of an exemplary Her2 antibody are show in FIGS. 17C and 17D, respectively) for further evaluation. The nucleic acid encoding the anti-Her2 antibody human wild type Kappa constant region was removed from the expression vector by restriction enzyme digestion and replaced with a nucleic acid encoding human light chain constant Kappa regions comprising the single engineered cysteine residues using T4 DNA Ligase (New England Biolabs Inc., Ipswich, Mass.). The resulting nucleic acid was sequence confirmed for each construct. These data demonstrate that nucleic acids encoding the engineered Kappa light chains comprising mutations to introduce reactive cysteines in the constant region were produced.

Example 12

Production of Anti-Her2 Antibody Single Cysteine Engineered Human Kappa Variants from Transient HEK-293 Expression System To produce sufficient material for conjugation studies and to determine whether the variants could produced in larger quantities, HEK-293 cells in 10 L wave bags were transiently co-transfected with heavy and light chain DNA encoding the six anti-Her2 single-cysteine Kappa engineered antibody variants described previously using standard methods. Next, the single-cysteine Kappa variant antibodies were purified using a standard two step purification strategy, Protein-A affinity capture followed by size exclusion chromatography (SEC). These results shown in Table 25 demonstrate that acceptable levels of high molecular weight (HMW) aggregated species were detected following elution from Protein A resin for all six single cysteine Kappa variants and that this HMW species could be removed using size exclusion chromatography. Final purified single cysteine engineered Kappa anti-Her2 antibody protein preparations were shown not to form high molecular weight aggregated species upon storage at 4° C. for 1 week or when submitted to three (3) freeze/thaw cycles (Table 25).

TABLE 25

| Kappa Cysteine Variant | % HMW after ProA | % HMW final protein | % HMW 4° C. 1 week | % HMW 3x freeze/thaw | Final Yield [mg/Liter] |
|---|---|---|---|---|---|
| A111C | 9 | <1 | <1 | <1 | 19.0 |
| K183C | 7 | <1 | <1 | <1 | 18.9 |
| N210C | 13 | <1 | <1 | <1 | 18.2 |

Summary of anti-Her2 single cysteine engineered Kappa antibody variants in transient HEK-293 expression system. These data demonstrate that the engineered Kappa light chains comprising a mutation at A111, K183, and N210, to introduce a reactive cysteine, could be readily produced with no significant effect on the antibody yield and propensity to aggregate.

Example 13

In Vitro Stability of Engineered ADCs

The stability of the maleimide-cysteine linkage has become an area of increasing interest in recent years. Recent reports have shown that maleimides can be transferred both in vitro and in vivo to exogenous thiol nucleophiles (see, e.g., Shen et al., 2012, Nature Biotech. 30(2):184-185). In order to assess the stability of ADCs and prioritize samples for in vivo evaluation, a novel assay was developed that involves the treatment of the maleimide-linked ADC with excess aqueous glutathione (GSH) or plasma. Aliquots of the reaction mixture are analyzed at various timepoints to determine the loading of ADCs. This method, described below, was used to assess the stability of a series of cysteine mutant antibodies of the invention that were linked to mcMMAD and other payload-linkers. The results indicate that the drug-antibody linkage is slowly cleaved in a GSH-dependent manner (Table 26). Importantly, the rate of cleavage is highly dependent upon the site of modification, thereby allowing a ranking of the cysteine mutants based on stability. The GSH stability assay results shown in Table 26 demonstrate that particular mutants (for example, E388C and L443C) are significantly more stable than other mutants (for example, E380C and V422C).

Assay Protocol:

The ADC sample (30 μg) in PBS was mixed with glutathione (GSH) solution to produce final concentration of GSH of 0.5 mM and 3 mg/mL protein concentration. A control sample (without GSH) was likewise prepared from 30 μg ADC diluted to 3 mg/mL in PBS. The GSH-treated ADC sample and the control ADC sample were incubated at 37° C. and were sampled at 0, 3, and 6 days. Aliquots were reduced with excess TCEP, acidified by adding 0.1% formic acid solution with 10% acetonitrile and analyzed by for loading by LC/MS as described below.

Sample Analysis:

Analysis was performed using an Agilent 1100 capillary HPLC coupled with Waters Xevo G2 Q-TOF mass spectrometer. The analytes were loaded onto a Zorbax Poroshell 300SB C8 column (0.5 mm×75 mm, maintained at 80° C.) with 0.1% formic acid, and eluted using a gradient of 20-40% buffer B (80% acetonitrile, 18% 1-propanol, 2% water with 0.1% formic acid) at a flow rate of 20 μl/min over 5.5 minutes. Mass spectrometric detection was carried out in positive, sensitivity mode with capillary voltage set at 3.3 kV. Data analyses were performed with MaxEnt 1 function in MassLynx and intensities were used for loading calculation based on the previously described formula (i.e., Equation 1 set forth previously elsewhere herein). Results of the analyses are shown in Table 26 below.

TABLE 26

| Antibody | Payload | Original loading Day 0 | Loading at Day 3 (+GSH) | Loading at day 6 (+GSH) | % Loading remaining at Day 3 (+GSH) | % Loading remaining at day 6 (+GSH) |
|---|---|---|---|---|---|---|
| 5T4-E380C | mcMMAD | 2.0 | 1.0 | 0.6 | 48% | 31% |
| 5T4-E380C + L398C | mcMMAD | 3.9 | 3.7 | 2.9 | 94% | 74% |
| 5T4-E380C + L443C | mcMMAD | 4.0 | 3.0 | 2.8 | 77% | 70% |
| 5T4-E380C + V422C | mcMMAD | 3.0 | 2.4 | 2.2 | 81% | 73% |
| 5T4-K388C | mcMMAD | 1.9 | 2.0 | 2.0 | 101% | 101% |
| 5T4-K392C + L443C | MalPeg6C2_MMAD | 3.8 | 3.6 | 3.6 | 95% | 95% |
| 5T4-K392C + L443C | MalPeg3C2_MMAD | 3.9 | 3.9 | 3.9 | 100% | 100% |
| 5T4-K392C + L443C | mcMMAD | 3.9 | 3.8 | 3.7 | 97% | 95% |
| 5T4-L398C | mcMMAD | 2.0 | 1.9 | 1.6 | 96% | 84% |
| 5T4-L398C + L443C | MalPeg3C2_MMAD | 3.9 | 3.9 | 4.0 | 100% | 103% |
| 5T4-L398C + L443C | MalPeg6C2_MMAD | 3.8 | 3.8 | 3.9 | 100% | 103% |
| 5T4-L398C + L443C | mcMMAD | 3.9 | 3.7 | 3.5 | 95% | 90% |
| 5T4-L398C + L443C | mcMMAD | 3.9 | 3.1 | 3.3 | 80% | 84% |
| 5T4-L398C + V422C | MalPeg6C2_MMAD | 3.6 | 3.8 | 3.8 | 106% | 106% |
| 5T4-L398C + V422C | MalPeg3C2_MMAD | 3.9 | 3.9 | 4.0 | 100% | 103% |
| 5T4-L398C + V422C | mcMMAD | 3.8 | 3.6 | 3.3 | 95% | 87% |
| 5T4-L443C | mcMMAD | 2.0 | 2.0 | 2.0 | 101% | 99% |
| 5T4-V422C | mcMMAD | 1.7 | 1.1 | 0.9 | 65% | 53% |
| Her2-E380C | mcMMAD | 1.8 | 0.7 | 0.4 | 39% | 22% |
| Her2-E380C + L443C | mcMMAD | 2.6 | 2.7 | 2.3 | 104% | 88% |
| Her2-E388C | MalPeg6C2_MMAD | 1.9 | 1.9 | 1.9 | 100% | 100% |
| Her2-E388C | mcMMAD | 2.0 | 1.9 | 1.9 | 95% | 95% |
| Her2-E388C + kappaA111C | mcMMAD | 3.7 | 3.5 | 3.5 | 95% | 95% |
| Her2-K392C + L443C | mcMMAD | 3.9 | 3.9 | 3.7 | 100% | 95% |
| Her2-kappaA111C | mcMMAD | 2.0 | 1.9 | 1.9 | 95% | 95% |
| Her2-kappaA111C | mcMMAD | 2.0 | 2.0 | 2.0 | 100% | 100% |
| Her2-kappaK183C | mcMMAD | 2.0 | 2.0 | 2.0 | 100% | 100% |
| Her2-kappaK183C | mcMMAD | 2.0 | 1.9 | 1.7 | 95% | 85% |
| Her2-L398C + L443C | mcMMAD | 3.9 | 3.6 | 3.2 | 92% | 82% |
| Her2-L443C | MalPeg6C2_MMAD | 2.0 | 1.9 | 1.8 | 95% | 90% |
| Her2-L443C | mcMMAD | 1.9 | 1.9 | 1.7 | 100% | 89% |
| Her2-L443C + kappaA111C | mcMMAD | 4.0 | 3.7 | 3.6 | 93% | 90% |
| Her2-L443C + kappaK183C | mcMMAD | 3.9 | 3.8 | 3.6 | 97% | 92% |
| Her2-L443C + kappaK207C | mcMMAD | 3.5 | 3.5 | 3.5 | 100% | 100% |
| Her2-N421C | MalPeg6C2_MMAD | 1.9 | 2.0 | 2.0 | 105% | 105% |
| Her2-Q347C | MalPeg6C2_MMAD | 2.0 | 2.0 | 2.0 | 100% | 100% |
| Her2-Q347C | mcMMAD | 2.0 | 1.8 | 2.0 | 90% | 100% |
| Her2- | mcMMAD | 3.6 | 3.4 | 3.4 | 94% | 94% |

TABLE 26-continued

| Antibody | Payload | Original loading Day 0 | Loading at Day 3 (+GSH) | Loading at day 6 (+GSH) | % Loading remaining at Day 3 (+GSH) | % Loading remaining at day 6 (+GSH) |
|---|---|---|---|---|---|---|
| Q347C + kappaA111C | | | | | | |
| Her2-Q421C | mcMMAD | 2.0 | 2.0 | 2.0 | 100% | 100% |
| Her2-S375C | mcMMAD | 2.0 | 2.0 | 1.8 | 100% | 90% |
| Her2-Y373C | MalPeg6C2_MMAD | 1.7 | 1.4 | 1.0 | 82% | 59% |
| Her2-Y373C | mcMMAD | 1.6 | 1.5 | 1.4 | 94% | 88% |

Example 14

Engineered Lambda Constant Region Comprising Reactive Cysteines for Site-Specific Conjugation The engineered reactive cysteines selected in the Lambda light chain constant region disclosed herein expand diversity of positions for site-specific conjugation and enable conjugation of 4 toxic payloads per antibody by combining engineered Lambda regions with select single Fc-region cysteine mutants. Preferred positions for engineered cysteines in the Lambda constant region of the invention have predicted pKa values of 9.5-11.5 and predicted side chain solvent accessibility of 15-60 Å$^2$. Without wishing to be bound by any particular theory, these properties are shared with the preferred conjugated cysteine mutants disclosed previously herein, including, but not limited to, the heavy chain constant domain cysteines engineered at the following positions: Q347C, E380C, K392C, and L443C.

Predictions of the desired properties were performed on several Lambda domain crystal structures (two unpublished structures, plus PDB entries 3H42 and 3G6A, described in Chan et al., 2009, Proc. Natl. Acad. Sci. USA 106:9820-9825 and Teplyakov et al., 2009, J. Mol. Bio. 389:115-123, respectively), and positions giving optimal property predictions on multiple structures were preferred. Each position was examined in each crystal structure by first mutating the position to cysteine and predicting the rotamer with SCWRL4 (Krivov et al., 2009, Proteins 77(4):778-795), then by predicting the cysteine side chain pKa (using methods such as those described in, inter alia, Spassov and Yan, 2008, Protein Sci. 17:1955-1970) and side chain solvent accessibility using Discovery Studio 3.0 (Accelrys, Inc., San Diego, Calif.). Table 27 sets forth the location of the mutations relative to wild type endogenous human Lambda constant region wherein the amino acid residue was mutated to cysteine for thiol reactive site-specific conjugation. Table 27 indicates the positions where human Lambda residues were replaced with reactive cysteines. Positions were defined by the Lambda numbering system as set forth in Kabat et al. (1991, NIH Publication 91-3242, National Technical Information Service, Springfield, Va.), such that all positions are numbered according to the Kabat system.

TABLE 27

| Position (Kabat Numbering) | SEQ ID NO of full Cλregion | Amino Acids Flanking Engineered Cysteine | SEQ ID NO of portion showing engineered amino acid |
|---|---|---|---|
| Wild type human Cλ | 170 | Not applicable | Not applicable |
| Wild type human Cλ Amino Acid | 171 | Not applicable | Not applicable |
| K110C | 172 | GQPCAAPSVTLFPP | 189 |
| A111C | 173 | GQPKCAPSVTLFPPS | 190 |
| L125C | 174 | VTLFPPSSEECQANKATLVCL | 191 |
| K149C | 175 | FYPGAVTVAWCADSSPVKAGV | 192 |
| V155C | 176 | TVAWKADSSPCKAGVETTTPS | 193 |
| G158C | 177 | WKADSSPVKACVETTTPSKQS | 194 |
| T161C | 178 | DSSPVKAGVECTTPSKQSNNK | 195 |
| Q185C | 179 | ASSYLSLTPECWKSHRSYSCQ | 196 |
| S188C | 180 | YLSLTPEQWKCHRSYSCQVTH | 197 |
| H189C | 181 | LSLTPEQWKSCRSYSCQVTHE | 198 |
| S191C | 182 | LTPEQWKSHRCYSCQVTHEGS | 199 |
| T197C | 183 | EQWKSHRSYSCQVCHEGSTVE | 200 |
| V205C | 184 | SCQVTHEGSTCEKTVAPTECS | 201 |

TABLE 27-continued

| Position (Kabat Numbering) | SEQ ID NO of full CLregion | Amino Acids Flanking Engineered Cysteine | SEQ ID NO of portion showing engineered amino acid |
|---|---|---|---|
| E206C | 185 | CQVTHEGSTVCKTVAPTECS | 202 |
| K207C | 186 | QVTHEGSTVECTVAPTECS | 203 |
| T208C | 187 | VTHEGSTVEKCVAPTECS | 204 |
| A210C | 188 | HEGSTVEKTVCPTECS | 205 |

Example 15

In Vivo Characterization of Engineered Antibodies for Site-Specific Conjugation

Figure 21A:
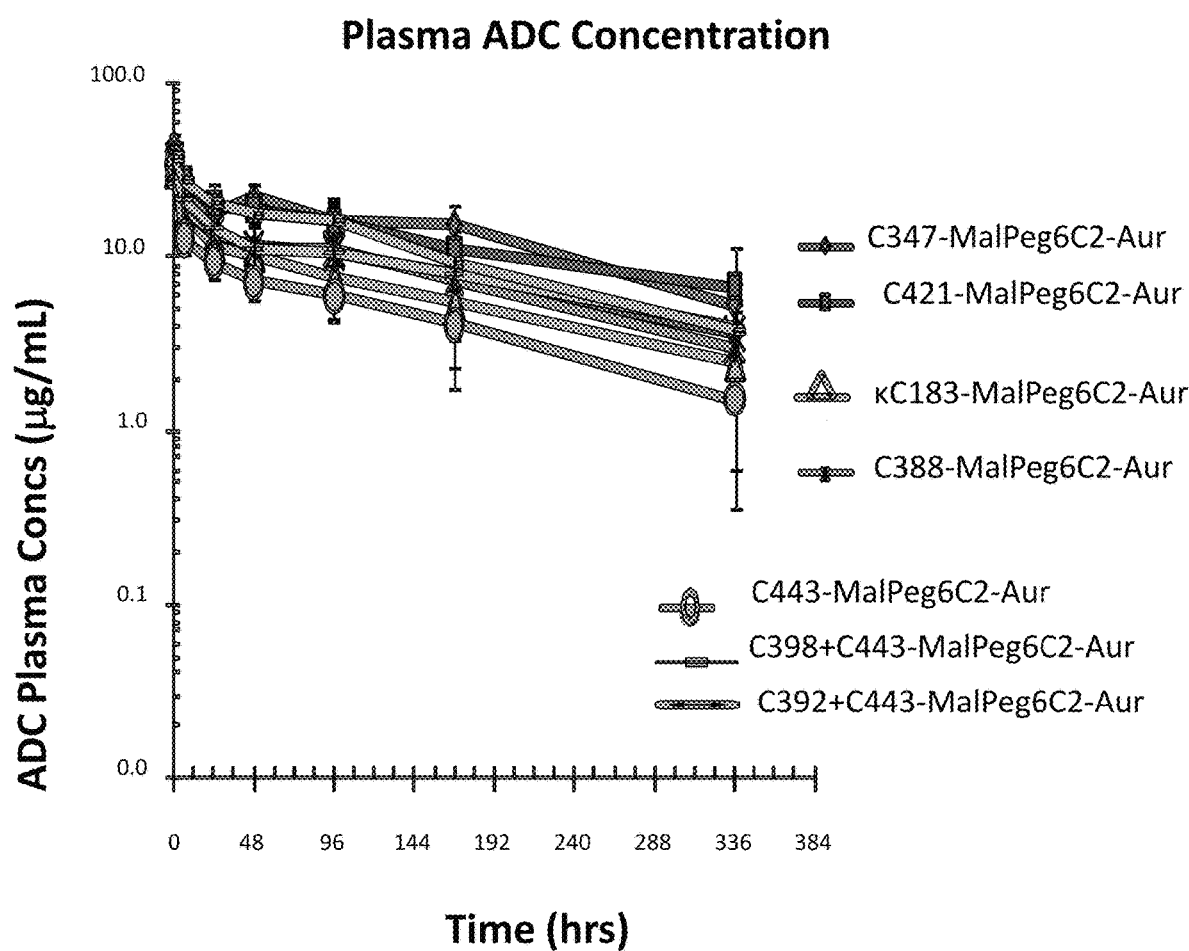
FIG. 21A is a graph illustrating the plasma concentration over time of site-specific conjugated ADCs where an anti-Her2 antibody was conjugated, at the specific site(s) indicated, via a MalPeg6C2 linker to Aur. The engineered conjugation sites were: Q347C; N421C; kappa K183C; K388C; L443C; L398C+FL443C; and K392C+FL443C.
Figure 21B:
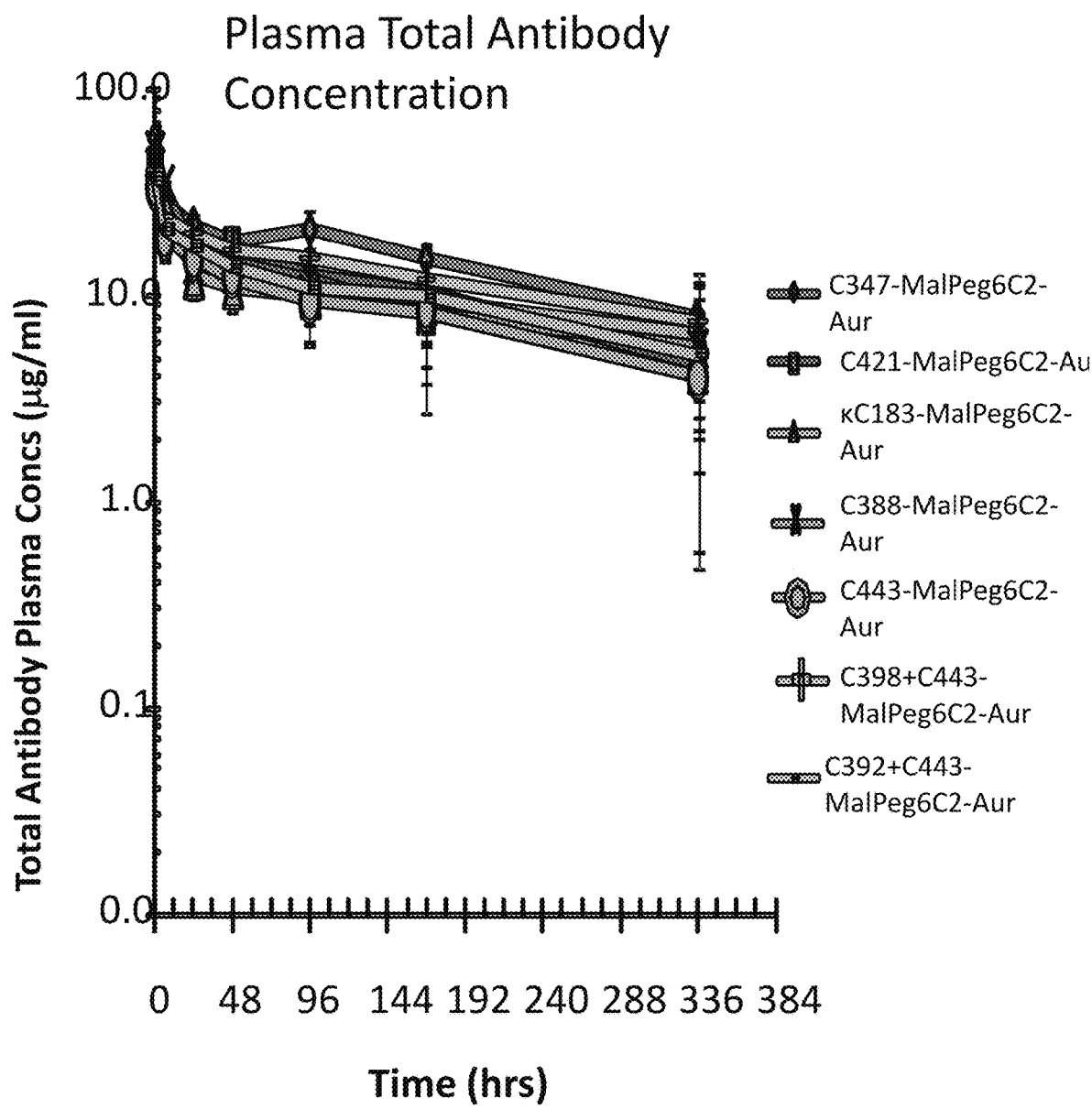
FIG. 21B is a graph illustrating the total anti-Her2 ADC plasma concentration for various site-specific conjugate ADCs. Anti-Her2 antibody was conjugated, via a MalPeg6C2 linker, to a proprietary auristatin payload "Aur" (also referred to herein as "8261"). The specific engineered conjugation sites were as follows: Q347C; N421C; kappa K183C; K388C; L443C; L398C+L443C; and K392C+L443C.

The in vivo PK parameters of various site-specific conjugated ADCs of the invention were assessed in a mouse model. Briefly, the PK of various site-specific anti-Her2 conjugated ADCs loaded with mcMMAD using a MalPeg6C2_Aur linker-payload, where "Aur" is a proprietary auristatin payload also referred to as "8261" and disclosed in International Patent Application No. PCT/IB2012/056224 filed Nov. 7, 2012, which is incorporated by reference as if set forth in its entirety herein, were determined and the results are shown in FIG. 21. No significant detectable PK differences were observed for site-specific ADCs regardless of the site (Fc C347, Fc C421, kappa 183, Fc C388, Fc C443, Fc C398+C443, and Fc C392+C443) used for conjugation (FIG. 21A). The data disclosed in FIG. 21B demonstrate that site-specific conjugates showed at least about 70% ADC/Antibody AUC ratios, with the majority near 100%, unlike those typically observed for conventional conjugates. The ratios of ADC AUC to antibody AUC were typically lower and in the range of 40-60%. The data disclosed herein demonstrate that two double-engineered (i.e. DAR=4) MalPeg6C2_Aur site-specific ADCs (L398C+L443C and K392C+L443C) exhibited comparable PK to the single-engineered ADCs (DAR=2). Both types of site specific ADCs had significant improvement in ADC/antibody ratios. Additionally, anti-Her2-mcMMAD PK data correlated with the PK parameters determined for comparable ADCs on an anti-5T4 antibody, suggesting that the engineered cysteine positions can be used across multiple antibody platforms to generate stable conjugates.

N87 Gastric Carcinoma Model

Figure 22A:
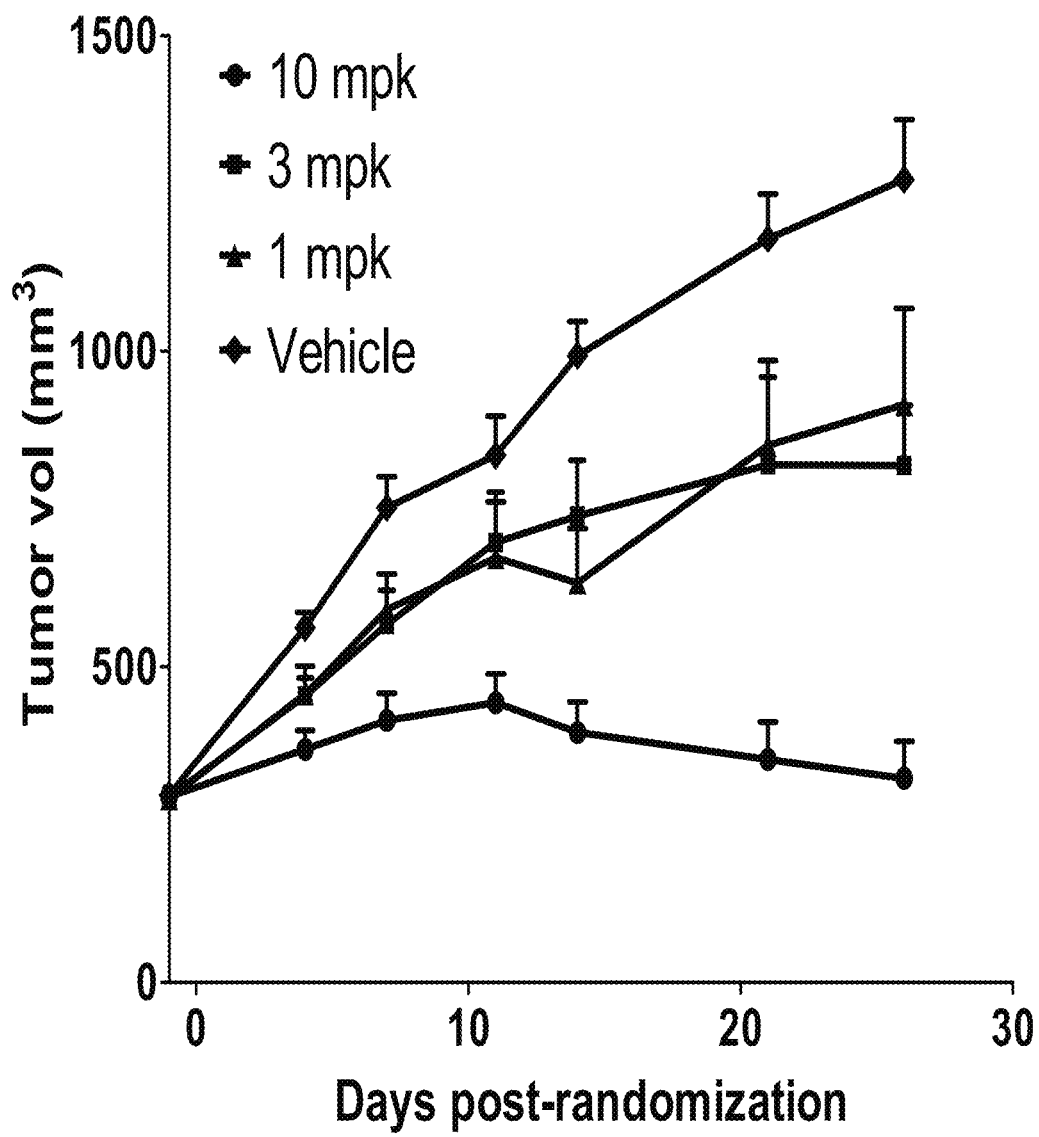
FIG. 22A depicts a graph illustrating the tumor size in an N87 mouse model of gastric carcinoma where anti-Her2-L443C was conjugated to MMAD via a MalPeg6C2 linker and administered at 1 mg/kg, 3 mg/kg and 10 mg/kg compared with a negative control (Vehicle).
Figure 22B:
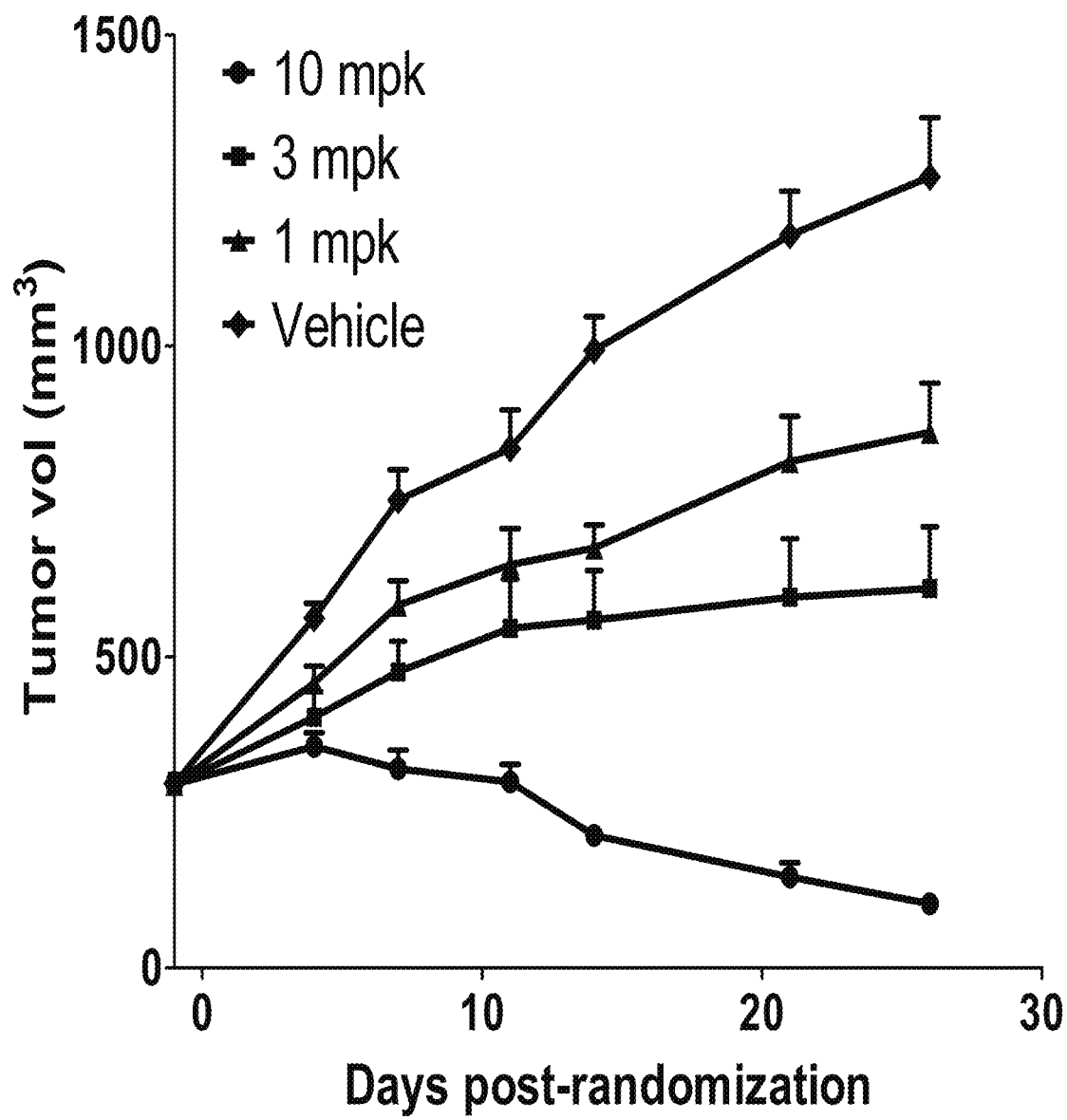
FIG. 22B depicts a graph illustrating the tumor size in an N87 mouse model of gastric carcinoma where anti-Her2-L443C was conjugated to Aur (also referred to as "8261", a novel auristatin-based cytotoxic compound) via a MalPeg6C2 linker (abbreviated herein as "MP6") and administered at 1 mg/kg, 3 mg/kg and 10 mg/kg compared with a negative control (Vehicle).
Figure 22C:
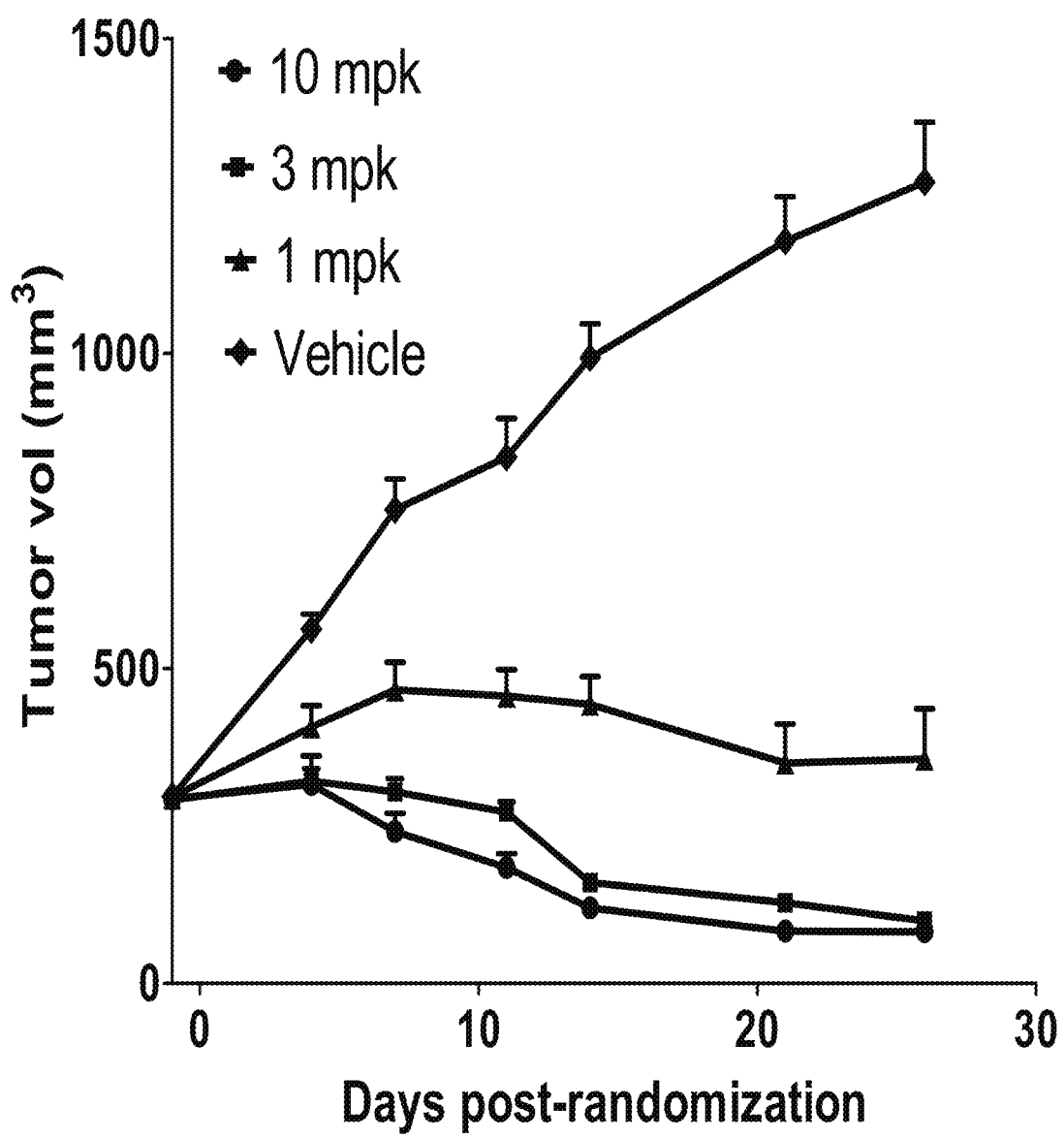
FIG. 22C depicts a graph illustrating the tumor size in an N87 mouse model of gastric carcinoma where anti-Her2-L443C was conjugated to a proprietary payload (referred to as "0101") via a vc linker and administered at 1 mg/kg, 3 mg/kg and 10 mg/kg compared with a negative control (Vehicle).

The efficacy of anti-Her2-L443C ADC variants, conjugated with select lead proprietary linker-payloads, was determined in the in vivo N87 gastric carcinoma model. Results show comparable in vivo efficacy for the anti-Her2-L443C-Mal-Peg6-C2-MMAD (FIG. 22A), anti-Her2-L443C-MalPeg6C2-Aur (FIG. 22B) and anti-Her2-L443C-vc0101 (a novel cytotoxic compound disclosed in International Patent Application No. PCT/IB2012/056224) (FIG. 22C) ADCs relative to historical data for conventional non-site specific conjugates despite approximately 50% lower loading per antibody. That is, the average for anti-Her2-L443C ADCs is DAR=2 compared with a DAR=4 for conventional non-specific anti-Her2 conjugates (T-DM1; drug maytansinoid 1).

DYT2 Xenograft Tumor Model

Figure 23:
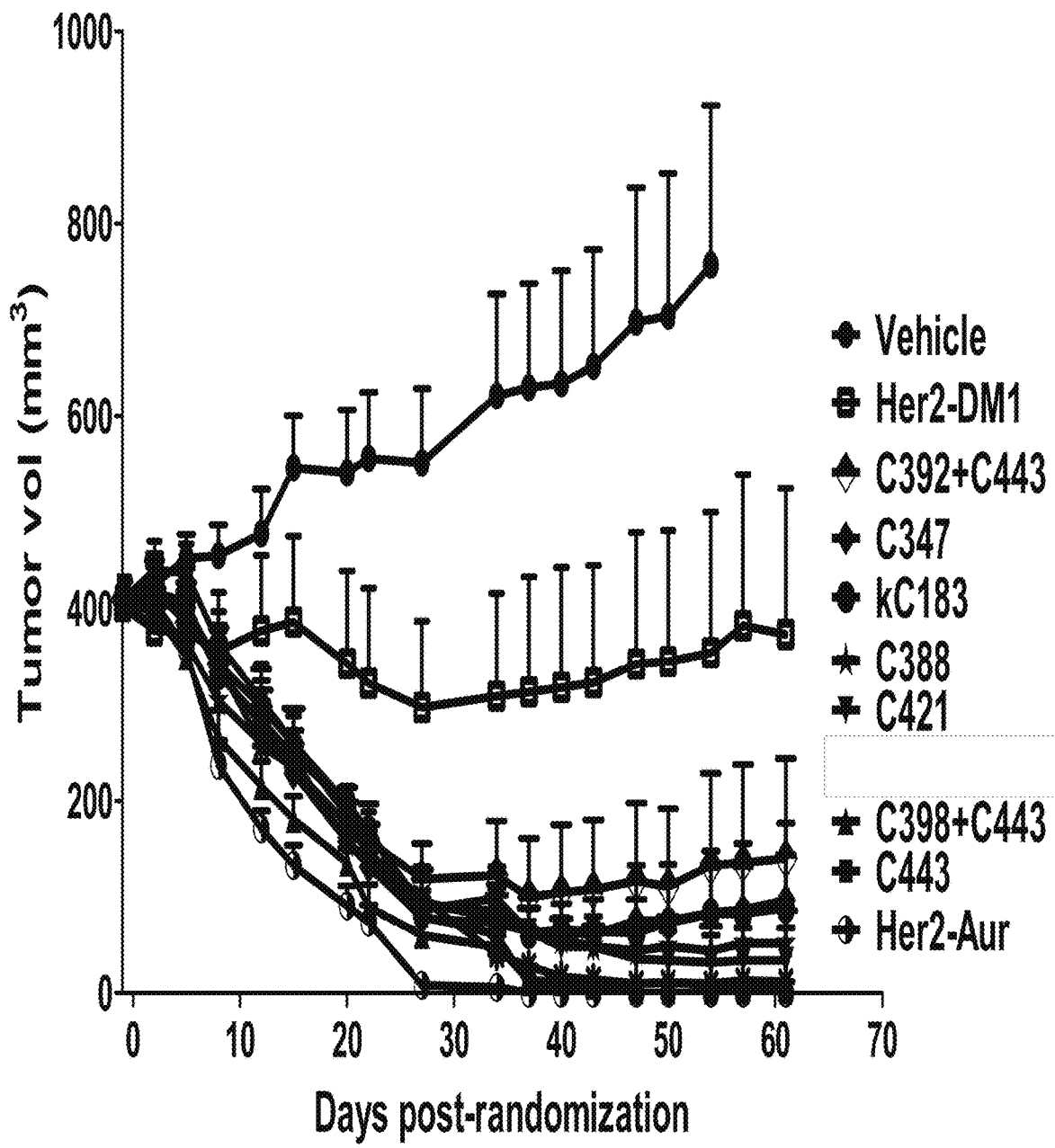
FIG. 23 depicts a graph demonstrating the efficacy of site-specific conjugated anti-Her2 ADCs in the DYT2 Her2+ carcinoma model. The anti-Her2 ADCs were conjugated at various engineered cysteines (K392C+L443C, Q347C, kappa K183C; K388C; N421C, kappa K207C; L398C+L443C; L443C; and their efficacy was compared with vehicle only and the anti-Her2 antibody conventionally conjugated with DM1 (Her2-DM1) and Aur (Her2-Aur).

The efficacy of anti-Her2 site-specific conjugated ADCs was assessed in another tumor model. Eight MalPeg6C2-Aur engineered site-specific cysteine mutant ADCs were compared to a conventional conjugate at 1 mg/kg in the DYT2 xenograft model and the results are shown in FIG. 23. Data from this study indicated that the L443C, K388C, and N421C single mutants and the L398C+L443C double mutant had equivalent potency relative to the conventional conjugate. However, the K392C+L443C double mutant, and Q347C and kappa-K183C single mutants were not as efficacious as the conventional conjugate (FIG. 23). Overall, in vivo potency of site-specifically conjugated ADCs using various linker-payload combinations is comparable to that observed for conventional conjugates.

In Vivo Toxicology Studies

Rat toxicology studies were performed using anti-Her2-L443C-vc0101, anti-Her2-MalPeg6C2-MMAD and anti-Her2-MalPeg6C2-Aur conjugates in the N87 gastric carcinoma model. One site-specific conjugate of the invention, L443C-vc0101, demonstrated a better toxicity profile at the highest payload dose tested than the conventionally conjugated Her2-vc0101. Similar, but slightly less pronounced improvement in safety relative to the conventional conjugate was also observed for Her2-L443C-MalPeg6C2-Aur site-specific ADC.

Determination of Therapeutic Index (TI) Values for Site-Specific Conjugated ADCs The therapeutic Index (TI) values of conventional versus site-specific conjugated mcMMAD, vc0101 and mcAur anti-Her2 conjugates of the invention were determined and the results are shown in FIG. 23. TI values were determined by using the ratio of cNOAEL (statistically derived No Observed Adverse Effect Levels based on the continuous response variable) from rat toxicology studies to efficacy defined as Tumor Static Concentration (TSC). Anti-Her2 site-specific L443C-vc0101 ADC showed a greater than two-fold increase in the TI value relative to a conventionally conjugated ADC. This was due to a three-fold decrease in efficacy (TSC) that was compensated with a 6-fold increase in safety (improved cNOAEL). The data disclosed herein suggest that the novel site-specific antibody conjugates of the invention can be used with certain linker-payload combinations, such as vc0101, and could exhibit a better therapeutic window than conventionally conjugated antibodies.

The data disclosed herein demonstrate that the novel identified positions to engineer reactive cysteines for enabling site-specific conjugation yielded stable, efficacious ADCs with improved PK and TI relative to conventional conjugates across multiple antibody, payload and linker platforms.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An engineered human IgG heavy chain constant domain ($C_\gamma$) polypeptide, wherein the engineered Cγ polypeptide comprises at least one amino acid substitution to introduce a cysteine residue useful for conjugation, and wherein the engineered $C_\gamma$ polypeptide comprises a substitution at amino acid position K334, according to the EU index of Kabat.

2. The engineered Cγ polypeptide of claim 1, wherein the polypeptide comprises the amino acid sequence of SEQ ID NO: 131.

3. The engineered Cγ polypeptide of claim 1, wherein the polypeptide is selected from an IgG1, IgG2, IgG3, or an IgG4 subclass.

4. The engineered Cγ polypeptide of claim 1, wherein the polypeptide is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, and wherein the conjugation is at the at least one amino acid substitution.

5. The engineered Cγ polypeptide of claim 4, wherein the cytotoxic agent is conjugated to the polypeptide via a linker.

6. The engineered $C_\gamma$ polypeptide of claim 5, where the linker is selected from the group consisting of mc (maleimidocaproyl), val-cit (valine-citrulline), mc-val-cit (maleimidocaproyl-valine-citrulline), mc-val-cit-PRBC (maleimidocaproyl-valine-citrulline-p-aminobenzylcarbamate), Mal-PEG2C2 (maleimido-$[CH_2CH_2O]_2CH_2CH_2C(=O)$), Mal-PEG3C2 (maleimido-$[CH_2CH_2O]_3CH_2CH_2C(=O)$), and Mal-PEG6C2 (maleimido-$[CH_2CH_2O]_6CH_2CH_2C(=O)$).

7. An engineered human IgG heavy chain constant domain ($C_\gamma$) polypeptide, wherein the engineered Cγ polypeptide comprises at least one amino acid substitution to introduce a cysteine residue useful for conjugation,
wherein the at least one amino acid substitution is selected from the group consisting of a substitution at amino acid position K334, Q347, Y373, E380 and E388, according to the EU index of Kabat,
wherein the polypeptide is conjugated to a cytotoxic agent via a linker,
wherein the conjugation is at the at least one amino acid substitution and wherein the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCit-PABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG2C2-3377, Mal-PEG2C2-8261, Mal-PEG3C2-8261, and Mal-PEG6C2-8261.

8. An antibody, or antigen-binding portion thereof, comprising an engineered human kappa light chain constant domain ($C_K$) polypeptide wherein the engineered $C_k$ polypeptide comprises an amino acid substitution to introduce a cysteine residue useful for conjugation, and wherein the amino acid substitution is at position K183, according to the numbering of Kabat.

9. An antibody, or antigen-binding portion thereof, comprising
an engineered human IgG heavy chain constant domain ($C_\gamma$) polypeptide comprising at least one amino acid substitution selected from the group consisting of K334, Q347, Y373, E380 and E388, according to the EU index of Kabat; and an engineered human kappa light chain constant domain ($C_k$) polypeptide comprising a CL domain of a $C_k$, and further comprising an amino acid substitution at position K183, according to the numbering of Kabat.

10. An Fc fusion protein comprising the engineered Cy polypeptide of claim 1.

11. A pharmaceutical composition comprising the antibody, or antigen-binding portion thereof, of claim 8 and a pharmaceutically acceptable carrier.

12. A pharmaceutical composition comprising the antibody, or antigen-binding portion thereof, of claim 9 and a pharmaceutically acceptable carrier.

13. A method of treating cancer, autoimmune, inflammatory, or infectious diseases or disorders in a subject in need thereof, the method comprising administering to the subject a therapeutically effective amount of an antibody, or antigen-binding portion thereof, or an Fc fusion protein, wherein the antibody, or antigen-binding portion thereof, or the Fc fusion protein, comprises the engineered $C_\gamma$ polypeptide of claim 1.

14. The method of claim 13, wherein the engineered $C_\gamma$ polypeptide is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, and wherein conjugation is at the at least one amino acid substitution.

15. The method of claim 14, wherein the one or more of a cytotoxic agent is conjugated to the engineered Cy polypeptide via a linker and wherein the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCitPABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261.

16. A nucleic acid encoding the engineered $C_\gamma$ polypeptide of claim 1.

17. A host cell comprising the nucleic acid of claim 16.

18. A method of producing an engineered antibody, or antigen-binding portion thereof, comprising incubating the host cell of claim 17 under suitable conditions for expressing the engineered $C_\gamma$ polypeptide, and isolating the antibody or antigen-binding portion thereof.

19. An antibody, or antigen-binding portion thereof, comprising
(a) an engineered human IgG heavy chain constant domain (Cy) polypeptide comprising at least one amino acid substitution selected from the group consisting of K246, D249, D265, S267, D270, N276, Y278, E283, R292, E293, E294, Y300, V302, V303, L314, N315, E318, K320, 1332, E333, K334, 1336, E345, Q347, S354, M358, K360, Q362, K370, Y373, D376, A378, E380, E382, Q386, E388, N390, K392, T393, D401, F404, T411, D413, K414, R416, Q418, Q419, N421, M428, A431, L432, T437, Q438, K439, and L443, according to the EU index of Kabat; and (b) an engineered human kappa light chain constant domain ($C_K$) polypeptide comprising a CL domain of a $C_K$, and further comprising an amino acid substitution at position K183, according to the numbering of Kabat.

20. A pharmaceutical composition comprising the antibody, or antigen-binding portion thereof, of claim 19 and a pharmaceutically acceptable carrier.

21. The antibody, or antigen-binding portion thereof of claim 8, wherein the engineered $C_K$ polypeptide is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, and wherein the conjugation is at the K183 amino acid substitution.

22. The antibody, or antigen-binding portion thereof of claim 21, wherein the cytotoxic agent is conjugated to the engineered $C_K$ polypeptide via a linker.

23. The antibody, or antigen-binding portion thereof of claim 22, where the linker is selected from the group consisting of mc (maleimidocaproyl), val-cit (valine-citrulline), mc-val-cit (maleimidocaproyl-valine-citrulline), mc-val-cit-PABC (maleimidocaproyl-valine-citrulline-p-aminobenzylcarbamate), Mal-PEG2C2 (maleimido-[$CH_2CH_2O$]$_2CH_2CH_2C(=O)$)), Mal-PEG3C2 (maleimido-[$CH_2CH_2O$]$_3CH_2CH_2C(=O)$)), and Mal-PEG6C2 (maleimido-[$CH_2CH_2O$]$_6CH_2CH_2C(=O)$)).

24. The antibody, or antigen-binding portion thereof of claim 23, wherein the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCitPABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261.

25. A method of treating cancer, autoimmune, inflammatory, or infectious diseases or disorders in a subject in need thereof, the method comprising administering to the subject a therapeutically effective amount of an antibody, or antigen-binding portion thereof, of claim 8.

26. The method of claim 25, wherein the engineered $C_K$ polypeptide of the antibody, or antigen-binding portion thereof, is conjugated to one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin, and wherein the conjugation is at the K183 amino acid substitution.

27. The method of claim 26, wherein the one or more of a cytotoxic agent is conjugated to the engineered $C_K$ polypeptide via a linker and wherein the linker and the cytotoxic agent are selected from the group consisting of maleimidocaproyl-monomethyl auristatin D (mcMMAD), maleimidocaproyl-0101 (mc0101), maleimidocaproyl-3377 (mc3377), maleimidocaproyl-8261 (mc8261), valine-citrulline-monomethyl auristatin D (vcMMAD), valine-citrulline-0101 (vc0101), valine-citrulline-3377 (vc3377), valine-citrulline-8261 (vc8261), mcValCitPABCMMAD (maleimidocaproyl-valine-citrulline-monomethyl auristatin D), mcValCit0101 (maleimidocaproyl-valine-citrulline-0101), mcValCit3377 (maleimidocaproyl-valine-citrulline-3377), mcValCit8261 (maleimidocaproyl-valine-citrulline-8261), Mal-PEG2C2-MMAD, Mal-PEG3C2-MMAD, Mal-PEG6C2-MMAD, Mal-PEG2C2-0101, Mal-PEG3C2-0101, Mal-PEG6C2-0101, Mal-PEG2C2-3377, Mal-PEG3C2-3377, and Mal-PEG6C2-3377, Mal-PEG2C2-8261, Mal-PEG3C2-8261, and Mal-PEG6C2-8261.

* * * * *